United States Patent
Jablons et al.

(10) Patent No.: US 11,479,601 B2
(45) Date of Patent: Oct. 25, 2022

(54) ANTIBODIES SPECIFIC TO SONIC HEDGEHOG AND METHOD OF USE THEREOF

(71) Applicant: The Regents of the University of California, Oakland, CA (US)

(72) Inventors: David M. Jablons, San Francisco, CA (US); Bhairavi Tolani, San Francisco, CA (US); Biao He, Foster City, CA (US); Etienne Giroux-Leprieur, Boulogne-Billancourt (FR)

(73) Assignee: The Regents of the University of California, Oakland, CA (US)

( * ) Notice: Subject to any disclaimer, the term of this patent is extended or adjusted under 35 U.S.C. 154(b) by 295 days.

(21) Appl. No.: 16/313,413

(22) PCT Filed: Jun. 28, 2017

(86) PCT No.: PCT/US2017/039831
§ 371 (c)(1),
(2) Date: Dec. 26, 2018

(87) PCT Pub. No.: WO2018/005697
PCT Pub. Date: Jan. 4, 2018

(65) Prior Publication Data
US 2019/0161538 A1     May 30, 2019

Related U.S. Application Data

(60) Provisional application No. 62/356,276, filed on Jun. 29, 2016.

(51) Int. Cl.
| | |
|---|---|
| *A61K 39/395* | (2006.01) |
| *C07K 16/18* | (2006.01) |
| *C07K 16/30* | (2006.01) |
| *A61P 35/00* | (2006.01) |
| *A61K 47/68* | (2017.01) |
| *A61K 39/00* | (2006.01) |
| *A61K 45/06* | (2006.01) |
| *G01N 33/574* | (2006.01) |

(52) U.S. Cl.
CPC .......... *C07K 16/18* (2013.01); *A61K 39/0011* (2013.01); *A61K 39/3955* (2013.01); *A61K 45/06* (2013.01); *A61K 47/6843* (2017.08); *A61K 47/6857* (2017.08); *A61P 35/00* (2018.01); *C07K 16/3023* (2013.01); *G01N 33/57492* (2013.01); *A61K 2039/505* (2013.01); *A61K 2039/54* (2013.01); *A61K 2039/545* (2013.01); *A61K 2039/572* (2013.01); *C07K 2317/24* (2013.01); *C07K 2317/34* (2013.01); *C07K 2317/52* (2013.01); *C07K 2317/565* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,622,929 | A | 4/1997 | Willner et al. |
| 6,214,345 | B1 | 4/2001 | Firestone et al. |
| 8,071,733 | B2 | 12/2011 | Beachy et al. |
| 2007/0149592 | A1 | 6/2007 | He et al. |
| 2009/0035320 | A1 | 2/2009 | Suzuki et al. |
| 2010/0196388 | A1* | 8/2010 | Jenkins ............... A61P 25/28 424/142.1 |
| 2011/0059469 | A1 | 3/2011 | Aburatani et al. |
| 2015/0361048 | A1 | 12/2015 | He et al. |

FOREIGN PATENT DOCUMENTS

| | | |
|---|---|---|
| WO | 2018005678 | 1/2018 |

* cited by examiner

*Primary Examiner* — Laura B Goddard
(74) *Attorney, Agent, or Firm* — Rudy J. Ng; Bozicevic, Field & Francis LLP

(57) ABSTRACT

Antibodies that specifically bind to a Sonic Hedgehog (Shh) polypeptide, or an antigen binding fragment thereof, are provided. Also provided are methods of treating an individual for cancer using the Shh polypeptide antibodies. Methods of analyzing a tissue sample for cell-surface expression of a full-length Shh polypeptide are also provided.

40 Claims, 83 Drawing Sheets

Specification includes a Sequence Listing.

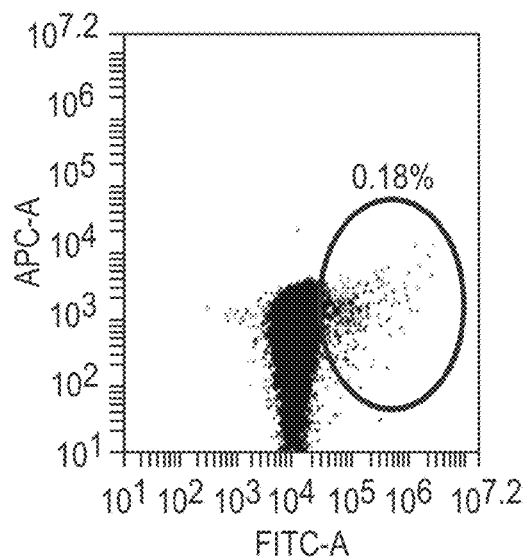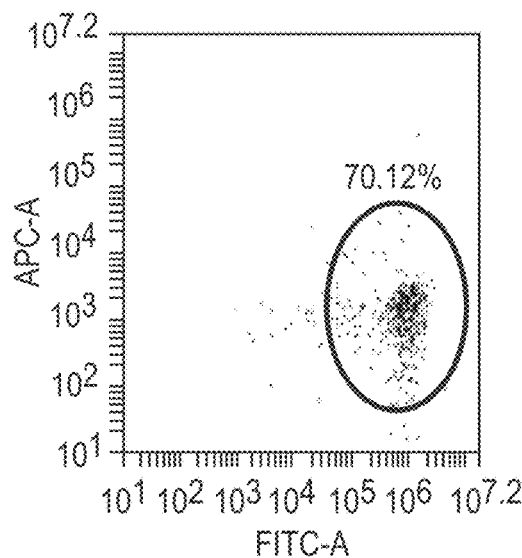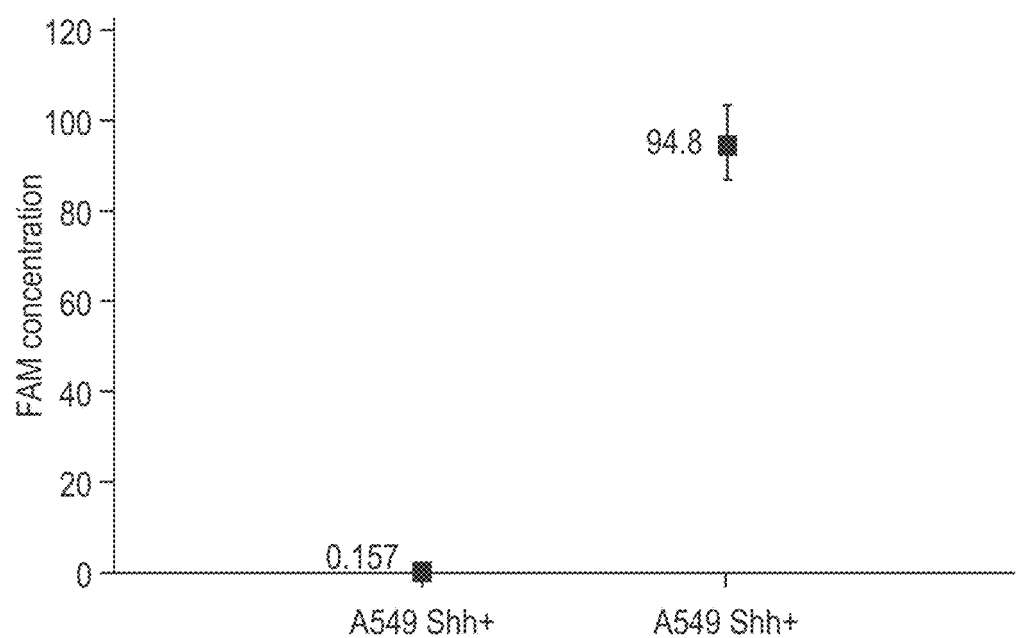

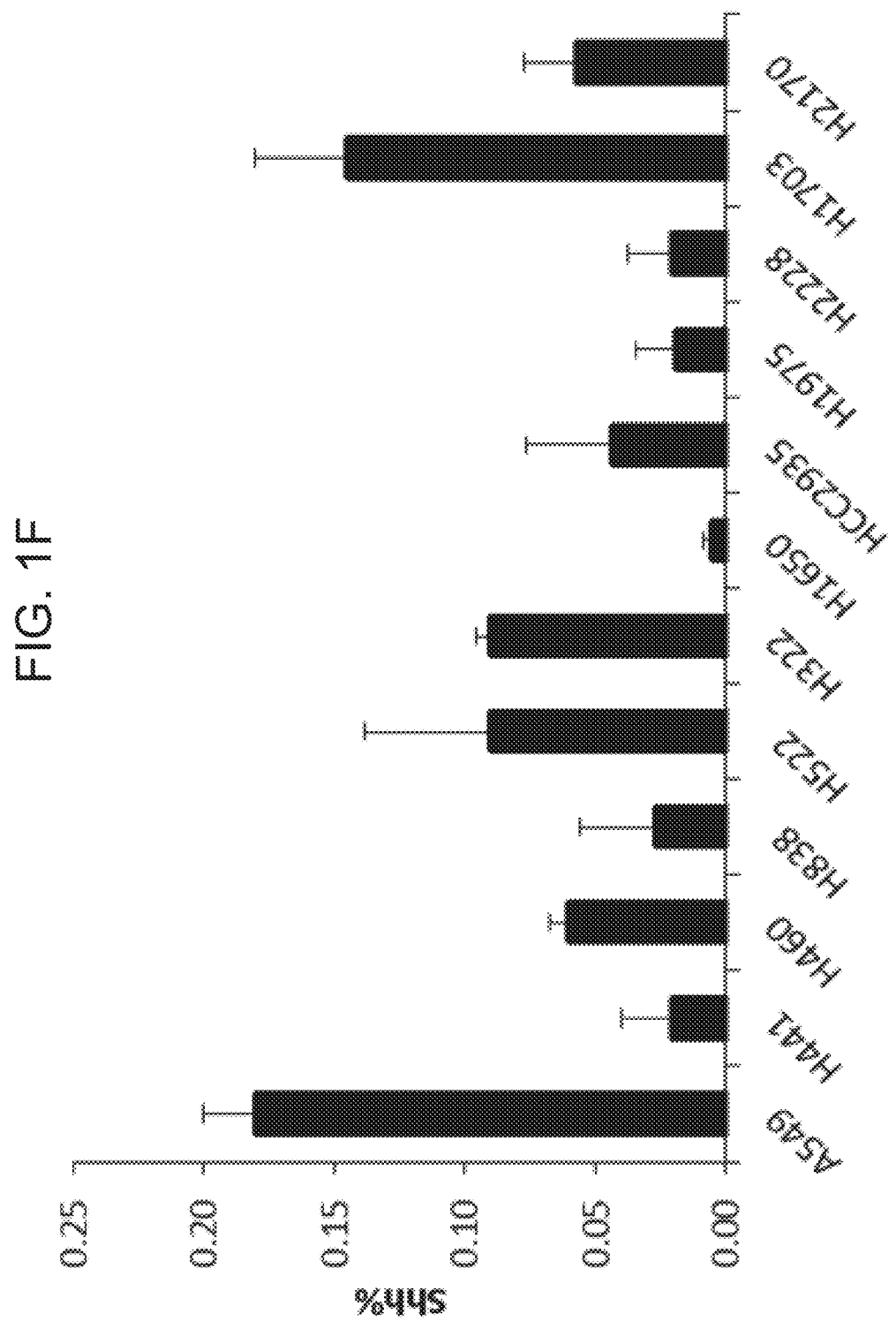

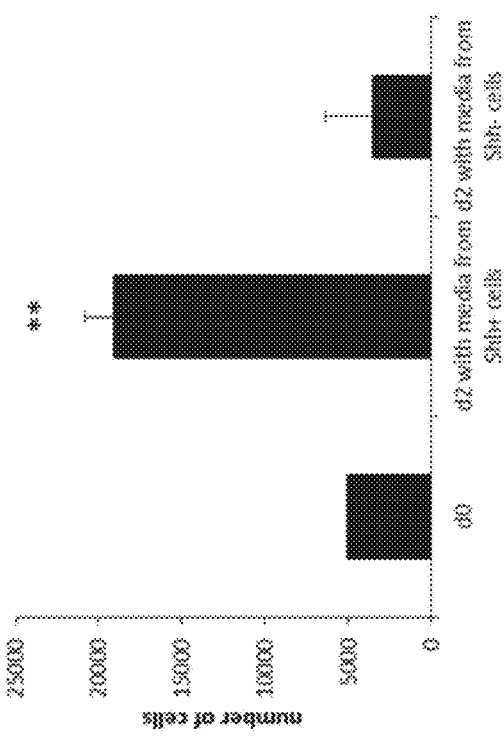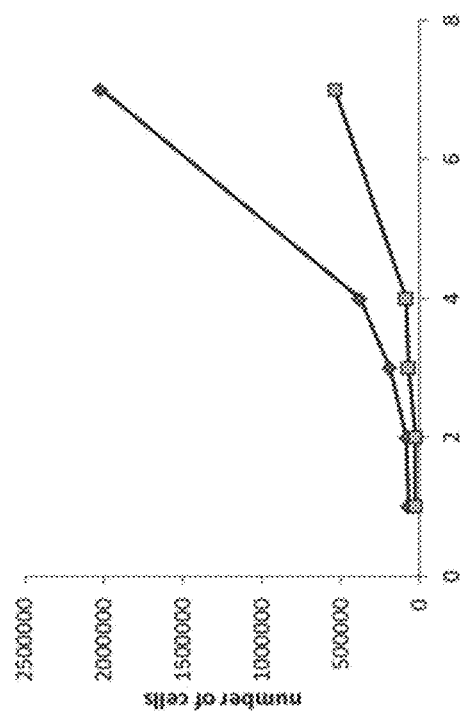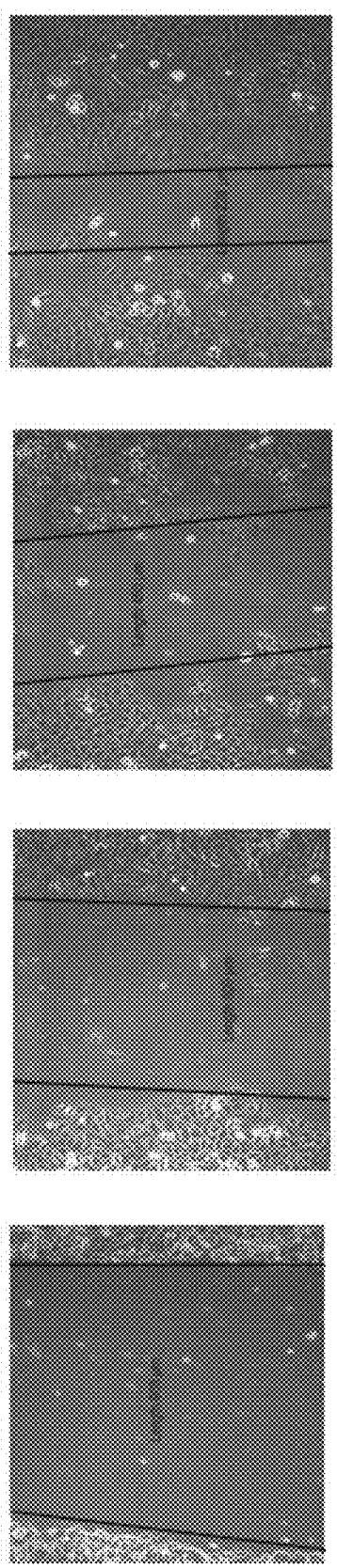

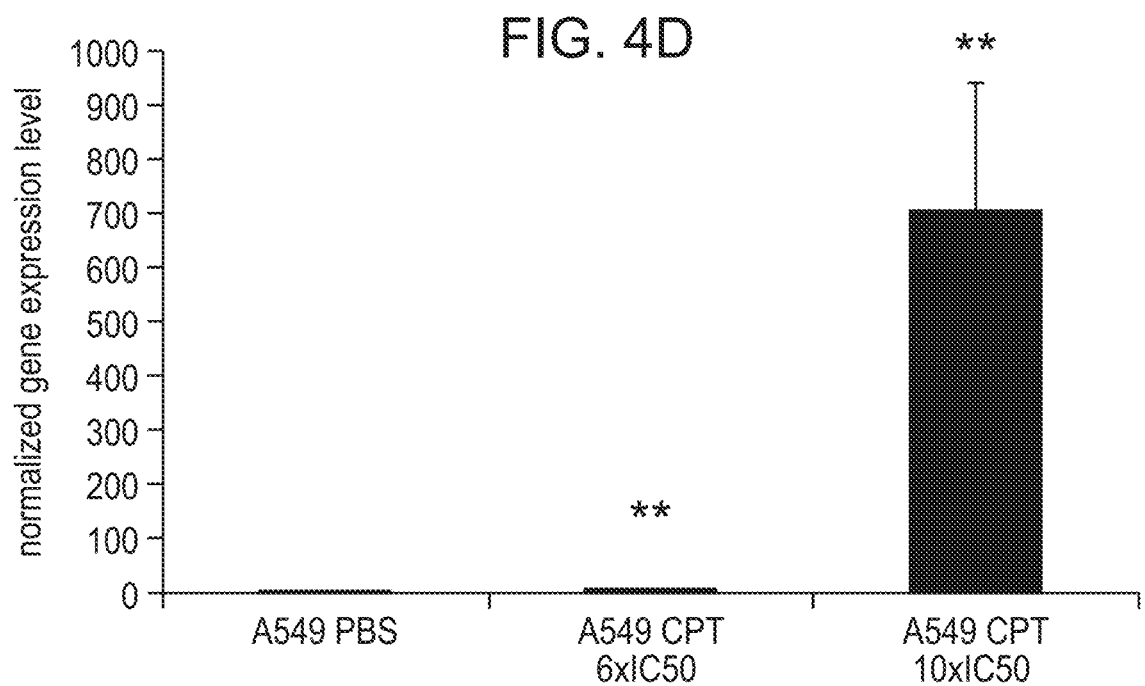
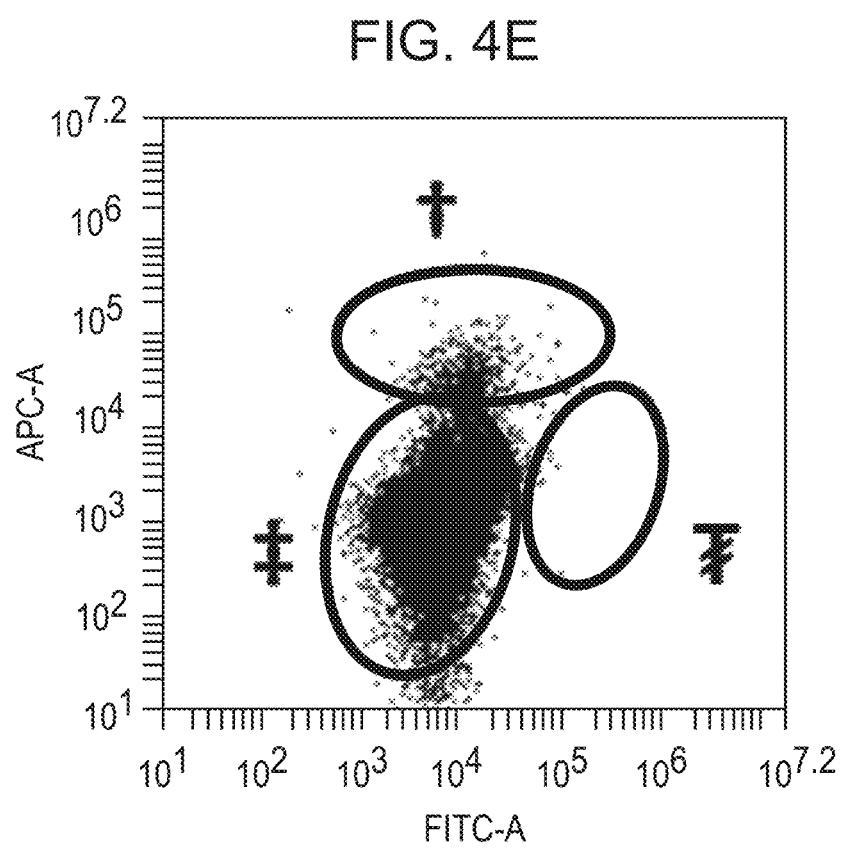

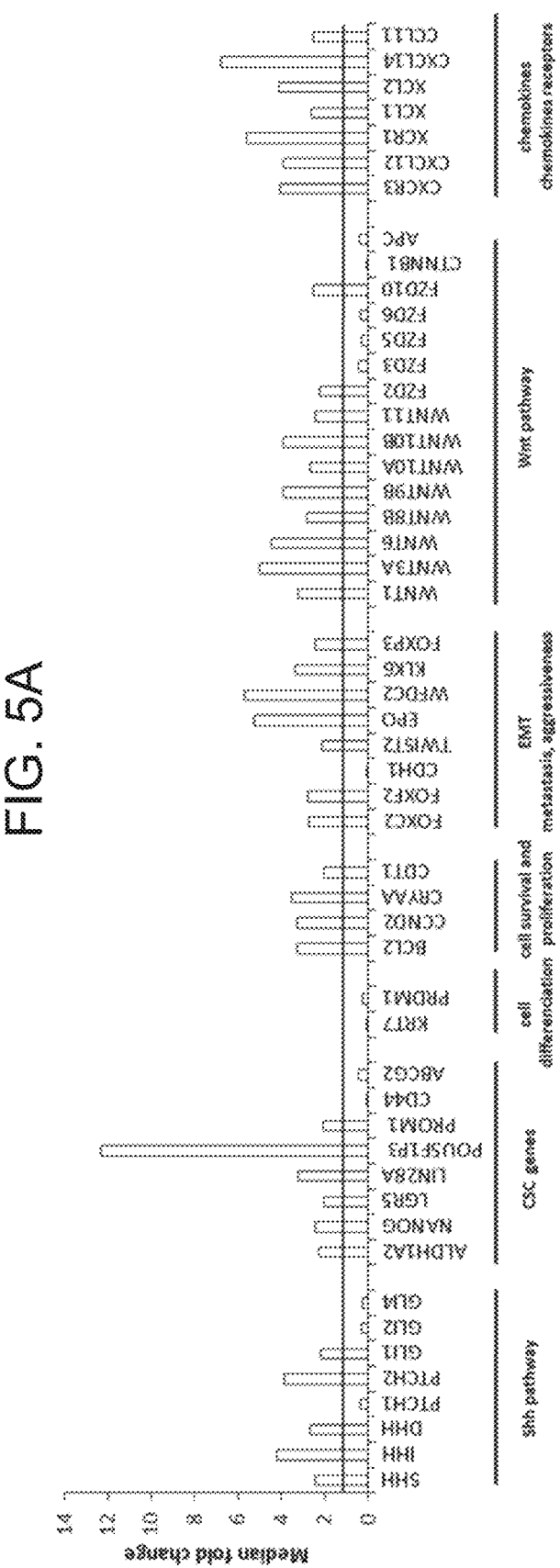
FIG. 5A
FIG. 5B
FIG. 5C

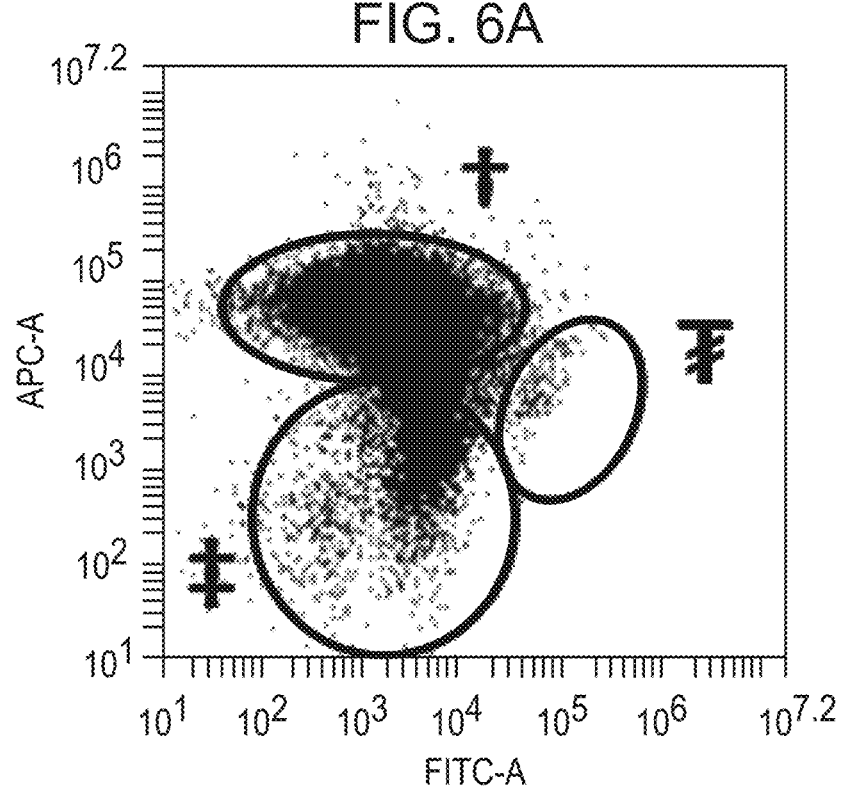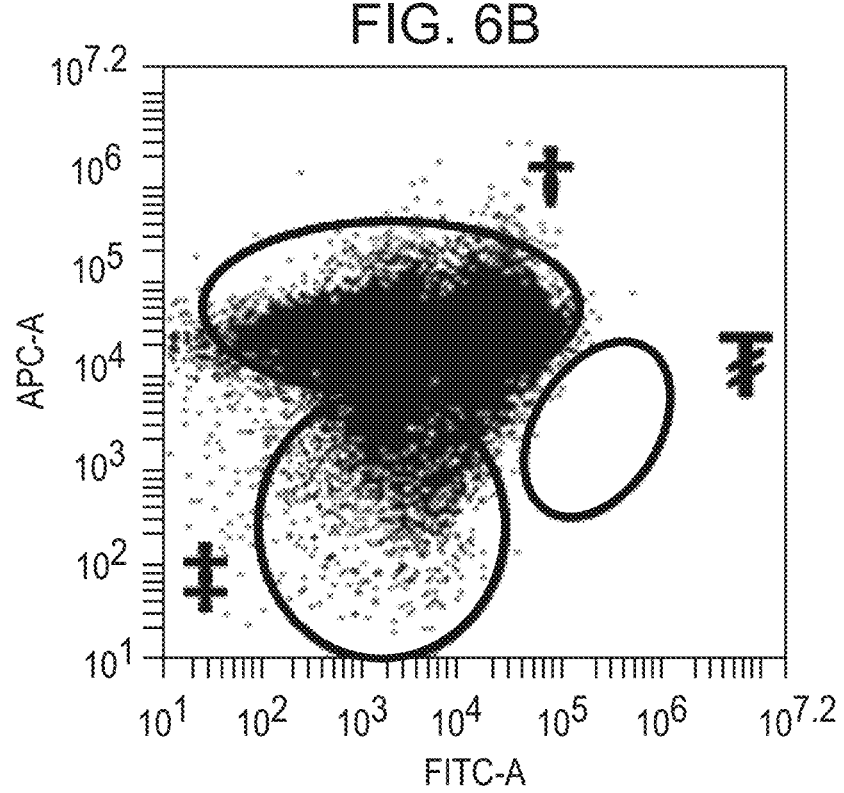

FIG. 14

Table 2

| Pathological type of lung metastases | n | Shh rate (%) |
|---|---|---|
| Malignant pleural mesothelioma | 7 | 0.07 (IQR 0.02-0.13) |
| Melanoma | 5 | 0.10 (IQR 0-0.42) |
| Sarcoma | 3 | 0.02 (IQR 0.02-0.04) |
| Prostatic carcinoma | 1 | 0.07 |
| Renal carcinoma | 1 | 0.06 |
| Breast carcinoma | 1 | 0.01 |
| Colorectal carcinoma | 1 | 0.01 |
| Hepatocarcinoma | 1 | 0.01 |

1 = PHX cells
2 = PHX + SHh
3 = A549 cells

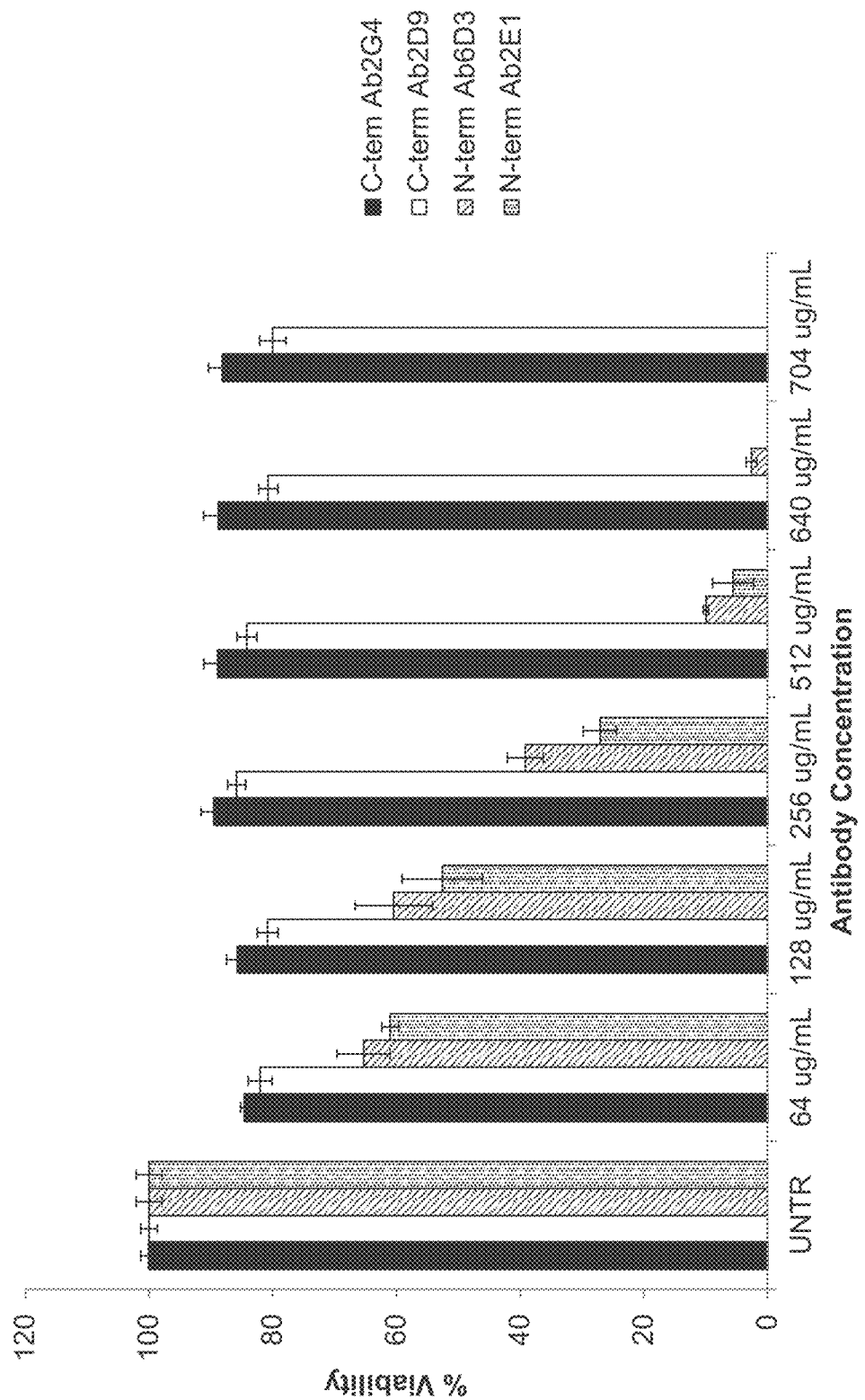

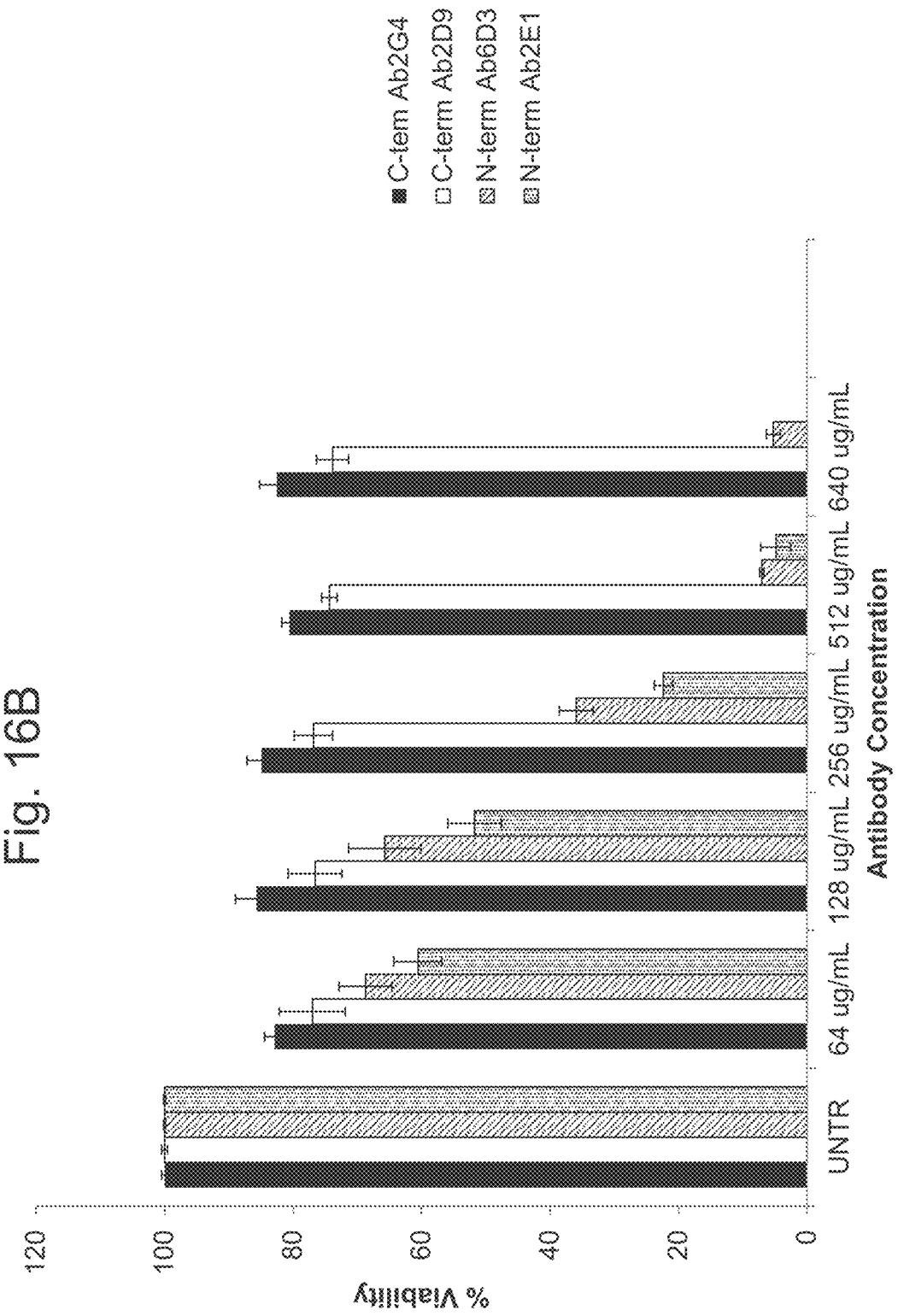

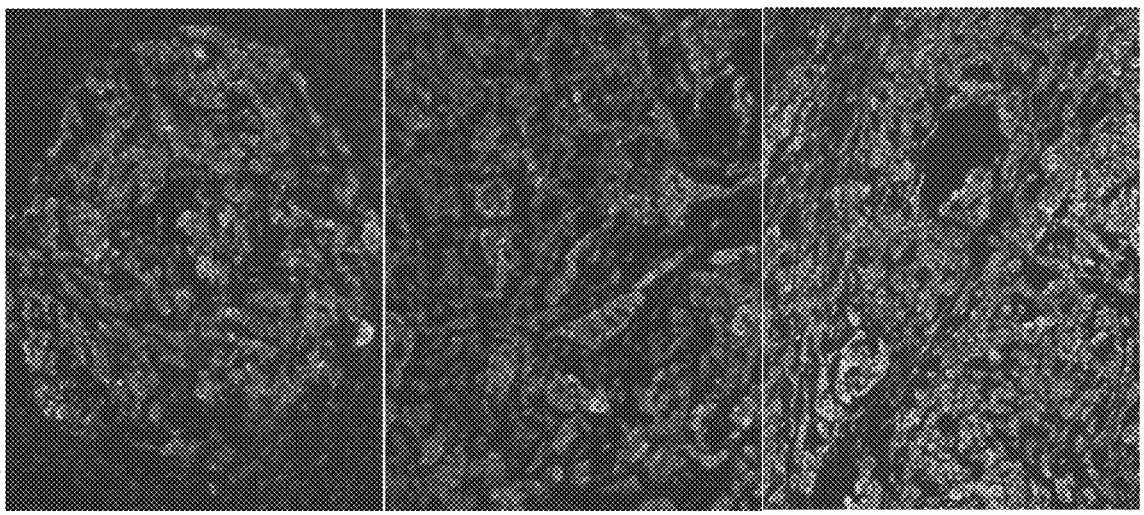
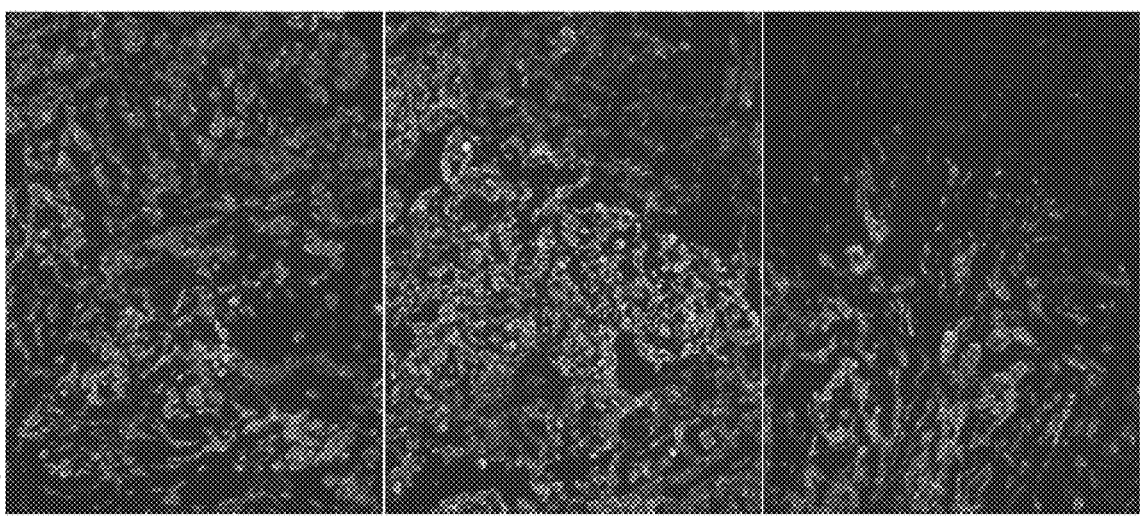
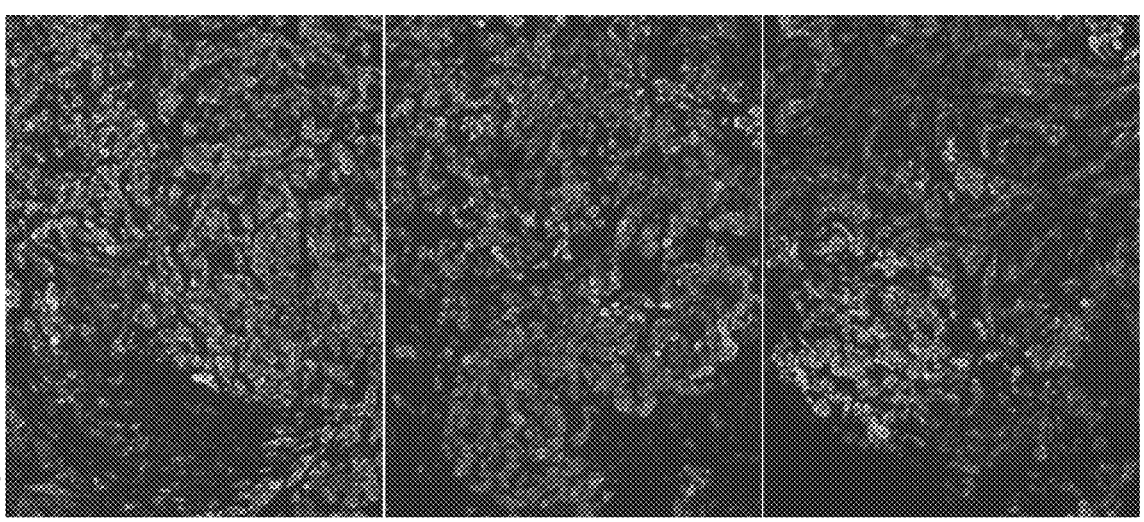

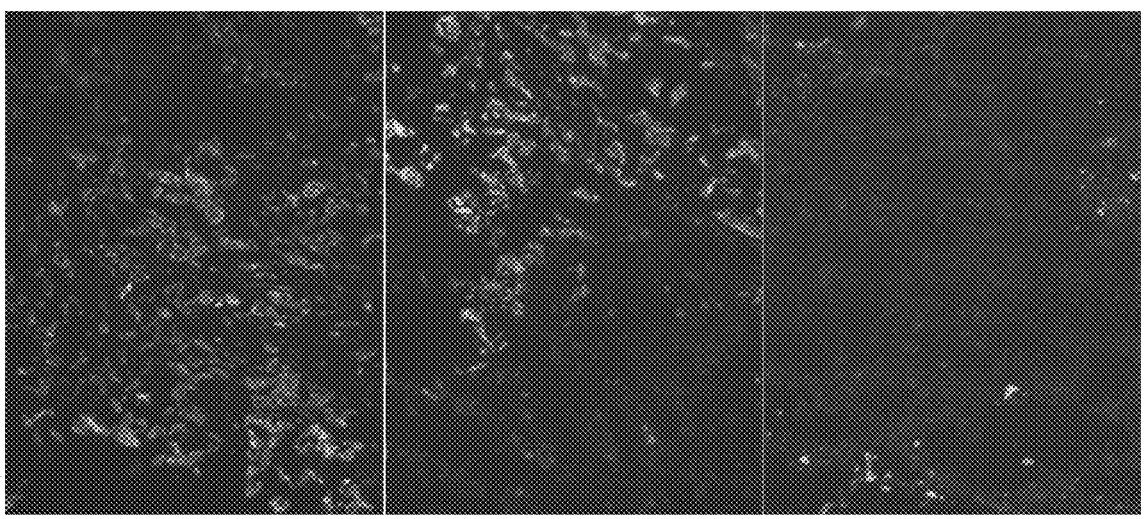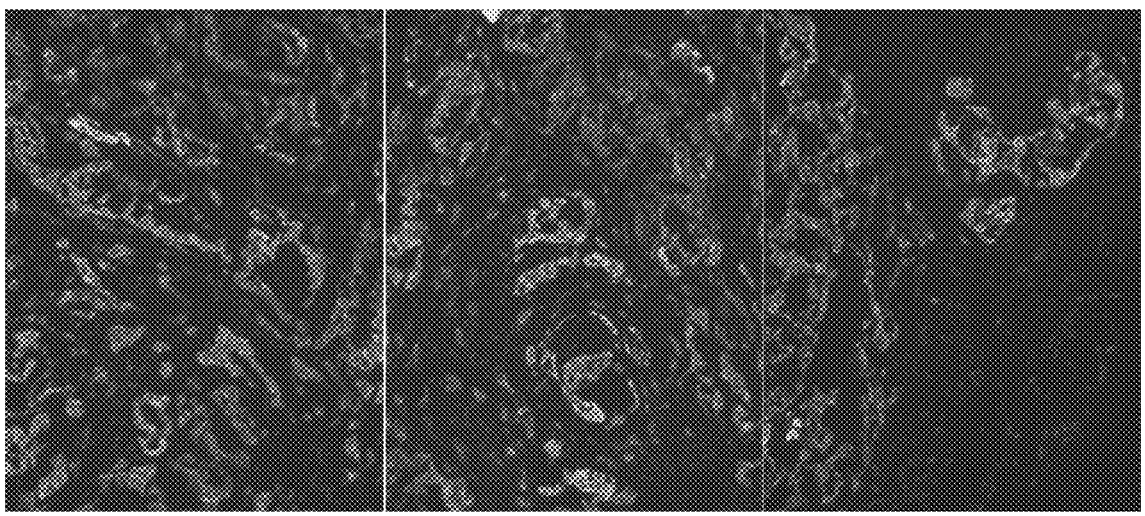

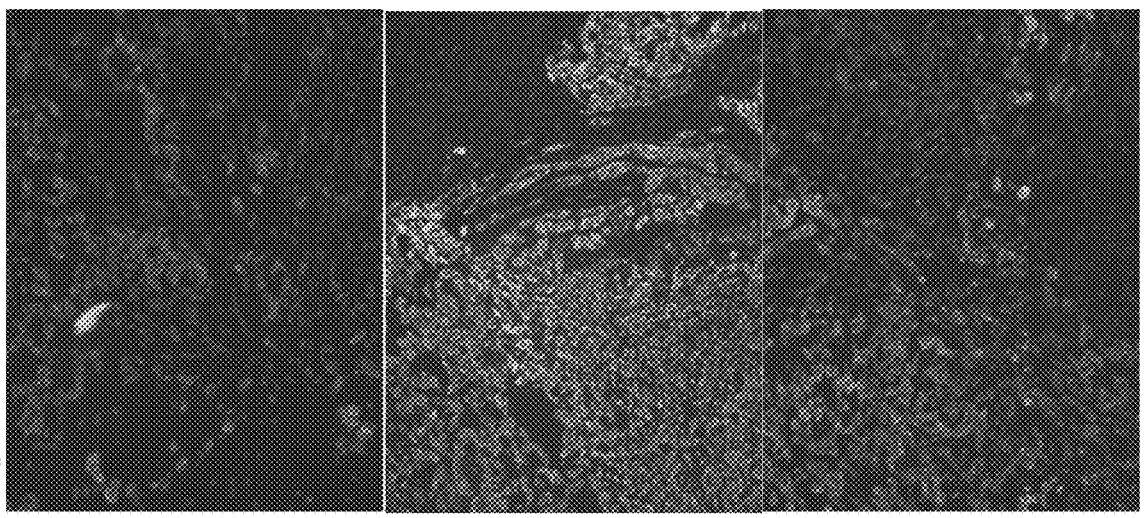
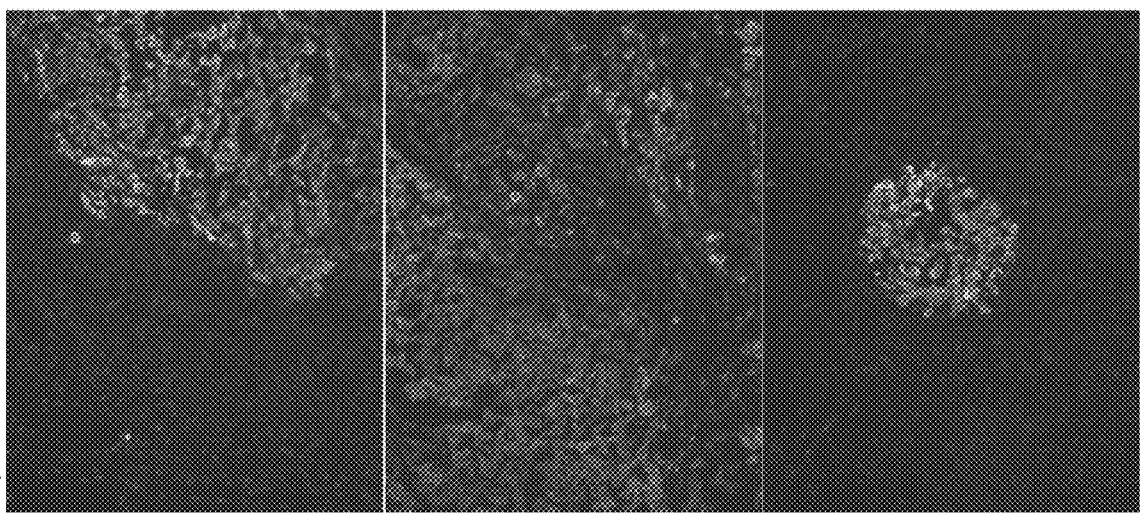
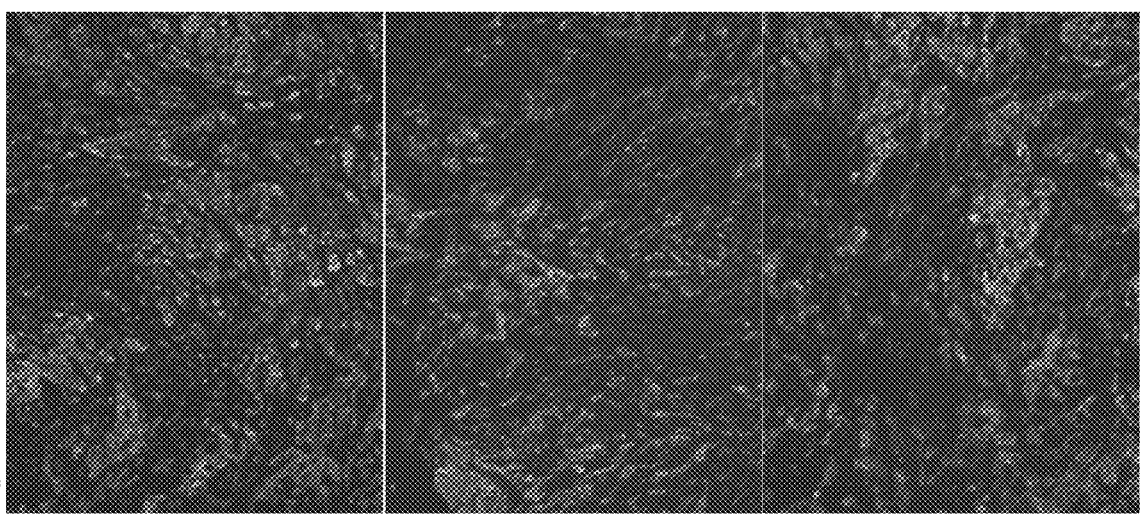

Fig. 22

Table 8: Expression of GLI1 in tumors after antibody treatment

|  | Control | Control | Control | Avg | Fold change | |
|---|---|---|---|---|---|---|
| Mouse # tag | 980 | 981 | 990 | | | |
| GLI1 | 0.033906 | 0.008164 | 0.018195 | 0.020089 | 1 | |
| | 2G4 | 2G4 | 2G4 | Avg | | |
| Mouse # tag | 468 | 469 | 478 | | | |
| GLI1 | 0.019194 | 0.027071 | 0.006787 | 0.017684 | 0.8803074 | down |
| | 2D9 | 2D9 | 2D9 | Avg | | |
| Mouse # tag | 479 | 480 | NT | | | |
| GLI1 | 0.026555 | 0.009136 | 0.007746 | 0.014479 | 0.7207577 | down |

Fig. 23

Human full length sonic hedgehog (SHH); Genbank accession: NP_000184 mlllarclllvlvssllvcsglacgpgrgfgkrrhpkkltplaykqfipnvaektlgasgryegkisrns
erfkeltpnynpdiifkdeentgadrlmtqrckdklnalaisvmnqwpgvklrvtegwdedghhseeslh
yegravdittsdrdrskygmlarlaveagfdwvyyeskahihcsvkaensvaaksggcfpgsatvhleqg
gtklvkdlspgdrvlaaddqgrllysdfltfldrddgakkvfyvietreprerllltaahllfvaphnds
atgepeassqsgppsggalgpralfasrvrpgqrvyvvaerdgdrrllpaavhsvtlseeaagayaplta
qgtilinrvlascyavieehswahrafapfrlahallaalapartdrggdsgggdrggggrvaltapga
adapgagatagihwysqllyqigtwlldsealhplgmavkss    (SEQ ID NO:1)

Note: C-terminal peptide (residues 198-462) is underlined; signal
peptide is double underlined.

Table: 9

| Sequence | Clones sequenced | Clones with >99% sequence identity |
|---|---|---|
| $V_H$ | 5 | 5 |
| $C_H$ | 5 | 5 |
| $V_L$ | 5 | 5 |
| $C_L$ | 5 | 5 |

Fig. 25B

1C11/2G4
Heavy chain

ATGAACTTCGGGCTCAGCTTGATTTTCCTTGTCCTTGTTTTAAAAGGTGTGTCCAGTGTGAAGTGAAGCTGG
TGGAGTCTGGGGGAGGCTTAGTGAAGCCTGGAGGGTCCCTGAAACTCTCCTGTGCAGCCTCTGGATTCAC
TTTCAGTAGCTATACCATGTCTTGGGTTCGCCAGACTCCGGCGAAGAGGCTGGAGTGGGTCGCAACCATT
AGTAGTGGTGGTGGTAACACCTACTATCCAGACAGTGTGAAGGGCCGATTCACCATCTCCAGAGACAATG
CCAGGAACACCCTGTACCTGCAAATGAGCAGTCTGAGGTCTGAGGACACGGCCATGTATTACTGTGCAAG
AGACTATAGGTCCCTGTTTGCTTACTGGGGCCAAGGGACTCTGGTCACTGTCTCTGCAGCCAAAACGACA
CCCCCATCTGTCTATCCACTGGCCCCTGGATCTGCTGCCCAAACTAACTCCATGGTGACCCTGGGATGCC
TGGTCAAGGGCTATTTCCCTGAGCCAGTGACAGTGACCTGGAACTCTGGATCCCTGTCCAGCGGTGTGCA
CACCTTCCCAGCTGTCCTGCAGTCTGACCTCTACACTCTGAGCAGCTCAGTGACTGTCCCCTCCAGCACC
TGGCCCAGCGAGACCGTCACCTGCAACGTTGCCCACCCGGCCAGCAGCACCAAGGTGGACAAGAAAATTG
TGCCCAGGGATTGTGGTTGTAAGCCTTGCATATGTACAGTCCCAGAAGTATCATCTGTCTTCATCTTCCC
CCCAAAGCCCAAGGATGTGCTCACCATTACTCTGACTCCTAAGGTCACGTGTGTTGTGGTAGACATCAGC
AAGGATGATCCCGAGGTCCAGTTCAGCTGGTTTGTAGATGATGTGGAGGTGCACACAGCTCAGACGCAAC
CCCGGGAGGAGCAGTTCAACAGCACTTTCCGCTCAGTCAGTGAACTTCCCATCATGCACCAGGACTGGCT
CAATGGCAAGGAGTTCAAATGCAGGGTCAACAGTGCAGCTTTCCCTGCCCCCATCGAGAAAACCATCTCC
AAAACCAAAGGCAGACCGAAGGCTCCACAGGTGTACACCATTCCACCTCCCAAGGAGCAGATGGCCAAGG
ATAAAGTCAGTCTGACCTGCATGATAACAGACTTCTTCCCTGAAGACATTACTGTGGAGTGGCAGTGGAA
TGGGCAGCCAGCGGAGAACTACAAGAACACTCAGCCCATCATGGACACAGATGGCTCTTACTTCATCTAC
AGCAAGCTCAATGTGCAGAAGAGCAACTGGGAGGCAGGAAATACTTTCACCTGCTCTGTGTTACATGAGG
GCCTGCACAACCACCATACTGAGAAGAGCCTCTCCCACTCTCCTGGTAAATGA (SEQ ID NO:2)

FIG. 25C

1C11/2G4
Heavy chain

MNFGLSLIFLVLVLKGVQCEVKLVESGGGLVKPGGSLKLSCAASGFTFSSYTMSWVRQTPAKRLEWVATI
SSGGGNTYYPDSVKGRFTISRDNARNTLYLQMSSLRSEDTAMYYCARDYRSLFAYWGQGTLVTVSAAKTT
PPSVYPLAPGSAAQTNSMVTLGCLVKGYFPEPVTVTWNSGSLSSGVHTFPAVLQSDLYTLSSSVTVPSST
WPSETVTCNVAHPASSTKVDKKIVPRDCGCKPCICTVPEVSSVFIFPPKPKDVLTITLTPKVTCVVVDIS
KDDPEVQFSWFVDDVEVHTAQTQPREEQFNSTFRSVSELPIMHQDWLNGKEFKCRVNSAAFPAPIEKTIS
KTKGRPKAPQVYTIPPPKEQMAKDKVSLTCMITDFFPEDITVEWQWNGQPAENYKNTQPIMDTDGSYFIY
SKLNVQKSNWEAGNTFTCSVLHEGLHNHHTEKSLSHSPGK (SEQ ID NO:3)

Fig. 25D

1C11/2G4
Light chain

ATGCATTTTCAAGTGCAGATTTTCAGCTTCCTGCTAATCAGTGCCTCAGTCATAATGTCCAGAGGACAAA
TTGTTCTCACCCAGTCTCCAGCAATCATGTCTGCATCTCCAGGGGAGAAGGTCACCATAACCTGCAGTGC
CAGCTCAAGTGTAAGTTACATGCACTGGTTCCAGCAGAAGCCAGGCACTTCTCCCAAACTCTGGATTTAT
AGCACATCCAACCTGGCTTCTGGAGTCCCTGCTCGCTTCAGTGGCAGTGGATCTGGGACCTCTTACTCTC
TCACAATCAGCCGAATGGAGGCTGAAGATGCTGCCACTTATTACTGCCAGCAAAGGAGTAGTTACCCATT
CACGTTCGGCTCGGGGACAAAGTTGGAAATAAAACGGGCTGATGCTGCACCAACTGTATCCATCTTCCCA
CCATCCAGTGAGCAGTTAACATCTGGAGGTGCCTCAGTCGTGTGCTTCTTGAACAACTTCTACCCCAAAG
ACATCAATGTCAAGTGGAAGATTGATGGCAGTGAACGACAAAATGGCGTCCTGAACAGTTGGACTGATCA
GGACAGCAAAGACAGCACCTACAGCATGAGCAGCACCCTCACGTTGACCAAGGACGAGTATGAACGACAT
AACAGCTATACCTGTGAGGCCACTCACAAGACATCAACTTCACCCATTGTCAAGAGCTTCAACAGGAATG
AGTGTTG (SEQ ID NO:4)

FIG. 25E

1C11/2G4
Light chain

MHFQVQIFSFLLISASVIMSRGQIVLTQSPAIMSASPGEKVTITCSASSSVSYMHWFQQKPGTSPKLWIY
STSNLASGVPARFSGSGSGTSYSLTISRMEAEDAATYYCQQRSSYPFTFGSGTKLEIKRADAAPTVSIFP
PSSEQLTSGGASVVCFLNNFYPKDINVKWKIDGSERQNGVLNSWTDQDSKDSTYSMSSTLTLTKDEYERH
NSYTCEATHKTSTSPIVKSFNRNEC (SEQ ID NO:5)

Fig. 26A

Table: 10

| Sequence | Clones sequenced | Clones with >99% sequence identity |
|---|---|---|
| $V_H$ | 5 | 5 |
| $C_H$ | 5 | 5 |
| $V_L$ | 5 | 5 |
| $C_L$ | 5 | 5 |

Fig. 26B

1C11/2D9
Heavy chain

ATGAACTTCGGGCTCAGCTTGATTTTCCTTGTCCTTGTTTTAAAAGGTGTCCAGTGTGAAGTGAAGCTGG
TGGAGTCTGGGGGAGGCTTAGTGAAGCCTGGAGGGTCCCTGAAACTCTCCTGTGCAGCCTCTGGATTCAC
TTTCAGTAGCTATACCATGTCTTGGGTTCGCCAGACTCCGGCGAAGAGGCTGGAGTGGGTCGCAACCATT
AGTAGTGGTGGTGGTAACACCTACTATCCAGACAGTGTGAAGGGCCGATTCACCATCTCCAGAGACAATG
CCAGGAACACCCTGTACCTGCAAATGAGCAGTCTGAGGTCTGAGGACACGGCCATGTATTACTGTGCAAG
AGACTATAGGTCCCTGTTTGCTTACTGGGGCCAAGGGACTCTGGTCACTGTCTCTGCAGCCAAAACGACA
CCCCCATCTGTCTATCCACTGGCCCCTGGATCTGCTGCCCAAACTAACTCCATGGTGACCCTGGGATGCC
TGGTCAAGGGCTATTTCCCTGAGCCAGTGACAGTGACCTGGAACTCTGGATCCCTGTCCAGCGGTGTGCA
CACCTTCCCAGCTGTCCTGCAGTCTGACCTCTACACTCTGAGCAGCTCAGTGACTGTCCCCTCCAGCACC
TGGCCCAGCGAGACCGTCACCTGCAACGTTGCCCACCCGGCCAGCAGCACCAAGGTGGACAAGAAAATTG
TGCCCAGGGATTGTGGTTGTAAGCCTTGCATATGTACAGTCCCAGAAGTATCATCTGTCTTCATCTTCCC
CCCAAAGCCCAAGGATGTGCTCACCATTACTCTGACTCCTAAGGTCACGTGTGTTGTGGTAGACATCAGC
AAGGATGATCCCGAGGTCCAGTTCAGCTGGTTTGTAGATGATGTGGAGGTGCACACAGCTCAGACGCAAC
CCCGGGAGGAGCAGTTCAACAGCACTTTCCGCTCAGTCAGTGAACTTCCCATCATGCACCAGGACTGGCT
CAATGGCAAGGAGTTCAAATGCAGGGTCAACAGTGCAGCTTTCCCTGCCCCCATCGAGAAAACCATCTCC
AAAACCAAAGGCAGACCGAAGGCTCCACAGGTGTACACCATTCCACCTCCCAAGGAGCAGATGGCCAAGG
ATAAAGTCAGTCTGACCTGCATGATAACAGACTTCTTCCCTGAAGACATTACTGTGGAGTGGCAGTGGAA
TGGGCAGCCAGCGGAGAACTACAAGAACACTCAGCCCATCATGGACACAGATGGCTCTTACTTCATCTAC
AGCAAGCTCAATGTGCAGAAGAGCAACTGGGAGGCAGGAAATACTTTCACCTGCTCTGTGTTACATGAGG
GCCTGCACAACCACCATACTGAGAAGAGCCTCTCCCACTCTCCTGGTAAATGA(SEQ ID NO:6)

FIG. 26C

1C11/2D9
Heavy chain

MNFGLSLIFLVLVLKGVQCEVKLVESGGGLVKPGGSLKLSCAASGFTFSSYTMSWVRQTPAKRLEWVATI
SSGGGNTYYPDSVKGRFTISRDNARNTLYLQMSSLRSEDTAMYYCARDYRSLFAYWGQGTLVTVSAAKTT
PPSVYPLAPGSAAQTNSMVTLGCLVKGYFPEPVTVTWNSGSLSSGVHTFPAVLQSDLYTLSSSVTVPSST
WPSETVTCNVAHPASSTKVDKKIVPRDCGCKPCICTVPEVSSVFIFPPKPKDVLTITLTPKVTCVVVDIS
KDDPEVQFSWFVDDVEVHTAQTQPREEQFNSTFRSVSELPIMHQDWLNGKEFKCRVNSAAFPAPIEKTIS
KTKGRPKAPQVYTIPPPKEQMAKDKVSLTCMITDFFPEDITVEWQWNGQPAENYKNTQPIMDTDGSYFIY
SKLNVQKSNWEAGNTFTCSVLHEGLHNHHTEKSLSHSPGK (SEQ ID NO:7)

Fig. 26D

1C11/2D9
Light chain

ATGCATTTTCAAGTGCAGATTTTCAGCTTCCTGCTAATCAGTGCCTCAGTCATAATGTCCAGAGGACAAA
TTGTTCTCACCCAGTCTCCAGCAATCATGTCTGCATCTCCAGGGGAGAAGGTCACCATAACCTGCAGTGC
CAGCTCAAGTGTAAGTTACATGCACTGGTTCCAGCAGAAGCCAGGCACTTCTCCCAAACTCTGGATTTAT
AGCACATCCAACCTGGCTTCTGGAGTCCCTGCTCGCTTCAGTGGCAGTGGATCTGGGACCTCTTACTCTC
TCACAATCAGCCGAATGGAGGCTGAAGATGCTGCCACTTATTACTGCCAGCAAAGGAGTAGTTACCCATT
CACGTTCGGCTCGGGGACAAAGTTGGAAATAAAACGGGCTGATGCTGCACCAACTGTATCCATCTTCCCA
CCATCCAGTGAGCAGTTAACATCTGGAGGTGCCTCAGTCGTGTGCTTCTTGAACAACTTCTACCCCAAAG
ACATCAATGTCAAGTGGAAGATTGATGGCAGTGAACGACAAAATGGCGTCCTGAACAGTTGGACTGATCA
GGACAGCAAAGACAGCACCTACAGCATGAGCAGCACCCTCACGTTGACCAAGGACGAGTATGAACGACAT
AACAGCTATACCTGTGAGGCCACTCACAAGACATCAACTTCACCCATTGTCAAGAGCTTCAACAGGAATG
AGTGTTG (SEQ ID NO:8)

FIG. 26E

1C11/2D9
Light chain

MHFQVQIFSFLLISASVIMSRGQIVLTQSPAIMSASPGEKVTITCSASSSVSYMHWFQQKPGTSPKLWIY
STSNLASGVPARFSGSGSGTSYSLTISRMEAEDAATYYCQQRSSYPFTFGSGTKLEIKRADAAPTVSIFP
PSSEQLTSGGASVVCFLNNFYPKDINVKWKIDGSERQNGVLNSWTDQDSKDSTYSMSSTLTLTKDEYERH
NSYTCEATHKTSTSPIVKSFNRNEC (SEQ ID NO:9)

Fig.37A
Fig.37B
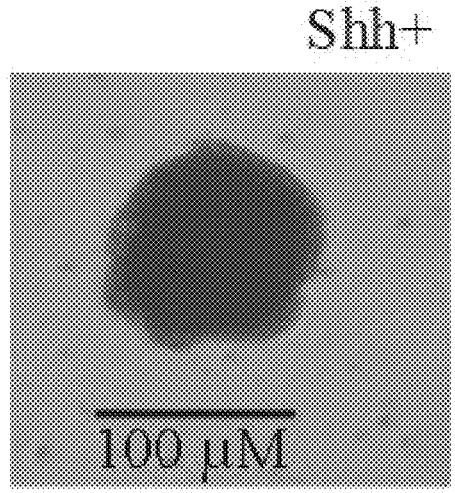
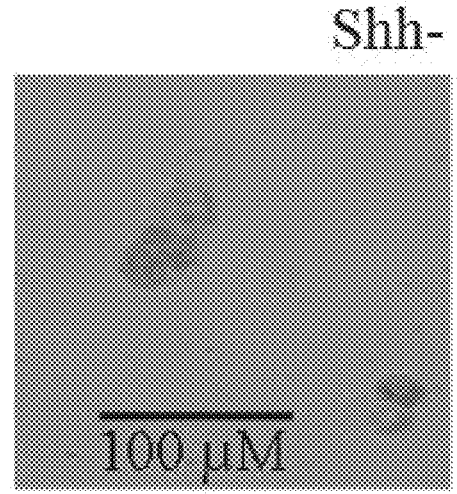
Fig.37C
Fig.37D
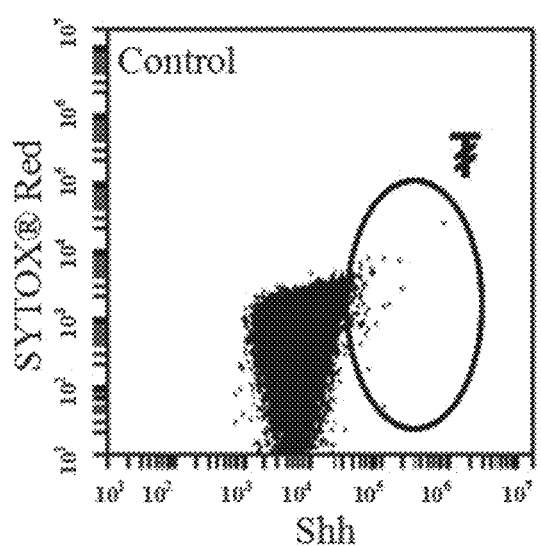
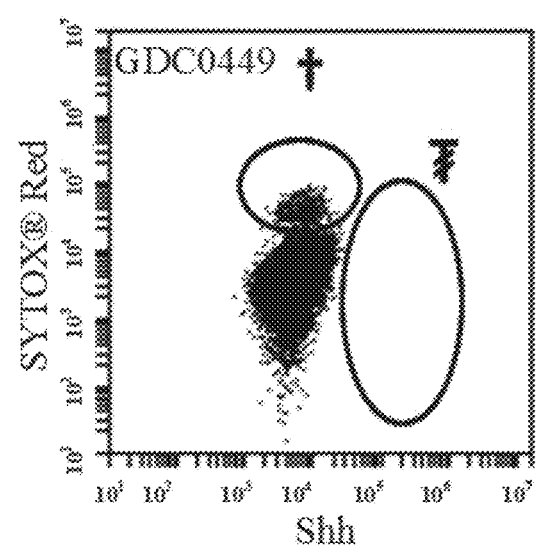

Shh+

Shh-

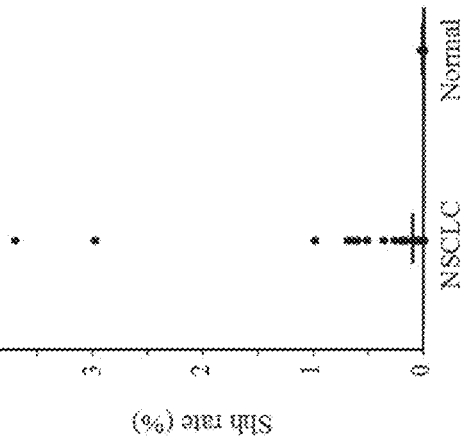
Fig. 38A Fig. 38B Fig. 38C
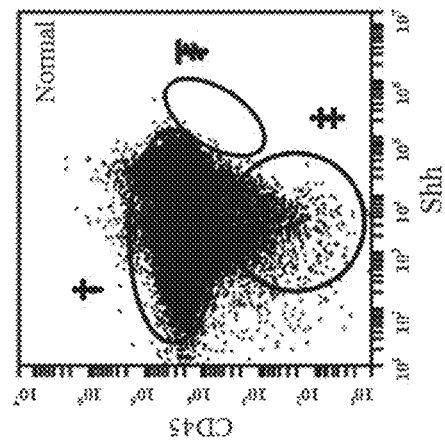
Fig. 38D Fig. 38E Fig. 38F
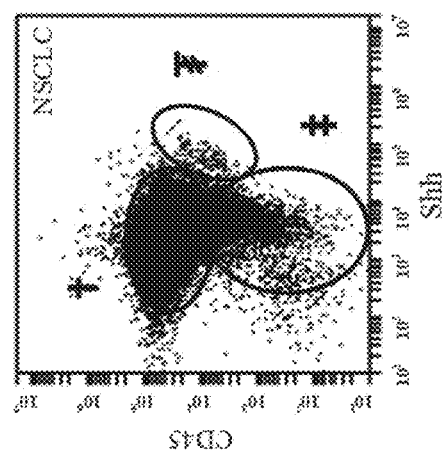
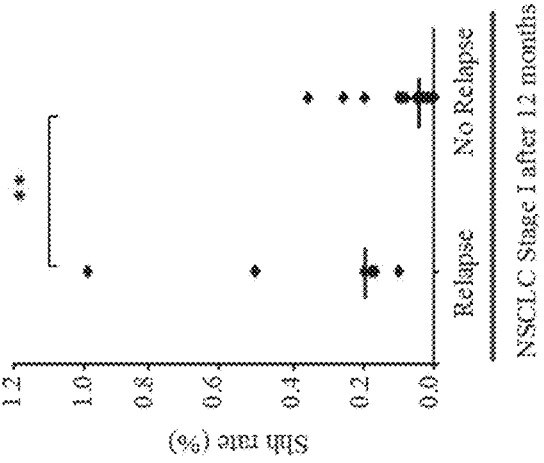
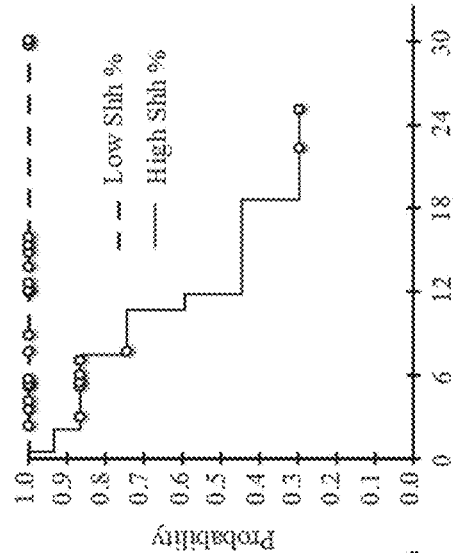
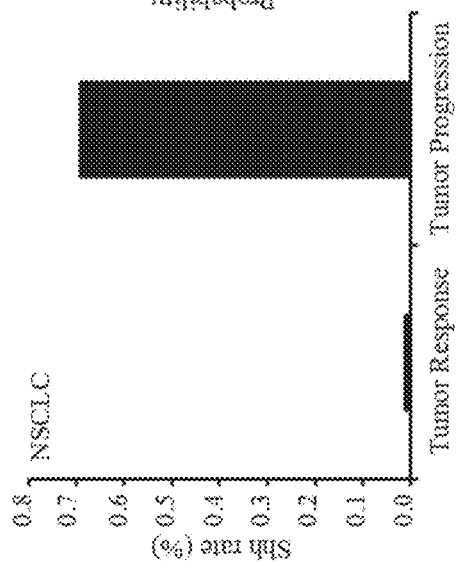

Fig. 40

| Pathological type of lung metastases | n | Shh rate (%) |
|---|---|---|
| Malignant pleural mesothelioma | 7 | 0.07 (IQR 0.02-0.13) |
| Melanoma | 5 | 0.10 (IQR 0-0.42) |
| Sarcoma | 3 | 0.02 (IQR 0.02-0.04) |
| Prostatic carcinoma | 1 | 0.07 |
| Renal carcinoma | 1 | 0.06 |
| Breast carcinoma | 1 | 0.01 |
| Colorectal carcinoma | 1 | 0.01 |
| Hepatocarcinoma | 1 | 0.01 |

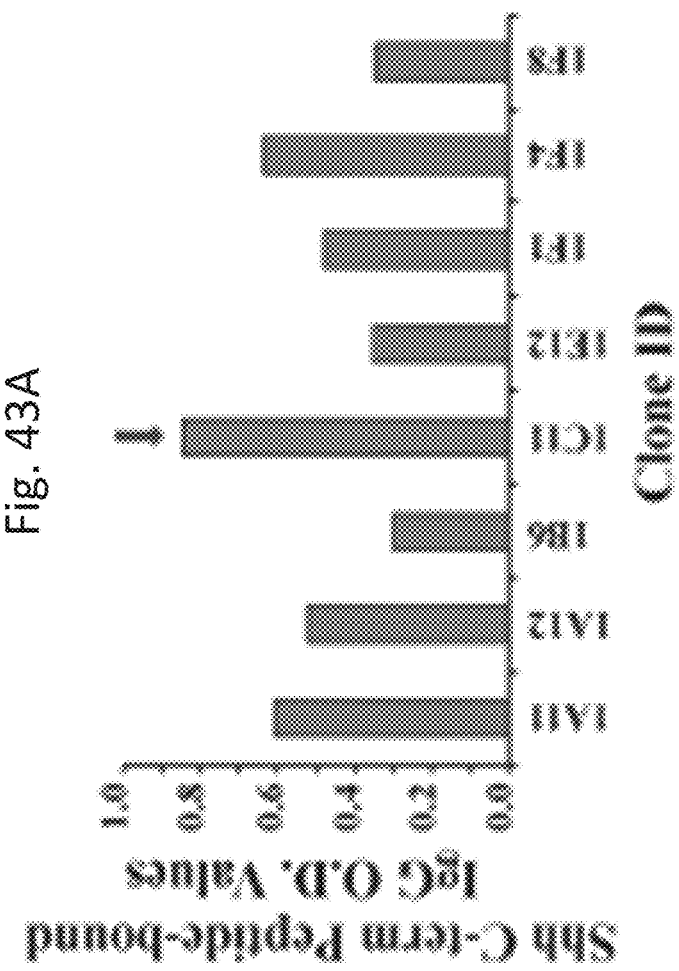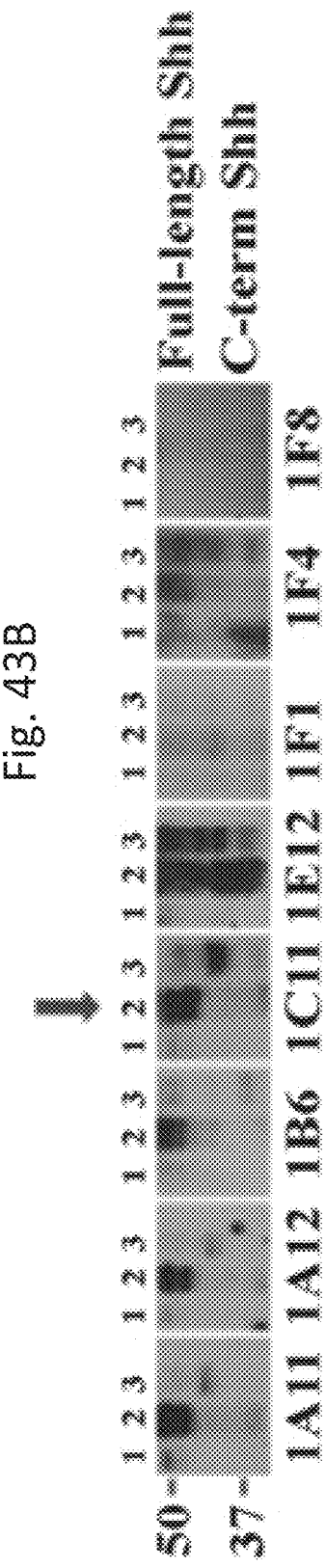

| Antibody | Isotype |
|---|---|
| 1C11-2G4 | IgG$_{1b}$, κ |
| 1C11-2D9 | IgG$_1$, κ |

| C-term Shh Antibody | Total Cells Sorted | % Shh+ Cells | # Shh+ Cells |
|---|---|---|---|
| Commercial (Abcam) | 19 million | 0.06% | 3,808 |
| 1C11-2G4 | 3 million | 0.11% | 1346 |
| 1C11-2D9 | 3 million | 0.05% | 647 |

| Tumor Volume (mm³) | | | | | |
|---|---|---|---|---|---|
| | #990 | #980 | #981 | #989 | #995 |
| Control IgG | 462 | 365 | 903 | 1991 | 726 |
| | #481 | #476 | #468 | #470 | #469 |
| Ab 1C11-2G4 | 234 | 239 | 466 | 656 | 307 |

ANTIBODIES SPECIFIC TO SONIC HEDGEHOG AND METHOD OF USE THEREOF

CROSS-REFERENCE TO RELATED APPLICATIONS

This application claims priority pursuant to 35 U.S.C. § 119(e) to U.S. Provisional Application No. 62/356,276, filed Jun. 29, 2016, the disclosure of which is incorporated herein by reference in its entirety.

INTRODUCTION

Lung cancer is the main cause of cancer-related mortality in the United States, with a predominance of non-small cell lung cancer (NSCLC) histological subtype. Because the majority of NSCLC patients at presentation have metastases without a targetable oncogenic signature, systemic chemotherapy plays a major part in the management of most patients' malignancies.

Sonic Hedgehog (Shh) is a protein physiologically involved in vertebrate development. The full-length protein is cleaved in the cytosol into N- and C-terminal products. While the C-terminal peptide is freely secreted, the N-terminal peptide is modified by lipid hydrophobic modifications and retained in the membrane before its secretion.

SUMMARY

Antibodies that specifically bind to a Sonic Hedgehog (Shh) polypeptide, or an antigen binding fragment thereof, are provided. Also provided are methods of treating an individual for cancer using the Shh polypeptide antibodies. Methods of analyzing a tissue sample for cell-surface expression of a full-length Shh polypeptide are also provided.

An antibody (i.e., a C-terminal Shh antibody), or an antigen binding fragment thereof, of the present disclosure may include: a heavy chain variable ($V_H$) region containing: a complementarity determining region ($CDR_H1$) having the amino acid sequence: SYTMS (SEQ ID NO:10); a $CDR_H2$ having the amino acid sequence: TISSGGGNTYYPDSVKG (SEQ ID NO:11); and a $CDR_H3$ having the amino acid sequence: DYRSLFAY (SEQ ID NO:12); and a light chain variable ($V_L$) region containing: a $CDR_L1$ having the amino acid sequence: SASSSVSYMH (SEQ ID NO:13); a $CDR_L2$ having the amino acid sequence: STSNLAS (SEQ ID NO:14); and a $CDR_L3$ having the amino acid sequence: QQRSSYPFT (SEQ ID NO:15). In some embodiments, the antibody, or an antigen binding fragment thereof, includes a $V_H$ region having an amino acid sequence at least about 80% identical to the sequence: EVKLVESGGGLVKPGGSLKLSCAASGFTFSSYTMSWVRQTPAKRLEWVATISSGGGNTYYPDSVKGRFTISRDNARNTLYLQMSSLRSEDTAMYYCARDYRSLFAYWGQGTLVTVSA (SEQ ID NO:16). In some embodiments, the antibody, or an antigen binding fragment thereof, includes a $V_L$ region having an amino acid sequence at least 80% identical to the sequence: QIVLTQSPAIMSASPGEKVTITCSASSSVSYMHWFQQKPGTSPKLWIYSTSNLASGVPARFSGSGSGTSYSLTISRMEAEDAATYYCQQRSSYPFTFGSGTKLEIK (SEQ ID NO:17). In some embodiments, the antibody, or antigen binding fragment thereof, is a scFV antibody, F(ab')$_2$, Fab', or Fab fragment or a diabody.

In any embodiment, the antibody may specifically bind a C-terminal Shh polypeptide.

In any embodiment, the antibody, or the antigen binding fragment thereof, may be humanized.

Also provided herein is an antibody conjugate that includes an antibody, or an antigen binding fragment thereof, having an immunoglobulin (Ig) polypeptide attached to a therapeutic agent, wherein the antibody specifically binds to full-length Shh polypeptide expressed on a cell's surface. In some embodiments, the antibody, or the antigen binding fragment thereof, is a C-terminal Shh antibody, or antigen binding fragment thereof, as described above.

In any embodiment, the cell surface may be a surface of a tumor cell. In some embodiments, the tumor cell is a cancer stem cell.

In any embodiment, the therapeutic agent may be covalently attached to the Ig polypeptide. In certain embodiments, the therapeutic agent is covalently attached through a cysteine residue in the Ig polypeptide. In certain embodiments, the therapeutic agent is attached to the polypeptide by a disulfide linkage. In certain embodiments, the therapeutic agent is attached to the Ig polypeptide through a linking group. In certain embodiments, the Ig polypeptide comprises a light chain polypeptide. In certain embodiments, the Ig polypeptide includes a heavy chain polypeptide. In certain embodiments, the therapeutic agent is attached to a constant region.

In any embodiment, the therapeutic agent may be an inhibitor of the Shh signaling pathway. In certain embodiments, the inhibitor is a GLI inhibitor or a Smoothened (Smo) inhibitor. In certain embodiments, the GLI inhibitor is a compound, for example a compound described in U.S. Provisional Application No. 62/356,261 titled "Compounds and Compositions for the Treatment of Cancer", filed Jun. 29, 2016, and PCT Application titled "Compounds and Compositions for the Treatment of Cancer", filed herewith, the disclosures of which are incorporated herein by reference.

Also provided herein is a nucleic acid that includes a nucleotide sequence encoding one or more Ig polypeptides of a C-terminal Shh antibody, or antigen binding fragment thereof, as described above. Also provided herein is an expression vector that includes the nucleic acid, as described above, wherein the nucleotide sequence encoding the antibody, or the antigen binding fragment thereof, is operably linked to a promoter.

Also provided herein is a composition that includes: a C-terminal Shh antibody, or the antibody conjugate, as described above; and a pharmaceutically acceptable excipient. In some embodiments, the antibody is present in a therapeutically effective amount. In some embodiments, the composition includes a therapeutic agent in a therapeutically effective amount. In certain embodiments, the therapeutic agent is a chemotherapeutic agent. In certain embodiments, the chemotherapeutic agent is an alkylating agent, antimetabolite, anti-microtubule agent, topoisomerase inhibitor, or a cytotoxic antibiotic. In certain embodiments, the therapeutic agent is an inhibitor of the Shh signaling pathway. In certain embodiments, the antibody is present in an amount such that the therapeutically effective amount of the therapeutic agent in the composition containing the amount of the antibody is less than the therapeutically effective amount of the therapeutic agent in the composition that does not contain the antibody. In certain embodiments, the therapeutically effective amount of the therapeutic agent in the composition containing the amount of the antibody is at least about 10% less than the therapeutically effective amount of the therapeutic agent in the composition that does not contain the antibody.

Also provided herein is a method of treating an individual for a cancer, the method including administering to an individual, a therapeutically effective amount of a C-terminal Shh antibody, or the antibody conjugate, as described above. In certain embodiments, the method includes co-administering with the antibody, a therapeutically effective amount of a therapeutic agent. In certain embodiments, the co-administering includes simultaneously administration the antibody and the therapeutic agent. In certain embodiments, the method includes administering a therapeutically effective amount of the antibody conjugate, wherein the antibody conjugate comprises a C-terminal Shh antibody, as described above.

In any embodiment, the therapeutic agent may be a chemotherapeutic agent. In certain embodiments, the chemotherapeutic agent is an alkylating agent, antimetabolite, anti-microtubule agent, topoisomerase inhibitor, or a cytotoxic antibiotic. In certain embodiments, the therapeutic agent is an inhibitor of the Shh signaling pathway. In certain embodiments, the antibody is administered in an amount sufficient to reduce the therapeutically effective amount of the Shh signaling pathway inhibitor in comparison to the therapeutically effective amount of the Shh signaling pathway inhibitor administered without co-administering with the antibody. In certain embodiments, the therapeutically effective amount of the Shh signaling pathway inhibitor co-administered with the antibody is reduced by at least about 10% in comparison to the therapeutically effective amount of the Shh signaling pathway inhibitor administered without co-administering with the antibody.

In any embodiment, the individual may have or may be suspected of having a cancer associated with cancer stem cells. In certain embodiments, the cancer stem cells are Shh+ cells. In certain embodiments, the method includes determining the presence and/or the prevalence of Shh+ cells in a biopsy sample of a tumor from the individual. In some embodiments, the determining includes: contacting cells of a tumor tissue sample from an individual having or suspected of having a cancer with a detectable binding agent that specifically binds to a Shh polypeptide, under conditions sufficient for the detectable binding agent to preferentially bind full-length Shh polypeptide expressed on a cell surface; and measuring an amount of the detectable binding agent bound to the cells, wherein the measured amount indicates a level of full-length Shh polypeptide expressed on the cell surface. In certain embodiments, the detectable binding agent is an anti-Shh antibody that specifically binds to the Shh polypeptide. In certain embodiments, the anti-Shh antibody specifically binds to a C-terminal Shh polypeptide. In certain embodiments, the anti-Shh antibody is a C-terminal Shh antibody, as described above.

In any embodiment, the individual may have or may be suspected of having pancreatic, colon, gastric, lung, breast, prostate or blood cancer, but may also include other cancers. In certain embodiments, the individual has or is suspected of having non-small cell lung cancer (NSCLC). In certain embodiments, the blood cancer is leukemia or multiple myeloma.

Also provided herein is a method of analyzing a tissue sample, the method includes: contacting cells of a tissue sample with a first detectable binding agent that specifically binds to a Shh polypeptide, under conditions sufficient for the first detectable binding agent to preferentially bind full-length Shh polypeptide expressed on a cell surface; and measuring an amount of the first detectable binding agent bound to the cells, wherein the measured amount indicates a level of full-length Shh polypeptide expressed on the cell surface.

In any embodiment, the tissue sample may be a biopsy sample from an individual. In certain embodiments, the individual has or is suspected of having a cancer, and wherein the tissue sample is a tumor sample.

Also provided herein is a method of diagnosing a cancer in an individual, the method including: contacting cells of a tumor tissue sample from an individual having or suspected of having a cancer with a first detectable binding agent that specifically binds to a Shh polypeptide, under conditions sufficient for the first detectable binding agent to preferentially bind full-length Shh polypeptide expressed on a cell surface; measuring an amount of the first detectable binding agent bound to the cells, wherein the measured amount indicates a level of full-length Shh polypeptide expressed on the cell surface; and diagnosing the cancer based on the measured amount.

In any embodiment, the diagnosing may include providing a prognosis of the cancer, based on the measured amount. In certain embodiments, the prognosis includes a relative risk for relapse after surgery, for metastasis of the cancer, and/or of clinical progression. In certain embodiments, the diagnosing includes determining that there is a higher risk of clinical progression when a proportion of cells having full-length Shh polypeptide expressed on the cell surface in the tumor sample is above or equal to a first reference proportion, and that there is a lower risk of clinical progression when the proportion of cells having full-length Shh polypeptide expressed on the cell surface in the tumor sample is below the reference proportion. In certain embodiments, the diagnosing includes determining that there is a higher risk of relapse after surgical removal of a tumor from the individual when a proportion of cells having full-length Shh polypeptide expressed on the cell surface in the tumor sample is above or equal to a first reference proportion, and that there is a lower risk of relapse after surgical removal of the tumor when the proportion of cells having full-length Shh polypeptide expressed on the cell surface in the tumor sample is below the reference proportion. In certain embodiments, the first reference proportion is based on a comparison between a measured amount of the first detectable binding agent bound to the cells of a healthy tissue sample and a measured amount of the first detectable binding agent bound to the cells of a tumor tissue sample. In certain embodiments, the method further includes selecting a recommended treatment for the cancer based on the measured amount. In certain embodiments, the recommended treatment includes administration of a Shh signaling pathway inhibitor to the individual, if a proportion of cells having full-length Shh polypeptide expressed on the cell surface in the tumor sample is above or equal to a second reference proportion. In certain embodiments, the recommended treatment includes co-administration of the Shh signaling pathway inhibitor with a chemotherapeutic agent to the individual. In certain embodiments, the second reference proportion is based on a comparison between a measured amount of the first detectable binding agent bound to the cells of a healthy tissue sample and a measured amount of the first detectable binding agent bound to cells of a tumor tissue sample.

In any embodiment, the first detectable binding agent may be an anti-Shh antibody that specifically binds to the Shh polypeptide. In certain embodiments, the anti-Shh antibody specifically binds to a C-terminal Shh polypeptide. In certain embodiments the anti-Shh antibody is a C-terminal Shh antibody, as described above.

In any embodiment, the cells may not be permeabilized before the contacting.

In any embodiment, the first detectable binding agent may include a detectable label. In certain embodiments, the detectable label is a fluorescent label.

In any embodiment, the method may include dissociating the cells before the measuring. In certain embodiments, the measuring includes using flow cytometry.

In any embodiment, the measuring may include measuring the amount the first detectable binding agent bound to a subset of the cells that are determined to be non-immune cells. In certain embodiments, the contacting further includes contacting the cells with a second detectable binding agent that specifically binds to an immune cell marker, and wherein the measuring includes: measuring a first amount of the first detectable binding agent bound to the cells; and a second amount of the second detectable binding agent bound to the cells, to determine the subset of cells that are non-immune cells. In certain embodiments, the second detectable binding agent is an antibody that specifically binds to an immune cell marker. In certain embodiments, the antibody that specifically binds to an immune cell marker is an anti-CD45 antibody.

Also provided herein is a method of immunizing an individual, the method includes administering to an individual an antigenic peptide that contains a fragment of a C-terminal Shh polypeptide, in a manner sufficient to elicit an adaptive immune response against a cell of the individual, wherein the cell expresses full-length Shh polypeptide on its surface. In some embodiments, the cell is a tumor cell. In certain embodiments, the cell is a cancer stem cell. In certain embodiments, the individual is diagnosed with a cancer. In certain embodiments, the individual is predisposed to developing a cancer. In certain embodiments, the cancer is lung cancer. In certain embodiments, the lung cancer is NSCLC.

In any embodiment, the adaptive immune response may include generation of an antibody that specifically binds to a cell that expresses the full-length Shh polypeptide expressed on the cell surface.

In any embodiment, the administering may include administering one or more antigenic peptides, each antigenic peptide containing a fragment of the C-terminal Shh polypeptide having an amino acid sequence set forth in SEQ ID NOs:18 or 20.

In any embodiment, the administering may include administering an immunogenic composition comprising the antigenic peptide and an adjuvant.

In any embodiment, the antigenic peptide may include the fragment of the C-terminal Shh polypeptide conjugated to a carrier.

Kits that include the present C-terminal Shh antibody, or an antigen binding fragment thereof, or the present antigenic peptide, as described above, are provided.

BRIEF DESCRIPTION OF THE DRAWINGS

FIGS. 1A-1F are a collection of images and graphs showing that Shh+ cells are Shh-producing cells and represent a rare population in vitro, according to embodiments of the present disclosure.

FIGS. 3A-3E are a collection of images and graphs showing that Shh+ cells have a paracrine effect on Shh− cells, according to embodiments of the present disclosure.

FIGS. 4A-4I are a collection of graphs showing that Shh+ cells are resistant to cisplatin but sensitive to GDC0449, according to embodiments of the present disclosure.

FIGS. 5A-5J are a collection of graphs and images showing that Shh+ cells have cancer stem cell features, according to embodiments of the present disclosure.

FIGS. 6A-6G are a collection of graphs showing the presence of Shh+ cells in fresh human NSCLC tissue samples, according to embodiments of the present disclosure.

FIG. 14 shows Table 2, showing expression of Shh in various fresh cancer tissue samples, according to embodiments of the present disclosure.

FIGS. 16A and 16B are a collection of graphs showing cytotoxicity of Shh antibodies, according to embodiments of the present disclosure.

FIGS. 21A-21I is a collection of images showing antibody staining of tumor tissue sections using a C-terminal Shh antibody, after administration of the C-terminal Shh antibody in vivo, according to embodiments of the present disclosure.

FIG. 22 shows Table 8, showing the expression level of GLI1 in tumors after administration of a C-terminal Shh antibody in vivo, according to embodiments of the present disclosure.

FIG. 23 shows an annotated amino acid sequence of full-length sonic hedgehog.

FIG. 24 is a schematic diagram of an antibody, showing the relative position of the variable region of the heavy ($V_H$) and light ($V_L$) chains, and constant region of the heavy ($C_H1$, $C_H2$, $C_H3$) and light (CO chains. The framework regions (FRs) and the complementarity determining regions (CDRs) of the variable regions are also indicated.

FIGS. 25A-25E shows Table 9, and the nucleotide and amino acid sequences of the light chain and heavy chain of a C-terminal Shh antibody from clone 2G4, according to embodiments of the present disclosure.

FIGS. 26A-26E shows Table 10, and the nucleotide and amino acid sequences of the light chain and heavy chain of a C-terminal Shh antibody from clone 2D9, according to embodiments of the present disclosure.

FIG. 27A shows immunofluorescence (IF) analysis of A549 cells without membrane permeabilization, which showed positive Shh (red) and nuclear staining (blue, DAPI). White arrows: positive membranous Shh staining in relatively few cells. FIG. 27B shows IF analysis of A549 cells with membrane permeabilization (Triton X-100), which showed positive Shh (red) and nuclear staining (blue, DAPI) in a majority of the cells probed. FIG. 27C shows flow cytometric analysis of A549 cells without membrane permeabilization probed for Shh (0.18%). FIG. 27D shows flow cytometric analysis of A549 cells with membrane permeabilization (Tween 20) probed for Shh (70.12%). FIG. 27E shows IF analysis of sorted A549 cells without membrane permeabilization, which showed strong positive membranous Shh staining (green, white arrows) in Shh+ cells and low/no staining in Shh− cells/controls without the primary antibody. Red: membranous staining (lipophilic dye); blue: nuclear staining (DAPI). FIG. 27F shows Shh gene expression analysis by ddPCR in A549 Shh+ and Shh− cells. FIG. 27G shows a graph of Shh rate (%, mean±SD) in several NSCLC cell lines.

FIG. 28A shows an immunoblot of A549 cells transiently transfected with wild-type Shh and probed for the Sonic Hedgehog (Shh) protein in whole cell and membrane extracts (left), and immunoblot of supernatants from non-transfected Shh-sorted A549 cells (right) with secreted MMP2 as a loading control. FIG. 28B shows a schematic representation of Shh constructs showing the sizes and locations of N-term HA and C-term FLAG tags stably expressed in NSCLC cells. FIG. 28C shows immunofluorescence analysis of H838 cells showing cytosolic and membrane staining of N-term, C-term, wild-type Shh and C198A Shh constructs probed for the presence of HA (red) and FLAG (yellow). FIG. 28D shows a graph of NSCLC cell lines (A549 and H838) used in FIG. 28C analyzed for increases in viability (MTS assay) relative to the vector control after 4 days ($p<0.01$). FIG. 28E shows a graph of supernatants from NSCLC cells that were applied to parental cells and analyzed as in FIG. 28D ($p<0.01$).

FIG. 30A shows a proliferation assay (MTS) on A549 Shh+ and Shh− cells (d0, d3, d4, d7). FIG. 30B shows a proliferation assay (MTS) of A549 Shh− cells supplemented with culture media from Shh+ or Shh− cells [conditioned media: fresh media (1:1) at d1 after cell sorting]. **$p<0.01$, compared with cells supplemented with media from Shh− cells. FIG. 30C shows a migration/wound healing assay on A549 Shh− cells at d0 (far left) and d3 (left to right: control, 1,200 ng/mL Shh recombinant protein, media from Shh+ cells). FIG. 30D and FIG. 30E show graphs of gene expression levels of downstream Shh pathway targets analyzed by qRT-PCR in A549 (FIG. 30D) or H838 (FIG. 30E) Shh− cells cultured with media from Shh+ cells (normalized to Shh− cells). *$p<0.05$; **$p<0.01$, compared with Shh− cells cultured with media from Shh− cells.

FIG. 31A shows correlation between Shh rate (%) and cisplatin $IC_{50}$ in NSCLC cell lines. FIG. 31B shows a graph of Shh rate (%) in A549 cells treated with cisplatin (1 mM, 72 h). †dead cells; ‡Shh− cells; ⊤ Shh+ cells (5% of live cells). FIG. 31C shows a graph of Shh rate (%) in A549 cells treated by cisplatin (600 μM and 1 mM, 72 h). *$p<0.05$; $p<0.01$, compared to baseline. FIG. 31D shows a graph of Shh expression level (qRT-PCR) in A549 cells treated with cisplatin (600 μM and 1 mM, 72 h) (normalized to PBS-treated cells, log-scale). $p<0.01$, compared to PBS. FIG. 31E shows a graph of Shh rate (%) in A549 cells treated with GDC0449 (40 μM, 72 h). †dead cells; ‡Shh− cells; ⊤ Shh+ cells (0%). FIG. 31F shows a graph of Shh expression level (qRT-PCR) in A549 cells treated with GDC0449 (20 μM and 40 μM, 72 h) (normalized to DMSO-treated cells). $p<0.01$, compared to DMSO. FIG. 31G shows a graph of MTS assay of A549 cells treated with DSMO or GDC0449 (40 μM, 72 h). $p<0.01$, compared to day 0. FIG. 31H shows a graph of Shh rate (%) in A549 cells treated with cisplatin and DMSO/GDC0449 (40 μM, 72 h) or docetaxel and DMSO/GDC0449 (40 μM, 72 h). **$p<0.01$, compared to cisplatin/docetaxel and DMSO. i: Shh rate (%) in A549 xenograft model treated with cisplatin (CPT, 10 mg/kg, IV weekly), followed by vehicle or GDC0449 (20 mg/kg, IP daily). *$p<0.05$.

FIG. 34C: GDC0449 20 μM; FIG. 34D: GDC0449 40 μM).

Figure 36:
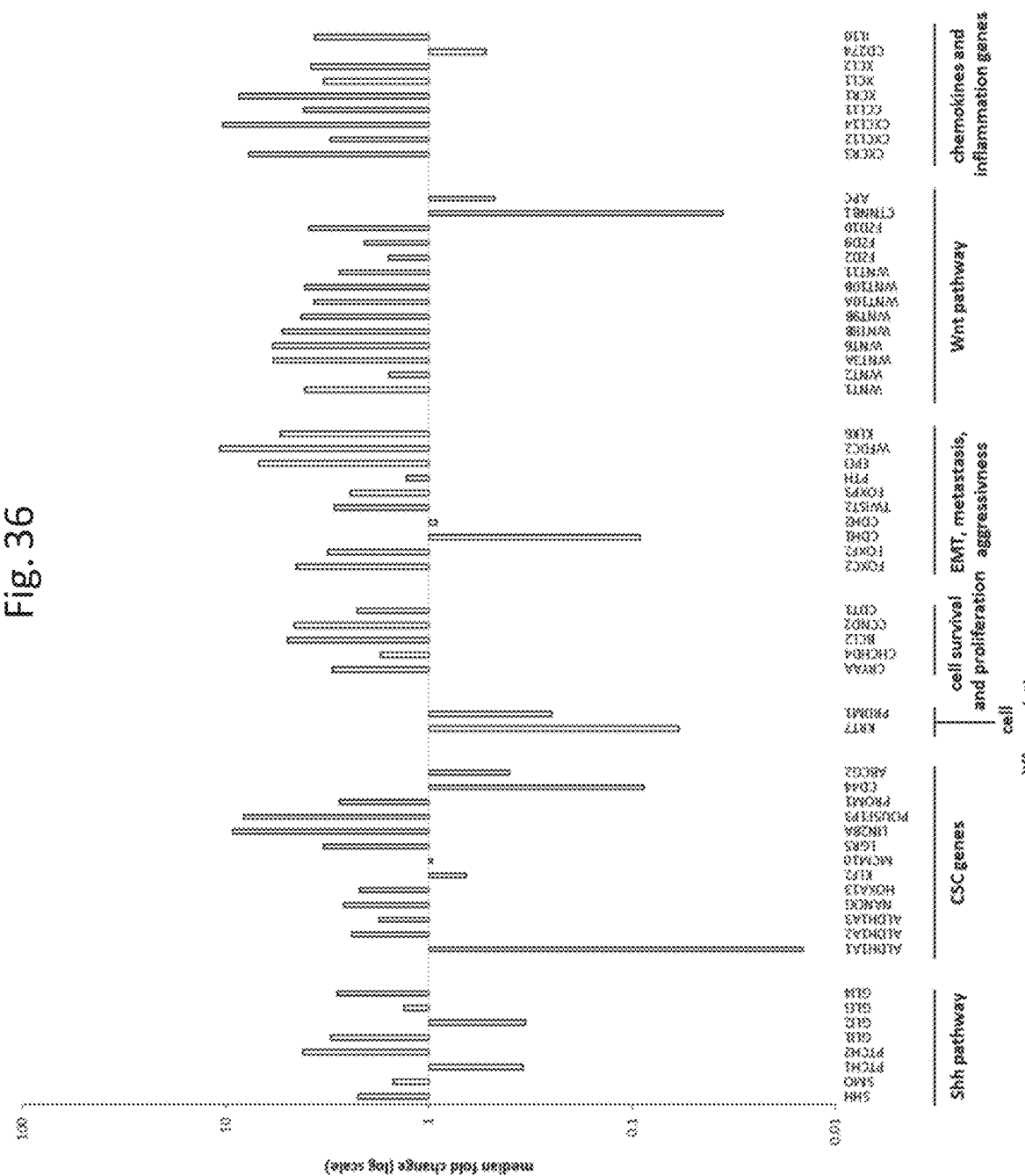

FIG. 36 shows a graph of microarray gene expression analysis on A549 Shh+ cells (normalized to Shh– cells, log-scale). CSC: cancer stem cell. EMT: epithelial-mesenchymal transition.

Figure 37E:
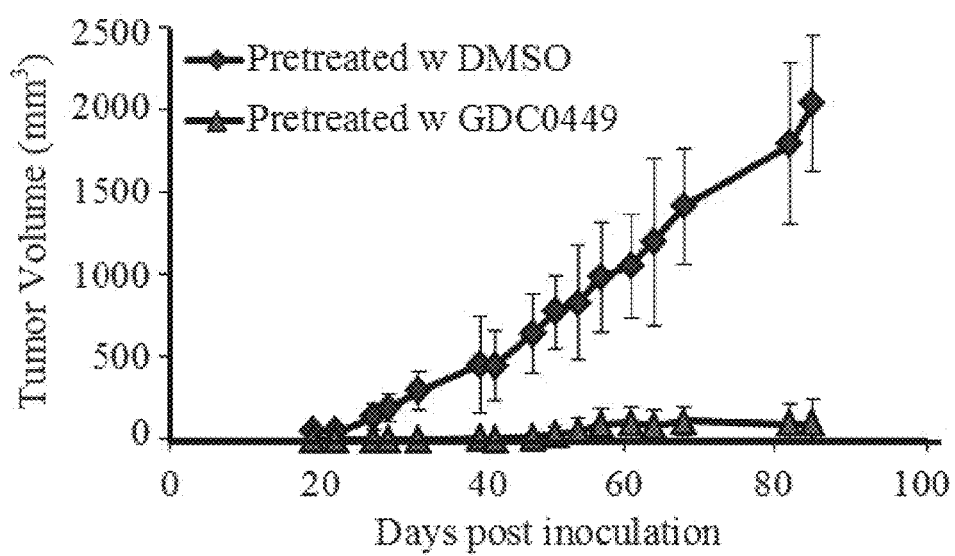
Figure 37F:
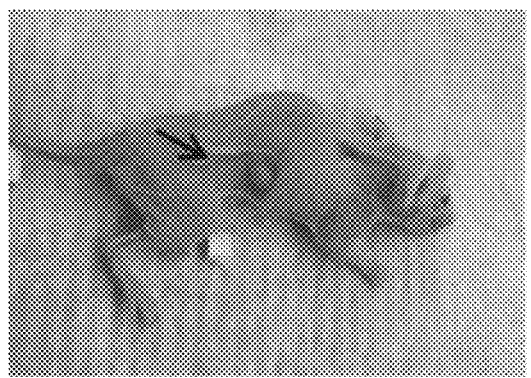
Figure 37G:
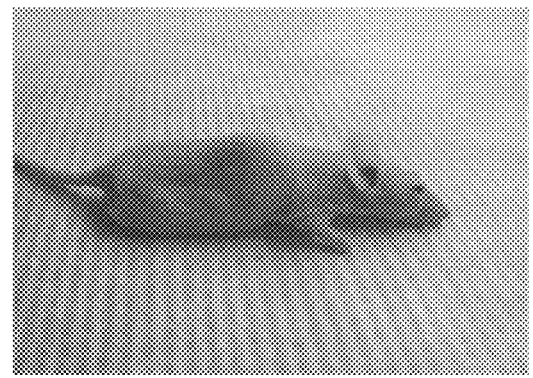
Figure 37H:
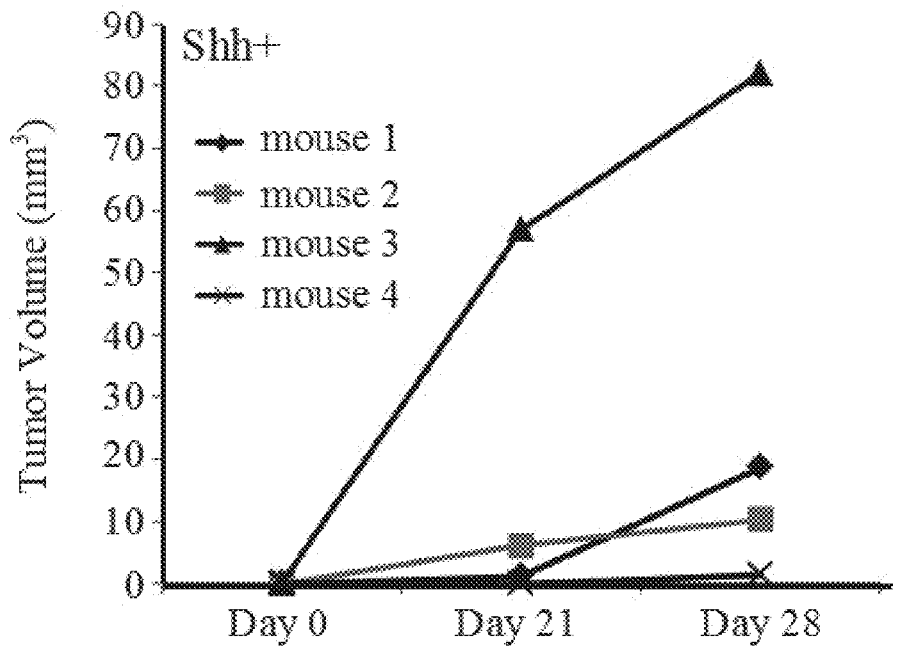
Figure 37I:
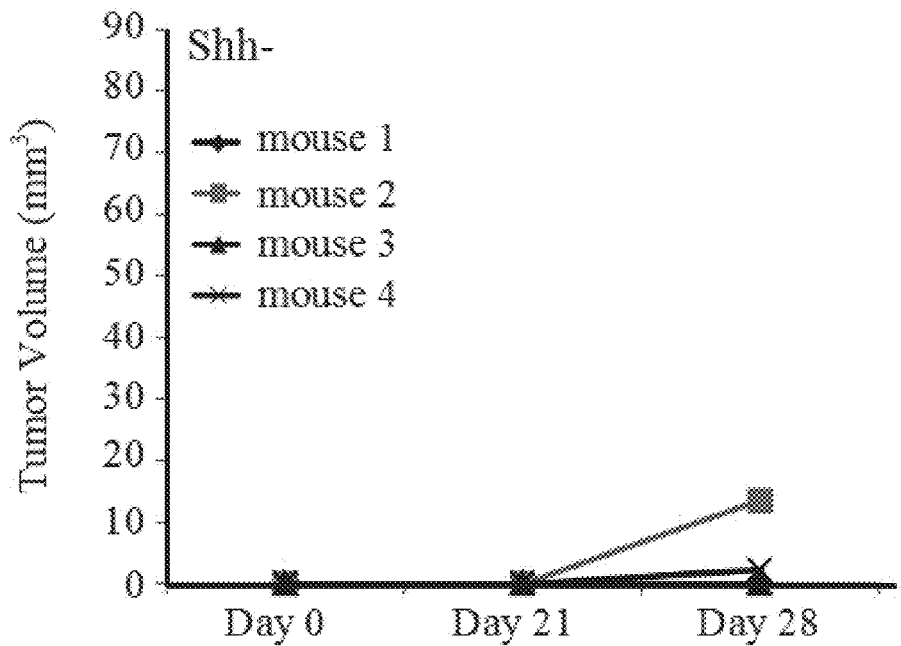

FIGS. 37A-37I show a collection of images showing that Shh+ cells have cancer stem cells features. FIG. 37A shows growth of A549 Shh+ cells cultured under serum-free conditions at d14 led to spheroid formation (scale bar: 100 µm). FIG. 37B shows that culture of A549 Shh– cells in serum-free media at d14 did not lead to spheroid formation (scale bar: 100 µm). FIG. 37C shows a flow cytometric analysis of pre-inoculated A549 cells treated with DMSO (d3). ⊤ Shh+ cells (0.10%). FIG. 37D shows a flow cytometric analysis of pre-inoculated A549 cells treated with GDC0449 (40 d3), †dead cells (SytoxRed); ⊤ Shh+ cells (0%). FIG. 37E shows a graph of change in A549 xenograft tumor volume in nude mice after inoculation of pre-treated cells. FIG. 37F shows nude mice inoculated with a low amount (1,500) of A549 Shh+ cells with tumor formation at 3 weeks. FIG. 37G shows nude mice inoculated with a low amount (1,500) of A549 Shh– cells, without tumor formation at 3 weeks. FIGS. 37H-37I show graphs of subcutaneous tumor volumes in nude mice 3-4 weeks after inoculation of a low amount (1,500) of A549 Shh+ (FIG. 37H) or Shh– cells (FIG. 37I).

FIGS. 38A-38F shows a collection of images showing the presence of Shh+ cells in fresh human NSCLC tissue samples. FIG. 38A shows a flow cytometric analysis of Shh in a fresh human NSCLC sample [†CD45+ cells; ‡CD45-Shh– cells; ⊤ CD45-Shh+ cells (2.99% of CD45– cells)]. FIG. 38B shows a flow cytometric analysis of Shh in a fresh human normal lung sample [†CD45+ cells; ‡CD45-Shh– cells; ⊤ CD45-Shh+ cells (0%)]. FIG. 38C shows a graph of Shh rate (%) in fresh human NSCLC samples and corresponding normal lung tissues (n=48). FIG. 38D shows a graph of Shh rate (%) in primary lung adenocarcinoma with a tumor response after chemotherapy and the corresponding adrenal metastasis with tumor progression after chemotherapy in the same patient. FIG. 38E shows a graph of time-to-progression (TTP) according to high (>0.10%) or low (<0.10%) Shh rate (p<0.01 for log-rank test) in stage I NSCLC tissue samples (n=32). FIG. 38F shows a graph of Shh rate (%) in stage I NSCLC with tumor relapse <12 months after surgery (n=6) and in stage I NSCLC without relapse within 12 months after surgery (n=16) (**p<0.01).

Figure 39:
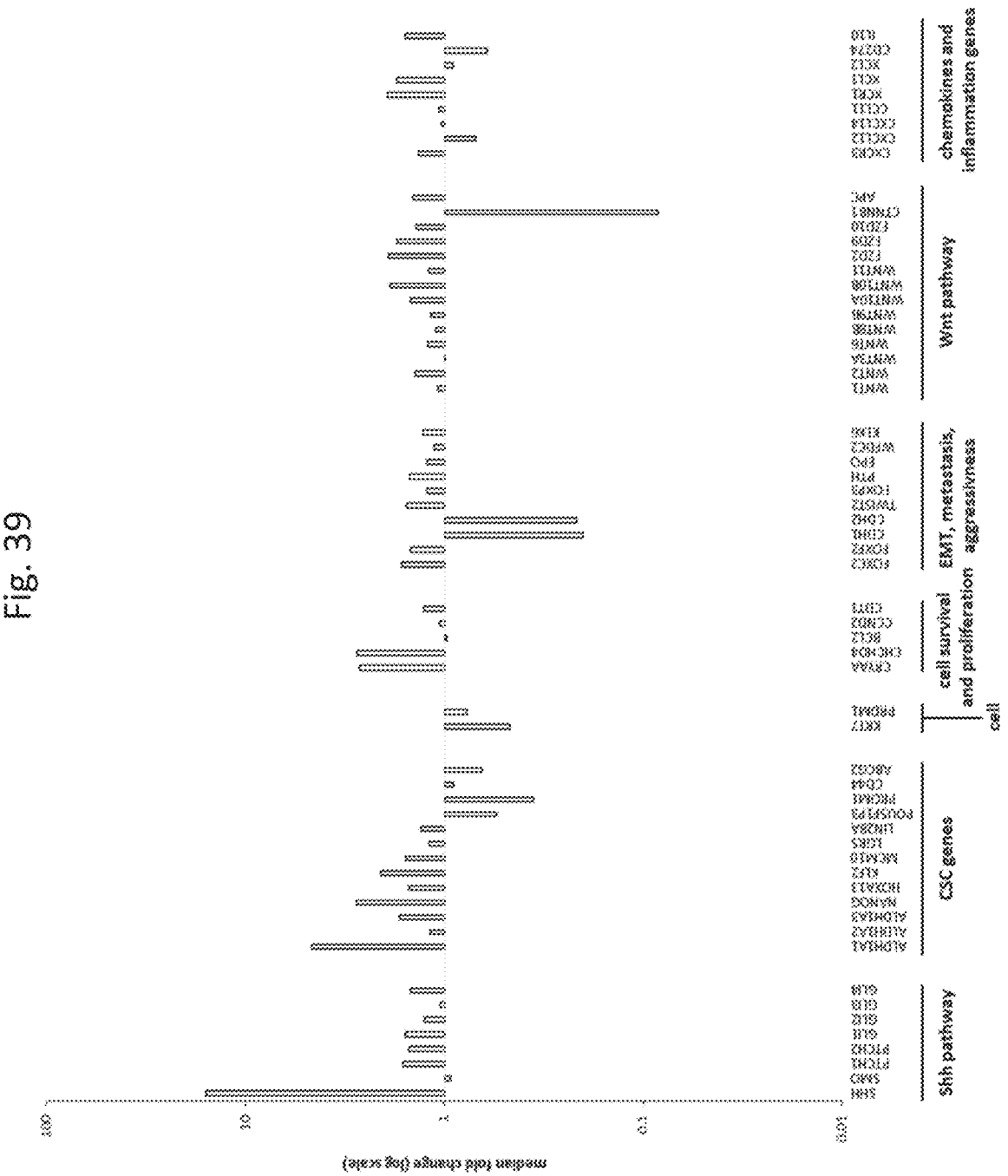

FIG. 39 shows a graph of microarray gene expression analysis on Shh+ cells from fresh lung adenocarcinoma (normalized to Shh– cells; log-scale; Shh rate at 0.69% assessed via flow cytometry). CSC: cancer stem cell. EMT: epithelial-mesenchymal transition.

FIG. 40 shows a table of Shh rate (%) evaluated by flow cytometry in various fresh tumor samples. Shh rate expressed as median (IQR) if several samples were tested for each pathological subtype.

Figure 41:
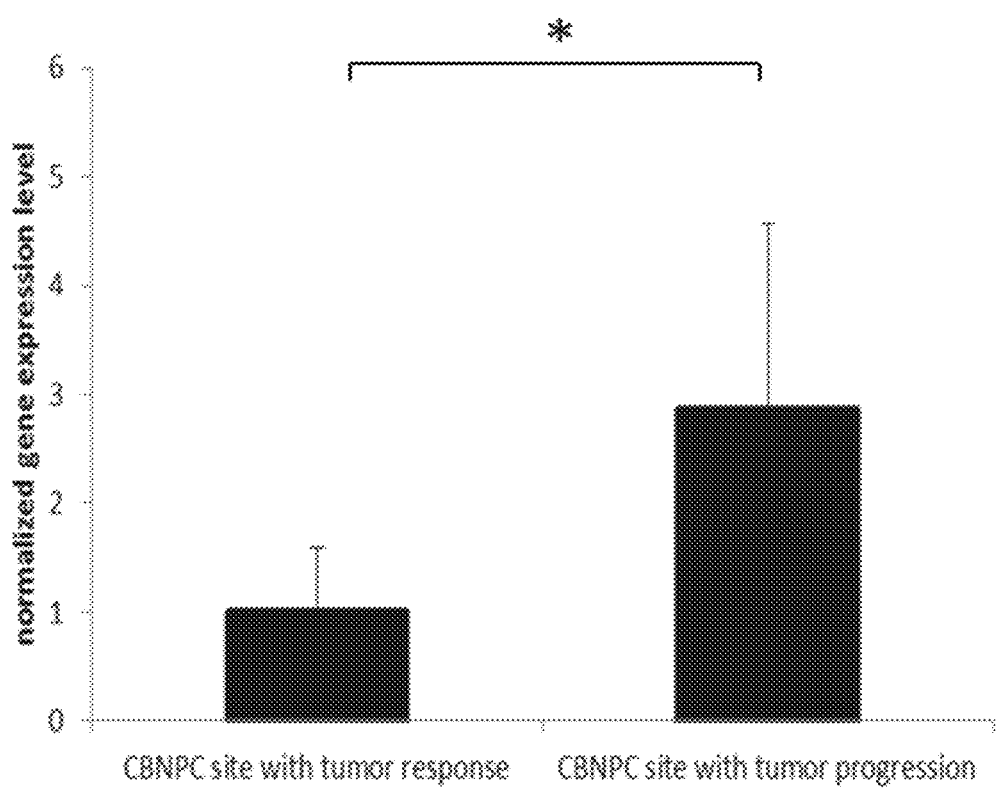

FIG. 41 shows a graph of Shh gene expression level (qRT-PCR) in the primary lung adenocarcinoma with tumor response after chemotherapy, and the corresponding adrenal metastasis with tumor progression after chemotherapy in the same patient. **p<0.01.

Figure 42:
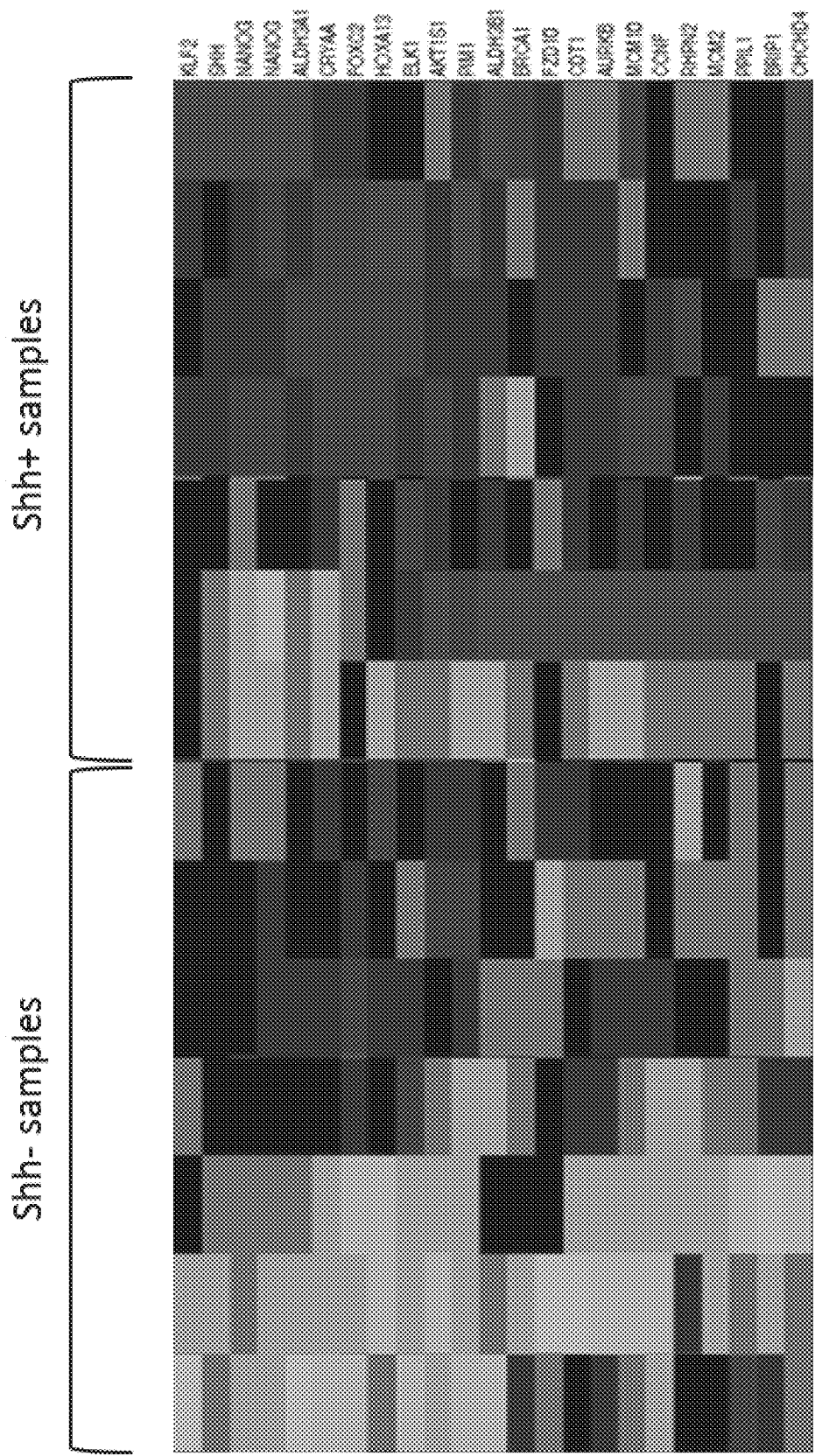

FIG. 42 shows a heat map of microarray gene expression analysis in Shh+ and Shh– cells isolated from human fresh lung tumor samples (n=7). Genes analyzed were from the Shh pathway (Shh), Wnt pathway (Fzd10), those involved with CSC features (NANOG, HOXA13, KLF2, ALDH3A1, ALDH3B1), cell proliferation (CRYAA, CDT1, AURKB, MCM2, MCM10, CCNF, RHPN2, AKT1S1, PIM1), EMT (FOXC2), hypoxia and tumor proliferation (CHCHD4), and chemoresistance (BRCA1, BRIP1, ELK1).

FIGS. 43A-43D are a collection of images showing the screens performed to identify murine hybridoma for candidate therapeutic anti-Shh antibodies directed at the C-terminal of the Sonic Hedgehog protein using an ELISA-based assay, Western blotting, flow cytometry and an isotyping kit, according to embodiments of the present disclosure.

FIGS. 44A-44E are a collection of table, images, and graphs showing that anti-Shh antibodies directed at the C-terminal of the Shh protein recognize Shh+ cell populations using fluorescence activated cell sorting (FACS), that the antibody is internalized over time using immune fluorescent staining and that the antibody directed at the C-terminal of the Shh protein reduces cell viability of cancer cells in a dose-dependent manner using CellTiter-Glo Luminescent Cell Viability Assay, according to embodiments of the present disclosure.

FIGS. 45A-45D are a collection of graphs, images and tables showing that an anti-Shh antibody directed at the C-terminal of the Sonic Hedgehog protein inhibits in vivo growth of non-small cell lung cancer NSCLC in a mouse xenograft model, according to embodiments of the present disclosure.

FIGS. 46A-46D are a collection of graphs and images showing that treatment of tumors with an anti-Shh antibody directed at the C-terminal of the Sonic hedgehog protein reduces Shh staining detection by flow cytometry and immunofluorescent staining ex vivo and that treatment with the C-terminal antibody impairs GLI expression by qRT-PCR and Western blotting, according to embodiments of the present disclosure.

Figure 47A:
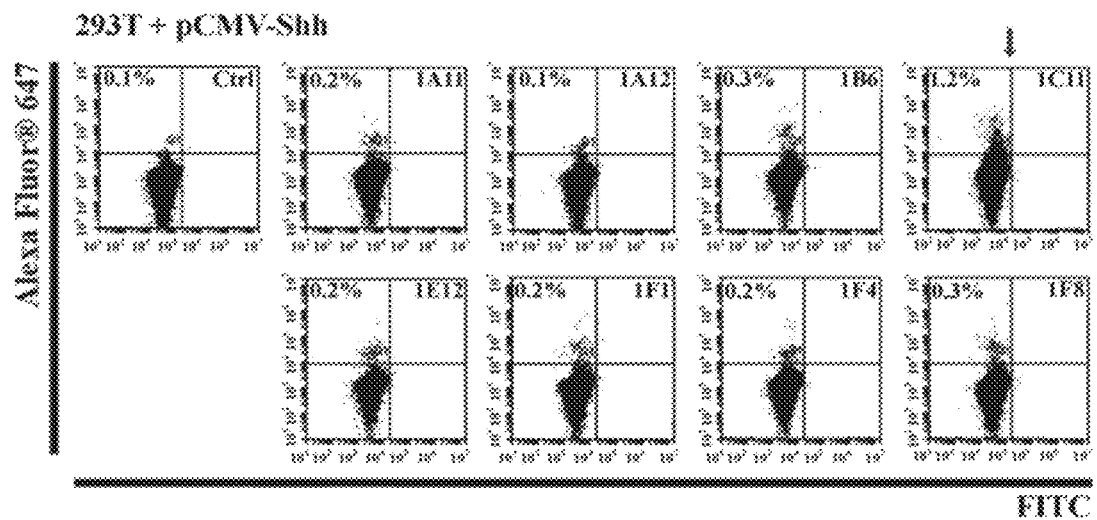
Figure 47B:
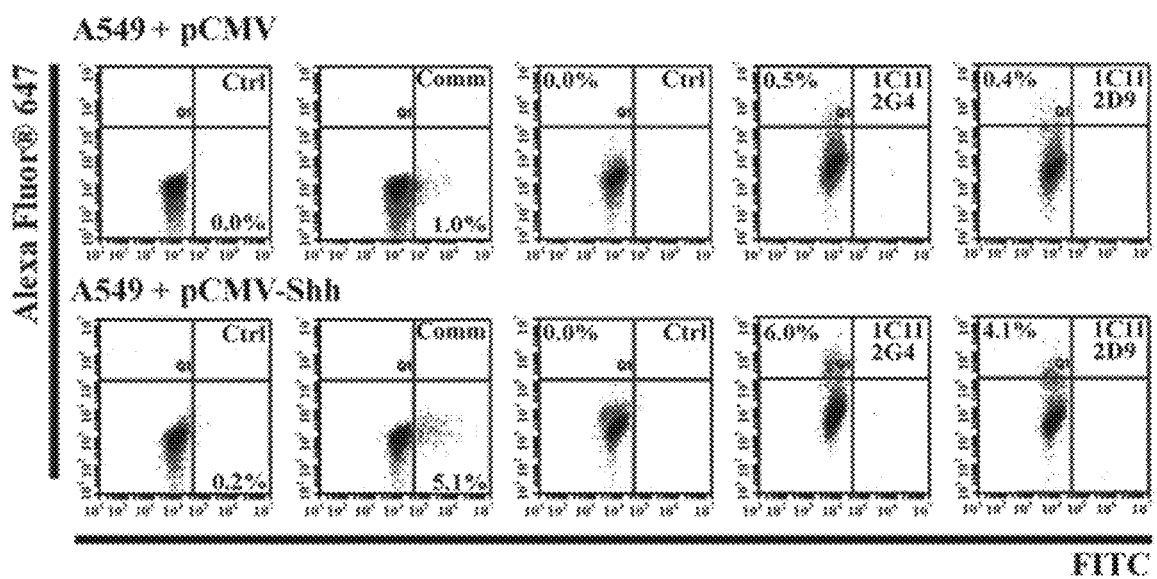

FIGS. 47A-47B graphs showing that anti-Shh antibodies directed at the C-terminal of the Sonic hedgehog protein can detect Shh protein transfected in 293T cells and A549 cells as well as endogenous Shh in A549 non-transfected cells, according to embodiments of the present disclosure. Purified antibodies Ab 1C11-2G4, Ab 1C11-2D9 and a commercial (Comm) C-term antibody were used in Flow cytometric evaluations and compared with their negative controls of cells incubated with secondary antibody alone.

Figure 48A:
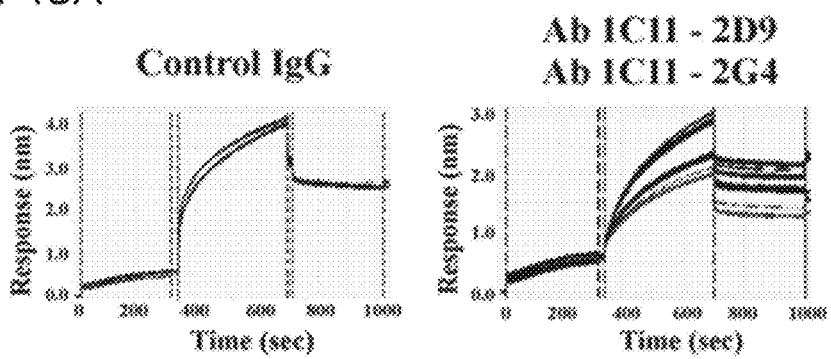
Figure 48B:
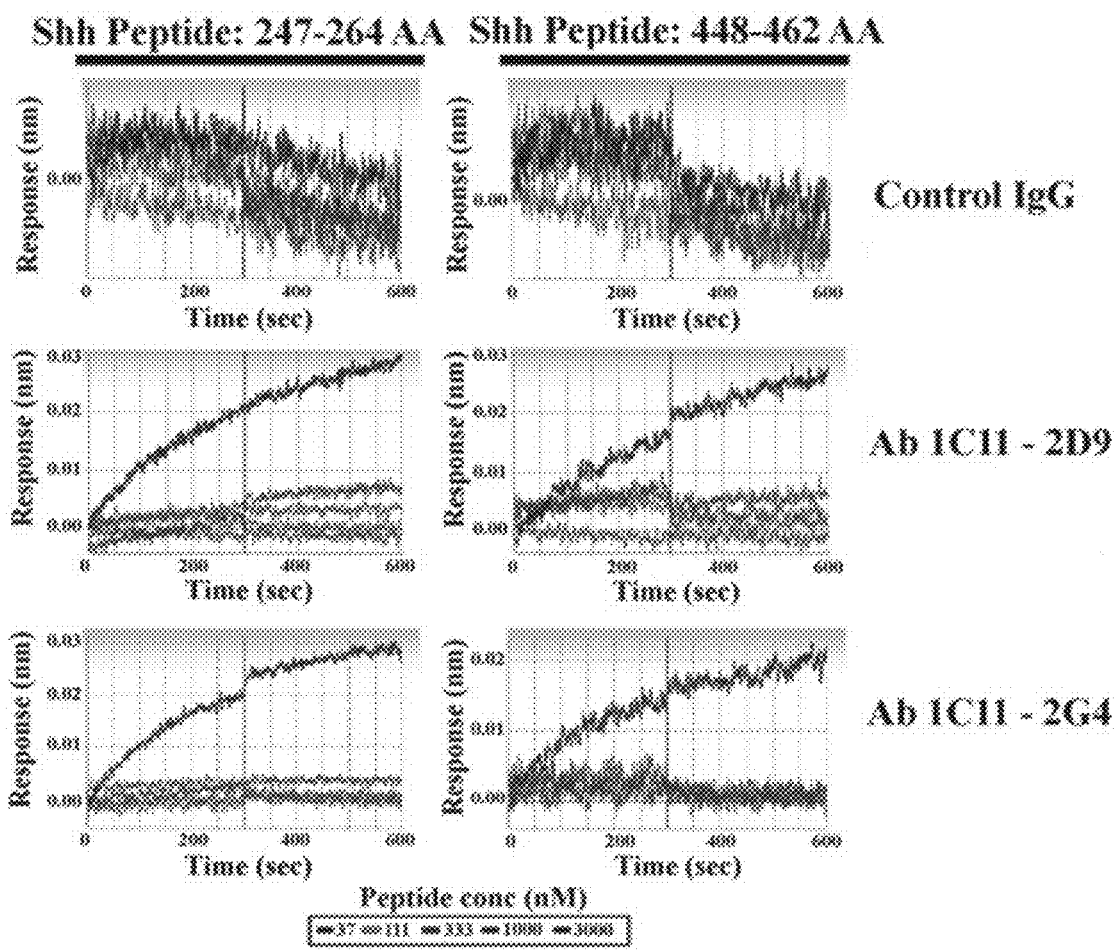
Figure 48C:
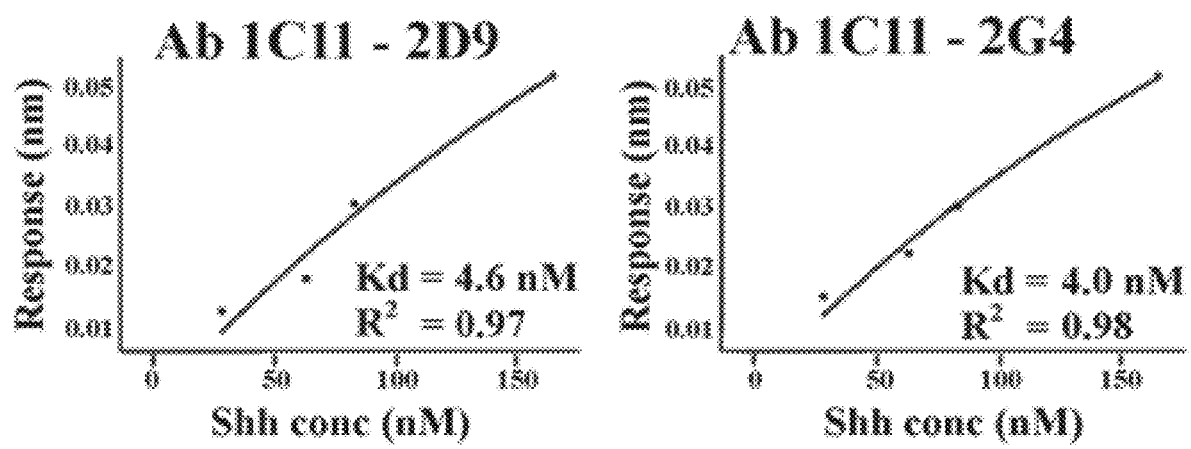

FIGS. 48A-48C are graphs showing that anti-Shh antibodies directed at the C-terminal of the Sonic Hedgehog protein, Ab 1C11-2G4 and Ab 1C11-2D9, can bind synthetic Shh peptides in a concentration dependent manner using a cell-free system (Octet Red 384 system). $K_d$ values indicate the binding of affinities of Ab 1C11-2G4 and Ab 1C11-2D9 for recombinant full-length Shh protein according to embodiments of the present disclosure.

Figure 49A:
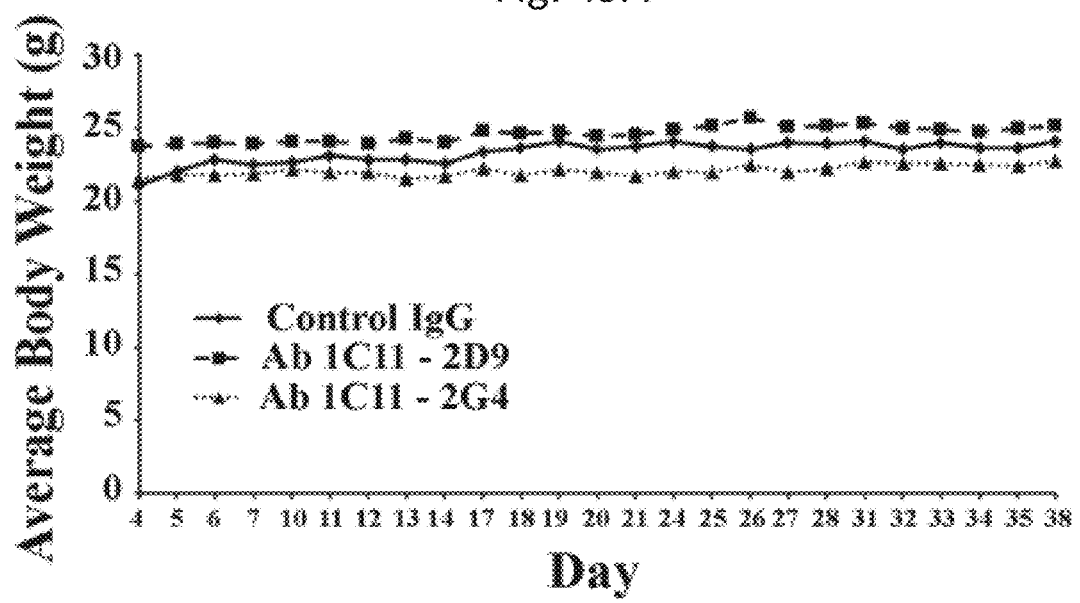
Figure 49B:
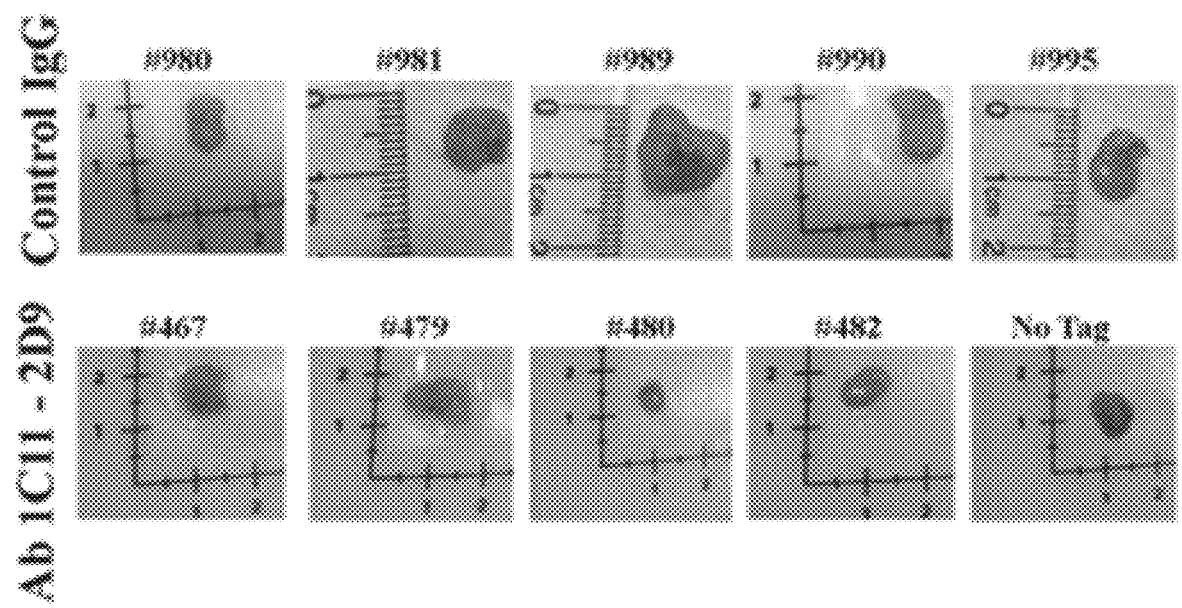

FIGS. 49A-49B are a collection images showing that treatment with anti-Shh antibodies directed at the C-terminal of the Sonic Hedgehog protein, Ab 1C11-2G4 and Ab 1C11-2D9, of mice bearing A549-derived NSCLC xenografts reduces tumor size without significantly reducing the mices' body weight compared to treatment with IgG alone, according to embodiments of the present disclosure.

DEFINITIONS

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are typical of measurements characterizing the disclosed compositions or appropriate to perform the disclosed methods.

The terms "polynucleotide", "nucleotide", "nucleotide sequence", "nucleic acid", "nucleic acid molecule", "nucleic acid sequence" and "oligonucleotide" are used interchangeably, and can also include plurals of each respectively depending on the context in which the terms are utilized. They refer to a polymeric form of nucleotides of any length, either deoxyribonucleotides (DNA) or ribonucleotides (RNA), or analogs thereof. Polynucleotides may have any three-dimensional structure, and may perform any function. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA, ribozymes, small interfering RNA, (siRNA), microRNA (miRNA), small nuclear RNA (snRNA), cDNA, recombinant polynucleotides, branched polynucleotides, plasmids, vectors, isolated DNA (A, B and Z structures) of any sequence, PNA, locked nucleic acid (LNA), TNA (treose nucleic acid), isolated RNA of any sequence, nucleic acid probes, and primers. LNA, often referred to as inaccessible RNA, is a modified RNA nucleotide. The ribose moiety of an LNA nucleotide is modified with an extra bridge connecting the 2' and 4' carbons. The bridge "locks" the ribose in the 3'-endo structural conformation, which is often found in the A-form of DNA or RNA, which can significantly improve thermal stability.

The terms "polypeptide," "peptide," and "protein" are used interchangeably herein to refer to a polymeric form of amino acids of any length. Unless specifically indicated otherwise, "polypeptide," "peptide," and "protein" can include genetically coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, proteins which contain at least one N-terminal methionine residue (e.g., to facilitate production in a recombinant bacterial host cell); immunologically tagged proteins; and the like.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure M. O. Dayhoff ed.*, 5 Suppl. 3:353-358, National biomedical Research Foundation, Washington, D.C., which adapts the local homology algorithm of Smith and Waterman *Advances in Appl. Math.* 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present disclosure is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST®, used with default parameters. For example, BLAST®N and BLAST®P can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank®+EMBL®+DDBJ+PDB+GenBank® CDS translations+Swiss protein+Spupdate+PIR. Details of these programs are readily available.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art.

"Binding," as used herein, refers to a specific interaction between any two members, e.g., two proteins, two nucleic acids, a protein and a nucleic acid, etc., where the affinity between two specific binding members is characterized by a $K_D$ (dissociation constant) of $10^{-5}$ M or less, $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, including $10^{-16}$ M or less. "Affinity" refers to the strength of binding, increased binding affinity being correlated with a lower $K_D$.

As used herein, "antigen" refers to any substance that, when introduced into a body, e.g., of a patient or individual, stimulates an immune response such as the production of an antibody that recognizes the antigen.

The term "antibody" is used in the broadest sense and includes monoclonal antibodies (including full-length monoclonal antibodies), polyclonal antibodies, and multispecific antibodies (e.g., bispecific antibodies), humanized antibodies, single-chain antibodies, chimeric antibodies, antibody fragments (e.g., Fab fragments), and the like. An antibody is capable of binding a target antigen. (Janeway, C., Travers, P., Walport, M., Shlomchik (2001) Immuno Biology, 5th Ed., Garland Publishing, New York). A target antigen can have one or more binding sites, also called epitopes, recognized by complementarity determining regions (CDRs) formed by one or more variable regions of an antibody.

"Immunoglobulin polypeptide" as used herein refers to a polypeptide containing at least a variable region or a constant region of a light chain polypeptide of an antibody, or at least a variable region or a constant region of a heavy chain polypeptide of an antibody.

Figures 24, 25A:
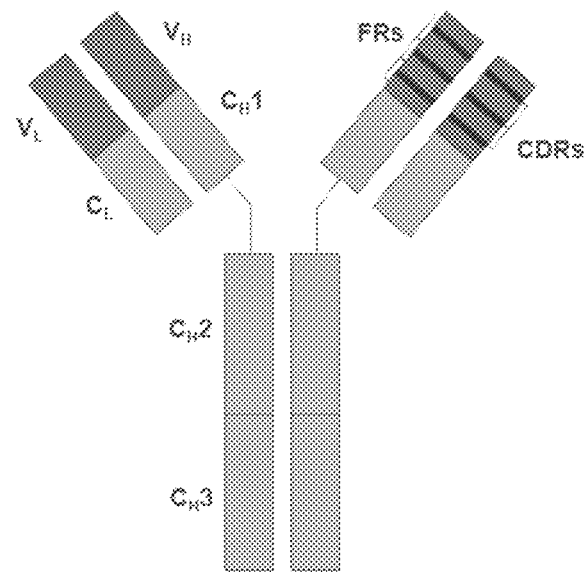

An immunoglobulin polypeptide immunoglobulin light or heavy chain variable region is composed of a framework region (FR) interrupted by three hypervariable regions, also called "complementarity determining regions" or "CDRs" (See also, FIG. 24). The extent of the framework region and CDRs have been defined. The residues that make up the six CDRs according to Kabat are as follows: residues 24-34 (CDRL1), 50-56 (CDRL2) and 89-97 (CDRL3) in the light chain variable region and 31-35 (CDRH1), 50-65 (CDRH2) and 95-102 (CDRH3) in the heavy chain variable region (see, "Sequences of Proteins of Immunological Interest," E. Kabat et al., U.S. Department of Health and Human Services, 1991). The framework region of an antibody, that is the combined framework regions of the constituent light and heavy chains, serves to position and align the CDRs. The CDRs are primarily responsible for binding to an epitope of an antigen.

In the context of an Ig polypeptide, the term "constant region" is well understood in the art, and refers to a C-terminal region of an Ig heavy chain, or an Ig light chain. An Ig heavy chain constant region includes CH1, CH2, and CH3 domains (and CH4 domains, where the heavy chain is a µ or an ε heavy chain). In a native Ig heavy chain, the CH1, CH2, CH3 (and, if present, CH4) domains begin immediately after (C-terminal to) the heavy chain variable (VH) region, and are each from about 100 amino acids to about 130 amino acids in length. In a native Ig light chain, the constant region begins begin immediately after (C-terminal to) the light chain variable (VL) region, and is about 100 amino acids to 120 amino acids in length.

An immunoglobulin light chain may have a structure schematically represented, from N- to C-terminus, as: FR1-$CDR_L1$-FR2-$CDR_L2$-FR3-$CDR_L3$-FR4-$C_L$, where $CDR_L1$, $CDR_L2$ and $CDR_L3$ are hypervariable regions interposed between the framework into four regions (FR1, FR2, FR3 and FR4) and $C_L$ is the constant region. An immunoglobulin heavy chain may have a structure schematically represented, from N- to C-terminus, as: FR1-$CDR_H1$-FR2-$CDR_H2$-FR3-$CDR_H3$-FR4-$C_H1$-H—$C_H2$-$C_H3$, where $CDR_H1$, $CDR_H2$ and $CDR_H3$ are hypervariable regions interposed between the framework into four regions (FR1, FR2, FR3 and FR4), $C_H1$, $C_H2$ and $C_H3$ are constant regions and H is a hinge region.

The term "humanized antibody" or "humanized immunoglobulin" refers to a non-human (e.g., mouse or rabbit) antibody containing one or more amino acids (in a framework region, a constant region or a CDR, for example) that have been substituted with a correspondingly positioned amino acid from a human antibody. In general, humanized antibodies produce a reduced immune response in a human host, as compared to a non-humanized version of the same antibody. Antibodies can be humanized using a variety of techniques known in the art including, for example, CDR-grafting, and chain shuffling (U.S. Pat. No. 5,565,332). In certain embodiments, framework substitutions are identified by modeling of the interactions of the CDR and framework residues to identify framework residues important for antigen binding and sequence comparison to identify unusual framework residues at particular positions. Accordingly, the antibodies described above may be humanized using methods that are well known in the art.

By "conjugate" is meant a first moiety that is stably associated with a second moiety. By "stably associated" is meant that a moiety is bound to another moiety or structure under standard conditions. In certain embodiments, the first and second moieties are bound to each other through one or more covalent bonds. The first or the second moiety of a conjugate may be referred to as a "payload".

The term "control sequences" refers to DNA sequences that facilitate expression of an operably linked coding sequence in a particular expression system, e.g. mammalian cell, bacterial cell, cell-free synthesis, etc. The control sequences that are suitable for prokaryote systems, for example, include a promoter, optionally an operator sequence, and a ribosome binding site. Eukaryotic cell systems may utilize promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate the initiation of translation. Generally, "operably linked" means that the DNA sequences being linked are contiguous, and, in the case of a secretory leader, contiguous and in reading frame. Linking is accomplished by ligation or through amplification reactions. Synthetic oligonucleotide adaptors or linkers may be used for linking sequences in accordance with conventional practice.

The term "expression cassette" as used herein refers to a segment of nucleic acid, usually DNA, that can be inserted into a nucleic acid (e.g., by use of restriction sites compatible with ligation into a construct of interest or by homologous recombination into a construct of interest or into a host cell genome). In general, the nucleic acid segment comprises a polynucleotide that encodes a polypeptide of interest (e.g., a light chain or heavy chain Ig polypeptide of a C-terminal Shh antibody), and the cassette and restriction sites are designed to facilitate insertion of the cassette in the proper reading frame for transcription and translation. Expression cassettes can also comprise elements that facilitate expression of a polynucleotide encoding a polypeptide of interest in a host cell. These elements may include, but are not limited to: a promoter, a minimal promoter, an enhancer, a response element, a terminator sequence, a polyadenylation sequence, and the like.

As used herein the term "isolated" is meant to describe a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound that is removed from its natural environment and is at least 60% free, at least 75% free, at least 80% free, at least 85% free, at least 90% free, at least 95% free, at least 98% free, or more than 98% free, from other components with which it is naturally associated.

An "individual" as used herein, includes any animal, such as a mammal, and may be a murine, canine, feline, ungulate, non-human primate, etc. The animal may be, without limitation, a mouse, rat, dog, cat, livestock (e.g., pig), or a human.

As used herein, the terms "treat", "treating", and "treatment" include: (1) preventing a disease, such as cancer, i.e. causing the clinical symptoms of the disease not to develop in an individual that may be predisposed to the disease but does not yet experience any symptoms of the disease; (2)

inhibiting the disease, i.e. arresting or reducing the development of the disease or its clinical symptoms; or (3) relieving the disease, i.e. causing regression of the disease or its clinical symptoms. Treatment means any manner in which the symptoms or pathology of a condition, disorder, or disease are ameliorated or otherwise beneficially altered. In certain embodiments, the individual in need of such treatment is a mammal, such as a human.

A "therapeutically effective amount" refers to an amount effective, at dosages and for periods of time necessary, to achieve the desired therapeutic result. A therapeutically effective amount of a therapeutic agent may vary according to factors such as the disease state, age, sex, and weight of the individual, and the ability of the therapeutic agent to elicit a desired response in the individual. A therapeutically effective amount is also one in which any toxic or detrimental effects of the therapeutic agent are outweighed by the therapeutically beneficial effects.

"Co-administer", as used herein, may refer to administering two or more therapeutic agents to an individual to treat a disease. The two or more therapeutic agents may be administered with dosage schedules that are independent of one another (e.g., at different frequencies or intervals of administration). In some cases, two or more therapeutic agents may be administered at the same time, and in some cases, two or more therapeutic agents may be administered at different times (e.g., one before another, in alternating sequence, etc.).

The terms "cancer, "neoplasm," and "tumor" are used interchangeably herein to refer to cells which exhibit relatively autonomous growth, so that they exhibit an aberrant growth phenotype characterized by a significant loss of control of cell proliferation. Cells of interest that may exhibit uncontrolled proliferation include precancerous, malignant, pre-metastatic, metastatic, and non-metastatic cells, as well as carcinoma in situ. Cancer also refers to the pathological condition caused by the uncontrolled proliferation of cells.

"Cancer stem cell" may refer to a cell found within a tumor or among blood cancer cells, that exhibits characteristics associated with stem cells, such as the ability to give rise to cell types found in the tumor or cancer (e.g., exhibits pluripotency) and self-renewal (e.g., divide to give rise to another pluripotent stem cell of the cancer). The cell may be able to form or initiate a tumor, and may be involved in the development of the tumor. In some cases, cancer stem cells are resistant to chemotherapy.

"Marker" as used herein, refers to a gene whose level of expression (RNA transcript expression or protein expression) is specific to a type of cell (e.g., cancer stem cell, immune cell), at least among a collection of different types of cells commonly found associated with the type of cell identified by expression of the gene in a tissue.

"Surface" as used in reference to a cell, is meant to refer to the side of the plasma membrane of the cell that is exposed to the extracellular environment in the absence of permeabilization of the plasma membrane. The side of the plasma membrane may be accessible for binding of an antibody to its antigen, or epitope, that is positioned thereon.

"Sonic Hedgehog", "Shh", "Sonic Hedgehog polypeptide", and equivalents thereof, refer to a protein encoded by the human SHH gene (Gene ID: 6469). The full-length human Shh protein may have an amino acid sequence as set forth in SEQ ID NO:1, shown in FIG. 23. Shh is a protein physiologically involved in vertebrate development. The full-length protein is cleaved in the cytosol into N- and C-terminal products. The C-terminal Shh polypeptide may have an amino acid sequence from residues 198 to 462 of SEQ ID NO:1, shown in FIG. 23. The N-terminal Shh polypeptide may or may not include a signal sequence at the N-terminal end. Thus, an N-terminal Shh polypeptide without the signal sequence may have an amino acid sequence from residues 24 to 197 of SEQ ID NO:1, shown in FIG. 23. An N-terminal Shh polypeptide with the signal sequence may have an amino acid sequence from residues 1 to 197 of SEQ ID NO:1, shown in FIG. 23.

"Shh+" and "Shh−" are meant to indicate the expression status of full-length Shh on the surface of a cell, e.g., as determined by labeling unpermeabilized cells with a detectably labeled C-terminal Shh antibody, and using flow cytometry or immunohistochemistry. A cell may express Shh on the cell surface, and therefore be classified as Shh+, when the detectable signal (e.g., fluorescence) from the C-terminal Shh antibody (e.g., fluorescently labeled C-terminal Shh antibody) is above a threshold, and may not express Shh on the cell surface, and therefore be classified as Shh−, when the detectable signal from the C-terminal Shh antibody is below the threshold. The threshold may be determined based on an appropriate control (e.g., cells known to express or not express full-length Shh on the cell surface, or cells labeled without the C-terminal Shh antibody, etc.).

The "Shh signaling pathway" includes a plasma membrane complex of Patched (Ptc) and Smoothened (Smo) that transduce the Shh signal into the cell. Ptc is considered to repress Shh signaling by binding to Smo in the cell membrane. Upon binding of the Shh ligand, Ptc repression is relieved and Smo is able to signal. In vertebrates, the zinc finger proteins GLI1, GLI2 and GLI3 are downstream mediators of Shh signaling and are involved in controlling the transcriptional response of target genes in a Shh dependent manner.

"Therapeutic agent" as used herein may refer to any chemical compound, small molecule, antibody, nucleic acid molecule, or polypeptide, or fragments thereof, useful for treatment of a disease. Examples include, but are not limited to, a drug, a toxin, an affinity ligand, a detection probe, or a combination thereof. In some cases, the active agent is an anti-cancer agent.

"Chemotherapeutic agent" as used herein may refer to a chemical compound used to treat cancer (i.e., an anti-cancer agent). The chemical compound is generally a non-specific cytotoxin, such as an inhibitor of mitosis. In some cases, the chemical compound is not an anti-cancer agent that targets specific growth signaling pathways, such as the Shh signaling pathway.

Before the present disclosure is further described, it is to be understood that the disclosed subject matter is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosed subject matter. The upper and lower limits of these smaller ranges may independently be included in the smaller ranges, and are also encompassed within the disclosed subject matter, subject to any specifically excluded limit in the stated range. Where the stated range includes one or both of the limits, ranges excluding either or both of those included limits are also included in the disclosed subject matter.

Unless defined otherwise, all technical and scientific terms used herein have the same meaning as commonly understood by one of ordinary skill in the art to which the disclosed subject matter belongs. Although any methods and materials similar or equivalent to those described herein can also be used in the practice or testing of the disclosed subject matter, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an antibody" includes a plurality of such antibodies and reference to "the conjugate" includes reference to one or more conjugates and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the disclosed subject matter, which are, for clarity, described in the context of separate embodiments, may also be provided in combination in a single embodiment. Conversely, various features of the disclosed subject matter, which are, for brevity, described in the context of a single embodiment, may also be provided separately or in any suitable sub-combination. All combinations of the embodiments pertaining to the disclosure are specifically embraced by the disclosed subject matter and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein.

The publications discussed herein are provided solely for their disclosure prior to the filing date of the present application. Nothing herein is to be construed as an admission that the disclosed subject matter is not entitled to antedate such publication by virtue of prior invention. Further, the dates of publication provided may be different from the actual publication dates which may need to be independently confirmed.

DETAILED DESCRIPTION

As summarized above, antibodies that specifically bind to a Sonic Hedgehog (Shh) polypeptide, or an antigen binding fragment thereof, are provided. The antibodies of the present disclosure specifically binds to a population of cells expressing full-length Shh on the cell surface (Shh+ cells) in a tumor, where the Shh+ cells may exhibit properties of cancer stem cells. Thus the Shh antibodies can be used to detect and quantitate the prevalence of Shh+ cells in a tumor sample, and/or can be used to target therapeutic agents, e.g., anti-cancer drugs, to the Shh+ cells in a tumor, by conjugating the therapeutic agent to the antibody, to thereby treat an individual for cancer. The antibodies themselves may have cytotoxic properties on cancer cells, and may be administered, with or without co-administration of other anti-cancer agents, to an individual for cancer treatment.

The Shh+ cells identified by the present antibodies exhibit certain characteristics of cancer stem cells, and it may be therapeutically effective to target them during cancer treatment. For example, tumors containing Shh+ cells may be formed, developed and/or maintained by elevated signaling through the Shh signaling pathway. Thus, detecting the presence of the Shh+ cells in a tumor sample from an individual, e.g., a patient with cancer, may aid in providing patient-specific treatment of the cancer (e.g., administering a chemotherapeutic agent, with or without co-administration of a Shh signaling pathway inhibitor).

Further aspects of the present disclosure are now described.

Antibodies

The present Shh antibodies include antibodies raised against a C-terminal Shh polypeptide in a suitable animal model, e.g., a suitable mouse, for generating monoclonal antibodies. The present Shh antibody may be obtained by a method that includes inoculating a suitable organism, e.g., a suitable mouse, with one or more (e.g., two or more) peptides that includes an amino acid sequence of a C-terminal Shh polypeptide, where the amino acid sequence is from about 15 to 18 amino acids long, as described below. A C-terminal Shh antibody of the present disclosure (including that which may be part of an antibody conjugate, as described below), may be a monoclonal antibody. A C-terminal Shh antibody generally binds specifically to full-length Shh polypeptide, expressed on a cell surface, in the cytosol, and/or isolated in vitro, e.g., in a Western blot, on a biosensor chip, etc. An antibody or antibody conjugate of the present disclosure can bind a full-length Shh polypeptide with a suitable binding affinity, e.g., from about $5 \times 10^{-8}$ M to about $10^{-9}$ M, such as, from about $10^{-8}$ M to about $2 \times 10^{-9}$ M, including from about $6 \times 10^{-9}$ M to about $3 \times 10^{-9}$ M, as measured by, e.g., biolayer interferometry. In some embodiments, the C-terminal Shh antibody specifically binds to a C-terminal Shh polypeptide. In some embodiments, the C-terminal Shh antibody does not bind to an N-terminal Shh polypeptide. Also provided are antigen-binding fragments of the C-terminal Shh antibodies (e.g., fragments of the antibody that includes the complementarity determining regions (CDRs) that define antigen specificity of the antibody).

In some embodiments, a C-terminal Shh antibody of the present disclosure includes 3 heavy chain complementarity determining regions (CDRs) and 3 light chain CDRs (e.g., as defined by Kabat, supra), each having an amino acid sequence as follows:

```
Heavy chain variable (V_H) region CDRs:
CDR_H1:
                                      (SEQ ID NO: 10)
SYTMS;

CDR_H2:
                                      (SEQ ID NO: 11)
TISSGGGNTYYPDSVKG;

CDR_H3:
                                      (SEQ ID NO: 12)
DYRSLFAY;
```

-continued

```
Light chain variable (V_L) region CDRs:
CDR_L1:
                                       (SEQ ID NO: 13)
SASSSVSYMH;

CDR_L2:
                                       (SEQ ID NO: 14)
STSNLAS;
and

CDR_L3:
                                       (SEQ ID NO: 15)
QQRSSYPFT.
```

Also provided herein are single-chain antibodies and antibody fragments that include the antigen binding portions of the C-terminal Shh antibody. A single chain antibody may include, e.g., scFv, having $V_H$ and $V_L$ regions containing the respective CDRs and connected by a suitable linker. In some cases, a single chain antibody may be a multimer (e.g., a diamer (i.e., a diabody), trimer, or tetramer, etc.) of scFvs. Antibody fragments include, without limitation, F(ab')$_2$, Fab' and Fab fragments of the C-terminal Shh antibody.

The heavy chain CDRs may be conveniently positioned within any suitable framework of a $V_H$ region of the antibody. In some cases, the framework regions are from a non-human (e.g., mouse) antibody $V_H$ region. In some cases, the framework region is humanized, where one or more amino acids of the non-human antibody heavy chain framework region are substituted with an amino acid at a corresponding position of the framework region of a human antibody $V_H$ region.

The light chain CDRs may be conveniently positioned within any suitable framework of a $V_L$ region of the antibody. In some cases, the framework regions are from a non-human (e.g., mouse) antibody $V_L$ region. In some cases, the framework region is humanized, where one or more amino acids of the non-human antibody light chain framework region are substituted with an amino acid at a corresponding position of the framework region of a human antibody $V_L$ region.

The C-terminal Shh antibody may have any suitable constant regions. In some embodiments, the C-terminal Shh antibody includes a heavy chain constant region (e.g., $C_H1$, $C_H2$, $C_H3$ and/or H regions) of a non-human (e.g., mouse) antibody. In some embodiments, the constant region is humanized, where one or more amino acids of the non-human antibody heavy chain constant region are substituted with an amino acid at a corresponding position of the framework region of a human antibody heavy chain constant region. In some embodiments, the heavy chain constant region of the C-terminal Shh antibody is a heavy chain constant region from a human antibody. In some embodiments, the C-terminal Shh antibody includes a light chain constant region of a non-human (e.g., mouse) antibody. In some embodiments, the constant region is humanized, where one or more amino acids of the non-human antibody light chain constant region are substituted with an amino acid at a corresponding position of the framework region of a human antibody light chain constant region. In some embodiments, the light chain constant region of the C-terminal Shh antibody is a light chain constant region from a human antibody.

The C-terminal Shh antibody may include any suitable isotype for the heavy chain and/or the light chain. Suitable antibody isotypes include, without limitation, IgA, IgD, IgG, IgE and IgM. In some cases, the C-terminal Shh antibody is an IgG$_1$, IgG$_2$, IgG$_3$, or IgG$_4$ antibody. In some cases, the C-terminal Shh antibody includes a non-human (e.g., mouse) isotype. In some embodiments, the C-terminal Shh antibody includes a human isotype. Suitable isotypes for the heavy chain include, without limitation, alpha, delta, gamma, epsilon and mu isotypes. In some cases, the heavy chain isotype is a human light chain isotype. Suitable isotypes for the heavy chain include, without limitation, kappa and lambda light chains. In some cases, the light chain isotype is a human light chain isotype.

In some embodiments, a C-terminal Shh antibody has a $V_H$ region having an amino acid sequence that is at least about 80%, e.g., at least about 85%, at least about 90%, at least about 95%, at least about 97% at least about 99%, or 100% identical to the sequence:

```
                                       (SEQ ID NO: 16)
EVKLVESGGGLVKPGGSLKLSCAASGFTFSSYTMSWVRQTPAKRLE

WVATISSGGGNTYYPDSVKGRFTISRDNARNTLYLQMSSLRSEDTA

MYYCARDYRSLFAYWGQGTLVTVSA,
``` where the amino acid sequences of the $V_H$ region corresponding to positions 31-35 (CDR$_H$1), 50-66 (CDR$_H$2), and 99-106 (CDR$_H$3) of SEQ ID NO:16 are as set forth in SEQ ID NOs: 10, 11 and 12, respectively.

In some embodiments, a C-terminal Shh antibody has a $V_L$ region having an amino acid sequence that is at least about 80%, e.g., at least about 85%, at least about 90%, at least about 95%, at least about 97% at least about 99%, or 100% identical to the sequence:

```
                                       (SEQ ID NO: 17)
QIVLTQSPAIMSASPGEKVTITCSASSSVSYMHWFQQKPGTSPKLW

IYSTSNLASGVPARFSGSGSGTSYSLTISRMEAEDAATYYCQQRSS

YPFTFGSGTKLEIK,
``` where the amino acid sequences of the $V_L$ region corresponding to positions 24-33 (CDR$_L$1), 49-55 (CDR$_L$2), and 88-96 (CDR$_L$3) of SEQ ID NO:17 are as set forth in SEQ ID NOs: 13, 14 and 15, respectively.

In some embodiments, a C-terminal Shh antibody has a heavy chain Ig polypeptide amino acid sequence that is at least about 70%, e.g., at least about 75%, at least about 80%, at least about 85%, at least about 90%, at least about 95%, at least about 97% at least about 99%, or 100% identical to the sequence:

```
                                       (SEQ ID NO: 3)
MNFGLSLIFLVLVLKGVQCEVKLVESGGGLVKPGGSLKLSCAASGF

TFSSYTMSWVRQTPAKRLEWVATISSGGGNTYYPDSVKGRFTISRD

NARNTLYLQMSSLRSEDTAMYYCARDYRSLFAYWGQGTLVTVSAAK

TTPPSVYPLAPGSAAQTNSMVTLGCLVKGYFPEPVTVTWNSGSLSS

GVHTFPAVLQSDLYTLSSSVTVPSSTWPSETVTCNVAHPASSTKVD

KKIVPRDCGCKPCICTVPEVSSVFIFPPKPKDVLTITLTPKVTCVV

VDISKDDPEVQFSWFVDDVEVHTAQTQPREEQFNSTFRSVSELPIM

HQDWLNGKEFKCRVNSAAFPAPIEKTISKTKGRPKAPQVYTIPPPK

EQMAKDKVSLTCMITDFFPEDITVEWQWNGQPAENYKNTQPIMDTD

GSYFIYSKLNVQKSNWEAGNTFTCSVLHEGLHNHHTEKSLSHSPGK,
``` where the amino acid sequences of the heavy chain Ig polypeptide corresponding to positions 50-54 (CDR$_H$1), 69-85 (CDR$_H$2), and 118-125 (CDR$_H$3) of SEQ ID NO:3 are as set forth in SEQ ID NOs: 10, 11 and 12, respectively.

In some embodiments, a C-terminal Shh antibody has a light chain Ig polypeptide amino acid sequence that is at least about 70%, e.g., at least about 75%, at least about 80%, at least about 85%, at least about 90%, at least about 95%, at least about 97% at least about 99%, or 100% identical to the sequence:

(SEQ ID NO: 5)
MHFQVQIFSFLLISASVIMSRGQIVLTQSPAIMSASPGEKVTITC<u>SA</u>

<u>SSSVSYMH</u>WFQQKPGTSPKLWIY<u>STSNLAS</u>GVPARFSGSGSGTSYSL

TISRMEAEDAATYYC<u>QQRSSYPFT</u>FGSGTKLEIKRADAAPTVSIFPP

SSEQLTSGGASVVCFLNNFYPKDINVKWKIDGSERQNGVLNSWTDQD

SKDSTYSMSSTLTLTKDEYERHNSYTCEATHKTSTSPIVKSFNRNEC, where the amino acid sequences of the light chain Ig polypeptide corresponding to positions 46-55 (CDR$_L$1), 71-77 (CDR$_L$2), and 110-118 (CDR$_L$3) of SEQ ID NO:5 are as set forth in SEQ ID NOs: 13, 14 and 15, respectively.

Antibody Conjugates

Also provided herein are antibody conjugates, where an antibody (e.g., a C-terminal Shh antibody, as described above), or an antigen binding fragment thereof, is conjugated to a payload, e.g., a therapeutic agent for treating a disease, such as cancer. As used herein, "conjugated to the antibody" is used to refer to a payload that is attached, via physical interaction, to one or more immunoglobulin (Ig) polypeptides (i.e., heavy chain or light chain) of the antibody. Thus, the payload of the present antibody conjugate may be conjugated to any one or more Ig polypeptides (i.e., heavy chain or light chain) of the antibody. The cell may be any suitable cell that expresses full-length Shh polypeptide on the cell surface (i.e, on the extracellular leaflet of the plasma membrane). In some cases, the cell is a tumor cell. In some cases, the cell is a cancer stem cell in a tumor. Thus, the antibody conjugate may specifically bind to full-length Shh polypeptide that is expressed on the surface of the cell, and thereby enhance targeting of the conjugated payload, e.g., therapeutic agent, to physiological sites containing Shh+ cells, such as targeting to tumors with Shh+ cancer stem cells.

The antibody portion of the antibody conjugate may be any suitable antibody, or an antigen binding fragment thereof, that specifically binds to full-length Shh polypeptide that is expressed on the surface of a cell (e.g., surface of a cancer stem cell in a tumor). In some embodiments, the antibody, or the antigen binding fragment thereof, specifically binds to a C-terminal Shh polypeptide. In some embodiments, the antibody does not bind to an N-terminal Shh polypeptide. In some embodiments, the antibody, or the antigen binding fragment thereof, is a C-terminal Shh antibody (i.e., an antibody raised against a C-terminal Shh polypeptide, and that specifically binds to a Shh polypeptide), or an antigen binding fragment thereof, as described above. In some embodiments, the antibody, or the antigen binding fragment thereof, binds the same antigen epitope as the antigen epitope of the C-terminal Shh antibody, and may compete with the C-terminal Shh antibody for binding to the epitope.

The therapeutic agent may be attached to the antibody in any suitable manner, and in a manner compatible with the activity of the payload, e.g., the therapeutic activity of the therapeutic agent when administered to an individual to treat a cancer. Thus, in some cases, the therapeutic agent is attached non-covalently to the antibody. In some cases, the antibody is functionalized with a carrier, (e.g., a polymeric carrier, a liposome, etc.), and the therapeutic agent may interact non-covalently with the carrier, to attach the therapeutic agent to the antibody.

In some cases, the therapeutic agent is attached covalently to the antibody in the present antibody conjugate. The antibody conjugate may then be represented schematically as: X-(L-)Y, where X is the antibody, L is an optional linking group, Y is the payload (e.g., therapeutic agent), and "-" represent covalent bonds. The therapeutic agent may be covalently attached to the antibody in the conjugate in any suitable manner. Therapeutic agents may be attached, for example to reduced SH groups (e.g., of a cysteine residue) to form a disulfide bond between the therapeutic agent and an Ig polypeptide of the antibody, and/or to carbohydrate side chains of an Ig polypeptide of the antibody, which may involve a secondary amine formed via reduction of an initial Schiff base (imine) linkage between an oxidized carbohydrate of the Ig polypeptide and a free amine group. A therapeutic agent may be attached at the hinge region of a reduced antibody component via disulfide bond formation. Alternatively, such agents can be attached using a heterobifunctional cross-linker, such as N-succinyl 3-(2-pyridyldithio) propionate (SPDP). Thus, a suitable Ig polypeptide of an antibody included in the present antibody conjugates may be engineered to include a suitable conjugation site for attaching a payload and/or a linking group, e.g., by modifying one or more amino acids in the amino acid sequence of the Ig polypeptide compared to a parent Ig polypeptide which may lacked suitable sites for conjugation of the payload and/or linking group. The modification may include one or more of insertion, deletion, and substitution of one or more amino acids of the parent Ig polypeptide, as is appropriate to introduce a conjugation site that is accessible to the conjugation chemistry.

In some embodiments, the payload, e.g., therapeutic agent, is conjugated via a carbohydrate moiety in the Fc region of the antibody. The Fc region may be absent if the antibody component of the antibody conjugate is an antibody fragment. However, it is possible to introduce a carbohydrate moiety into the light chain variable region of a full-length antibody or antibody fragment.

In some embodiments, the payload, e.g., therapeutic agent, is attached to an antibody or fragment through the use of click chemistry reactions. Any suitable click chemistry may be used, such as the Huisgen 1,3-dipolar cycloaddition copper catalyzed reaction, which links a conjugating moiety (e.g., the therapeutic agent) to the antibody through a chemically stable 1,4-disubstituted 1,2,3-triazole group. Other alternatives include cycloaddition reactions such as the Diels-Alder, nucleophilic substitution reactions (such as to small strained rings like epoxy and aziridine compounds), carbonyl chemistry formation of urea compounds and reactions involving carbon-carbon double bonds, such as alkynes in thiol-yne reactions.

Any suitable linking group (L) may be used to conjugate the present antibody (i.e., an Ig polypeptide of the present antibody) with a payload, e.g., therapeutic agent. The linking group may be a cleavable linking group, or a non-cleavable linking group.

For example, in some embodiments, the linking group is cleavable by a cleaving agent that is present in the intracellular environment (e.g., within a lysosome or endosome or caveolea). The linking group can be, e.g., a peptidyl linking group that is cleaved by an intracellular peptidase or protease enzyme, including, but not limited to, a lysosomal or endosomal protease. Typically, the peptidyl linking group is at least two amino acids long or at least three amino acids long. Cleaving agents can include cathepsins B and D and plasmin, which may hydrolyze the peptidyl linking group, resulting in the release of the payload, e.g., therapeutic agent, inside target cells. For example, a peptidyl linking group that is cleavable by the thiol-dependent protease cathepsin-B, which is highly expressed in cancerous tissue, can be used (e.g., a Phe-Leu or a Gly-Phe-Leu-Gly linking group). Other such linking groups are described, e.g., in U.S. Pat. No. 6,214,345. In specific embodiments, the peptidyl linking group cleavable by an intracellular protease is a Val-Cit linking group or a Phe-Lys linking group.

In other embodiments, the cleavable linking group is pH-sensitive, i.e., sensitive to hydrolysis at certain pH values. Typically, the pH-sensitive linking group hydrolyzable under acidic conditions. For example, an acid-labile linking group that is hydrolyzable in the lysosome (e.g., a hydrazone, semicarbazone, thiosemicarbazone, cis-aconitic amide, orthoester, acetal, ketal, or the like) can be used. Such linking groups are relatively stable under neutral pH conditions, such as those in the blood, but are unstable at below pH 5.5 or 5.0, the approximate pH of the lysosome. In certain embodiments, the hydrolyzable linking group is a thioether linking group (such as, e.g., a thioether attached to the therapeutic agent via an acylhydrazone bond (see, e.g., U.S. Pat. No. 5,622,929)).

In yet other embodiments, the linking group is cleavable under reducing conditions (e.g., a disulfide linking group). A variety of disulfide linking groups are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene), SPDB and SMPT.

In yet other specific embodiments, the linking group is a malonate linking group, a maleimidobenzoyl linking group, or a 3'-N-amide analog.

The linking group may not be substantially sensitive to the extracellular environment. As used herein, "not substantially sensitive to the extracellular environment," in the context of a linking group, means that about 20% or less, e.g., about 15% or less, about 10% or less, about 5% or less, about 3% or less, including about 1% or less of the linking groups, in a sample of antibody conjugate, are cleaved when the antibody conjugate is present in an extracellular environment (e.g., in plasma), in the absence of a cleaving agent or a cleaving condition(s), as described above.

In some cases, the linking group is non-cleavable. A non-cleavable linking group is substantially resistant to cleavage, such as acid-induced cleavage, light-induced cleavage, peptidase-induced cleavage, esterase-induced cleavage, or disulfide bond cleavage. Examples of such non-cleavable linking groups include, without limitation, those that are or can be derived from a haloacetyl-based moiety selected from the group consisting of N-succinimidyl-4-(iodoacetyl)-aminobenzoate (SIAB), N-succinimidyl iodoacetate (SIA), N-succinimidyl bromoacetate (SBA), and N-succinimidyl 3-(bromoacetamido)propionate (SBAP). Alternatively, the non-cleavable linking group is or is derived from, without limitation, a maleimido-based moiety selected from the group consisting of N-succinimidyl 4-(maleimidomethyl)cyclohexanecarboxylate (SMCC), N-succinimidyl-4-(N-maleimidomethyl)-cyclohexane-1-carboxy-(6-amidocaproate) (LC-SMCC), K-maleimidoundecanoic acid N-succinimidyl ester (KMUA), γ-maleimidobutyric acid N-succinimidyl ester (GMBS), ε-maleimidcaproic acid N-hydroxysuccinimide ester (EMCS), m-maleimidobenzoyl-N-hydroxysuccinimide ester (MBS), N-(a-maleimidoacetoxy)-succinimide ester (AMAS), succinimidyl-6-(P-maleimidopropionamido)hexanoate (SMPH), N-succinimidyl 4-(p-maleimidophenyl)-butyrate (SMPB), and N-(p-maleimidophenyl)isocyanate (PMPI); another non-cleavable linking group is maleimidocaproyl.

The conjugated payload may be any suitable therapeutic agent. In some cases, the therapeutic agent is an anti-cancer agent, e.g., an anti-cancer drug. The anti-cancer agent may be any suitable anti-cancer agent, or anti-cancer drug. In some cases, the anti-cancer agent is a chemotherapeutic agent, e.g., a chemotherapeutic drug. In some cases, the anti-cancer agent is an inhibitor of the Shh signaling pathway. Suitable therapeutic agents, anti-cancer agents and Shh signaling pathway inhibitors for use in the present antibody conjugates are discussed further below.

Nucleic Acids

Also provided herein is a nucleic acid that includes a nucleotide sequence encoding one or more Ig polypeptides of the C-terminal Shh antibody, or an antigen binding fragment thereof, as described above, and expression vectors containing the same. The nucleic acid may include: 1) a nucleotide sequence encoding a $V_H$ region of a C-terminal Shh antibody, where the $V_H$ region includes: a $CDR_H1$ having an amino acid sequence as set forth in SEQ ID NO:10; a $CDR_H2$ having an amino acid sequence as set forth in SEQ ID NO:11, and a $CDR_H3$ having an amino acid sequence as set forth in SEQ ID NO:12; 2) a nucleotide sequence encoding a $V_H$ region of a C-terminal Shh antibody, where the $V_H$ region includes: a $CDR_H1$ having an amino acid sequence as set forth in SEQ ID NO:10; a $CDR_H2$ having an amino acid sequence as set forth in SEQ ID NO:11, and a $CDR_H3$ having an amino acid sequence as set forth in SEQ ID NO:12, and a nucleotide sequence encoding a heavy chain constant region in frame with and 3' of the nucleotide sequence encoding the $V_H$ region; 3) a nucleotide sequence encoding a $V_L$ region of a C-terminal Shh antibody, where the $V_L$ region includes: a $CDR_L1$ having an amino acid sequence as set forth in SEQ ID NO:13; a $CDR_L2$ having an amino acid sequence as set forth in SEQ ID NO:14, and a $CDR_L3$ having an amino acid sequence as set forth in SEQ ID NO:15; 4) a nucleotide sequence encoding a $V_L$ region of a C-terminal Shh antibody, where the $V_L$ region includes: a $CDR_L1$ having an amino acid sequence as set forth in SEQ ID NO:13; a $CDR_L2$ having an amino acid sequence as set forth in SEQ ID NO:14, and a $CDR_L3$ having an amino acid sequence as set forth in SEQ ID NO:15, and a nucleotide sequence encoding a light chain constant region in frame with and 3' of the nucleotide sequence encoding the $V_L$ region.

In some embodiments, the nucleic acid encodes a $V_H$ region having an amino acid sequence at least about 80%, e.g., at least about 85%, at least about 90%, at least about 95%, at least about 97% at least about 99%, or 100% identical to the sequence as set forth in SEQ ID NO:16, where the amino acid sequences of the $V_H$ region corresponding to positions 31-35 ($CDR_H1$), 50-66 ($CDR_H2$), and 99-106 ($CDR_H3$) of SEQ ID NO:16 are as set forth in SEQ ID NOs: 10, 11 and 12, respectively. In some embodiments, the nucleic acid encodes a $V_L$ region having an amino acid sequence at least about 80%, e.g., at least about 85%, at least about 90%, at least about 95%, at least about 97% at least about 99%, or 100% identical to the sequence as set forth in SEQ ID NO:17, where the amino acid sequences of the $V_L$ region corresponding to positions 24-33 ($CDR_L1$), 49-55 ($CDR_L2$), and 88-96 ($CDR_L3$) of SEQ ID NO:17 are as set forth in SEQ ID NOs: 13, 14 and 15, respectively.

In some embodiments, the nucleic acid encodes a heavy chain Ig polypeptide amino acid sequence that is at least about 70%, e.g., at least about 75%, at least about 80%, at least about 85%, at least about 90%, at least about 95%, at least about 97% at least about 99%, or 100% identical to the sequence set forth in SEQ ID NO:3, where the amino acid sequences of the heavy chain Ig polypeptide corresponding to positions 50-54 ($CDR_H1$), 69-85 ($CDR_H2$), and 118-125 ($CDR_H3$) of SEQ ID NO:3 are as set forth in SEQ ID NOs: 10, 11 and 12, respectively. In some embodiments, the nucleic acid encodes a light chain Ig polypeptide amino acid sequence that is at least about 70%, e.g., at least about 75%, at least about 80%, at least about 85%, at least about 90%, at least about 95%, at least about 97% at least about 99%, or 100% identical to the sequence set forth in SEQ ID NO:5, where the amino acid sequences of the light chain Ig polypeptide corresponding to positions 46-55 ($CDR_L1$), 71-77 ($CDR_L2$), and 110-118 ($CDR_L3$) of SEQ ID NO:5 are as set forth in SEQ ID NOs: 13, 14 and 15, respectively.

Also provided herein are expression vectors that include a nucleic acid that includes a nucleotide sequence encoding one or more Ig polypeptides of the C-terminal Shh antibody, or an antigen binding fragment thereof, as described above, where the nucleotide sequence is operably linked to a promoter (e.g., a bacterial, mammalian, or viral expression promoter, etc., for expressing the Ig polypeptide of the C-terminal Shh antibody).

Any suitable expression vector backbone may be used. Vectors which may be used include, without limitation, plasmids; cosmids; viral vectors (e.g., retroviral vectors); non-viral vectors; artificial chromosomes (yeast artificial chromosomes (YAC's), BAC's, etc.); mini-chromosomes; and the like. The choice of vector will depend upon a variety of factors such as the type of cell in which propagation is desired and the purpose of propagation.

Suitable vectors that may be used include but are not limited to those derived from recombinant bacteriophage DNA, plasmid DNA or cosmid DNA. For example, plasmid vectors such as pBR322, pUC 19/18, pUC 118, 119 and the M13 mp series of vectors may be used. Bacteriophage vectors may include λgt10, λgt11, λgt18-23, λZAP/R and the EMBL series of bacteriophage vectors. Cosmid vectors that may be utilized include, but are not limited to, pJB8, pCV 103, pCV 107, pCV 108, pTM, pMCS, pNNL, pHSG274, COS202, COS203, pWE15, pWE16 and the charomid 9 series of vectors. Alternatively, recombinant virus vectors may be engineered, including but not limited to those derived from viruses such as herpes virus, retroviruses, vaccinia virus, poxviruses, adenoviruses, adeno-associated viruses, or bovine papilloma virus.

Vectors can provide for extrachromosomal maintenance in a host cell or can provide for integration into the host cell genome. Vectors may provide for expression of the nucleic acids encoding a polypeptide of interest (e.g., an Ig polypeptide of a C-terminal Shh antibody), may provide for propagating the subject nucleic acids, or both.

For expression of a protein of interest (e.g., a C-terminal Shh antibody), an expression cassette of an expression vector may be employed. The expression vector provides a transcriptional and translational regulatory sequence, and may provide for inducible or constitutive expression, where the coding region is operably linked under the transcriptional control of the transcriptional initiation region, and a transcriptional and translational termination region. These control regions may be native to the gene encoding the polypeptide (e.g., an Ig polypeptide of a C-terminal Shh antibody), or may be derived from exogenous sources. In general, the transcriptional and translational regulatory sequences may include, but are not limited to, promoter sequences, ribosomal binding sites, transcriptional start and stop sequences, translational start and stop sequences, and enhancer or activator sequences. In addition to constitutive and inducible promoters, strong promoters (e.g., T7, CMV, and the like) find use in the constructs described herein, particularly where high expression levels are desired in an in vivo (cell-based) or in an in vitro expression system. Further exemplary promoters include mouse mammary tumor virus (MMTV) promoters, Rous sarcoma virus (RSV) promoters, adenovirus promoters, the promoter from the immediate early gene of human CMV (Boshart et al., *Cell* 41:521-530, 1985), and the promoter from the long terminal repeat (LTR) of RSV (Gorman et al., *Proc. Natl. Acad. Sci. USA* 79:6777-6781, 1982). The promoter can also be provided by, for example, a 5'UTR of a retrovirus.

Expression vectors generally have convenient restriction sites located near the promoter sequence to provide for the insertion of nucleic acid sequences encoding proteins of interest. A selectable marker operative in the expression host may be present to facilitate selection of cells containing the vector. In addition, the expression construct may include additional elements. For example, the expression vector may have one or two replication systems, thus allowing it to be maintained in organisms, for example in mammalian or insect cells for expression and in a prokaryotic host for cloning and amplification. In addition the expression construct may contain a selectable marker gene to allow the selection of transformed host cells.

Compositions

Therapeutic Compositions

Also provided herein is a composition (e.g., a therapeutic composition) that includes a C-terminal Shh antibody, as described above, and/or an antibody conjugate, as described above, and a pharmaceutically acceptable excipient. The present composition may be formulated for use in a treatment of an individual for a disease, e.g., cancer. In some embodiments, the cancer is lung cancer, such as, without limitation, non-small cell lung cancer (NSCLC). The present therapeutic composition may include the antibody, and/or the antibody conjugate, each in a therapeutically effective amount (e.g., an amount effective in treating a cancer when administered to an individual for treatment of the cancer).

As used herein, "carrier" or "excipient" includes any and all solvents, diluents, buffers (such as, e.g., neutral buffered saline or phosphate buffered saline), solubilizers, colloids, dispersion media, vehicles, fillers, chelating agents (such as, e.g., ethylenediaminetetraacetic acid (EDTA) or glutathione), amino acids (such as, e.g., glycine), proteins, disintegrants, binders, lubricants, wetting agents, emulsifiers, sweeteners, colorants, flavorings, aromatisers, thickeners, agents for achieving a depot effect, coatings, antibacterial and antifungal agents, preservatives, antioxidants, tonicity controlling agents, absorption delaying agents, and the like, and combinations thereof. Except insofar as any conventional media or agent is incompatible with the active substance, its use in the therapeutic compositions may be contemplated.

Illustrative, non-limiting carriers for use in formulating the pharmaceutical compositions may include, for example, oil-in-water or water-in-oil emulsions, aqueous compositions with or without inclusion of organic co-solvents suitable for intravenous (IV) use, liposomes or surfactant-containing vesicles, microspheres, microbeads and microsomes, powders, tablets, capsules, suppositories, aqueous suspensions, aerosols, and other carriers apparent to one of ordinary skill in the art.

In some embodiments, the present composition may include an additional therapeutic agent, e.g., a Shh signaling pathway inhibitor, where the composition is formulated for co-administering a C-terminal Shh antibody, as described above, with the therapeutic agent. The therapeutic agent may be any suitable therapeutic agent for formulating and co-administering with the C-terminal Shh antibody. Suitable therapeutic agents are described further below.

The C-terminal Shh antibody may have a synergistic effect with a Shh signaling pathway inhibitor, such as a GLI inhibitor, by enhancing the cytotoxic/growth-inhibiting effect of the inhibitor. Thus, when a C-terminal Shh antibody is co-administered with a Shh signaling pathway inhibitor, such as a GLI inhibitor, the therapeutic efficacy of the combined treatment may be greater than the apparent sum of the therapeutic efficacies of each of the C-terminal Shh antibody and the Shh signaling pathway inhibitor administered alone at the same respective amounts.

Thus, in some embodiments, the therapeutic composition includes, an effective amount of the C-terminal Shh antibody, or an antigen-binding fragment thereof, in the composition such that the Shh signaling pathway inhibitor, e.g., a GLI inhibitor, is present in a therapeutically effective amount that is at least about 10%, e.g., at least about 15%, at least about 20%, at least about 25%, at least about 30%, at least about 40%, including at least about 50% less than the amount of the Shh signaling pathway inhibitor present in a composition without the C-terminal Shh antibody and of similar therapeutic efficacy. For example, the composition that includes the C-terminal Shh antibody and the Shh signaling pathway inhibitor, e.g., a GLI inhibitor, may include the Shh signaling pathway inhibitor at an amount at least about 10%, e.g., at least about 15%, at least about 20%, at least about 25%, at least about 30%, at least about 40%, including at least about 50% below the $IC_{50}$ of the Shh signaling pathway inhibitor when administered alone (i.e., without the C-terminal Shh antibody).

The antibodies, or an antigen-binding fragment thereof, and antibody conjugates of the present disclosure can be formulated into a variety of different compositions. In general, the antibody or antibody conjugate is formulated in a manner compatible with the antibody, a therapeutic agent (e.g., an anti-cancer drug) conjugated to the antibody, the condition to be treated, and the route of administration to be used.

The antibody, or an antigen-binding fragment thereof, or antibody conjugate can be provided in any suitable form, e.g., in the form of a pharmaceutically acceptable salt, and can be formulated for any suitable route of administration, e.g., oral, topical or parenteral administration. Where the antibody, or an antigen-binding fragment thereof, or antibody conjugate is provided as a liquid injectable (such as in those embodiments where they are administered intravenously or directly into a tissue), the antibody or antibody conjugate can be provided as a ready-to-use dosage form, or as a reconstitutable storage-stable powder or liquid composed of pharmaceutically acceptable carriers and excipients.

Any convenient methods for formulating antibodies, or an antigen-binding fragment thereof, or antibody conjugates can be adapted in preparing the present compositions. For example, antibodies, or an antigen-binding fragment thereof, or antibody conjugates can be provided in a pharmaceutical composition comprising an effective amount of an antibody or antibody conjugate, and a pharmaceutically acceptable carrier (e.g., saline). The pharmaceutical composition may optionally include other additives (e.g., buffers, stabilizers, preservatives, and the like). Of particular interest in some embodiments are formulations that are suitable for administration to a mammal, particularly those that are suitable for administration to a human.

Immunogenic Compositions

Also provided herein is a composition (i.e., an immunogenic composition) for administering to an individual to eliciting an immune response (e.g., an adaptive immune response). "Adaptive immune response" as used herein, may refer to a response by the body to an antigen that includes generating an antibody that specifically binds to the antigen. The immunogenic composition may include one or more antigenic peptides that includes an amino acid sequence of at least a portion of a C-terminal Shh polypeptide. The antigenic peptide may elicit production of an antibody that can specifically bind to full-length Shh polypeptide that is expressed on the surface of a cell, e.g., on the surface of a cancer cell.

The antigenic peptide may include any suitable fragment of a C-terminal Shh polypeptide for eliciting an adaptive immune response when administered to an individual. The antigenic peptide may include a fragment of C-terminal Shh polypeptide of any suitable length, and in some cases, the C-terminal Shh polypeptide fragment has a length of 10 amino acids or more, e.g., 12 amino acids or more, 15 amino acids or more, 18 amino acids or more, 25 amino acids or more, including 50 amino acids or more, and in some embodiments, has a length of 265 amino acids or less, e.g., 200 amino acids or less, 150 amino acids or less, 100 amino acids or less, 50 amino acids or less, 25 amino acids or less, including 20 amino acids or less. In certain embodiments, the antigenic peptide includes a fragment of C-terminal Shh polypeptide having a length of from 10 to 265 amino acids, e.g., from 10 to 100 amino acids, from 12 to 50 amino acids, from 12 to 50 amino acids, including from 15 to 20 amino acids. In some embodiments, the antigenic peptide includes a fragment of C-terminal Shh polypeptide having the amino acid sequence GAKKVFYVIETREPRERL (SEQ ID NO:18). In some embodiments, the antigenic peptide includes a fragment of C-terminal Shh polypeptide having the amino acid sequence DSEALHPLGMAVKSS (SEQ ID NO:20).

In certain embodiments, the antigenic peptide includes a C-terminal Shh polypeptide fragment conjugated to a carrier, e.g., a protein carrier. Suitable carriers for conjugating to the C-terminal Shh polypeptide fragment e.g., to enhance antigenicity of the antigenic peptide, include keyhole limpet hemocyanin (KLH), thyroglobulin (THY), bovine serum albumin (BSA), ovalbumin (OVA), tetanus toxoid (TT), diphtheria toxoid, and tuberculin purified protein derivative. In some embodiments, KLH manufactured under Current Good Manufacturing Practice (cGMP) conditions is obtained from, e.g., Biosyn Arzneimittel GmbH and used for the preparation of C-terminal Shh polypeptide fragment-KLH conjugates.

The present immunogenic composition may include any other suitable components (e.g., pharmaceutical excipients, adjuvants, etc.). In some embodiments, the immunogenic composition includes granulocyte-macrophage colony stimulating factor (GM-CSF), which may serve as an immunological adjuvant.

Therapeutic Agents

Aspects of the present disclosure include a therapeutic agent that may be suitable: for conjugation to an antibody, or an antigen-binding fragment thereof, of the present disclosure; for formulating in a composition with an antibody or antibody conjugate of the present disclosure, as described above; or for use in methods of the present disclosure (e.g., for administering to an individual for treatment of a cancer), as described below. The therapeutic agent for use in the antibody conjugates, compositions and methods of the present disclosure may be any suitable chemical compound, small molecule, antibody, nucleic acid molecule, or polypeptide, or fragments thereof, useful for treatment of a disease, such as cancer. Suitable therapeutic agents may include drugs, toxins, oligonucleotides, immunomodulators, cytokine or chemokine inhibitors, proapoptotic agents, tyrosine kinase inhibitors, sphingosine inhibitors, hormones, hormone antagonists, enzymes, enzyme inhibitors, radionuclides, angiogenesis inhibitors, other antibodies or fragments thereof, etc.

In some embodiments, the therapeutic agent is a cytotoxic agent suitable for, e.g., treating a cancer. Suitable cytotoxic agents include, without limitation, vinca alkaloids, anthracyclines, gemcitabine, epipodophyllotoxins, taxanes, anti-metabolites, alkylating agents, antibiotics, SN-38, COX-2 inhibitors, anti-mitotics, anti-angiogenic and proapoptotic agents, particularly doxorubicin, methotrexate, taxol, CPT-11, camptothecins, proteosome inhibitors, mTOR inhibitors, HDAC inhibitors, tyrosine kinase inhibitors, and others. Other suitable cytotoxic agents include nitrogen mustards, alkyl sulfonates, nitrosoureas, triazenes, folic acid analogs, COX-2 inhibitors, antimetabolites, pyrimidine analogs, purine analogs, platinum coordination complexes, mTOR inhibitors, tyrosine kinase inhibitors, proteasome inhibitors, HDAC inhibitors, camptothecins, hormones, and the like.

Chemotherapeutic Agents

In some cases, a therapeutic agent that may be suitable for use for co-administration with an antibody or antibody conjugate of the present disclosure, or that may be suitable for use in methods of the present disclosure, include, without limitation, alkylating agents, anti-metabolites, anti-microtubule agents, topoisomerase inhibitors, and cytotoxic antibiotics. Suitable chemotherapeutic agents may include, without limitation, aplidin, azaribine, anastrozole, azacytidine, bleomycin, bortezomib, bryostatin-1, busulfan, calicheamycin, camptothecin, 10-hydroxycamptothecin, carmustine, celebrex, chlorambucil, cisplatin, irinotecan (CPT-11), SN-38, carboplatin, cladribine, cyclophosphamide, cytarabine, dacarbazine, docetaxel, dactinomycin, daunomycin glucuronide, daunorubicin, dexamethasone, diethylstilbestrol, doxorubicin, doxorubicin glucuronide, epirubicin glucuronide, ethinyl estradiol, estramustine, etoposide, etoposide glucuronide, etoposide phosphate, floxuridine (FUdR), 3',5'-O-dioleoyl-FudR (FUdR-dO), fludarabine, flutamide, fluorouracil, fluoxymesterone, gemcitabine, hydroxyprogesterone caproate, hydroxyurea, idarubicin, ifosfamide, L-asparaginase, leucovorin, lomustine, mechlorethamine, medroprogesterone acetate, egestrol acetate, melphalan, mercaptopurine, 6-mercaptopurine, methotrexate, mitoxantrone, mithramycin, mitomycin, mitotane, phenyl butyrate, prednisone, procarbazine, paclitaxel, pentostatin, PSI-341, semustine streptozocin, tamoxifen, taxanes, taxol, testosterone propionate, thalidomide, thioguanine, thiotepa, teniposide, topotecan, uracil mustard, velcade, vinblastine, vinorelbine, vincristine, ricin, abrin, ribonuclease, onconase, rapLR1, DNase I, Staphylococcal enterotoxin-A, pokeweed antiviral protein, gelonin, diphtheria toxin, *Pseudomonas* exotoxin, and *Pseudomonas* endotoxin.

In some embodiments, a chemotherapeutic agent is a platinum-containing compound, such as, but not limited to, cisplatin, carboplatin and oxaliplatin.

Shh Signaling Pathway Inhibitors

The therapeutic agent may be an inhibitor of the Shh signaling pathway. The Shh signaling pathway inhibitor may be any suitable chemical compound, small molecule, antibody, nucleic acid molecule, or polypeptide, or fragments thereof, that inhibits Shh signaling, and may target any suitable step of the Shh signaling pathway. The Shh signaling pathway inhibitor may inhibit, without limitation, SHH gene expression, Shh protein processing, Shh protein secretion, Shh protein activity, Patched (Ptc) activity, Smoothened (Smo) gene expression, Smo activity, GLI zinc finger protein expression, GLI zinc finger protein activity, etc. Suitable Shh signaling pathway inhibitors include, without limitation, GDC-0449 (also known as RG3616 or vismodegib); LDE-225 described, e.g., in Pan S. et al., *ACS Med. Chem. Lett.*, 2010; 1(3): 130-134; LEQ-506 described, e.g., in National Institute of Health Clinical Trial Identifier No. NCT01106508; Hedgehog pathway antagonists disclosed in U.S. patent application Publication No. 2010/0286114; SMOi2-17 described, e.g., U.S. patent application Publication No. 2010/0093625; SANT-1 and SANT-2 described, e.g., in Rominger C. M. et al., *J. Pharmacol. Exp. Ther.* 2009; 329(3):995-1005; 1-piperazinyl-4-arylphthalazines or analogues thereof, described in Lucas B. S. et al., *Bioorg. Med. Chem. Lett.* 2010; 20(12):3618-22; GANT61 (2,2'-{{dihydro-2-(4-pyridinyl)-1,3(2H,4H)-pyrimidinediyl]bis-(methylene)}bis{N,N-dimethylbenzenamine}); cyclopamine; sonidegib (N-[6-[(2S,6R)-2,6-Dimethylmorpholin-4-yl]pyridin-3-yl]-2-methyl-3-[4-(trifluoromethoxy)phenyl] benzamide); itraconazole ((2R,4S)-rel-1-(Butan-2-yl)-4-{4-[4-(4-{[(2R,4S)-2-(2,4-dichlorophenyl)-2-(1H-1,2,4-triazol-1-ylmethyl)-1,3-dioxolan-4-yl]methoxy}phenyl) piperazin-1-yl]phenyl}-4,5-dihydro-1H-1,2,4-triazol-5-one)); saridegib (N-((2S,3R,3aS,3'R,4a'R,6S,6a'R,6b'S,7aR, 12a'S,12b'S)-3,6,i r,12b'-tetramethyl-2',3a,3',4,4',4a',5,5',6, 6',6a',6b',7,7a,7',8',10',12',12a',12b'-icosahydro-rH,3H-spko [furo[3,2-b]pyridine-2,9'-naphtho[2,1-a]azulen]-3'-yl) methanesulfonamide); BMS 833923 (N-(2-methyl-5-((methylamino)methyl)phenyl)-4-((4-phenylquinazolin-2-yl)amino)benzamide); PF-04449913 (1-((2R,4R)-2-(1H-benzo[d]imidazol-2-yl)-1-methylpiperidin-4-yl)-3-(4-cyanophenyl)urea); and TAK-441 (6-Ethyl-N-[1-(hydroxyacetyl)piperidin-4-yl]-1-methyl-4-oxo-5-(2-oxo-2-phenylethyl)-3-(2,2,2-trifluoroethoxy)-4,5-dihydro-1H-pyrrolo[3,2-c]pyridine-2-carboxamide). In some cases, the Shh signaling pathway inhibitor is a Smo inhibitor, such as, without limitation, GDC-0449, PF-04449913, BMS-833923, LDE225, cyclopamine, sonidegib, jervine, XL-139, SANT 74-75 and SANT 1-4. In some cases, the Shh signaling pathway inhibitor is a Shh antagonist, such as, without limitation, Robotnikinin.

The Shh signaling pathway inhibitor may be an inhibitor of GLI zinc finger transcription factors. The GLI inhibitor may be an inhibitor of one or more of GLI1, GLI2 and GLI3. Suitable GLI inhibitors include, without limitation, GANT 58 and GANT 61. Other suitable GLI inhibitors are described in, e.g., US20070149592 and US20150361048, each of which are incorporated herein by reference. In some embodiments, a GLI inhibitor suitable for use in an antibody conjugate, a composition, or methods of the present disclosure is a compound, for example a compound described in U.S. Provisional Application No. 62/356,261 titled "Compounds and Compositions for the Treatment of Cancer", filed Jun. 29, 2016, and PCT Application titled "Compounds and Compositions for the Treatment of Cancer", filed herewith, the disclosures of which are incorporated herein by reference.

Methods

Methods of Treating an Individual

Also provided herein is a method of treating an individual for a cancer using a C-terminal Shh antibody, as described above, or an antibody conjugate, as described above. In general terms, the method may include administering a therapeutically effective amount of the C-terminal Shh antibody, or an antigen-binding fragment thereof, or a therapeutically effective amount of the antibody conjugate to an individual. The antibody or the antibody conjugate may be formulated in a pharmaceutical composition appropriate for the route and/or dose of administration, as described above.

The individual may be any individual having, or suspected of having, a cancer, such as a cancer associated with dysregulated or elevated Shh signaling, or a cancer associated with cancer stem cells. In some cases, the individual has or is suspected of having a cancer associated with Shh+ cancer stem cells. In some embodiments, the individual has or is suspected of having, without limitation, pancreatic, colon, gastric, lung, breast, prostate or blood cancer. In some embodiments, the individual has or is suspected of having lung cancer, such as non-small cell lung cancer (NSCLC). The individual may be exhibiting one or more diagnostic symptoms of the cancer, may have been diagnosed with the cancer, or may be at a high risk of developing the cancer. In some cases, the individual may have received treatment for the cancer, such as chemotherapy.

The C-terminal Shh antibody or the antibody conjugate may be administered at any suitable dosage and under any suitable dosing schedule for treating the cancer. Without limitation, depending on the type and severity of the disease, a typical daily dosage might range from about 1 µg/kg to 100 mg/kg of body weight or more. For repeated administrations over several days or longer, depending on the condition, the treatment may be sustained until a desired suppression of disease symptoms occurs. Without limitation, a dosage of the antibodies or antibody conjugates of the present disclosure may be in the range from about 1 µg/kg to about 150 mg/kg of body weight, e.g., from about 10 µg/kg to about 100 mg/kg of body weight, including from about 0.05 mg/kg to about 50 mg/kg of body weight. Thus, one or more doses of about 0.5 mg/kg, 2.0 mg/kg, 4.0 mg/kg, 10 mg/kg or 50 mg/kg (or any combination thereof) may be administered to the individual. Such doses may be administered intermittently, e.g., every week or every three weeks.

In some embodiments, the antibodies or antibody conjugates of the present disclosure is administered to the individual at a dosage that or in a dosage regimen that provides for a target tissue and/or blood concentration in the range of from about 0.001 µg/ml to about 1,000 µg/ml, e.g., about 0.01 µg/ml to about 500 µg/ml, about 0.05 µg/ml to about 250 µg/ml, about 0.05 µg/ml to about 100 µg/ml, about 0.01 µg/ml to about 50 µg/ml, about 0.01 µg/ml to about 10 µg/ml, including about 0.05 µg/ml to about 5 µg/ml.

In some cases, the present method includes co-administering the antibody with a therapeutically effective amount of another therapeutic agent, e.g., a chemotherapeutic agent. Co-administering may include any suitable combination of administration regimens for the antibody and the therapeutic agent. In some cases, the C-terminal Shh antibody and the chemotherapeutic agent are administered simultaneously, e.g., administered in the same composition, or administered in separate compositions taken at the same time. In some cases, the C-terminal Shh antibody and the chemotherapeutic agent are administered at different times over the course of the treatment, but may not be administered simultaneously, e.g., taken at different times during an administration regimen.

The therapeutic agent may be any suitable therapeutic agent, and in some cases, may be a chemotherapeutic agent or a Shh signaling pathway inhibitor, as described above. In some embodiments, the chemotherapeutic agent is a platinum-containing chemotherapeutic drug, such as cisplatin. In some cases, the Shh signaling pathway inhibitor is a GLI inhibitor, or a Smo inhibitor (such as, without limitation, GDC-0449, etc.).

Where the therapeutic agent is a Shh signaling pathway inhibitor, the C-terminal Shh antibody may have a synergistic effect of enhancing the cytotoxic/growth-inhibiting effect of the inhibitor, as described above. Thus, the therapeutic effect achieved by the present method of co-administering C-terminal Shh antibody with the Shh signaling pathway inhibitor may be greater than the apparent sum of the therapeutic effects achieved by a method of administering each of the C-terminal Shh antibody and the Shh signaling pathway inhibitor alone at the same respective amounts.

In some embodiments, the present method includes co-administering a C-terminal Shh antibody with a therapeutically effective amount of a Shh signaling pathway inhibitor, such as a GLI inhibitor, where the therapeutically effective amount of the Shh signaling pathway inhibitor is at least about 10%, e.g., at least about 15%, at least about 20%, at least about 25%, at least about 30%, at least about 40%, including at least about 50% less than the amount of the Shh signaling pathway inhibitor administered to an individual in the absence of the C-terminal Shh antibody in order to achieve a similar therapeutic effect (i.e., a therapeutic effect of within 30% or less, e.g., within 20% or less, within 10% or less, including within 5% or less). The therapeutic effect may be measured by, e.g., measuring tumor volume.

Administering the antibody, antibody conjugate, therapeutic agent and/or any therapeutic composition, as described herein, may be achieved by any suitable method. The routes of administration may be selected according to any of a variety of factors, such as properties of the therapeutic agent(s) to be delivered, the type of condition to be treated (e.g., type of autoimmune disease or cancer), and the like. In some cases, the antibody, antibody conjugate, therapeutic agent and/or any therapeutic composition can be administered by direct injection into a target tissue (e.g., into a tumor) or into the blood stream, and may be delivered by intradermal, subcutaneous, intravenous, intramuscular, intraosseous, or intraperitoneal injection. The antibody, antibody conjugate, therapeutic agent and/or any therapeutic compositions of the present disclosure can be administered by intracerebral, intrathecal, or epidural delivery to tissues of the central nervous system.

Methods of Analyzing a Tissue Sample

Also provided herein is a method of analyzing a tissue sample, e.g., for diagnosing an individual for a cancer, using the cell-surface expression of full-length Shh polypeptide as a marker. As Shh+ cells in a tumor may designate them as cancer stem cells, determining the presence or the abundance of Shh+ cells in a tumor tissue sample may facilitate diagnosing the cancer. Diagnosing may include classifying the type of cancer, providing a prognosis, determining a suitable treatment option for the cancer, monitoring a response to a treatment for a cancer, etc. In general terms, the present method may include contacting a tissue sample with a binding agent (e.g., an antibody) that specifically binds to a Shh polypeptide under conditions suitable for the binding agent to bind to full-length Shh polypeptide expressed on the surface of cells of the tissue sample; and measuring the amount of the binding agent bound to the cells. The measured amount may then indicate the level of full-length Shh polypeptide expressed on the cell surface. In some cases, a diagnosis is based on the proportion of cells that are classified as Shh+ (e.g., having a measured amount of the binding agent bound to the cell surface that is above a reference amount) in a tumor sample.

The binding agent may be an antibody that binds to full-length Shh polypeptide. In some cases, the antibody is a C-terminal Shh antibody, as described above. In some embodiments, the antibody binds the same antigen epitope as the antigen epitope of the C-terminal Shh antibody, and may compete with the C-terminal Shh antibody for binding to the epitope. In some embodiments, the antibody specifically binds to a C-terminal Shh polypeptide. In some embodiments, the antibody does not bind to an N-terminal Shh polypeptide.

The binding agent is generally a detectable binding agent, where the detectable feature may be any suitable feature for the detection method used. In some cases, an antibody binding agent can be detectable by binding a secondary antibody specific to the antibody binding agent, where the secondary antibody is conjugated to a detectable moiety, such as a fluorescent moiety or a suitable enzyme that can generate a detectable signal upon catalyzing a suitable substrate. In some embodiments, the antibody binding agent is conjugated to a detectable moiety, such as a fluorescent moiety or a suitable enzyme.

The contacting may be achieved by any suitable means, and may depend on the binding agent used, and the detection method used to measure binding. In general, the cells of the tissue are not permeabilized (e.g., not treated with a permeabilizing agent, such as a detergent or a surfactant) before applying the binding agent to the cells, in order to bind preferentially to full-length Shh polypeptide on the cell surface. In some cases, the cells may be permeabilized only to the extent that the binding agent will not enter the permeabilized cells, to allow preferential binding of the binding agent to full-length Shh polypeptide on the cell surface.

In some cases, the method includes using immunohistochemistry, where the tissue sample may be a tissue slice containing cells, or dissociated cells may be deposited on a solid support, such as a glass slide. Then, contacting may involve depositing a solution containing the binding agent in a suitable buffer to the cells on the solid support, and the amount of binding agent bound to the cells may be measured using a microscope, e.g., a fluorescence microscope. In some cases, the method includes using flow cytometry (including fluorescence-activated cell sorting (FACS)), in which case, the cells are dissociated cells from the tissue sample. Then, the contacting may include combining a liquid containing dissociated cells with a solution containing the binding agent, and the amount of binding agent bound to the cells may be measured using a flow cytometer.

The tissue sample may be any suitable sample. In some cases, the tissue sample is a biopsy. In some cases, the tissue sample, e.g., biopsy, is obtained from an individual having or is suspected of having a cancer, where the tissue sample is a tumor sample. In some embodiments, the tissue sample is a primary tumor, or a metastasis of a tumor. In some cases, the tumor is a lung tumor, e.g., from an individual with NSCLC. In some embodiments, the tissue sample includes cancerous cells from a leukemia or multiple myeloma.

The tissue sample may be prepared in any convenient manner such that the cells of the tissue sample may be accessible to the binding agent. In some embodiments, the tissue sample is sliced into thin sections (e.g., for immunohistochemistry). In some embodiments, the tissue sample is treated with an enzyme, such as collagenase, to dissociate the cells. In some cases, cells of the tissue sample are mechanically dissociated, e.g., by passing the tissue sample through an appropriate gauge syringe.

In some cases, the tissue sample, or cells thereof, is fixed using a suitable fixation method. In some cases, the tissue sample, or cells thereof, is a formalin-fixed paraffin embedded (PPFE) sample. In some cases, the cells are fixed with methanol. The fixed cells may be suitable for immunohistochemical analysis.

A cell whose measured amount of binding agent bound to the cell surface is above a reference level or reference range may be described as a Shh+ cell. The reference level or reference range may be any suitable level or range. In some cases, the reference level or range is a background level or range of signal detected in a control assay using, e.g., a control sample in which the target of binding of the detectable binding agent is substantially not present in the control sample, or in which the binding agent is omitted. In some embodiments, the reference level is based on a measured amount of the binding agent bound to the cells of a negative control sample, e.g., a healthy sample, and a measured amount of the binding agent bound to the cells of a positive control sample, e.g., a tumor tissue sample known to have Shh+ cells.

Cells that are found to have full-length Shh polypeptide expressed on the cell surface (i.e., Shh+ cells) may further be characterized by expression (RNA expression or protein expression) of one or more marker genes. Shh+ cells may have, on average, higher expression (e.g., at least about 2 fold higher, at least about 3 fold higher, at least about 4 fold higher, at least about 5 fold higher, at least about 6 fold higher, at least about 8 fold higher, including at least about 10 fold higher expression) of SHH, POU5F1P3, NANOG, LIN28A, ALDH1A2, PROM1, CCND2, BCL2, Wnt pathway genes, and chemokine-related genes, compared to Shh− cells. Shh+ cells may have, on average, reduced expression (e.g., about 2 fold lower, at least about 3 fold lower, at least about 4 fold lower, at least about 5 fold lower, at least about 6 fold lower, at least about 8 fold lower, including at least about 10 fold lower expression) of KRT7, PRDM1, compared to Shh− cells.

In some embodiments, the presence and/or the abundance of Shh+ cells in a tumor sample may indicate a higher risk of an adverse clinical outcome for the individual. The adverse clinical outcome may include clinical progression (e.g., as measured by time to progression (TTP), or relapse after surgery (e.g., surgical removal of the tumor from the individual). The abundance or proportion may be the relative number of Shh+ cells to the total number of Shh+ and Shh− cells in the tumor sample, e.g, using flow cytometry. In some embodiments, when flow cytometry is used to determine the proportion of Shh+ cells in a tissue sample, the analysis may exclude immune cells by labeling cells for an immune cell marker (e.g., CD45) and excluding cells that are labeled for the immune cell marker when determining the proportion of Shh+ cells in a tissue sample. The cells may be labeled for an immune cell marker using any suitable method. For example, an antibody specific to the immune cell marker (e.g., an anti-CD45 antibody) may be used to label the cells of the tissue sample.

In some embodiments, the individual may be diagnosed to have a higher risk of clinical progression when the proportion of Shh+ cells in the tumor sample from the individual is equal to or higher than a reference proportion, compared to when the proportion is lower than the reference proportion. The reference proportion may be any suitable proportion for stratifying a patient population based on the risk of clinical progression and the proportion of Shh+ cells in a tumor from each individual in the patient population. In some cases, the reference proportion is determined based on analyzing the proportion of Shh+ cells in healthy tissue samples and tumor tissue samples. In some cases, the reference proportion is determined based on analyzing the proportion of Shh+ cells in tumor tissue samples from a patient cohort that showed clinical progression of, e.g., from about 6 months to about 24 months (e.g., from about 9 months to about 18 months, from about 9 months to about 15 months, from about 10 months to about 13 months, or about 12 months) and from a control cohort diagnosed with the same type of cancer as the patient cohort, but that did not show clinical progression after, e.g., from about 6 months to about 24 months (e.g., from about 9 months to about 18 months, from about 9 months to about 15 months, from about 10 months to about 13 months, or about 12 months). In some embodiments, the reference proportion is from about 0.01% to about 0.5%, e.g., from about 0.05% to about 0.3%, from about 0.08% to about 0.2%, including about 0.1%.

In some embodiments, the individual may be diagnosed to have a higher risk of relapse after surgery when the proportion of Shh+ cells in the tumor sample from the individual is equal to or higher than a reference proportion, compared to when the proportion is lower than the reference proportion. The reference proportion may be any suitable proportion for stratifying a patient population based on the risk of relapse after surgery and the proportion of Shh+ cells in a tumor from each individual in the patient population. In some cases, the reference proportion is determined based on analyzing the proportion of Shh+ cells in healthy tissue samples and tumor tissue samples. In some cases, the reference proportion is determined based on analyzing the proportion of Shh+ cells in tumor tissue samples from a patient cohort that showed relapse after surgery within, e.g., from about 6 months to about 24 months (e.g., from about 9 months to about 18 months, from about 9 months to about 15 months, from about 10 months to about 13 months, or about 12 months) and from a control cohort diagnosed with the same type of cancer as the patient cohort, but that did not show relapse after surgery within, e.g., from about 6 months to about 24 months (e.g., from about 9 months to about 18 months, from about 9 months to about 15 months, from about 10 months to about 13 months, or about 12 months). In some embodiments, the reference proportion is from about 0.05% to about 0.5%, e.g., from about 0.06% to about 0.4%, from about 0.07% to about 0.3%, from about 0.08% to about 0.2%, including about 0.1%.

The presence and/or abundance of Shh+ cells in a tumor sample from an individual may be used to determine treatment options for the individual. Thus, in some cases, detection of the presence of Shh+ at a proportion above a reference proportion indicates the presence of cancer stem cells in the tumor sample, and a recommended treatment for the cancer may include administration of a therapeutic agent that targets the cancer stem cells. The recommended therapeutic agent may be a Shh signaling pathway inhibitor, such as a Smo inhibitor or a GLI inhibitor, as described above. In some cases, the recommended treatment may include co-administration of the Shh signaling pathway inhibitor with a chemotherapeutic agent, such as cisplatin. In some cases, the reference proportion is determined based on analyzing the proportion of Shh+ cells in healthy tissue samples and tumor tissue samples. In some cases, a treatment option that only includes a chemotherapeutic agent is avoided if the tumor includes Shh+ cells at a sufficient proportion.

Methods of Producing a C-Terminal Shh Antibody

Also provided herein is a method of producing a C-terminal Shh antibody. In general terms, the method may include inoculating a host organism having an adaptive immune system with a composition (e.g., an antigenic composition) that includes one or more peptides that includes an amino acid sequence of a C-terminal Shh polypeptide, for example where the amino acid sequence is from about 15 to 18 amino acids long, thereby inducing an adaptive immune response against the one or more peptides. The antigenic composition may include a peptide that includes the amino acid sequence GAKKVFYVIETREPRERL (SEQ ID NO:18) and/or a peptide that includes the amino acid sequence DSEALHPLGMAVKSS (SEQ ID NO:20).

The antigenic composition may be inoculated at any suitable site of the host organism to elicit the adaptive immune response. In some cases, the antigenic composition is inoculated into a lymph node of the host organism to elicit the adaptive immune response.

Upon inducing the adaptive immune response in the host organism, an antibody that specifically binds to full-length Shh polypeptide, as described herein, may be identified by screening antibody-producing B-cells from the host organism, in any suitable manner (e.g., making hybridoma clones form the B-cells, and screening antibodies produced by different the hybridoma clones). The screening may include any suitable means to determine binding (or lack thereof) of an antibody to an antigen of interest (i.e., full-length Shh polypeptide, and/or C-terminal Shh polypeptide and/or N-terminal Shh polypeptide). Suitable screening methods include, without limitation, flow cytometry, Western blotting and enzyme-linked immunosorbent assay (ELISA).

The host organism may be any suitable animal that can be inoculated to produce an antibody by the present methods. Suitable host organisms include, without limitation, rodents (such as mouse, rat, guinea pig, etc.), and lagomorphs (such as rabbit, etc.).

Methods of Immunizing an Individual

Also provide herein is a method of immunizing an individual, i.e., a vaccination method for a cancer. In general terms the method may include administering to an individual an antigenic peptide that includes a fragment of a C-terminal Shh polypeptide to elicit an adaptive immune response against a cell (e.g., against a cell in the individual's body) that expresses full-length Shh polypeptide on the cell surface. The present cancer vaccine may include any suitable antigenic peptide that includes a fragment of C-terminal Shh polypeptide, for use in an immunogenic composition, as described above. Thus, the present methods may include administering an immunogenic composition, as described above, in a manner sufficient to elicit the adaptive immune response against a cell that expresses full-length Shh polypeptide on the cell surface.

Administering the present antigenic peptide may be done in a manner sufficient to elicit the adaptive immune response against a cell that expresses full-length Shh polypeptide on the cell surface, where the adaptive immune response may include production of antibodies that specifically bind to cells that expresses full-length Shh polypeptide on the cell surface, in the individual's body. The cell may be a tumor cell, and may include a cancer stem cell. In some cases, the cell is a cell of a pancreatic, colon, gastric, lung, breast, prostate or blood cancer, such as, but not limited to, any of the tumor cells described herein.

The individual to whom the present antigenic peptide is administered may be any suitable individual in need of an adaptive immune response against a cell that expresses full-length Shh polypeptide on the cell surface. The individual, e.g., patient, may be diagnosed with a cancer, such as, without limitation, pancreatic, colon, gastric, lung, breast, prostate or blood cancer, or other cancers as described herein. In certain embodiments, the cancer is lung cancer, such as, without limitation, NSCLC. The individual may be diagnosed by having one or more clinical symptoms of the cancer. In some embodiments, the individual is predisposed to developing the cancer, e.g., by having known genetic and/or physiological markers associated with having a higher risk for developing cancer compared to a control cohort of individuals who do not have the genetic and/or physiological markers, and/or by having behavioral risk factors for the cancer, etc.

The administering may employ any suitable route, including but not limited to, administering orally, nasally, nasopharyngeally, parenterally, enterically, gastrically, topically, transdermally, subcutaneously, intramuscularly, in tablet, solid, powdered, liquid, aerosol form, locally or systemically, with or without added excipients. Where the route of administration is oral, the present antigenic peptide should be protected from digestion. Any suitable means of protecting the antigenic peptide from digestion may be used. In some cases, this is accomplished either by complexing the antigenic peptide with a composition to render it resistant to acidic and enzymatic hydrolysis, or by packaging in an appropriately resistant carrier such as a liposome.

In order to enhance serum half-life, an antigenic peptide of the present disclosure that is injected may also be encapsulated, introduced into the lumen of liposomes, prepared as a colloid. Any other conventional techniques may be employed which provide an extended serum half-life of the antigenic peptides. The antigenic peptide may also be provided in controlled release or slow-release forms for release and administration of the antigen preparations as a mixture or in serial fashion.

Single or multiple doses of the immunogenic composition may be administered depending on the dosage and frequency required and tolerated by the individual, e.g., patient, and route of administration. In general, immunization is provided so as to elicit an immune response in the individual, as described above.

In particular embodiments, the immunogenic compositions described herein are administered serially. First, an immunogenically effective dose of a first immunogenic composition that includes an antigenic peptide with a fragment of a C-terminal Shh polypeptide (which may be conjugated to a carrier, and may be with or without excipients) is administered to an individual. The first dose is generally administered in an amount effective to elicit an immune response (e.g., activation of B and/or T cells). Amounts for the initial immunization generally range from about 0.001 mg to about 1.0 mg per 70 kilogram patient, more commonly from about 0.001 mg to about 0.2 mg per 70 kilogram patient, usually about 0.005 mg to about 0.015 mg per 70 kilogram patient. Dosages from 0.001 up to about 10 mg per patient per day may be used, particularly when the antigen is administered to a secluded site and not into the blood stream, such as into a body cavity or into a lumen of an organ. Substantially higher dosages (e.g. 10 to 100 mg or more) are possible in oral, nasal, or topical administration.

After administration of the first immunogenic composition of the present antigenic peptide, a therapeutically effective dose of a second immunogenic composition (e.g. antigenic peptide that includes a fragment of a C-terminal Shh polypeptide, optionally conjugated and with or without excipients) is administered to the subject after the subject has been immunologically primed by exposure to the first dose. The booster may be administered days, weeks or months after the initial immunization, depending upon the patient's response and condition.

The presence of a desired immune response may be determined by any suitable methods (e.g. by obtaining serum from the individual before and after the initial immunization, and demonstrating a change in the individual's immune status, for example an immunoprecipitation assay, or an ELISA, or a Western blot, or flow cytometric assay, or the like) and/or demonstrating that the magnitude of the immune response to the second injection is higher than that of a control individual immunized for the first time with the composition used for the second injection (e.g. immunological priming). Immunologic priming and/or the existence of an immune response to the first immunogenic composition may also be assumed by waiting for a period of time after the first immunization that, based on previous experience, is a sufficient time for an immune response and/or priming to have taken place—e.g. 2, 4, 6, 10 or 14 weeks. Boosting dosages of the second immunogenic composition are typically from about 0.001 mg to about 1.0 mg of antigenic peptide, depending on the nature of the immunogen and route of immunization.

In certain embodiments, a therapeutically effective dose of a third immunogenic composition prepared from the present antigenic peptide is administered to the subject after the individual has been primed and/or mounted an immune response to the second immunogenic composition. The methods disclosed herein also contemplate administration of a fourth, fifth, sixth or greater booster immunization, using either a fourth, fifth or sixth immunogenic composition.

Utility

The antibodies, antibody-conjugates, compositions, kits and methods of the present disclosure find use in many applications where targeting Shh+ cells with a C-terminal Shh antibody is desired. In certain embodiments, the antibodies, antibody-conjugates, compositions, kits and methods of the present disclosure find use in treating a cancer, as described above. The cancer may be any cancer that is associated with dysregulated Shh signaling and can be treated by a C-terminal Shh antibody as described herein.

A cancer associated with dysregulated Shh signaling to be treated may include tumors and cancer cells that originate from Shh+ cells and/or rely on Shh+ cells for growth or maintenance of the cancerous tissue or in which Shh is overexpressed. In some cases, a cancer associated with dysregulated Shh signaling may include metastatic tumors that include Shh+ cells. In some cases, a cancer associated with dysregulated Shh signaling may include tumors resistant to chemotherapy, such as cisplatin chemotherapy. The Shh+ cells may be a marker for cancer stem cells.

Thus, a cancer treated by using the present antibodies, antibody-conjugates, compositions, kits and methods may be associated with cancer stem cells. In some embodiments, a cancer treated by the present antibodies, antibody-conjugates, compositions, kits and methods may be associated with Shh+ cancer stem cells. Suitable for cancer treatment, according to the present antibodies, antibody-conjugates, compositions, kits and methods include, without limitation, pancreatic, colon, gastric, lung, breast, prostate or blood cancer. In some embodiments, the present antibodies, antibody-conjugates, compositions, kits and methods may be used to treat non-small cell lung cancer (NSCLC). In some embodiments, the present antibodies, antibody-conjugates, compositions, kits and methods may be used to treat a leukemia or multiple myeloma.

Kits

Also provided herein are kits that include a C-terminal Shh antibody, or an antigen-binding fragment thereof, as described above, and/or an antibody conjugate, as described above. The kit may further include a suitable packaging configured to hold the antibody, or an antigen-binding fragment thereof, and/or the antibody conjugate. In some embodiments, the antibody, or an antigen-binding fragment thereof, and/or the antibody conjugate is in a buffer, which in some cases may be a pharmaceutically acceptable excipient.

Also provided is a kit that includes an antigenic peptide that includes at least a portion of a C-terminal Shh polypeptide, as described above, and an adjuvant.

Components of a subject kit can be in separate containers; or any combination or all of the components can be combined in a single container.

In some cases, the present kit includes instructions for using the antibodies and/or antibody conjugates of the present disclosure. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, digital versatile disc (DVD), flash drive, Blue-ray Disc™ etc. In yet other embodiments, the actual instructions are not present in the kit, but methods for obtaining the instructions from a remote source, e.g. via the internet, are provided. An example of this embodiment is a kit that includes a web address where the instructions can be viewed and/or from which the instructions can be downloaded. As with the instructions, the methods for obtaining the instructions are recorded on a suitable substrate.

EXAMPLES

The following examples are put forth so as to provide those of ordinary skill in the art with a complete disclosure and description of how to make and use the disclosed subject matter, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Membranous Full-Length Sonic Hedgehog Protein is a New Functional Cancer Stem Cell Marker in Lung Cancer Materials and Methods NSCLC Cell Lines and Culture Conditions All 12 NSCLC cell lines (A549, H322, H441, H460, H522, H838, H1650, H1975, H2228, HCC2935, H1703, H2170) were purchased from American Type Culture Collection (ATCC). Cells were cultured in RPMI 1640, supplemented with 10% fetal bovine serum and 2% antibiotics (Penicillin-Streptomycin). Cells were collected after trypsination and resuspended in PBS for further analysis. For serum-free medium culture conditions, sorted cells were seeded in non-tissue culture 96-wells plate (500 cells per well) and cultured in DMEM-F12 medium (Corning Cellgro), supplemented with basic Fibroblast Growth Factor (bFGF, Invitrogen, 10 ng/ml), Epidermal Growth factor (EGF, Invitrogen, 20 ng/ml) and insulin (Sigma, 5 µg/ml). Fresh medium with growth factors and insulin were added every 48 h. Spheroids formation (apparition of floating cell aggregates) was monitored daily.

Transfection Assays

For transfection assays, A549 and H838 cell lines were used. Transient transfection of Shh gene was performed with pCMV-Shh plasmid (Origene). For stable transfected cell lines, N-term peptide hemagglutinin (HA)-tagged Shh (1-197aa), C-term peptide FLAG-tagged Shh (198-462aa), double-tagged wild type Shh (N-HA and C-FLAG) and double-tagged cleavage mutant Shh C198A (N-HA and C-FLAG) were used with pCMV-Pig vector. Transfection assays were performed with Lipofectamine 2000 (Life Technologies), according to manufacturer instructions.

Human Fresh Tumor Samples

Fresh tumor samples were collected directly in the operative room (Surgery Department, University of California—San Francisco) in case of signed pre-operative consent from the patient. Samples were then processed the same day. Cell dissociation was performed with collagenase type IV (2 mg/ml, 30 min, Sigma), then completed with mechanical dissociation (syringe). Cells were resuspended in PBS for further analysis. Clinical follow-up data were collected prospectively through database (last time-point: Jul. 15, 2015).

Shh Antibody Production

To produce a Shh-C-terminal antibody, the corresponding peptide was first inoculated to mice for production of clones. Clones and sub-clones were selected by testing on A549 cell line and on Shh-transfected 293T cell line, in Western Blot (predicted band at 25 kDa (C-terminal peptide)±45 kDa (full-length Shh protein)) and flow cytometry. After identifying clones 2G4 and 2D9, large scale purification of the antibodies was performed and the purified antibodies were used for in vitro and in vivo experiments.

Flow Cytometry and FACS

The mouse Shh-C-terminal antibody (cf supra) was used for flow cytometry and

FACS (1:40). The secondary antibody was a donkey anti-mouse FITC-linked antibody (ab97029, 1:100, Abcam). For cell analysis after treatment assays (chemotherapy or GDC0449), a dead cell marker (SytoxRed, Invitrogen) was also used. For human fresh samples, an anti-CD45 APC-linked antibody (ab28106, 1:100, Abcam), and a dead cells marker (SytoxRed, Invitrogen) were added. For staining of stable transfected cell lines, mouse anti-HA antibody (Abcam, 1:100) and rabbit anti-FLAG antibody (Cell Signaling; 1:400) were used. Corresponding secondary antibodies were donkey anti-mouse AlexaFluor647 (Invitrogen, 1:1000) and donkey anti-rabbit AlexFluor594 (Invitrogen, 1:1000) antibodies. Flow cytometry analyses were performed on AccuriC6 flow cytometer (BD Biosciences), and FACS on FACSAria II (BD Biosciences). Flow analyses were based at least on 200,000 cells, and each test was made at least in triplicate. For all experiments, a negative control with cells processed without primary antibody was used. Sorted cells (Shh+ and Shh− cells) were collected on fresh media, and seeded on culture plates or freezed at −80° C. according to further analyses. Flow cytometry analysis was performed without membrane permeabilization prior to labeling the cells, unless otherwise indicated (e.g., FIG. 1D).

Immunofluorescence

Cells were fixed in 70% ice-cold methanol for 20 min and blocked in 5% BSA for 1 hour at room temp. For staining of commercial NSCLC cell lines, the present mouse Shh-C-terminal antibody (cf supra) as primary antibody was used. Corresponding secondary antibody was the donkey anti-mouse FITC-linked antibody (ab97029, 1:100, Abcam). For staining of transfected cell lines, mouse anti-HA antibody (Abcam, 1:100) and rabbit anti-FLAG antibody (Cell Signaling; 1:400) were used. Corresponding secondary antibodies were donkey anti-mouse AlexaFluor®647 (Invitrogen, 1:1000) and donkey anti-rabbit AlexFluor®594 (Invitrogen, 1:1000) antibodies. Three representative images per well were captured using an LSM 780 confocal microscope at 6300×. Background was subtracted by comparing images only incubated with the secondary antibodies and analyzed using Fiji software. The experiment was performed three separate times and representative images are presented.

Proliferation and Migration Assays, IC50 of Cisplatin and Doxetaxel

Proliferation assay was performed by MTS assay (CellTiter 96, Promega), according to manufacturer instructions. $IC_{50}$ for cisplatin and docetaxel was calculated for each cell lines at 72 hours.

Migration assay was performed by wound healing assay. Monolayers of cells were: cultured, scratched, treated with media containing proteins and/or drugs at different concentrations: Shh protein, DMSO, and GDC0449, and recorded 0 and 24, 72 and 96 hours after treatment.

Drugs

Cisplatin was purchased from Sigma, and freshly reconstituted in PBS (2 g/l). Docetaxel was purchased from Tocris Bioscience, reconstituted in DMSO (5 g/l stock dilution at −20° C.; further dilution in fresh culture medium) for in vitro assays, or reconstituted in ethanol/polysorbate 80 (1:1; 5 g/l stock dilution at −20° C.; further dilution in PBS) for in vivo assays. GDC0449 was purchased from Selleck Chemicals, and reconstituted in DMSO (30 mM stock dilution). Shh human recombinant protein was obtained from EBioscience, and used at 1200 ng/ml.

Western Blot

Proteins were extracted with M-PER Mammalian Protein Extraction Reagent (Thermo Scientific), according to manufacturer instructions. Western Blot was then processed following standard protocol. A rabbit anti-C-terminal Shh antibody (ab53281, Abcam, 1:1000) was used. As secondary antibody, donkey anti-rabbit HRP-conjugated antibody (ab16284, Abcam, 1:1000) was used.

Quantitative PCR and ddPCR

RNA from unsorted cells was extracted with Qiagen Rneasy® Minikit (Quiagen), according to manufacturer instructions. RNA from sorted cells was extracted with Arcturus PicoPure RNA Isolation Kit (Life technologies). cDNA was then synthesized with iScript cDNA Synthesis Kit (Bio-Rad), according to manufacturer instructions. Commercial primers for Shh gene were obtained from Origen. Quantitative PCR was performed on Applied Biosystems' 7900HT Fast Real-Time PCR System, with triplicate for each gene analysis. Gene expression analysis was calculated with deltaCT method, with normalization with endogenous control (18s gene) (normalized gene expression level=$2^{-deltaCT(test\ gene)-deltaCT(18s)}$). For ddPCR, droplets creation, PCR and results analysis were performed according to manufacturer instructions (BioRad, QX100 ddPCR System, Quantasoft software). Results of ddPCR were expressed as FAM concentrations (copies/µl).

Microarray

Total RNA (about 25 ng) was amplified into cRNA and made into cDNA using the Ambion WT Expression Kit (Life Technologies) or the Ovation Pico WTA System V2 kit (NuGen). The cDNA (5.5 µg for the Ambion WT Expression kit, 2.5 ug for the Ovation Pico WTA System V2 kit) was then fragmented using the Affymetrix GeneChip WT Terminal Labeling kit (Affymetrix, Santa Clara, Calif., USA) and confirmed by running 1 µl of each sample on the Agilent Bioanalyzer using the RNA 6000 kit (Agilent Technologies, Santa Clara, Calif., USA). The fragmented cDNA was labeled using the Affymetrix GeneChip WT Terminal Labeling kit and added into the hybridization cocktail that was>prepared according to the protocol included in the Affymetrix GeneTitan Hybridization Wash and Stain kit (Affymetrix). The samples were finally loaded into the Affymetrix GeneTitan MC for hybridization, washing and scanning.

Animals

For xenograft formation, female nude mice, 5 to 10 weeks old, were injected subcutaneously (SC) with 10 million A549 cells in the dorsal area in a volume of 1000. For SC inoculation of sorted cells, 1,500 cells of A549 Shh+ or Shh− cells were injected in a volume of 1500. For intra-veinous injection of sorted cells, 1,000 cells of A549 Shh+ or Shh− cells were injected in the tail vein. For the in vivo treatment assay, after xenograft formation, animals were injected intravenously with cisplatin (10 mg/kg weekly), docetaxel (10 mg/kg twice a week) or vehicle, and intraperitoneally with GDC0449 (20 mg/kg daily) or vehicle. Each group consisted in 4-5 mice. Tumor size was determined twice a week, and tumor volumes were calculated using width (x) and length (y) ($x^2y/2$, where x<y). Tumors were collected after mice euthanasia, and cell dissociation was performed as for fresh human samples (cf supra). Flow cytometry and FACS were done as described supra. All animals were cared in accord with University of California San Francisco (UCSF) guidelines.

Statistical Analyses

Distribution of variables was analyzed by Shapiro-Wilk test. In case of normal distribution, results were expressed as mean (±standard deviation SD), and comparison between 2 populations was performed by Student test. In case of non-normal distribution, results were expressed as median (interquartile range IQR), and comparison between 2 populations was performed by non-parametric Mann-Whitney test. For qPCR results analyses, the Student's test was used. For ddPCR results, Poisson law was used, with Poisson confidence intervals. Time to progression was calculated with Kaplan-Meyer method (log-rank test). For each test, results were considered as significant if p<0.05. Statistical analyses were performed using Xlstat 2.01 software (Addinsoft).

Results

Presence of NSCLC Shh+ Cells In Vitro

Figure 1A:
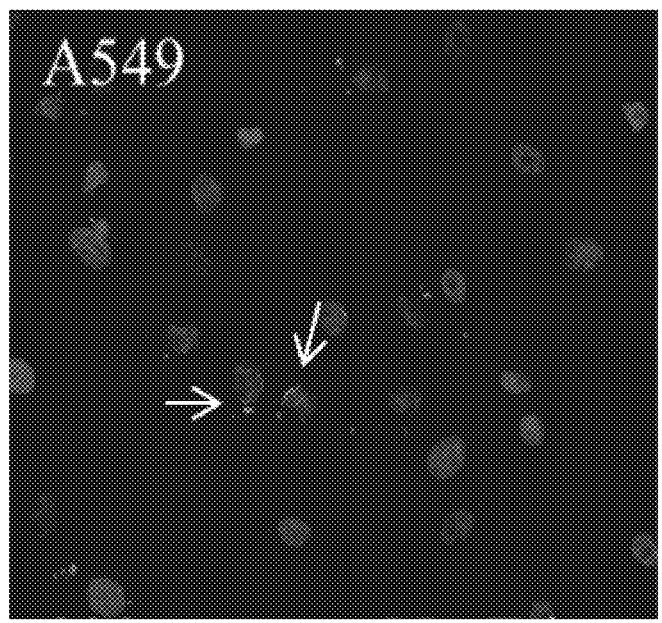
Figure 1B:
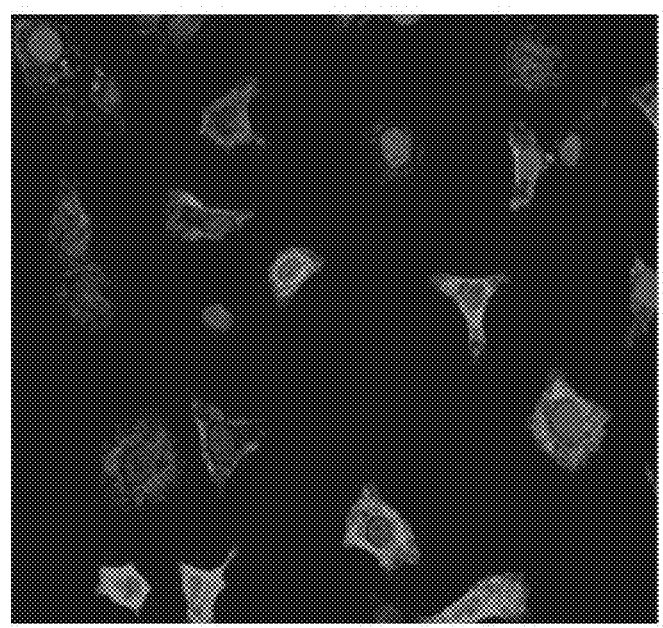

A peptide antibody against the C-terminal of Shh was developed and its specificity was tested with and without permeabilization on NSCLC cells. Surprisingly, upon immunofluorescence (IF) analysis, it was found that while only a very small number of cells stained positive (Shh+) without permeabilization, (FIG. 1A) a majority of them were positive with permeabilization (FIG. 1B). Flow cytometry analysis corroborated these findings, and it was observed that less than 0.20% (FIG. 1C) and more than 70% (FIG. 1D) of the cells were positive without and with permeabilization respectively. To better characterize these Shh+ cells by IF and flow cytometry, the cells were sorted via Fluorescence Activated Cell Sorting (FACS) without membrane permeabilization. Digital droplet PCR (ddPCR) analysis in sorted cells (Shh+ and Shh− cells) showed that Shh+ cells were Shh-producing cells. Shh+ cells expressed high levels of the Shh gene (FAM concentration=94.8 copies/µl (Poisson confidence interval: 87.1-103)), whereas Shh− cells did not express the Shh gene (FAM concentration=0.157 copies/µl (Poisson confidence interval: 0.01-0.75)) (FIG. 1E). Next, 12 NSCLC cell lines (10 adenocarcinoma cell lines: A549, H322, H441, H460, H522, H838, H1650, H1975, H2228, HCC2935; 2 squamous cell lines: H1703, H2170) were screened by flow cytometry on non-permeabilized cells. It was found that 0.06% (±0.05%) of the cells was Shh-positive via flow cytometry analysis (FIG. 1F). The highest rate was for A549 at 0.18% (±0.02%).

FIGS. 1A-1F. Shh+ cells are Shh-producing cells and represent a rare population in vitro. FIG. 1A: Immunofluorescence (IF) analysis of A549 cells without membrane permeabilization shows positive Shh and nuclear staining (DAPI). White arrows: positive membranous Shh staining in relatively few cells. FIG. 1B: IF analysis of A549 cells with membrane permeabilization (Triton® (octyl phenol ethoxylate)) shows positive Shh and nuclear staining (DAPI) in a majority of the cells probed. FIG. 1C: flow cytometry analysis of A549 cell line without membrane permeabilization probed for Shh (0.18%). FIG. 1D: flow cytometry analysis of A549 cell line with membrane permeabilization (Tween® 20 (polysorbate 20)) probed for Shh (70.12%). FIG. 1E: Shh gene expression analysis by ddPCR in A549 Shh+ and Shh− cells. FIG. 1F: Shh rate (%, mean±SD) in several NSCLC cell lines.

Secretion of Full-Length Shh Protein by Shh+ Cells

To characterize the localization of the Shh protein on the cell membrane/in the cytosol recognized by the C-terminal Shh antibody, NSCLC cell line A549 transiently transfected with the Shh gene was used. Since a C-terminal directed antibody was used, it was hypothesized that either the C-terminal Shh peptide, or the Shh full-length protein on the cell surface was identified. Western blotting indicated the presence of the full-length Shh protein, both in the cytosol and on the membrane (FIG. 2A) recognized by the C-term Shh antibody. To further characterize the localization and functional significance of the Shh protein and its cleaved products, retrovirus-mediated gene transfer was used to stably express several versions of the Shh gene in A549 and H838 cells. N-term peptide hemagglutinin (HA)-tagged Shh (1-197aa), C-term peptide FLAG-tagged Shh (198-462aa), double-tagged wild-type Shh (N-HA and C-FLAG) and double-tagged cleavage mutant Shh C198A (N-HA and C-FLAG) were used as shown in FIG. 2B. The presence of the C198A mutation is known to induce the production of a processing-defective full-length Shh protein. Next peptide expression and membrane/cytosolic localization of N-term, C-term, wild-type and C198A mutant Shh was confirmed via immunofluorescence in both A549 (FIG. 7A) and H838 cells (FIG. 2C) with antibodies directed at HA and FLAG respectively. Flow analysis revealed positive double staining in H838 cells for HA and FLAG in cells bearing wild-type and C198A constructs and single staining for N-term and C-term (FIG. 7B). Functional analyses with stably expressing N-term Shh in A549 and H838 cells resulted in a 20-30% growth advantage compared with the vector control (FIG. 2D) consistent with its role in biological development. Moreover, the wild-type and C198A expressing lines also showed significant increases in viability (10-20% and 10-15%, respectively). The C-term expressing lines only showed a 1-10 increase %. Analogous results were observed when the supernatants from cells expressing (vector, N-term, C-term, wild-type, C198A) were applied to their respective parental cell lines (FIG. 2E) confirming the paracrine effects of the Shh peptides, and notably the full-length Shh protein.

Figure 2A:
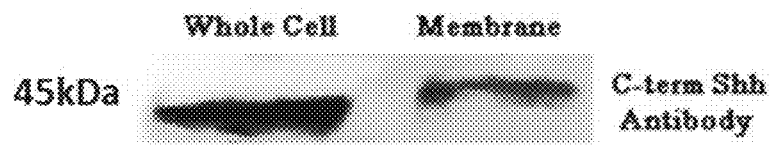
FIGS. 2A-2E are a collection of schematics, images and graphs showing that Shh+ cells produce Shh full-length protein, according to embodiments of the present disclosure.
Figure 2B:
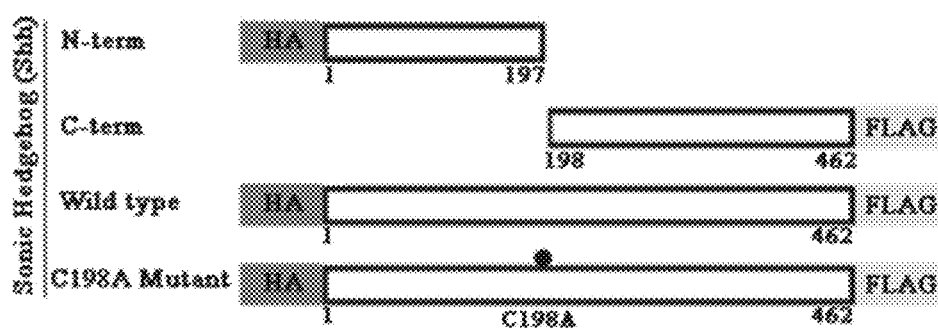
Figure 2C:
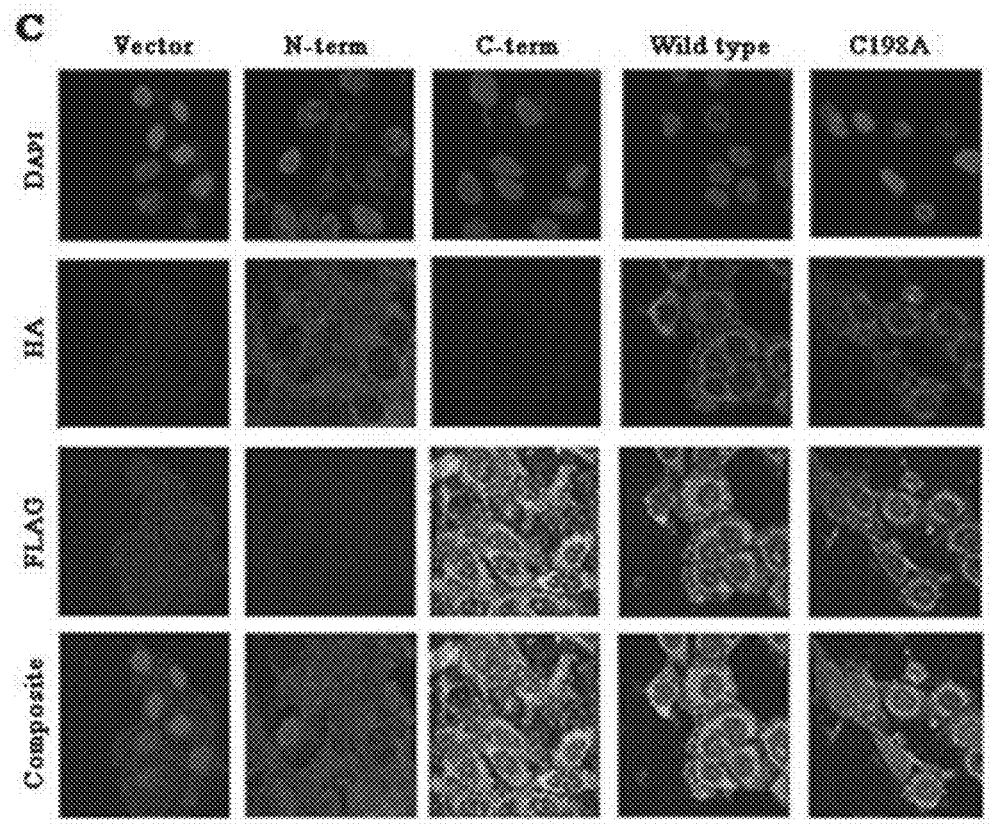
Figure 2D:
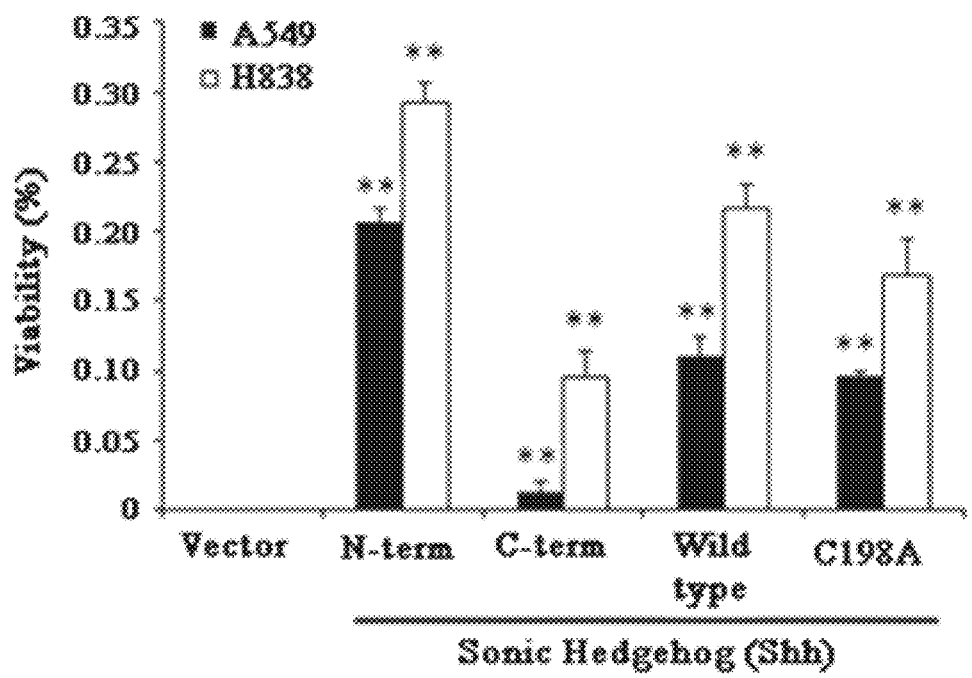
Figure 2E:
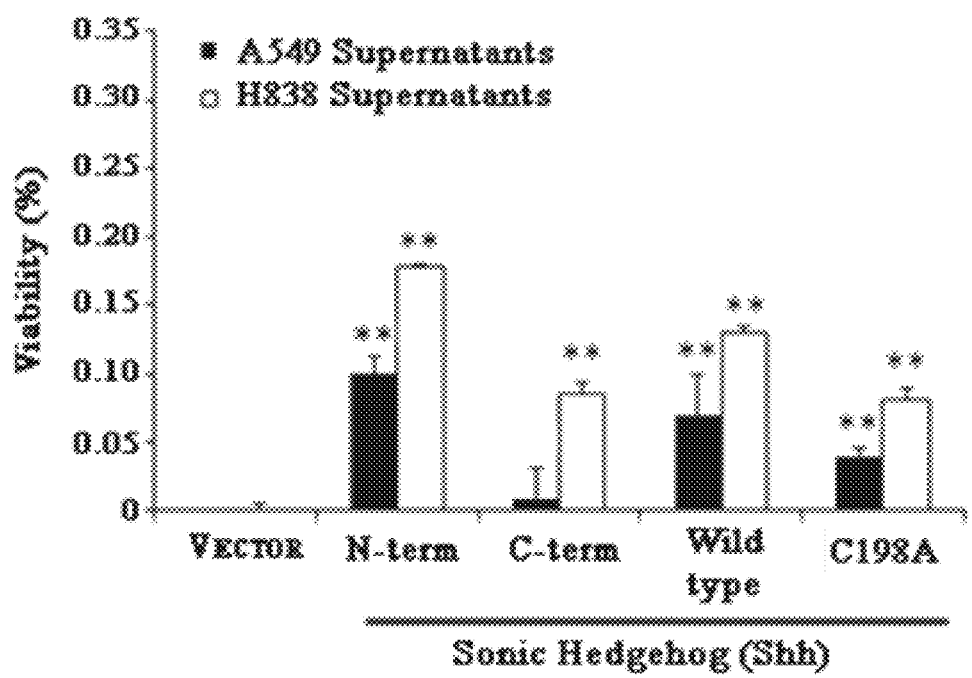

FIGS. 2A-2E. Shh+ cells produce Shh full-length protein. FIG. 2A: Immunoblot of A549 cells transiently transfected with wild-type Shh and probed for the Sonic Hedgehog (Shh) protein in whole cell and protein extracts. FIG. 2B: Schematic representation of Shh constructs showing the sizes and locations of N-term HA and C-term FLAG tags stably expressed in NSCLC cells. FIG. 2C: Immunofluorescence analysis of H838 cells showing cytosolic and membrane staining of N-term, C-term, wild-type Shh and C198A Shh constructs probed for the presence of HA and FLAG. FIG. 2D: NSCLC cell lines (A549 and H838) used in FIG. 2C analyzed for increases in viability (MTS assay) and compared with the vector control after 4 days (p<0.01). FIG. 2E: Supernatants from NSCLC cells were applied to parental cells and analyzed as in FIG. 2D (p<0.01).

Figure 7A:
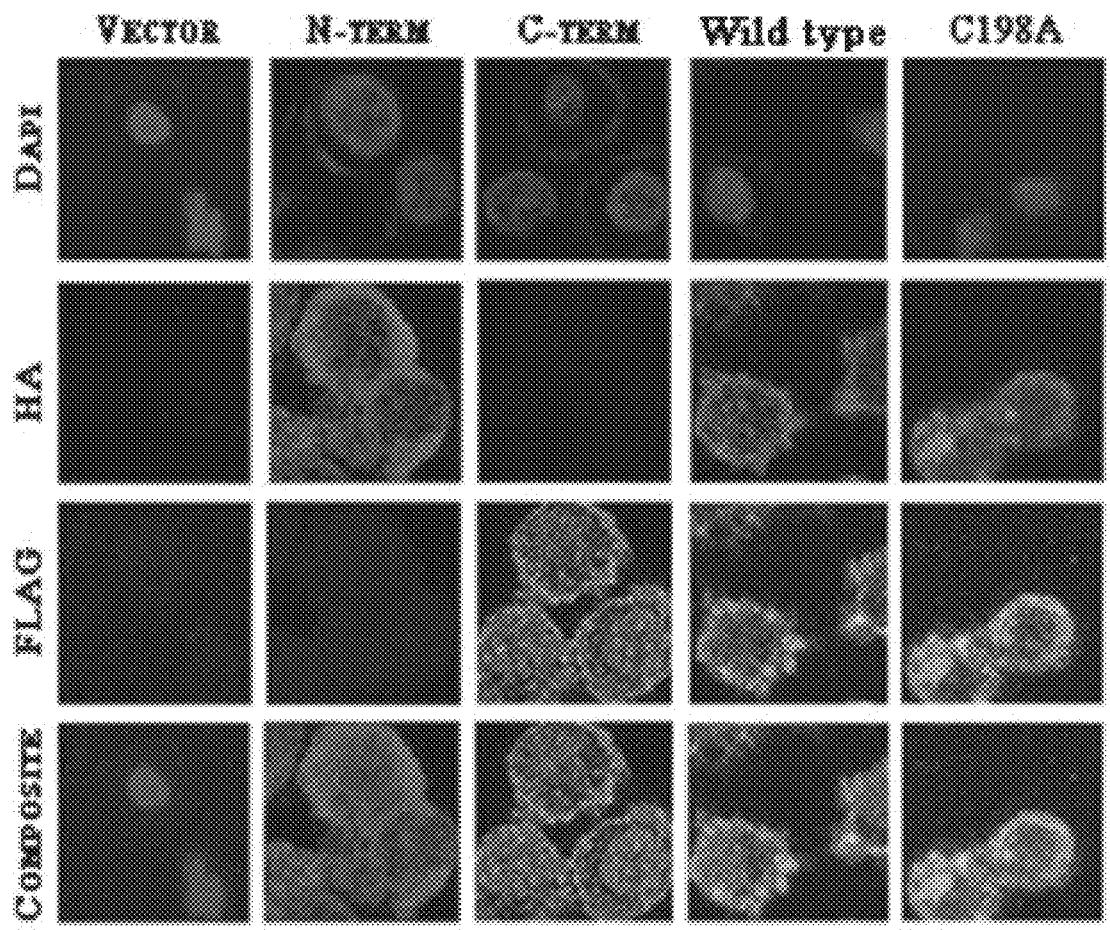
FIGS. 7A and 7B are a collection of images and graphs showing staining of tagged Shh constructs in cells, used as tools for this study, according to embodiments of the present disclosure.
Figure 7B:
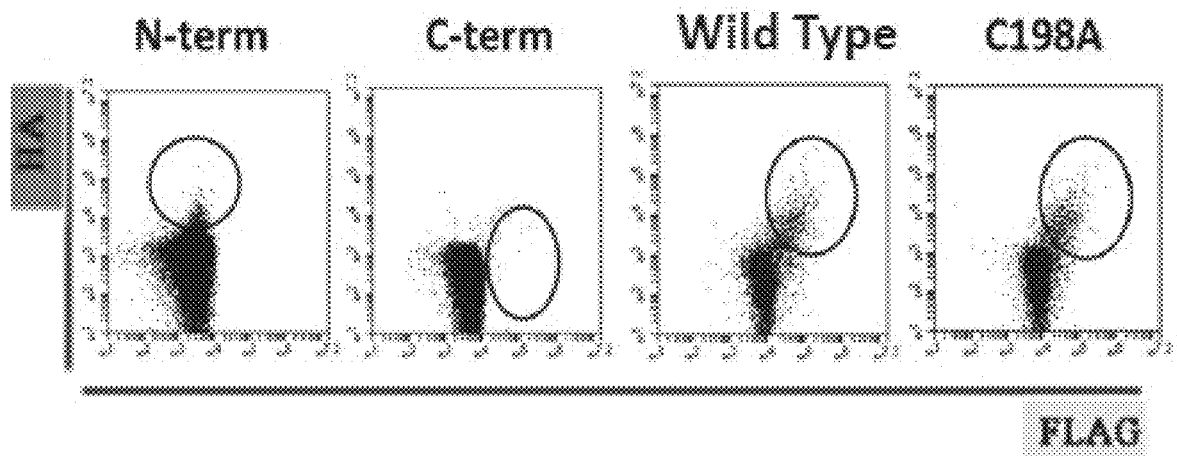

FIGS. 7A and 7B. FIG. 7A: Immunofluorescence analysis of A549 cells showing cytosolic and membrane staining of N-term, C-term, wild-type Shh and C198A Shh constructs probed for the presence of HA and FLAG. FIG. 7B: Flow analysis showing positive double staining in H838 cells for HA and FLAG in cells bearing wild-type and C198A constructs and single staining for N-term and C-term.

Paracrine Effect of Shh+ Cells on Other Cancer Cells

Figure 3D:
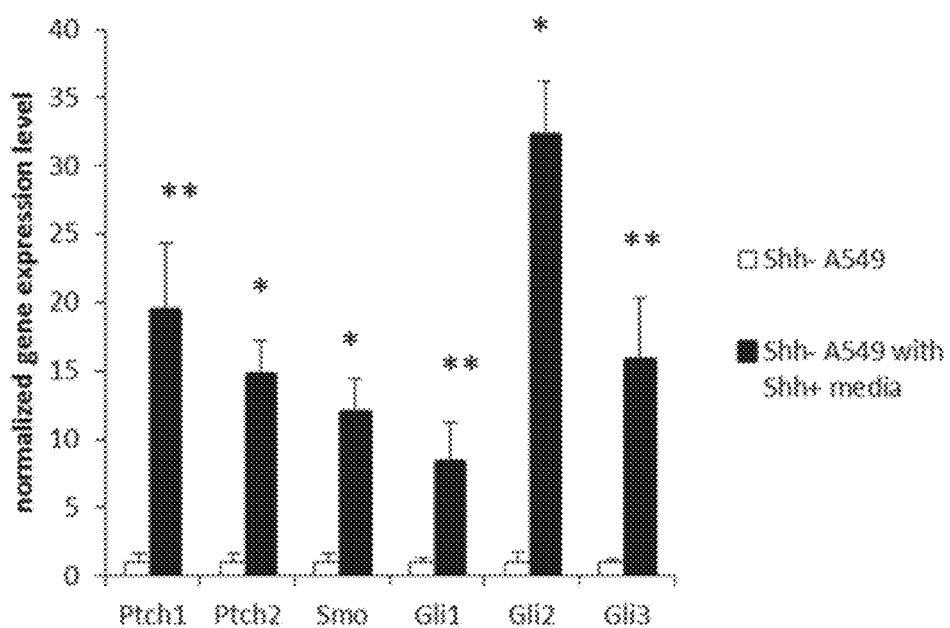
Figure 3E:
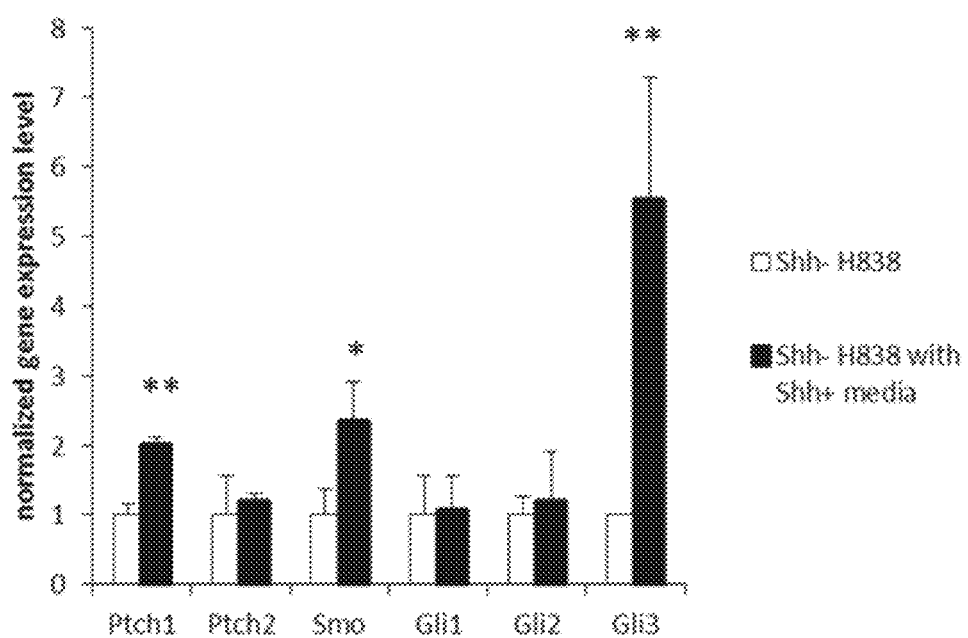

To better understand the properties of Shh+ and Shh− populations, functional analyses on sorted cells was performed in vitro. It was noted that the Shh+ cells had a 4 times higher proliferation rate in culture compared to the Shh− cells after 7 days (FIG. 3A). Moreover, the addition of media from Shh+ cells to Shh− cells induced a 4-times higher proliferation rate (FIG. 3B) and an augmentation in the migration rate of the Shh− cells by 50%. Addition of human recombinant N-terminal Shh peptide induced an augmentation in the migration rate by 15% (FIG. 3C). The addition of media from Shh+ cells to Shh− cells also induced gene overexpression of the downstream components of the Shh pathway such as Ptch, Sino, Gli1, Gli2, and Gli3 in quantitative PCR (qPCR) (FIGS. 3D & 3E). Taken together, these results suggest a paracrine role of Shh+ cells on Shh− cells, with activation of downstream factors of the Shh pathway putatively resulting in tumor proliferation and aggressiveness.

Figure 8A:
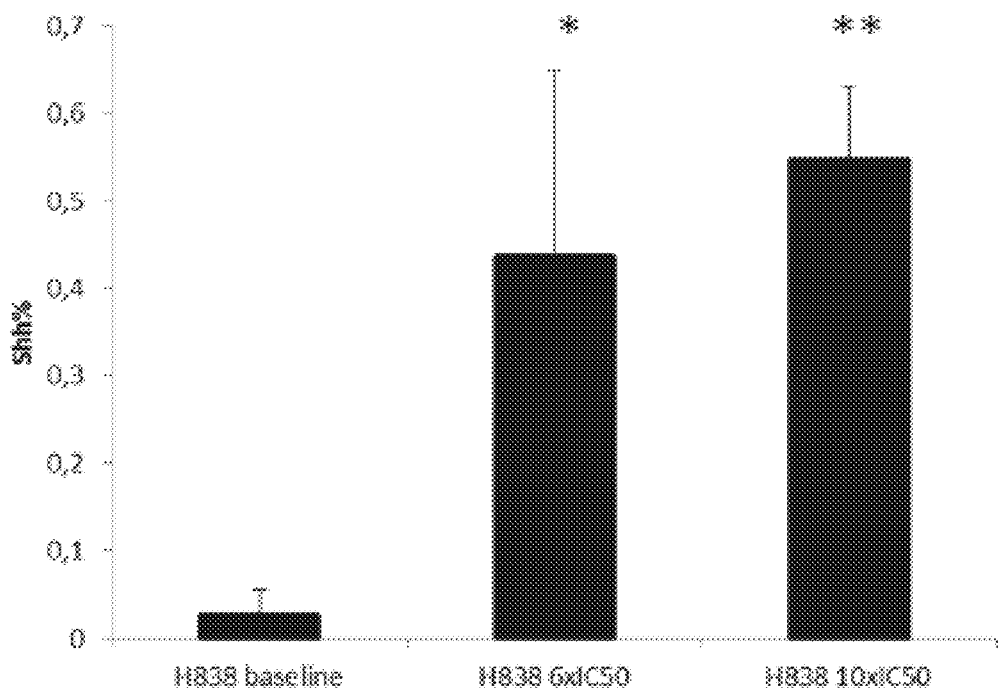
FIGS. 8A-8F are a collection of graphs showing Shh protein and Shh gene expression in cells treated with chemotherapy, according to embodiments of the present disclosure.
Figure 8B:
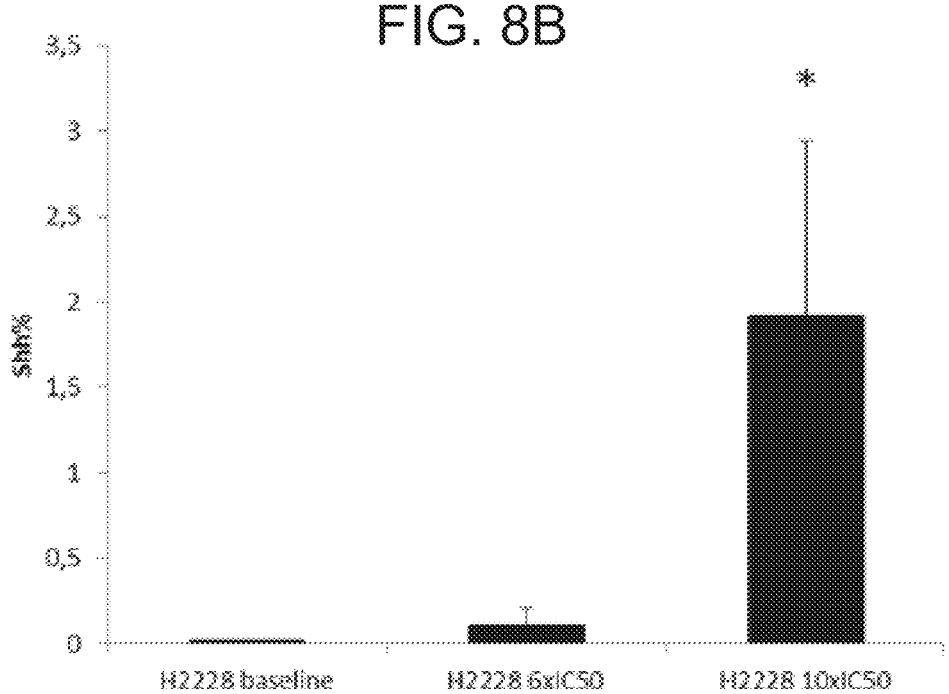
Figure 8C:
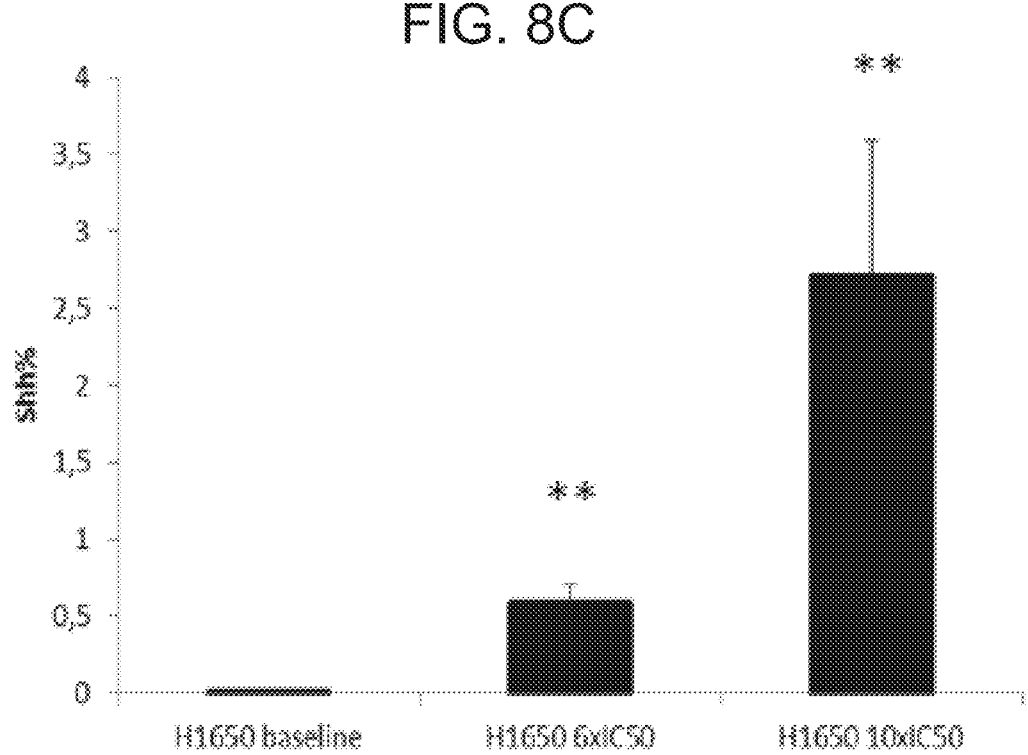
Figure 8D:
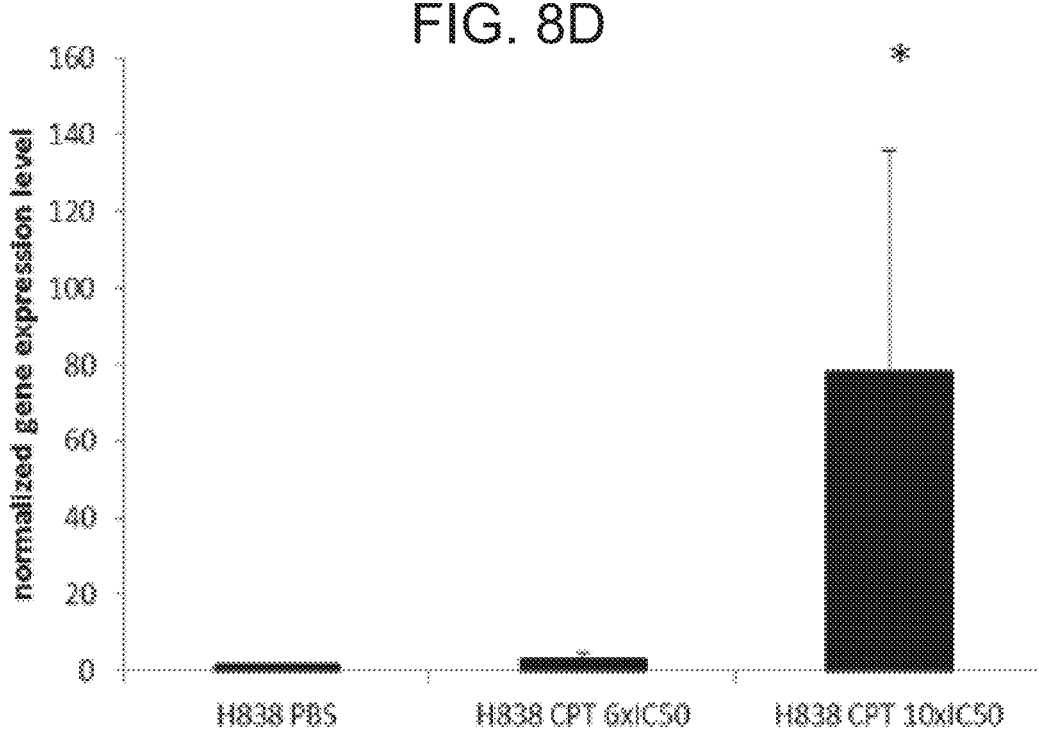
Figure 8E:
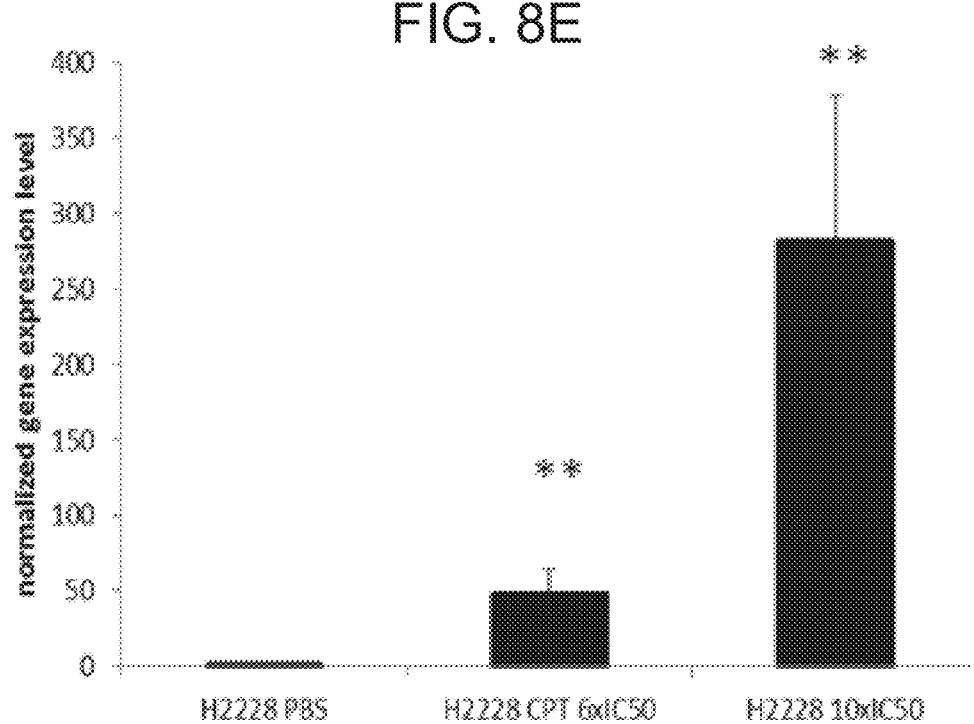
Figure 8F:
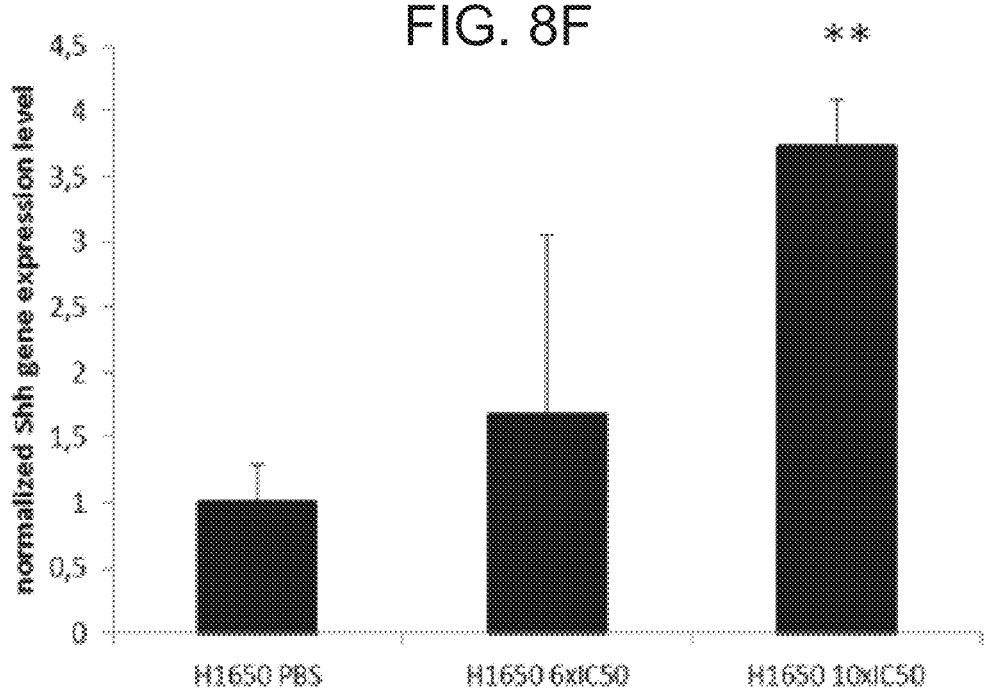

FIGS. 3A-3E. Shh+ cells have a paracrine effect on Shh− cells. FIG. 3A: proliferation assay (MTS) on A549 Shh+ and Shh− cells (day 0, day 3, day 4, day 7). FIG. 3B: proliferation assay (MTS) of A549 Shh− cells supplemented with culture media from Shh+ or Shh– cells (conditioned media: fresh media (1:1) at day 1 after cell sorting). **p<0.01, compared with cells supplemented with media from Shh– cells. FIG. 3C: migration/wound healing assay on A549 Shh– cells at day 0 (far left panel) and day 3 (three right panels, from left to right: control, with 1200 ng/mL Shh recombinant protein, with media from Shh+ cells). FIGS. 3D and 3E: gene expression levels of downstream Shh pathway targets analyzed by qPCR in A549 (FIG. 3D) or H838 (FIG. 3E) Shh– cells cultured with media from Shh+ cells (normalized to Shh– cells). *p<0.05; **p<0.01, compared with Shh– cells cultured with media from Shh– cells Evolution of the Shh Rate Following Cancer Treatment To examine the effect of cisplatin sensitivity on the rate of Shh+ cells, the resistance to cisplatin was compared with the level of Shh expression and observed a positive correlation between the $IC_{50}$ of cisplatin and the Shh+ rate assessed by flow cytometry (p=0.004, $R^2$=0.58, FIG. 4A). Further, when the cells were treated with escalating doses of chemotherapy, a corresponding augmentation in the Shh rate was seen (FIGS. 4B & 4C; FIGS. 8A-8C). This augmentation was absolute, with an increase in the total number of Shh+ cells subsequent to chemotherapy. An elevation in Shh gene expression was further confirmed by qPCR after cisplatin treatment (FIG. 4D; FIGS. 8D-8F).

Figure 4A:
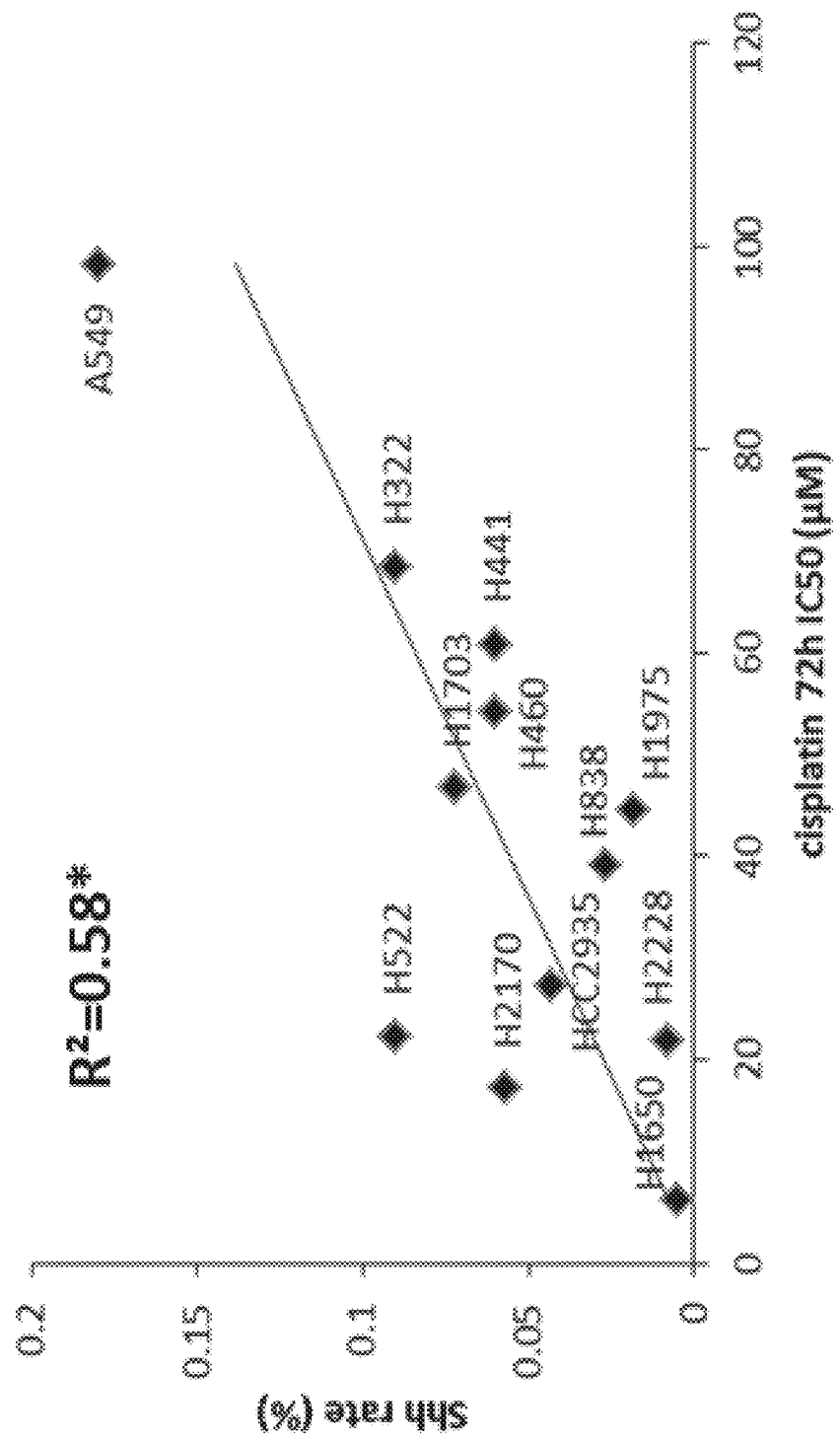
Figure 4B:
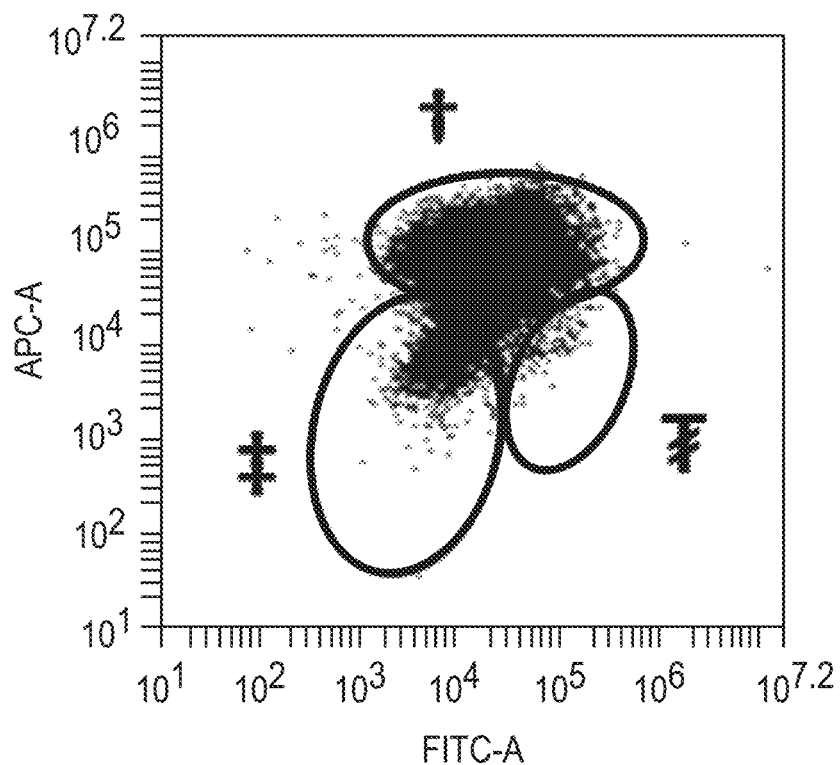
Figure 4C:
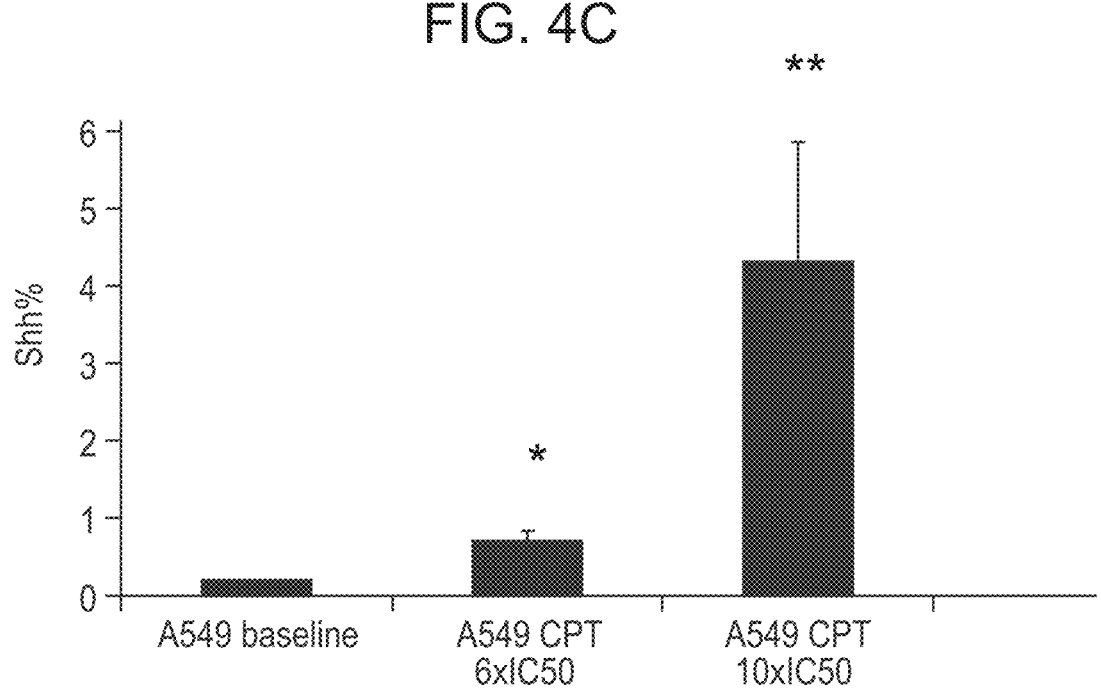
Figure 4F:
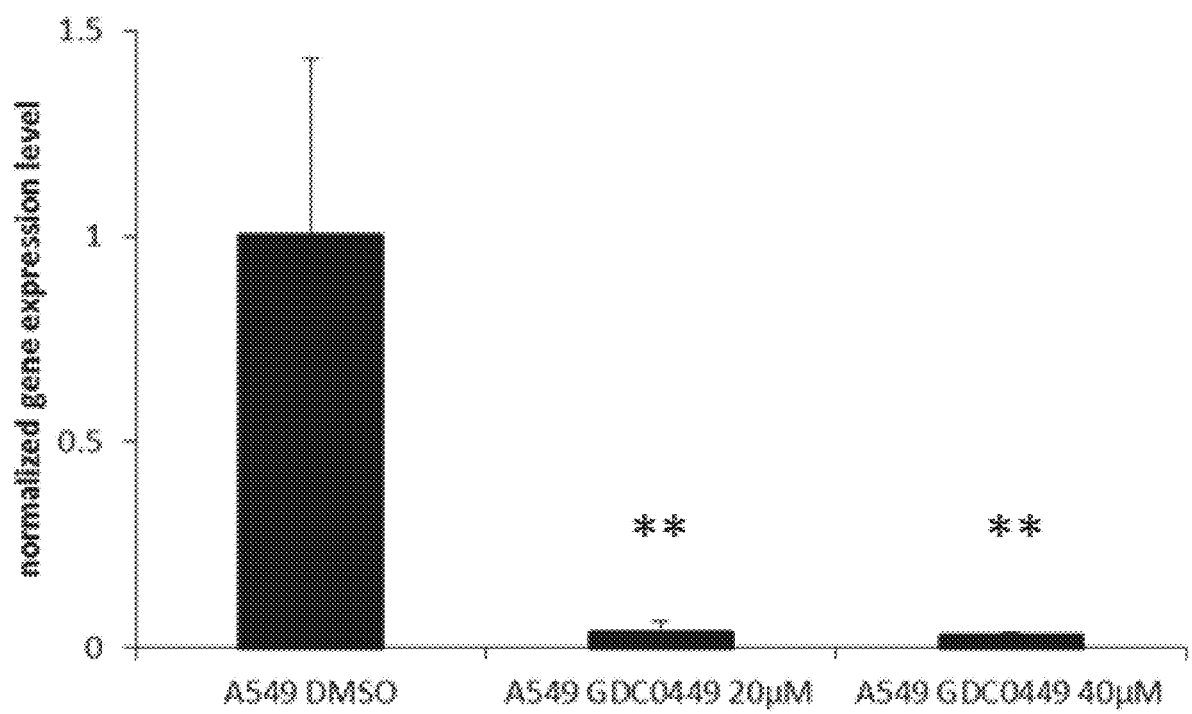
Figure 4G:
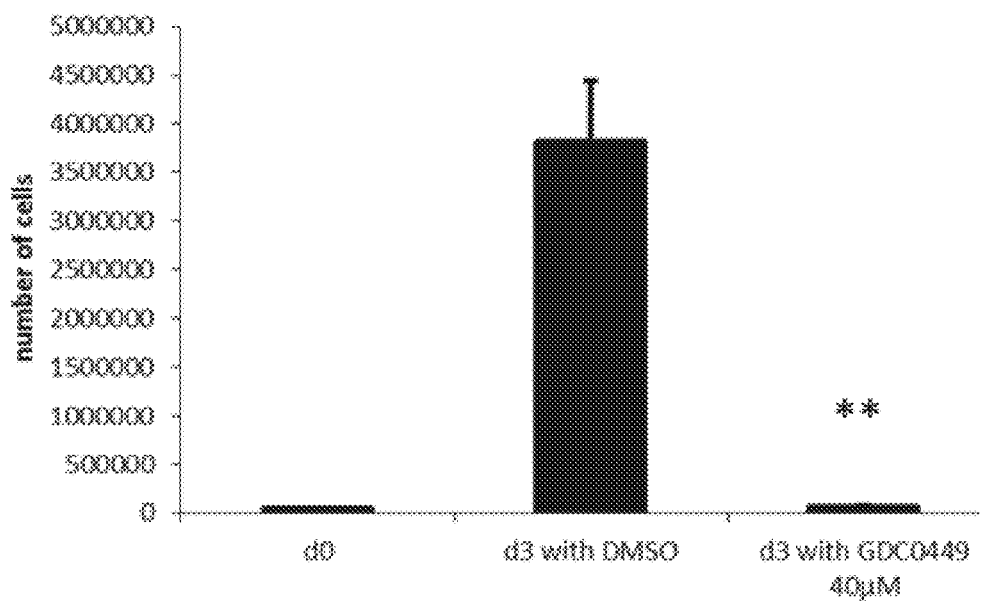
Figure 4H:
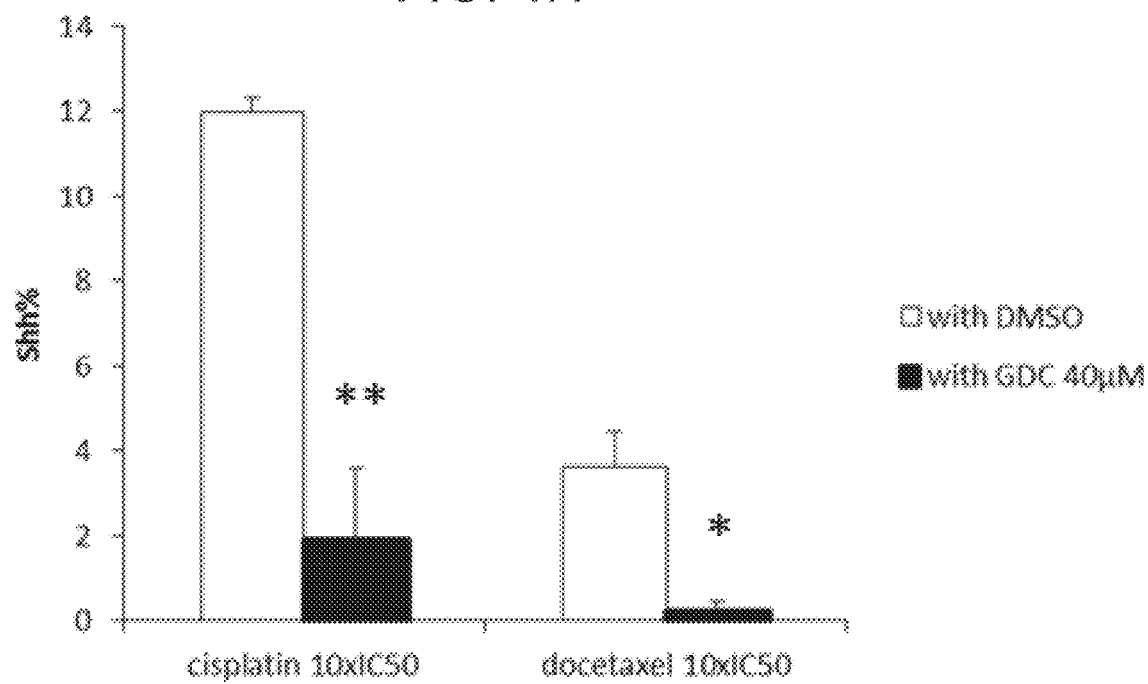
Figure 4I:
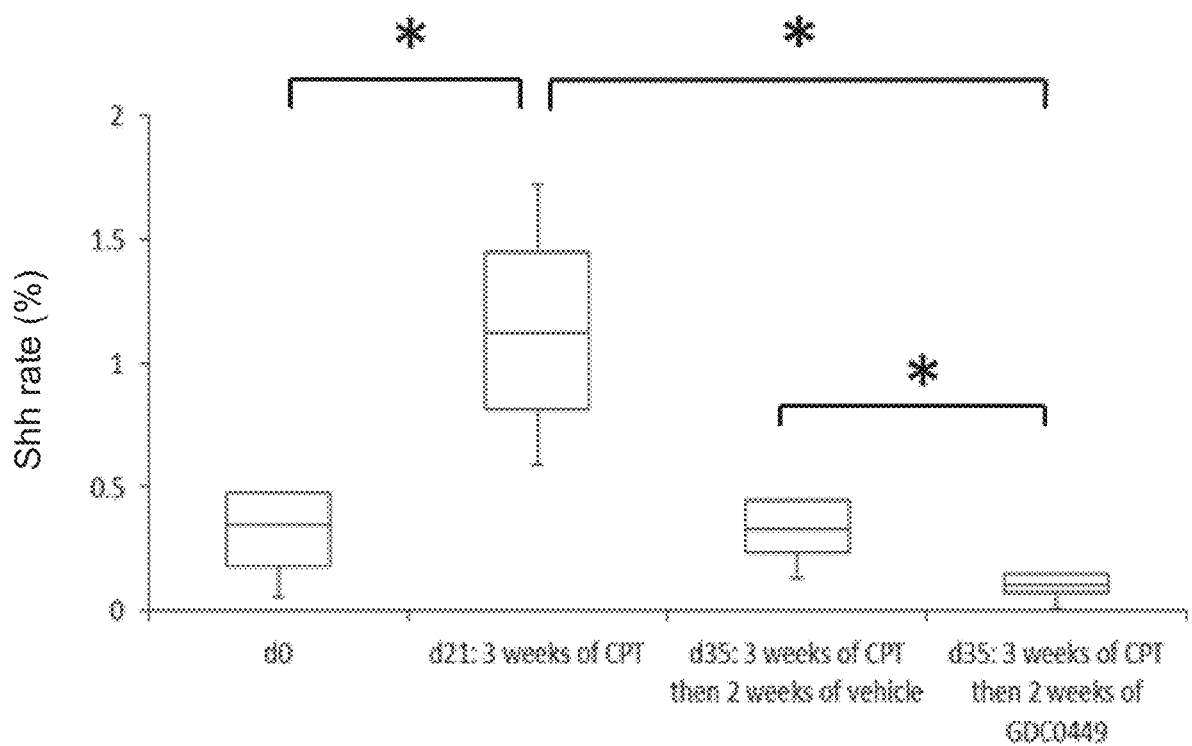

FIGS. 4A-4I. Shh+ cells are resistant to cisplatin but sensitive to GDC0449. FIG. 4A: correlation between Shh rate (%) and cisplatin $IC_{50}$ in NSCLC cell lines. FIG. 4B: Shh rate (%) in A549 cells treated with cisplatin (1 mM). †dead cells; ‡Shh– cells; ᵮ Shh+ cells (5% of live cells). FIG. 4C: Shh rate (%) in A549 cells treated by cisplatin (600 μM and 1 mM). *p<0.05; p<0.01, compared to baseline. FIG. 4D: Shh expression level (qPCR) in A549 cells treated with cisplatin (600 μM and 1 mM) (normalized to PBS-treated cells). p<0.01, compared to PBS. FIG. 4E: Shh rate (%) in A549 cells treated with GDC0449 (40 †dead cells; ‡Shh– cells; ᵮ: Shh+ cells (0%). FIG. 4F: Shh expression level (qPCR) in A549 cells treated with GDC0449 (20 μM and 40 μM) (normalized to DMSO-treated cells). p<0.01, compared to DMSO. FIG. 4G: MTS assay of A549 cells treated with DSMO or GDC0449 (40 μM). p<0.01, compared to day 0. FIG. 4H: Shh rate (%) in A549 cells treated with cisplatin and DMSO/GDC0449 (40 μM) or docetaxel and DMSO/GDC0449 (40 μM). **p<0.01, compared to cisplatin/docetaxel and DMSO. FIG. 4I: Shh rate (%) in A549 xenograft model treated with cisplatin (CPT, 10 mg/kg IV weekly), followed by vehicle or GDC0449 (20 mg/kg, IP daily). *p<0.05.

FIGS. 8A-8C: Shh rate (%) in flow cytometry in H838 (FIG. 8A), H2228 (FIG. 8B) and H1650 (FIG. 8C) cells according to the dose of cisplatin (6-fold and 10-fold IC50, ×72 h). FIGS. 8D, E and F: Shh gene expression level in H838 (FIG. 8D), H2228 (FIG. 8E) and H1650 (FIG. 8F) cells according to the dose of cisplatin (6-fold and 10-fold IC50, ×72 h) in qPCR (normalized to PBS-treated cells).

Figure 9A:
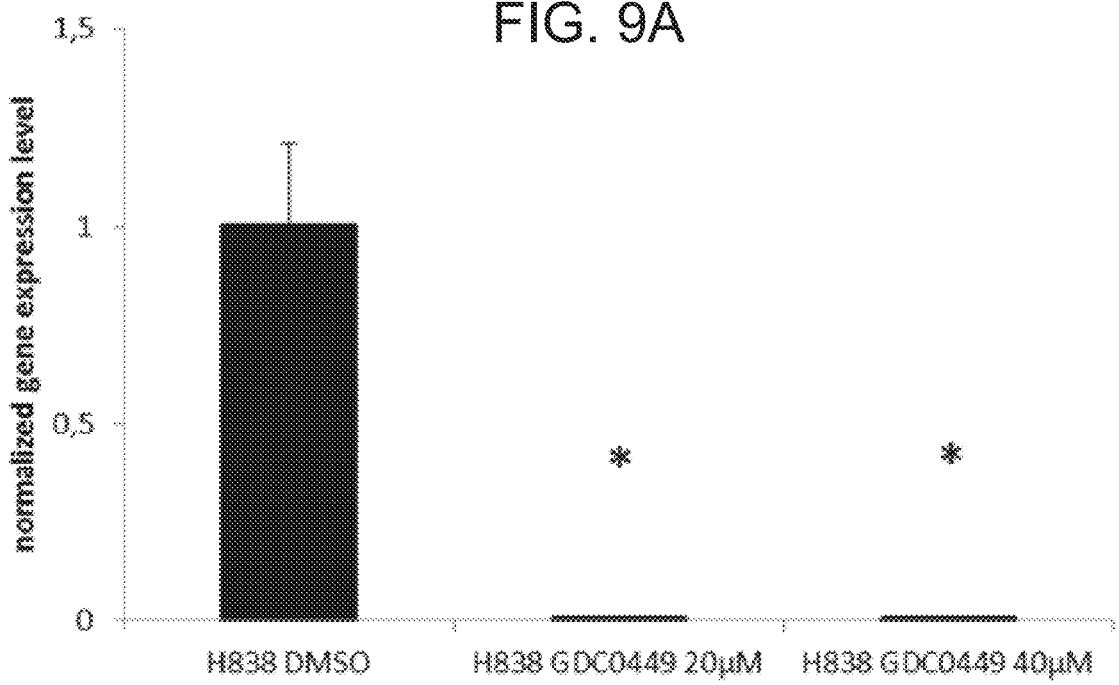
FIGS. 9A-9C are a collection of graphs showing Shh gene expression level in cells treated with chemotherapy, according to embodiments of the present disclosure.
Figure 9B:
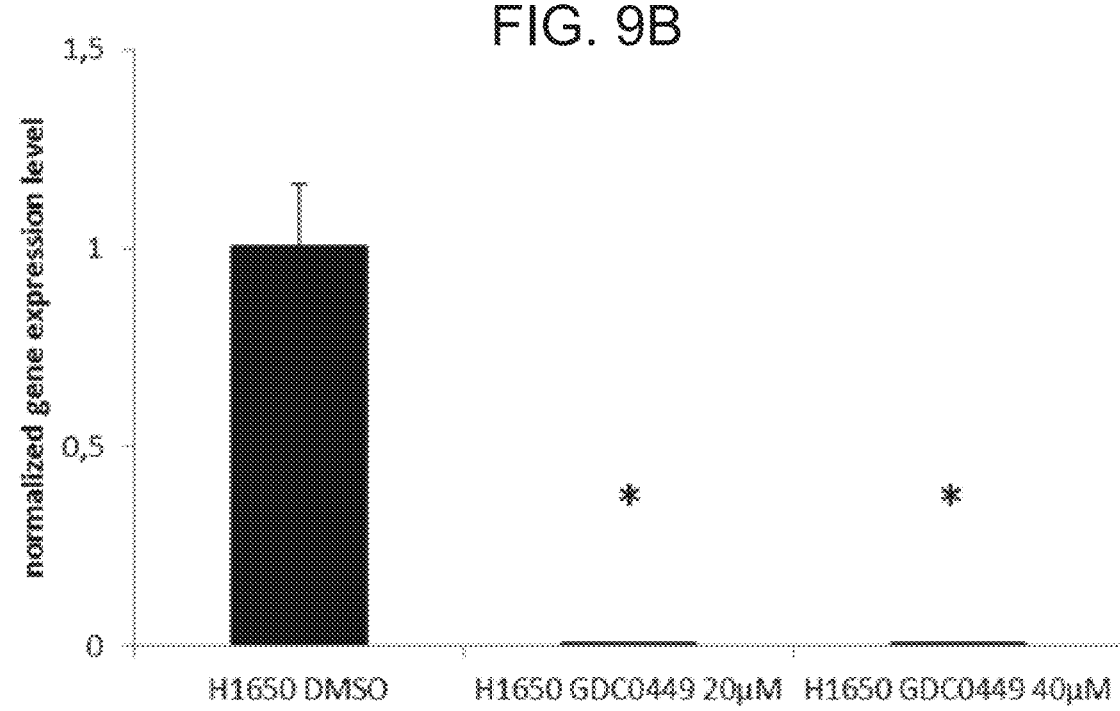

Treatment of A549 cells with 40 μM GDC0449 (Vismodegib/commercial Smoothened inhibitor) resulted in successful inhibition of the Shh pathway evidenced by a complete disappearance of Shh+ cells assessed by flow cytometry FIG. 4E). qPCR confirmed this dramatic decrease in Shh gene expression post-GDC0449 treatment (FIG. 4F; FIGS. 9A and 9B). Moreover, treatment with GDC0449 induced an inhibition of cell proliferation and migration (FIG. 4G; FIGS. 10A-10D). Also, a significant decrease in the Shh rate post-chemotherapy (cisplatin or docetaxel) combined with GDC0449 was observed compared to chemotherapy alone (FIG. 4H). In order to confirm these results in vivo, A549 xenografts in nude-mice treated were used with sequential treatments (cisplatin then GDC0449) or combined treatment (docetaxel and GDC0449). A significant augmentation in the Shh+ rate was observed after chemotherapy and a significant reduction in the Shh rate after GDC0449 treatment (sequential assay), and a significant reduction in the Shh rate following combination treatment, compared to chemotherapy alone (combined docetaxel and GDC0449 treatment) (FIG. 4I; FIG. 11).

Figure 9C:
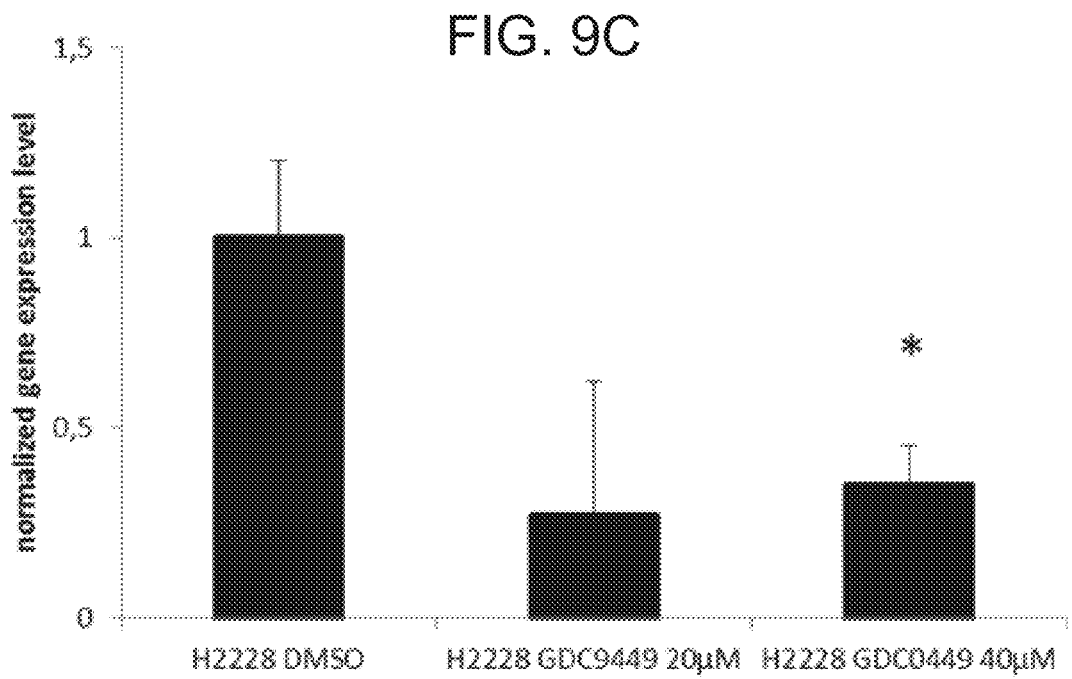

FIGS. 9A-9C. Shh gene expression level (qPCR) in H838 (FIG. 9A), H1650 (FIG. 9B) and H2228 (FIG. 9C) treated with GDC0449 (20 μM and 40 μM, ×72 h) (normalized to DMSO-treated cells).

Figure 10A:
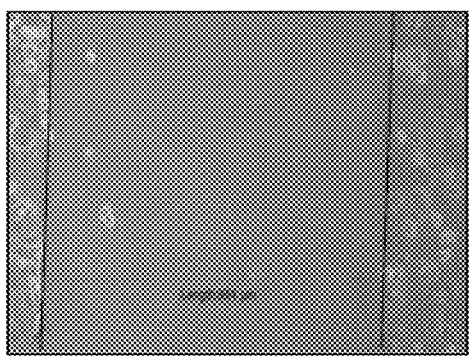
FIGS. 10A-10D are a collection of images showing migration/wound healing assay on A549 cells treated with chemotherapy, according to embodiments of the present disclosure.
Figure 10B:
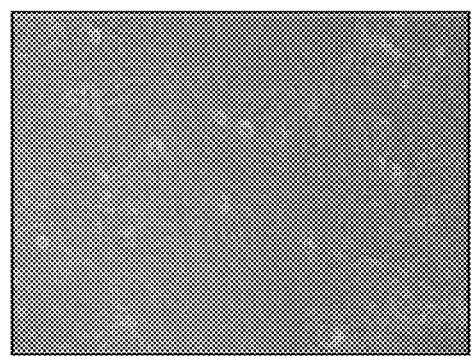
Figure 10C:
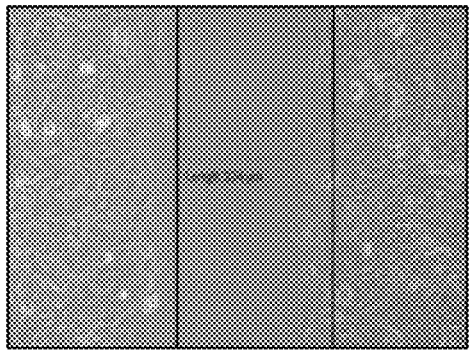
Figure 10D:
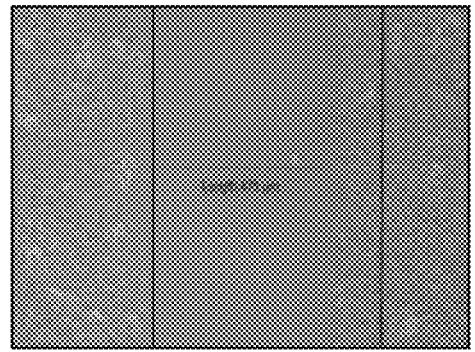
Figure 11:
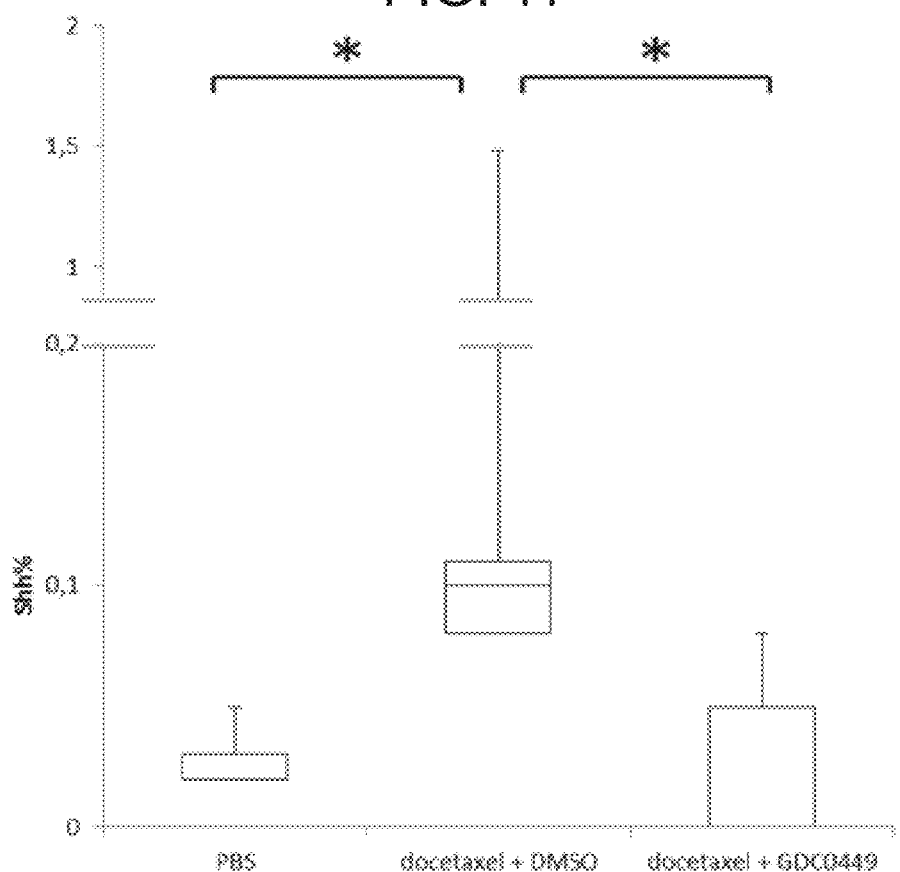
FIG. 11 is a graph showing expression of Shh in cells from tumor tissue from mice treated with chemotherapy, according to embodiments of the present disclosure.

FIGS. 10A-10D. Migration/wound healing assay on A549 cells at day 0 (FIG. 10A) and day 3 (FIG. 10B: DMSO; FIG. 10C: GDC0449 20 μM; FIG. 10D: GDC0449 40 μM).

FIG. 11. Shh rate (%) at day 21 in A549 xenografts (nude mice) treated with PBS or docetaxel (10 mg/kg twice a week) plus vehicle or docetaxel (10 mg/kg twice a week) plus GDC0449 (20 mg/kg IP daily). *p<0.05.

CSC Features of Shh+ Cells

To elucidate the features of the two populations, gene expression microarray profiling of sorted Shh+ and Shh– A549 cells was performed (FIG. 5A). Comparative gene expression profiling of Shh+ cells with Shh– cells, revealed an overexpression of Shh pathway genes (notably Shh), several well-known CSC genes (POU5F1P3, NANOG, LIN28A, ALDH1A2, PROM1), genes involved in cell survival and proliferation genes (Cyclin D2 (CCND2), BCL2), Wnt pathway genes (various Wnt protein genes), and chemokine-related genes. Interestingly, genes associated with differentiation (KRT7, PRDM1) were under-expressed in Shh+ cells.

Figure 5D:
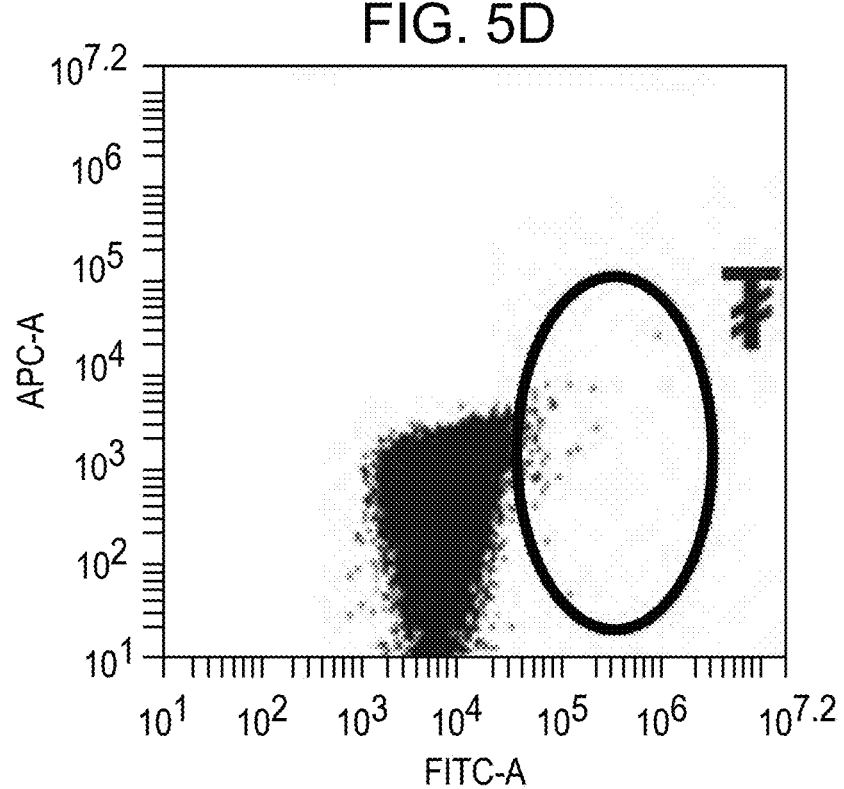
Figure 5E:
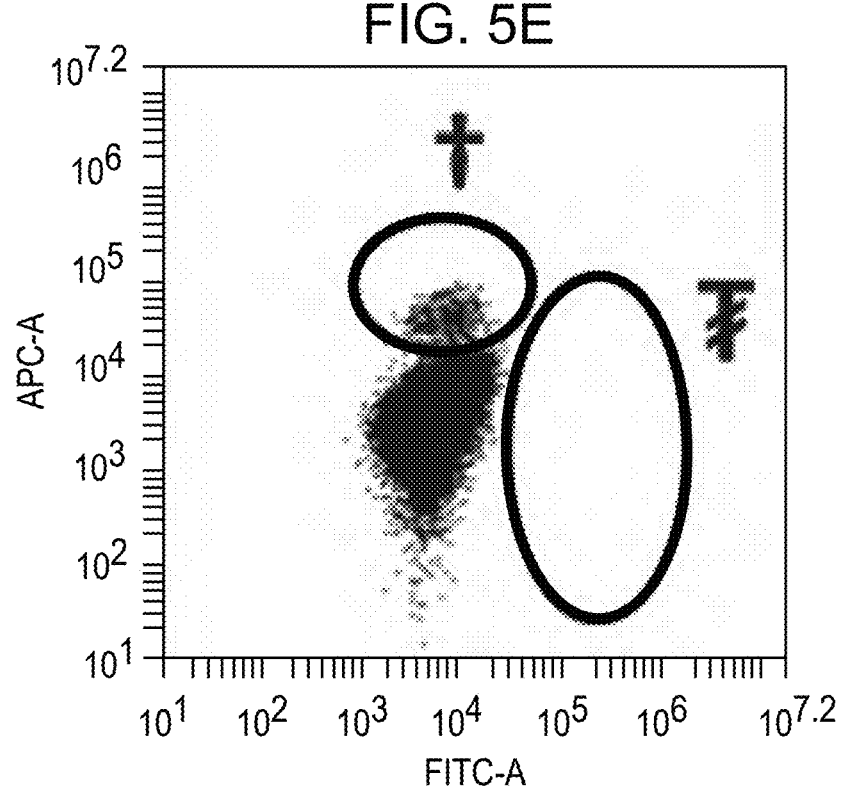
Figure 5F:
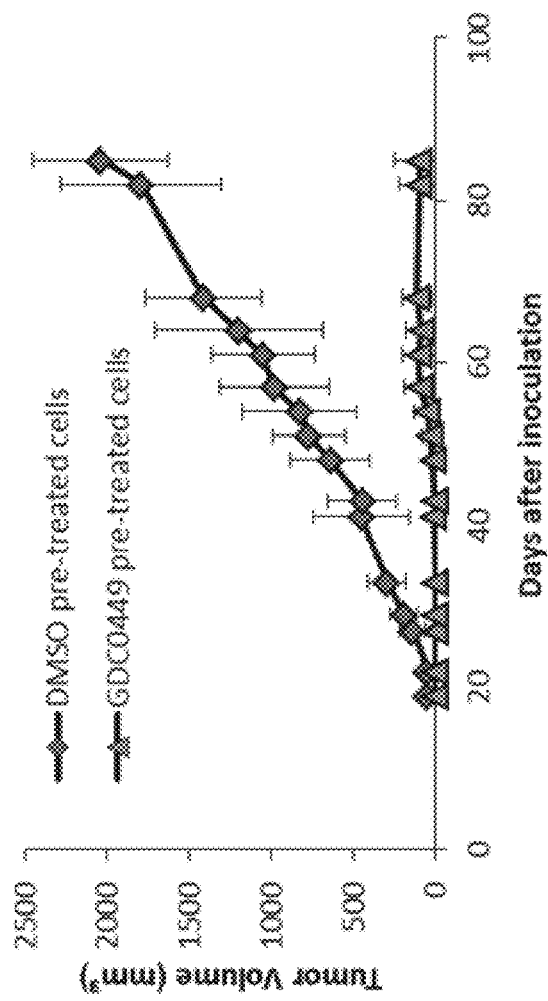

Upon culturing sorted cells in serum-free conditions, the formation of floating spheroids with A549 Shh+ cells was observed 10 to 15 days after sorting (FIG. 5B), but not with A549 Shh– cells (FIG. 5C). To prove the critical role of the Shh pathway in oncogenesis, cultured A549 cells were treated with 40 μM of GDC0449 (FIGS. 5D & 5E). Then, nude mice were inoculated (sub-cutaneous) with 1 million treated cells (still adherent to the culture flask after treatment with GDC0449). Tumor formation was completely inhibited with the pre-treated cells compared with the control group (DMSO pre-treated cells) (FIG. 5F). Next, nude mice, were inoculated with a small number (1,500 cells) of Shh+ or Shh– cells (sub-cutaneous). At 3 weeks, 3 out of 4 mice (75%) inoculated with Shh+ cells developed a measurable xenograft, whereas 0 of 4 mice (0%) inoculated with Shh– cells developed any tumors (FIGS. 5G-5J). Taken together, these data suggest that Shh+ cells are CSCs and that the Shh pathway is a key-component in oncogenesis.

Figure 5H:
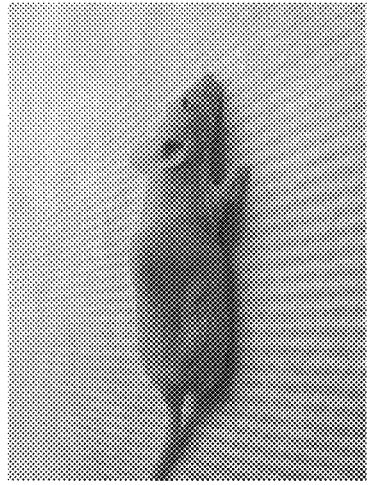
Figure 5G:
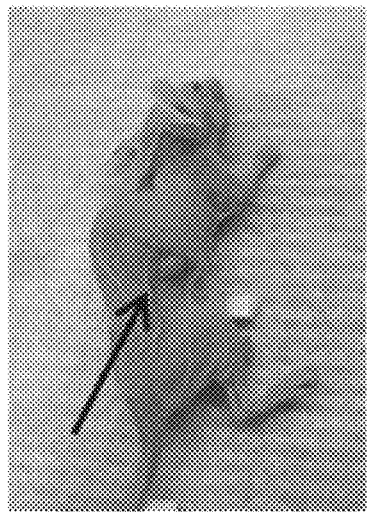

FIGS. 5A-5J. Shh+ cells have cancer stem cells features. FIG. 5A: microarray gene expression analysis on A549 Shh+ cells (normalized to Shh– cells). FIG. 5B: growth of A549 Shh+ cells cultured in serum-free conditions at day 14 led to spheroid formation (scale bar: 100 μm). FIG. 5C: culture of A549 Shh– cells in serum-free conditions at day 14 did not lead to spheroid formation (scale bar: 100 μm). FIG. 5D: flow cytometry analysis of pre-inoculated A549 cells treated with DMSO (day 3). ᵮ: Shh+ cells (0.10%). FIG. 5E: flow cytometry analysis of pre-inoculated A549 cells treated with GDC0449 (40 μM, day 3), t: dead cells (SytoxRed); ᵮ: Shh+ cells (0%). FIG. 5F: evolution of A549 xenograft volume in nude mice after inoculation of pre-treated cells. FIG. 5G: nude mice inoculated with low amount (1,500 cells) A549 Shh+ cells with tumor formation at 3 weeks.

Figure 5I:
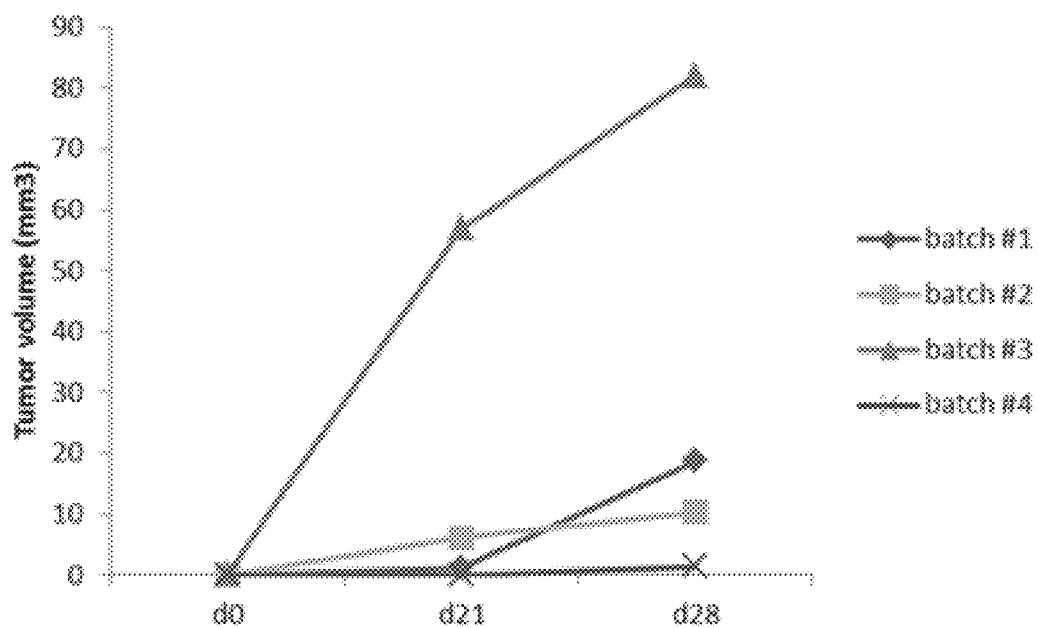
Figure 5J:
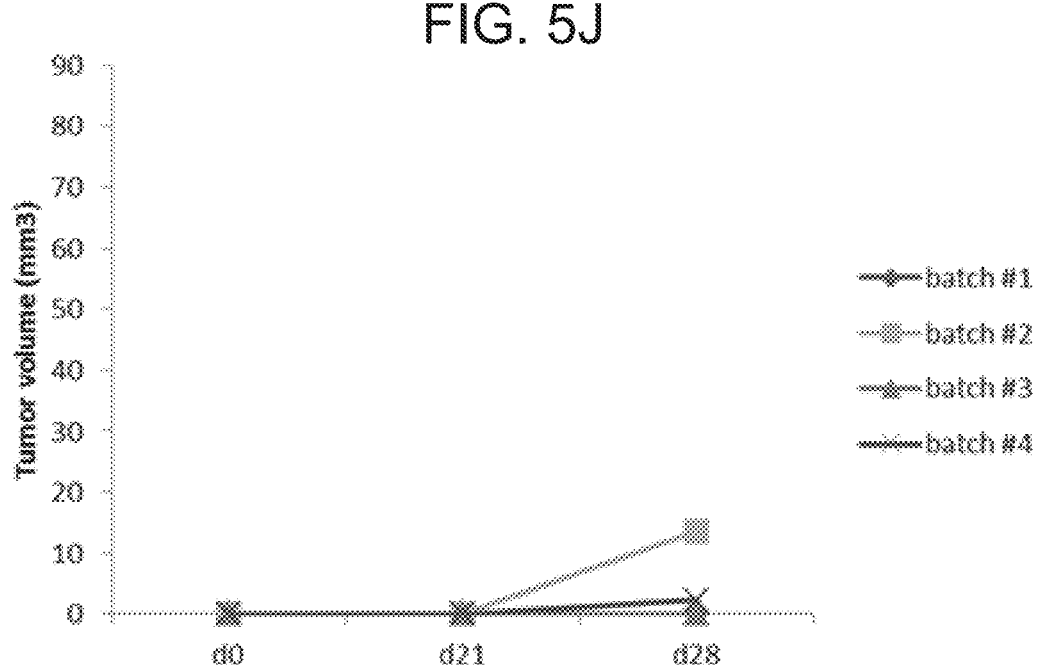

FIG. 5H: nude mice inoculated with low amount (1,500 cells) A549 Shh– cells, without tumor formation at 3 weeks. FIGS. 5I and 5J: subcutaneous tumor volumes in nude mice 3-4 weeks after inoculation of low amount (1,500 cells) A549 Shh+ (FIG. 5I) or Shh– (FIG. 5J) cells.

Presence of Shh+ Cells in Human Tumor Samples and Prognostic Impact

To evaluate the role of Shh as a prognostic marker in lung cancer, 48 fresh human surgical samples of 47 patients with NSCLC, obtained consecutively from the Surgery Department at UCSF, were tested. There were 46 primary lung tumors, one tumor pleural effusion, and one adrenal metastasis of lung adenocarcinoma. Patient samples were not only probed for Shh to assess the percentage of positive cells but also CD45 to exclude immune cells from the final analysis. While the overall median Shh rate was 0.06% (interquartile range IQR 0.02-0.20), the rate in corresponding fresh normal lung tissue (n=48) was 0% (IQR 0-0%) ($p<0.001$) (FIGS. 6A & 6B). The Shh rate (median) was 0.09% (IQR 0.03-0.21) for stage I (n=32), 0.02% (IQR 0.01-0.11) for stage II (n=6), 0.01% (IQR 0-0.02) for stage III (n=5) and 0.15% (IQR 0.01-0.56) for stage IV (n=5) ($p>0.05$ for each comparison). All the samples were chemo-naive, except for 3 samples (stage I: n=1; stage IV: n=2) which received pre-surgery chemotherapy. One patient underwent surgery twice after systemic chemotherapy, with 6-weeks delay between the 2 surgeries (the first surgery for the primary lung tumor, the second for an adrenal metastasis), and without any chemotherapy between the 2 surgeries. Initial post-chemotherapy evaluation showed a tumor response in the primary lung tumor, but a tumor burden on the adrenal metastasis. Both the primary tumor and adrenal metastasis were analyzed, and there was a nearly 70-fold higher Shh rate assessed via flow cytometry at the metastatic progressive site compared to the primary tumor that responded to chemotherapy (FIG. 6D). qPCR analysis confirmed this result as Shh gene overexpression at the site with tumor progression compared to the site with tumor response ($p=0.01$, FIG. 12). Fresh lung metastases from other pathological subtypes were also tested via flow cytometry and observed the presence of Shh+ cells in almost all of them (Table 2 in FIG. 14). Microarray analysis was then performed on 7 sorted fresh human tumor samples (4 primary lung adenocarcinoma and 3 secondary lung tumors (primary: melanoma (n=1); breast carcinoma (n=1); colorectal carcinoma (n=1)). Consistent with the microarray data from the NSCLC cell line, gene overexpression for Shh pathway genes, CSC genes, cell survival, EMT and aggressiveness genes, Wnt pathway and chemokines genes were found (FIG. 6E; FIG. 13).

Figure 6C:
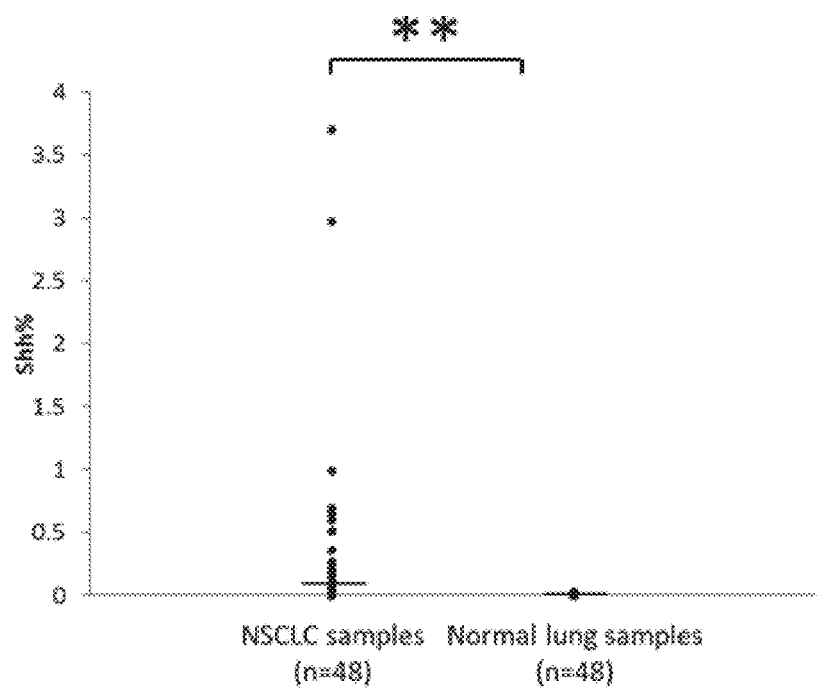
Figure 6D:
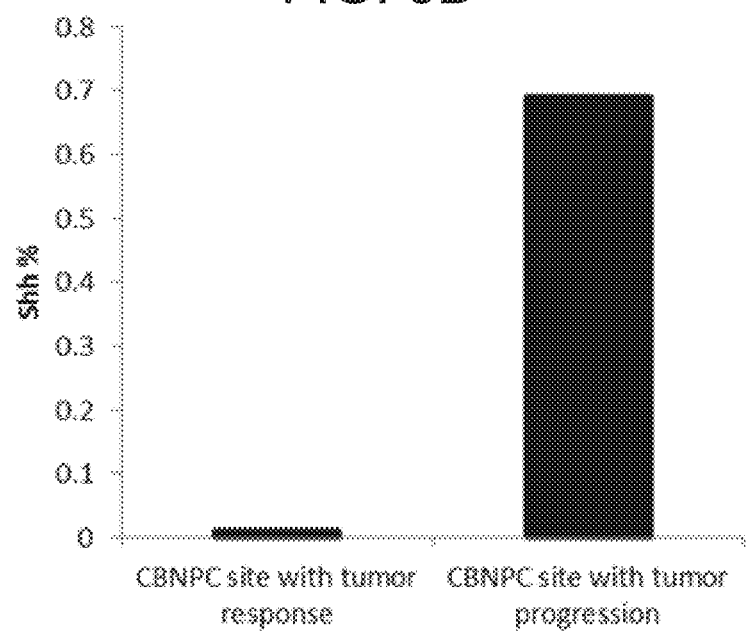
Figure 6E:
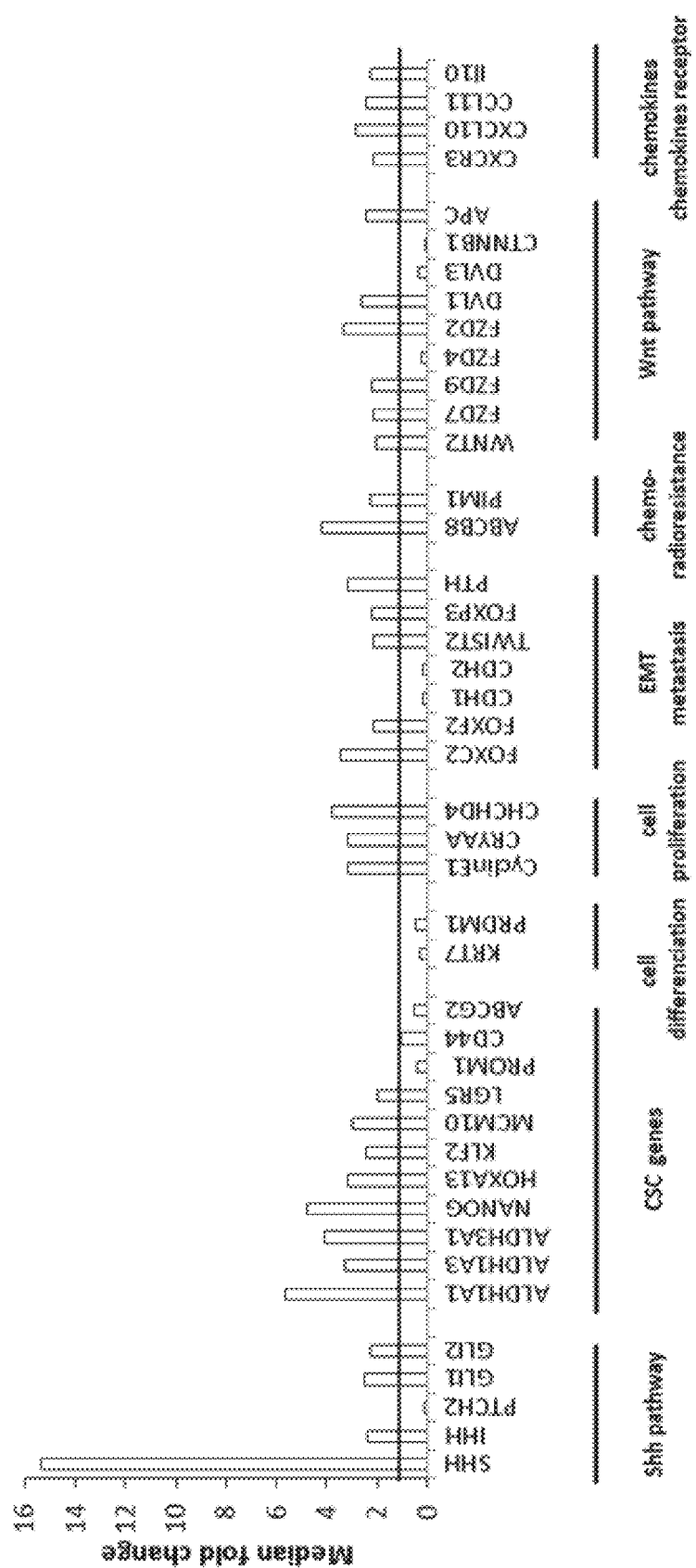
Figure 6F:
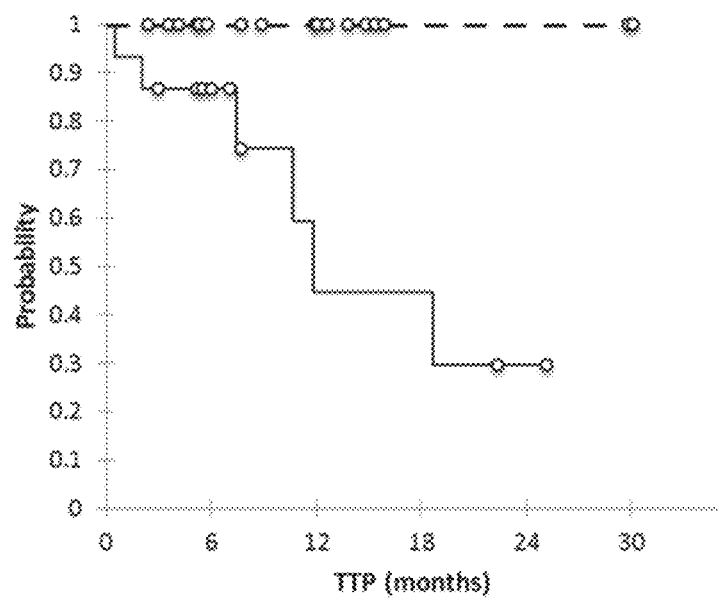
Figure 6G:
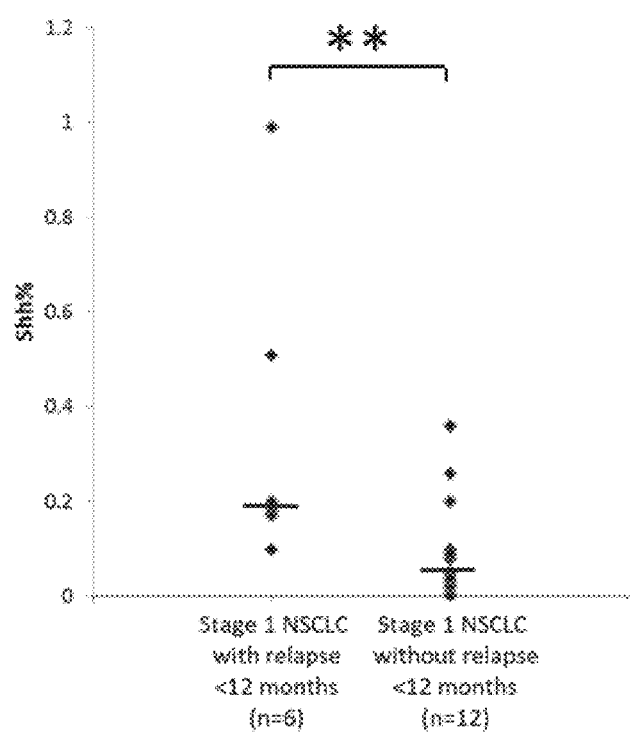

FIGS. 6A-6G. Presence of Shh+ cells in fresh human NSCLC tissue samples. FIG. 6A: flow cytometry analysis of Shh in a fresh human NSCLC sample (†CD45+ cells; ‡CD45-Shh– cells; ⊤ CD45-Shh+ cells (2.99% of CD45– cells). FIG. 6B: flow cytometry analysis of Shh in a fresh human normal lung sample (†CD45+ cells; CD45-Shh– cells; ⊤ CD45-Shh+ cells (0%). FIG. 6C: Shh rate (%) in fresh human NSCLC samples and corresponding normal lung tissues (n=48). FIG. 6D: Shh rate (%) in primary lung adenocarcinoma with a tumor response after chemotherapy and the corresponding adrenal metastasis with tumor progression after chemotherapy in the same patient. FIG. 6E: microarray gene expression analysis on Shh+ cells from fresh lung adenocarcinoma (normalized to Shh– cells; Shh rate at 0.69% assessed via flow cytometry). FIG. 6F: Time-to-progression (TTP) according to high (>0.10%) or low (<0.10%) Shh rate ($p<0.01$ for log-rank test) in stage I NSCLC tissue samples (n=32). FIG. 6G: Shh rate (%) in stage I NSCLC with tumor relapse within 12 months after surgery and in stage I NSCLC without relapse within 12 months after surgery (**$p<0.01$).

Figure 12:
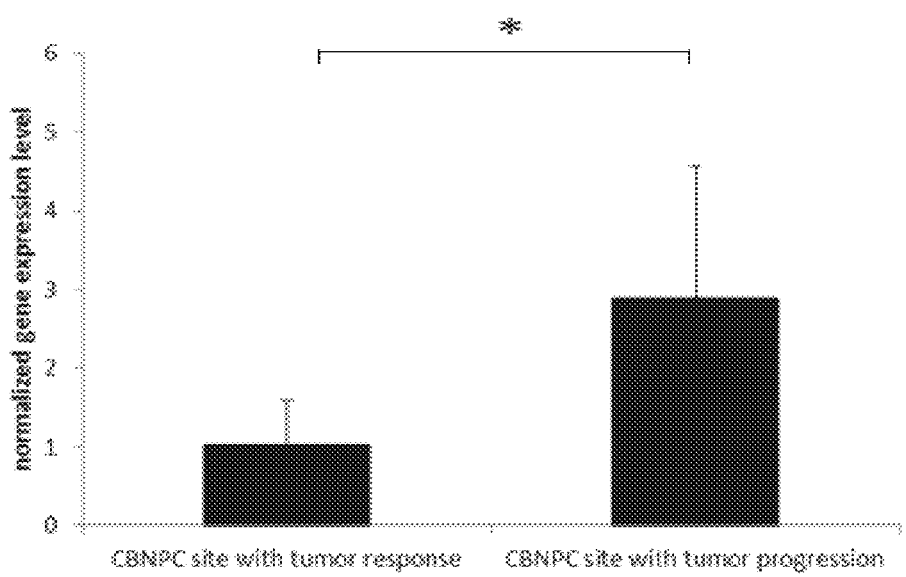
FIG. 12 is a graph showing Shh gene expression level in primary lung adenocarcinoma, according to embodiments of the present disclosure.
Figure 13:
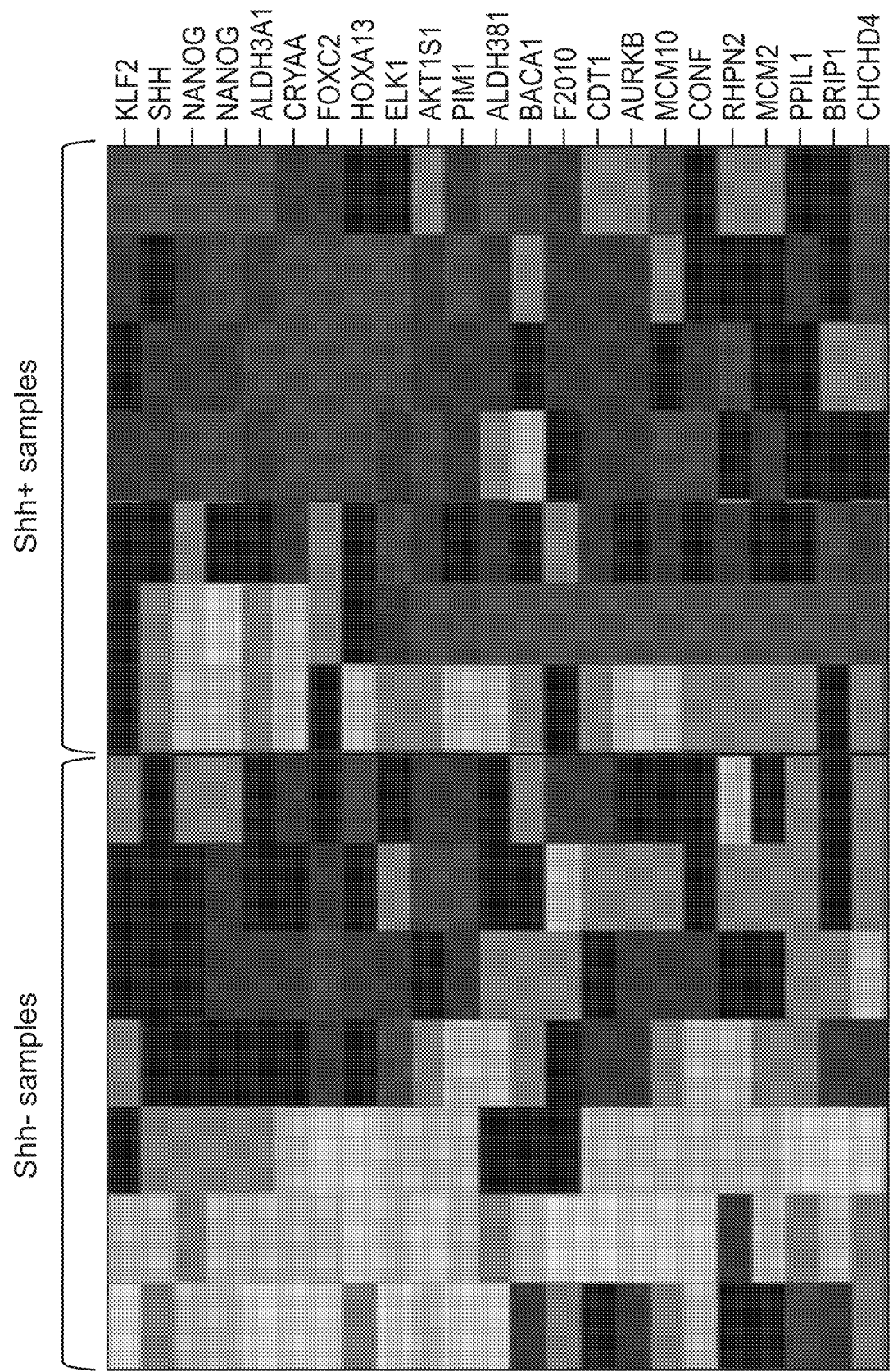
FIG. 13 shows a heat map of microarray gene expression analysis in Shh+ and Shh− cells isolated from human fresh lung tumor samples, according to embodiments of the present disclosure.

FIG. 12 Shh gene expression level (qPCR) in the primary lung adenocarcinoma with tumor response after chemotherapy, and the corresponding adrenal metastasis with tumor progression after chemotherapy, in the same patient. **$p<0.01$.

FIG. 13 Heat map of microarray gene expression analysis in Shh+ and Shh– cells isolated from human fresh lung tumor samples (n=7). Genes mentioned concerned Shh pathway (Shh), Wnt pathway (Fzd10), CSC features (NANOG, HOXA13, KLF2, ALDH3A1, ALDH3B1), cell proliferation (CRYAA, CDT1, AURKB, MCM2, MCM10, CCNF, RHPN2, AKT1S1, PIM1), EMT (FOXC2), hypoxia and tumor proliferation (CHCHD4) and chemoresistance (BRCA1, BRIP1, ELK1).

FIG. 14. Table 2: Shh rate (%) determined by flow cytometry in various fresh cancer tissue samples. Shh rate expressed as median (IQR) if several samples were tested for each pathological subtype.

Finally, a clinical impact of Shh+ cells in human NSCLC was ascertained. All the patients in this study was prospectively followed and a statistically significant association was found between the Shh+ rate and the time to progression (TTP) for stage I NSCLC. TTP (median) was 11.8 months in patients whose tumors showed a Shh+ rate of more than 0.10%, versus 'non reached' in those whose tumors showed a Shh+ rate of less than 0.10% ($p=0.004$, FIG. 6F). For stage I NSCLC, patients with tumor relapse within 12 months after surgery had a higher Shh+ rate in their tumors compared to those without tumor relapse within 12 months of surgery (median: 0.19% (IQR 0.14-0.36) versus 0.05% (IQR 0.02-0.09), respectively, $p=0.01$; analysis based on 22 stage I NSCLC with follow-up >12 months after surgery) (FIG. 6F).

Example 2: Shh Antibodies Raised Against C-Terminal Shh

To generate C-terminal Shh antibodies, mice were inoculated with the following peptides:

```
(SHH-247:264)
                                        (SEQ ID NO: 18)
GAKKVFYVIETREPRERL;
and (SHH-448:462)
                                        (SEQ ID NO: 19)
[C]-DSEALHPLGMAVKSS.
```

The lymph node protocol was used to obtain 15 clones, which were screened to identify clones that bind to full-length Shh polypeptide, via flow cytometry, Western blotting and ELISA, as described in Example 1 above. 3 of the clones were selected to isolate 12 subclones each for screening, and a total of 36 subclones were screened.

Expression of full-length Shh polypeptide in transfected cells increased the percentage of cells labeled with the Shh antibodies produced by two of the subclones (2D9 and 2G4) identified after the screening, compared to the percentage of untransfected cells labeled by the same antibodies, as measured by flow cytometry (Table 3).

TABLE 3

Binding of C-terminal Shh antibodies to full-length Shh expressed in transfected cells

| DNA Construct used | C-term Antibody | | |
|---|---|---|---|
| | Commercial @ 1:50 | 1C11/2D9 @ 1:10 | 1C11/2G4 @ 1:10 |
| No transfection | 0.11% | 0.17% | 0.17% |
| +SHh Full-Length | 2.45% | 1.43% | 2.24% |

Antibodies produced by the two clones (2G4, 2D9) bound to purified Shh (FIG. 15A) as well as Shh expressed endogenously and/or exogenously in cells (FIG. 15B), as determined by Western blot.

Figure 15A:
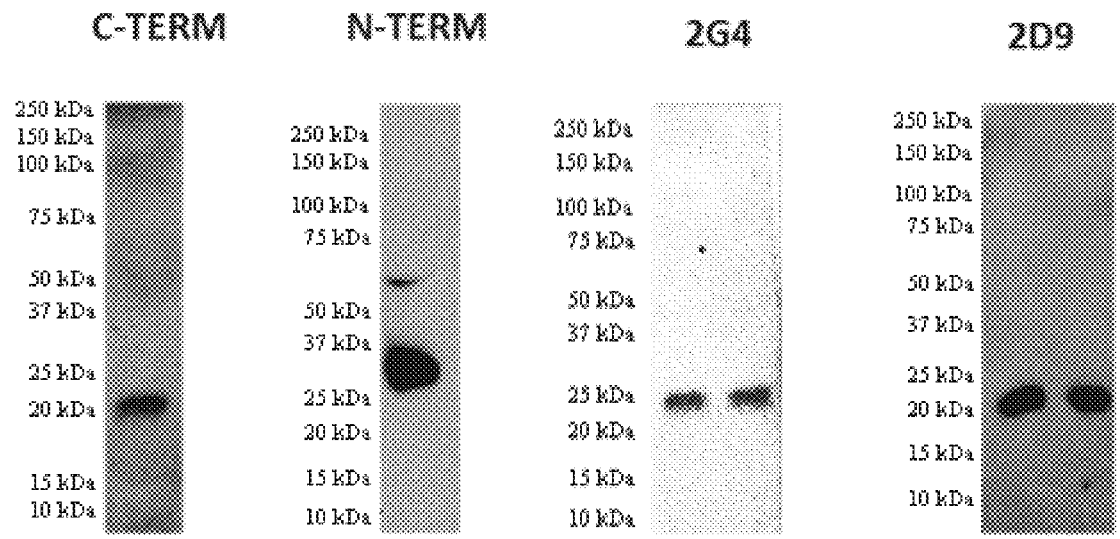
FIGS. 15A-15D are a collection of images and graphs showing binding of a C-terminal Shh antibody to full-length Shh and cleaved versions of Shh, according to embodiments of the present disclosure.
Figure 15B:
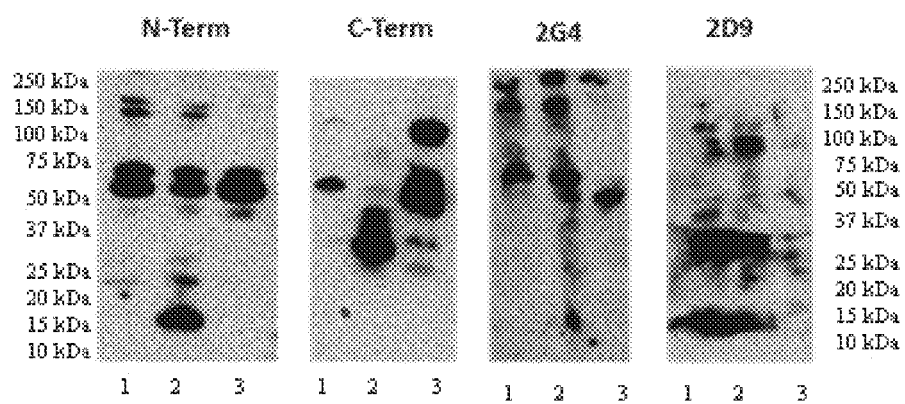

FIGS. 15A and 15B. Antibodies bind target SHh via Western blot. (FIG. 15A) Purified, recombinant human Shh (19.7 kDa, >98% purity by SDS-PAGE) was probed by the indicated antibodies. (FIG. 15B) Cell lysates from HEK-293T cells (PHX—Phoenix cells), with or without exogenous expression of full-length Shh, and A549 cells were probed with the antibodies produced by clones 2G4 and 2D9. Full-length Shh: ~50 kDa; N-terminal Shh: ~19 kDa; C-terminal Shh: ~25 kDa. Sample 2 was lysate from PHX cells transfected with full-length Shh DNA for about 24 hours. The exogenously expressed Shh appears to be cleaved into N-terminal and C-terminal Shh peptides. Both PHX cells and A549 cells endogenously express Shh.

The binding affinity of antibodies from clones and 2D9 were tested using a biosensor chip system (Octet®, Forte Bio, CA). Briefly, the antibody was covalently attached to the fiber-optic biosensor, and the attached antibody was exposed to increasing concentrations (28 nM, 63 nM, 83 nM, and 165 nM) of full-length recombinant Shh protein.

Figure 15C:
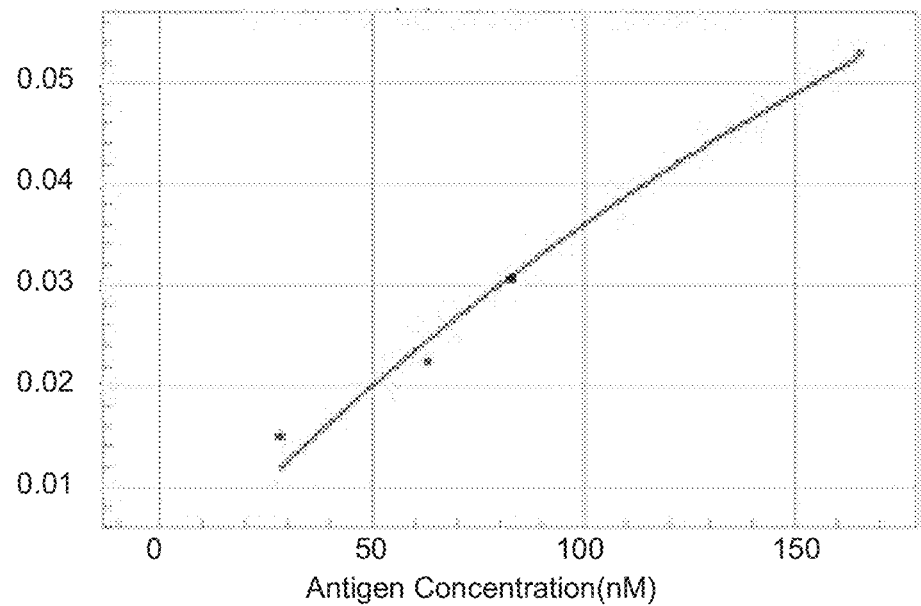
Figure 15D:
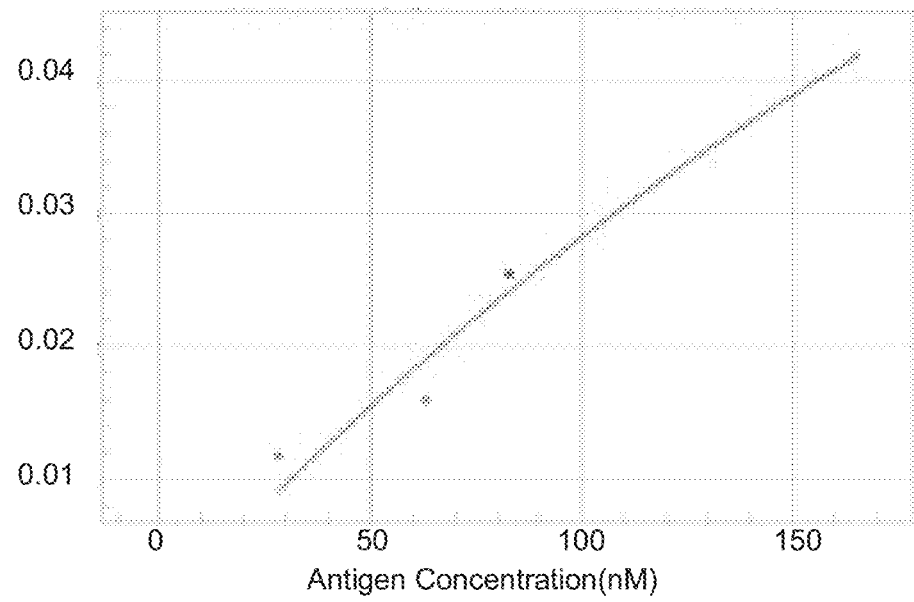

The binding affinity of antibodies from clone 2G4 for full-length recombinant Shh protein was 4.0 nM (FIG. 15C; $R^2$=0.98) and the binding affinity of antibodies from clone 2D9 for full-length recombinant Shh protein was 4.6 nM (FIG. 15D; $R^2$=0.97).

The amino acid sequence of the antibodies produced by clones 2G4 and 2D9 was deduced by sequencing RNA encoding the antibodies from individual cells (2G4: FIGS. 25A-25E; 2D9: FIGS. 26A-26E).

FIGS. 25A-25E. (FIG. 25A) RNA was extracted from 5 clones of 2G4, and sequences of cDNA encoding rearranged immunoglobulins were determined. (FIG. 25B) The nucleotide sequence of the heavy chain cDNA. (FIG. 25C) The amino acid sequence of the heavy chain deduced from the sequenced heavy chain cDNA. (FIG. 25D) The nucleotide sequence of the light chain cDNA. (FIG. 25E) The amino acid sequence of the light chain deduced from the sequenced heavy chain cDNA.

FIGS. 26A-26E. (FIG. 26A) RNA was extracted from 5 clones of 2D9, and sequences of cDNA encoding rearranged immunoglobulins were determined. (FIG. 26B) The nucleotide sequence of the heavy chain cDNA. (FIG. 26C) The amino acid sequence of the heavy chain deduced from the sequenced heavy chain cDNA. (FIG. 26D) The nucleotide sequence of the light chain cDNA. (FIG. 26E) The amino acid sequence of the light chain deduced from the sequenced heavy chain cDNA.

Example 3: Cytotoxicity of C-Terminal Sonic Hedgehog Antibodies, and Synergism with Cytotoxicity of a GLI Inhibitor The effect of the C-terminal Shh antibodies from clones 2G4 and 2D9 on the viability of A549 cells was determined. A549 cells were exposed to increasing concentrations of the C-terminal Shh antibodies (2G4, 2D9), or antibodies against the N-terminal portion of Shh protein (6D3, 2E1), and the effective dose ($ED_{50}$) was determined (assay 1: FIG. 16A; assay 2: FIG. 16B). For assay 1, the $ED_{50}$ were >700 µg/mL (2G4); >700 µg/mL (2D9); 189 µg/mL (6D3); and 128 µg/mL (2E1). For assay 2, the $ED_{50}$ were >700 µg/mL (2G4); >700 µg/mL (2D9); 224 µg/mL (6D3); and 128 µg/mL (2E1). Possibly due to the fact that very few cells express full-length Shh on the cell surface, the cytotoxic effect of the C-terminal Shh antibodies was not as potent as the cytotoxic effect of the N-terminal antibodies.

Next, the cytotoxicity of the C-terminal Shh antibodies was tested when the antibodies were used in conjunction with a small-molecule inhibitor of GLI zinc-finger transcription factor signaling, 249C (4-(5-chlorofuran-2-yl)-1,3-bis (2,4-difluorophenyl)-5-methyl-N-((4-methylmorpholin-2-yl)methyl)-4,5-dihydro-1H-pyrazole-5-carboxamide; Compound 135 above). A549 cells were exposed to varying concentrations of the C-terminal antibodies (2G4, 2D9) or the N-terminal antibodies (6D3, 2E1), in the presence or absence of a very low dose (40 nM) of 249C. (The $IC_{50}$ of 249C in A549 cells is ~70 nM.)

The GLI inhibitor, 249C, on its own had only a weak effect on cell viability, as expected; however, the presence of C-terminal Shh antibodies in addition to 249C greatly reduced the viability of A549 cells (Table 4). The synergistic effect between the C-terminal Shh antibodies and 249C was greater than that between the N-terminal Shh antibodies and 249C (compare, e.g., viability of A549 cells treated with antibody at 128 ng/mL+249C for the C-terminal Shh antibodies 2G4 and 2D9 with corresponding viability for the N-terminal Shh antibodies 6D3 and 2E1).

TABLE 4

Cell viability of A549 cells treated with Shh antibodies ±the GLI inhibitor, 249C

| | Treatment | | | | | | | |
|---|---|---|---|---|---|---|---|---|
| Ab conc. | C-term 2G4 | C-term 2G4 + 249C* | C-term 2D9 | C-term 2D9 + 249C* | N-term 6D3 | N-term 6D3 + 249C* | N-term 2E1 | N-term 2E1 + 249C* |
| 0 ng/mL | 100% | 88% | 100% | 92% | 100% | 92% | 100% | 93% |
| 32 ng/mL | 99% | 8% | 93% | 9% | 93% | 10% | 92% | 8% |
| 64 ng/mL | 95% | 11% | 65% | 18% | 65% | 19% | 81% | 15% |
| 128 ng/mL | 91% | 26% | 80% | 26% | 80% | 32% | 56% | 30% |

*249C added at 40 nM.

These results show that the C-terminal Shh antibodies derived from clones 2G4 and 2D9 act synergistically with a GLI inhibitor to reduce viability of non-small cell lung cancer cells.

Example 4: Effect of C-Terminal Sonic Hedgehog Antibody Administration on Tumors In Vivo The in vivo effect of the C-terminal Shh antibodies were tested using the A549 cell subcutaneous xenograft tumor model in mice, as described in Example 1. After xenograft formation, animals were intra-tumor injected with a C terminal Shh antibody (2G4 or 2D9; each at 158 µg), or a control solution, 3 times a week for about 3 weeks (at 2-3 day intervals). Tumor volume was determined, as described in Example 1, every 2 days. Weight and size of the excised tumor were determined after the antibody treatment. A portion of the excised tumor was sectioned for immunohistochemical analysis of Shh protein expression, and RNA was extracted from another portion of the excised tumor for analysis of Gli1 expression.

Figure 17A:
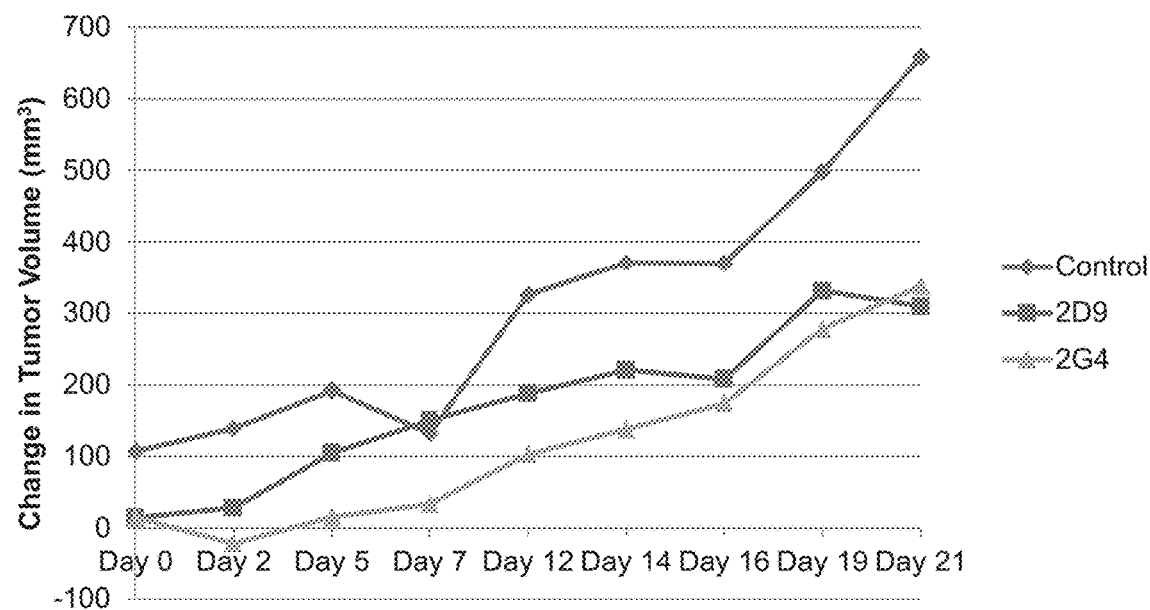
FIGS. 17A and 17B are a collection of graphs showing the effect of administering a C-terminal Shh antibody on tumor growth in vivo, according to embodiments of the present disclosure.
Figure 17B:
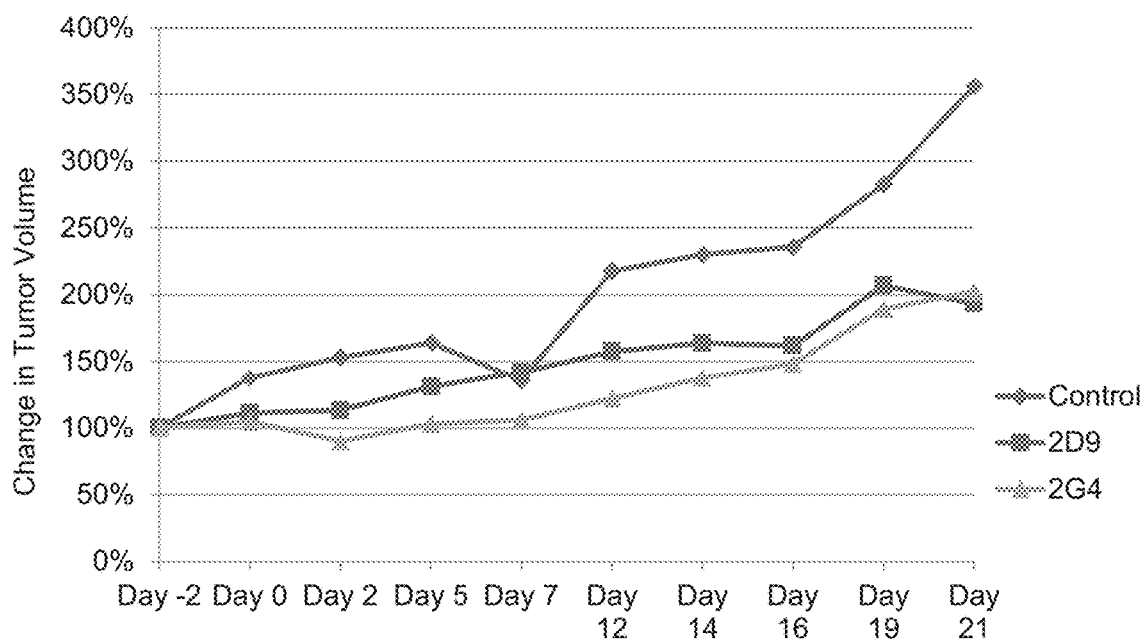

Intra-tumor administration of the C-terminal Shh antibodies significantly reduced the growth of treated tumor xenografts compared to the growth of tumor xenografts to which the antibodies were not administered (FIGS. 17A and 17B; and Tables 5 and 6).

TABLE 5

Average change in tumor volume (mm³)

|  | Control* | C-term Antibody 2D9 | 2G4 |
| --- | --- | --- | --- |
| Day 0 | 107 | 14.18 | 14.6 |
| Day 2 | 138.9 | 28.14 | −21.7 |
| Day 5 | 191.7 | 104.6 | 15.3 |
| Day 7 | 131.9 | 150.4 | 33.5 |
| Day 12 | 325.9 | 187.6 | 103 |
| Day 14 | 371.3 | 220.5 | 138.2 |
| Day 16 | 370.4 | 207.9 | 174.04 |
| Day 19 | 498.2 | 331.3 | 277.7 |
| Day 21 | 659 | 309.6 | 337.8 |
| T-test |  | 0.076038 | 0.021575 |

*control values indicate the measured tumor volume, in mm³

TABLE 6

Average % change in tumor volume, relative to day −2

|  | Control | C-term Antibody 2D9 | 2G4 |
| --- | --- | --- | --- |
| Day −2 | 100% | 100% | 100% |
| Day 0 | 137.50% | 111.10% | 104.50% |
| Day 2 | 153.30% | 113.30% | 90.20% |
| Day 5 | 164.00% | 131% | 103.10% |
| Day 7 | 135.80% | 141.70% | 105.80% |
| Day 12 | 217.70% | 157.70% | 121.90% |
| Day 14 | 230% | 163.90% | 137.70% |
| Day 16 | 236% | 162% | 148% |
| Day 19 | 282% | 206.90% | 189.60% |
| Day 21 | 356.50% | 193.60% | 202.40% |
| T-test |  | 0.066179 | 0.019543 |

Figure 18:
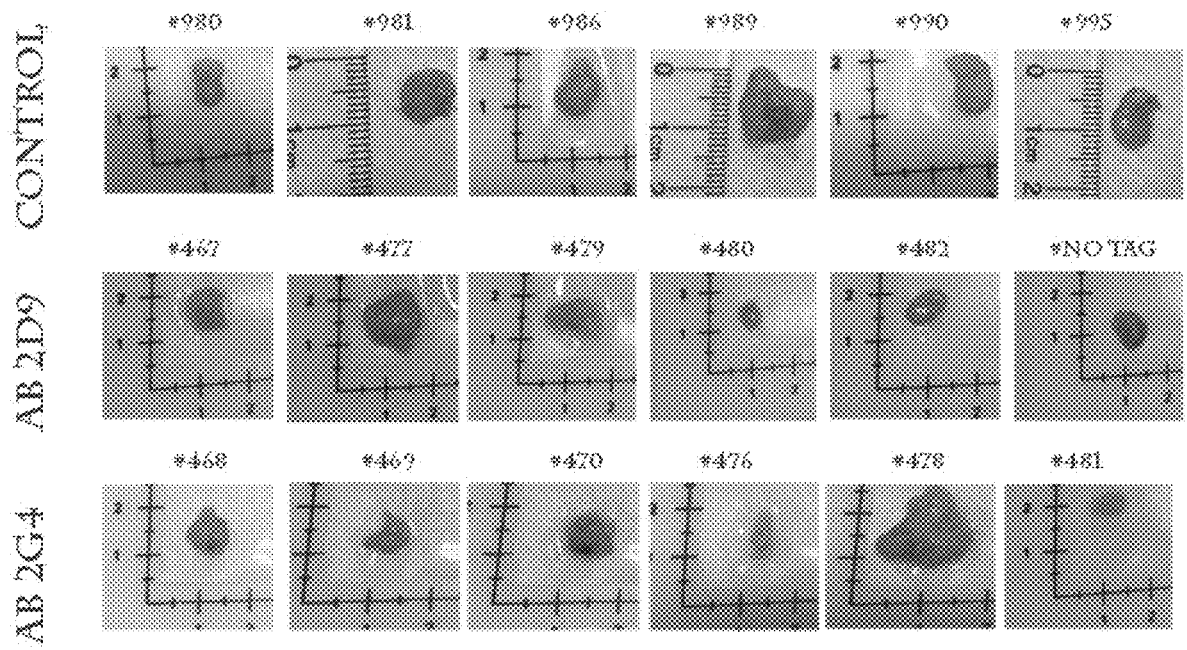
FIG. 18 is a collection of images showing the size of tumors after administering a C-terminal Shh antibody in vivo, according to embodiments of the present disclosure.
Figure 19:
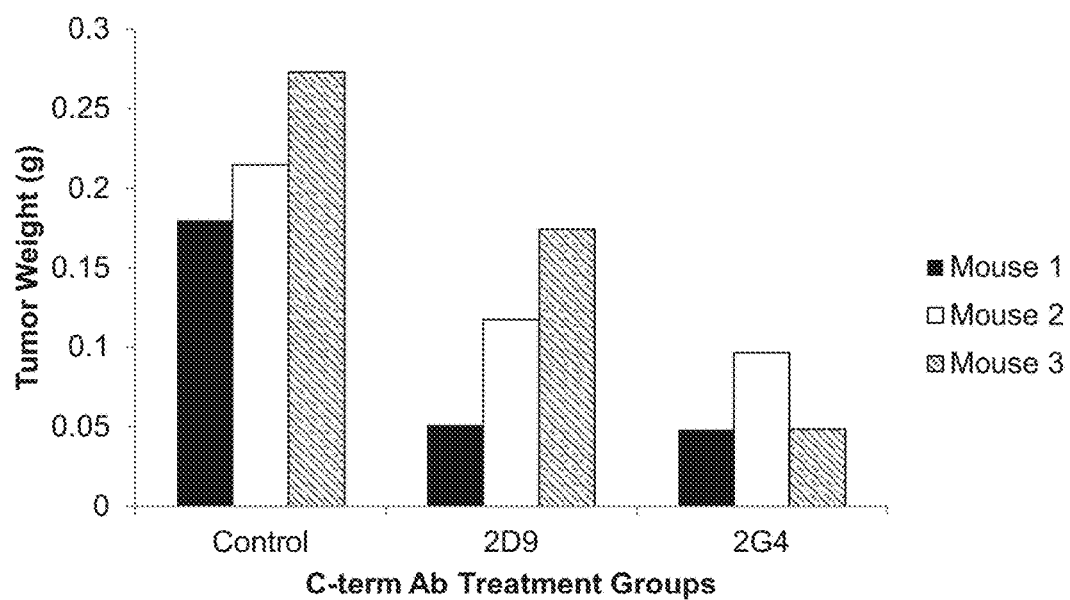
FIG. 19 is a graph showing weight of a tumor after administering a C-terminal Shh antibody in vivo, according to embodiments of the present disclosure.

After antibody treatment, the size of the excised tumor xenograft was smaller on average for an antibody-treated animal, compared to a control animal (FIG. 18). The weight of the excised tumor xenograft was on average smaller for the antibody-treated animals, compared to control animals (FIG. 19; and Table 7).

TABLE 7

Weight of tumor after treatment

|  |  | C-term Antibody |  |  |  |
| --- | --- | --- | --- | --- | --- |
| Control |  | 2D9 |  | 2G4 |  |
| #980 | 0.1798 | #480 | 0.0512 | #481 | 0.048 |
| #986 | 0.2146 | #482 | 0.1172 | #469 | 0.0966 |
| #990 | 0.2727 | No tag | 0.1742 | #476 | 0.0486 |
| AVG | 0.222367 |  | 0.1142 |  | 0.0644 |
| T-test |  |  | 0.072737 |  | 0.007429 |

Figure 20:
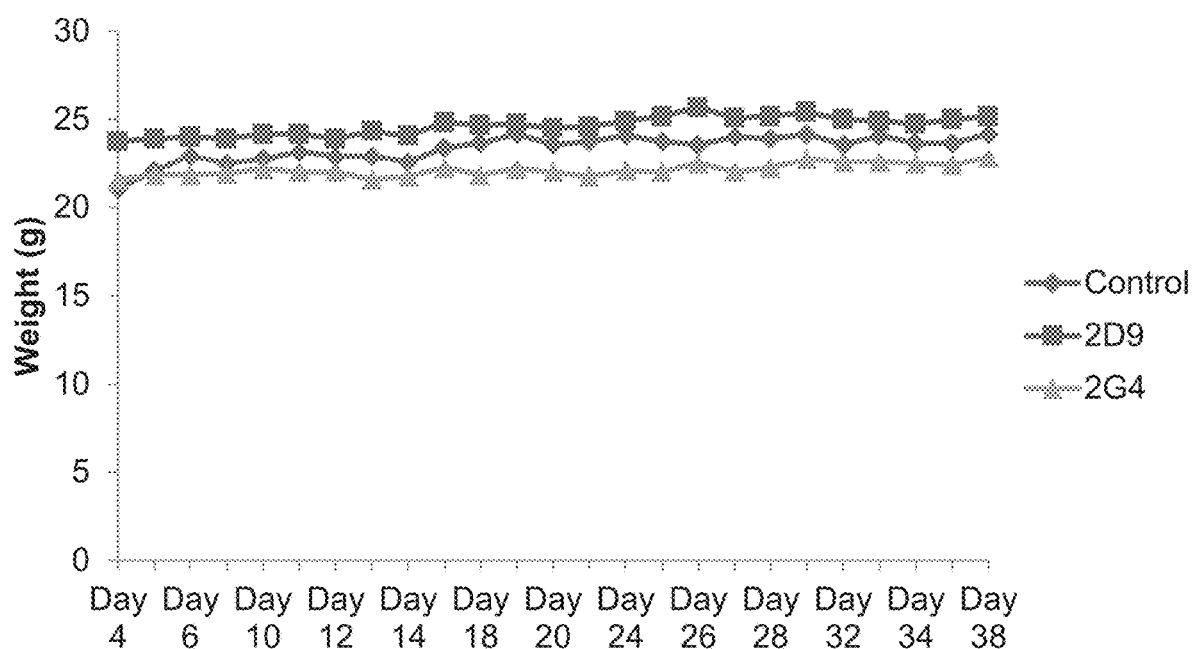
FIG. 20 is a graph showing body weight during administration of a C-terminal Shh antibody in vivo, according to embodiments of the present disclosure.

Antibody treatment did not have an effect on the average body weight of the animals (FIG. 20).

These results indicate that the C-terminal Shh antibodies derived from clones 2G4 and 2D9 reduce in vivo growth of tumors derived from non-small cell lung cancer cells.

To understand the effect of administering the C-terminal Shh antibodies on the tumor xenograft, the excised tumors were probed for expression of Shh protein, and RNA expression of a downstream target of Shh signaling, Gli1. Immunostaining the tumor xenografts excised with the C-terminal Shh antibodies after antibody treatment showed that tumor samples treated with the antibody (2G4: FIGS. 21D-21F; 2D9: FIGS. 21G-21I) had fewer cells expressing Shh protein compared to control tumor samples (FIGS. 21A-21C) that were not treated with the antibody. Furthermore, expression of Gli1 RNA was reduced in antibody-treated tumors compared to control (Table 8 in FIG. 22).

Example 5: Membrane-Bound Full-Length Sonic Hedgehog Identifies Cancer Stem Cells in Human Non-Small Cell Lung Cancer Materials and Methods
NSCLC Cell Lines and Culture Conditions All 12 NSCLC cell lines (A549, H322, H441, H460, H522, H838, H1650, H1975, H2228, HCC2935, H1703, H2170) were purchased from American Type Culture Collection (ATCC). Cells were cultured in RPMI 1640, supplemented with 10% fetal bovine serum and 2% antibiotics (Penicillin-Streptomycin). Cells were collected after trypsinization and resuspended in PBS for further analysis. For serum-free medium culture conditions, sorted cells were seeded in non-tissue culture 96-well plates (500 cells per well) and cultured in DMEM-F12 medium (Corning Cellgro), supplemented with basic fibroblast growth factor (bFGF, Invitrogen, 10 ng/ml), epidermal growth factor (EGF, Invitrogen, 20 ng/ml) and insulin (Sigma, 5 µg/ml). Fresh medium with growth factors and insulin was added every 48 h. Spheroid formation (appearance of floating cell aggregates) was monitored daily.

Transfection Assays

For transfection assays, A549 and H838 cell lines were used. Transient transfection of the Shh gene was performed with a pCMV-Shh plasmid (Origene). For stable transfected cell lines, N-term peptide hemagglutinin (HA)-tagged Shh (1-197aa), C-term peptide FLAG-tagged Shh (198-462aa), double-tagged wild type Shh (N-HA and C-FLAG) and double-tagged cleavage mutant Shh C198A (N-HA and C-FLAG) were used, all in pCMV-Pig vectors. Transfection assays were performed with Lipofectamine 2000 (Life Technologies), according to the manufacturer's instructions.

Fresh Human Tumor Samples

Fresh tumor samples were collected directly in the operating room (Surgery Department, University of California, San Francisco) when there was signed pre-operative consent from the patient. Samples were then processed on the same day. Cell dissociation was performed with collagenase type IV (2 mg/ml, 30 min, Sigma), then completed with mechanical dissociation (syringe). Cells were resuspended in PBS for further analysis. Clinical follow-up data were collected prospectively through a database (last time-point: Jul. 15, 2015).

Shh Antibody Production

Sp2/0-Ag14 mice were injected with both Shh 247-264 AA and Shh 448-462 AA peptides of the human Sonic Hedgehog protein (both are part of the C-term fragment of Shh; C-term: 198-462 AA) to mount an immune response. The free peptides were used to screen serum-positive samples via ELISA and the best animals were taken to the fusion phase. Approximately 51 antibody clones/sub-clones producing antibodies raised against the C-terminal Shh peptides were screened to identify clones that bind to full-length Shh polypeptide, as follows. First, expression of full-length Shh polypeptide in transfected cells increased the percentage of cells labeled with the Shh antibodies produced by two sub-clones (2D9 and 2G4) identified after the screening, compared to the percentage of untransfected cells labeled by the same antibodies, as measured by flow cytometry. Next, these antibodies produced by the two sub-clones (2G4, 2D9) were screened by Shh expressed endogenously and/or exogenously in cells, as determined by Western blot. Once 2G4 and 2D9 were chosen, a large-scale purification of the antibodies ensued and purified antibodies were employed for in vitro and in vivo experiments.

Flow Cytometry and FACS

The mouse Shh-C-terminal antibody (mentioned above) was used for flow cytometry and FACS (1:40). The secondary antibody was a donkey anti-mouse FITC-linked antibody (ab97029, 1:100, Abcam). For cell analysis after treatment assays (chemotherapy or GDC0449), a marker for dead cells (SytoxRed®, Invitrogen) was also used. For fresh human samples, an anti-CD45 APC-linked antibody (ab28106, 1:100, Abcam) was added, and a marker for dead cells (SytoxRed®, Invitrogen). For staining of stable transfected cell lines, a mouse anti-HA antibody (Abcam, 1:100) and a rabbit anti-FLAG antibody (Cell Signaling; 1:400) were used. Corresponding secondary antibodies were donkey anti-mouse AlexaFluor647 (Invitrogen, 1:1 000) and donkey anti-rabbit AlexFluor594 (Invitrogen, 1:1 000). Flow cytometry analyses were performed on an AccuriC6 flow cytometer (BD Biosciences), and FACS on a FACSAria II (BD Biosciences). Flow analyses were carried out with at least 200,000 cells, and each test was performed in triplicate. For all experiments, a negative control of cells processed without primary antibody was used. Sorted cells (Shh+ and Shh− cells) were collected in fresh media, and seeded in culture plates or frozen at −80° C. for further analyses.

Immunofluorescence

Cells were fixed in 70% ice-cold methanol for 20 min and blocked in 5% BSA for 1 hour at room temp. For staining of commercial NSCLC cell lines, the mouse Shh-C-terminal antibody (mentioned above) was used as the primary antibody and donkey anti-mouse FITC-linked antibody (ab97029, 1:100, Abcam) as the corresponding secondary antibody. For staining of non-permeabilized cells, Shh− sorted A549 cells were fixed in 4% paraformaldehyde for 20 minutes and blocked in 5% BSA for 1-2 hours at room temperature. Rabbit anti-Shh (Abcam, 1:200) and lipophilic/membrane-specific Vybrant® CM-DiI Cell-Labeling Solution (ThermoFisher, 1:200) were used according to the manufacturer's recommendations. A FITC-conjugated anti-rabbit secondary antibody (Abcam, 1:200) and VECTASHIELD DAPI (Vector Laboratories) mounting medium were used to stain cells prior to imaging. For staining of transfected cell lines, mouse anti-HA antibody (Abcam, 1:100) and rabbit anti-FLAG antibody (Cell Signaling; 1:400) were used. Corresponding secondary antibodies were donkey anti-mouse AlexaFluor647 (Invitrogen, 1:1,000) and donkey anti-rabbit AlexFluor594 (Invitrogen, 1:1,000) antibodies. Three representative images per well were captured using an LSM 780 confocal microscope at 6300×. Background was subtracted by comparing images only incubated with the secondary antibodies and analyzed using Fiji software. The experiment was performed three separate times and representative images are presented.

Proliferation and Migration Assays

MTS proliferation assays were performed (CellTiterGlo 96, Promega) according to the manufacturer's instructions. The $IC_{50}$ for cisplatin and docetaxel was calculated for each cell line at 72 hours in triplicates.

Wound healing assays were performed to study cell migration. Monolayers of cells were cultured, scratched, treated with media containing proteins and/or drugs at different concentrations: Shh protein, DMSO, and GDC0449-recorded at 0, 24, 72 and 96 hours after treatment.

Drugs

Cisplatin was purchased from Sigma and reconstituted in PBS (2 g/L). Docetaxel was purchased from Tocris Bioscience and reconstituted in DMSO (5 g/L stock dilution at −20° C.; further dilution in fresh culture medium) for in vitro assays, or reconstituted in ethanol/polysorbate 80 (1:1; 5 g/L stock dilution at −20° C.; further dilution in PBS) for in vivo assays. GDC0449 was purchased from Selleck Chemicals and reconstituted in DMSO (30 mM stock dilution). Shh human recombinant protein was obtained from eBioscience and used at 1,200 ng/mL.

Western Blot

Proteins were extracted with M-PER Mammalian Protein Extraction Reagent (Thermo Scientific), according to manufacturer's instructions. Western Blot was then processed following standard protocols. Western Blot for membrane proteins was processed using the Mem-PER™ Plus Membrane Protein Extraction Kit (Thermo Scientific). A rabbit anti-C-terminal Shh antibody (ab53281, Abcam, 1:1 000) was used. As a secondary antibody, a donkey anti-rabbit HRP-conjugated antibody (ab16284, Abcam, 1:1 000) was used. For immunoblotting of supernatants, Shh-sorted A549 cells were cultured for 3 days and the supernatants from Shh− and Shh+ cells were concentrated using Centrifugal Filter Units (Millipore) at 14,000 g for 10 minutes at 4° C. A Bradford assay was used to quantify concentrated supernatants for Western blot analysis. Sonic Hedgehog (Abcam, 1:1,000) and a loading control for secreted proteins, MMP2 (OneWorldLab, 1:1,000) antibodies were used to probe blots.

Quantitative RT-PCR and ddPCR

RNA from unsorted cells was extracted with Qiagen's RNeasy Mini kit (Qiagen) according to the manufacturer's instructions. RNA from sorted cells was extracted with an Arcturus PicoPure RNA Isolation Kit (Life Technologies). cDNA was then synthesized with an iScript cDNA Synthesis Kit (Bio-Rad) according to the manufacturer's instructions. Commercial primers for the Shh gene were obtained from Origene. Quantitative RT-PCR (qRT-PCR) was performed on an Applied Biosystems 7900HT Fast Real-Time PCR System, in triplicate for each sample. Gene expression analysis was calculated with the delta-deltaCT method normalized to an endogenous control (18S gene). For ddPCR, droplet creation, PCR and data analysis were performed according to the manufacturer's instructions (BioRad, QX100 ddPCR System, Quantasoft software). Results of ddPCR were expressed as FAM concentrations (copies/0).

Microarray

Total RNA (about 25 ng) was amplified into cRNA and made into cDNA using the Ambion WT Expression Kit (Life Technologies) or the Ovation Pico WTA System V2 kit (NuGen). The cDNA (5.5 µg for the Ambion WT Expression kit, 2.5 ug for the Ovation Pico WTA System V2 kit) was then fragmented using the Affymetrix GeneChip WT Terminal Labeling kit (Affymetrix, Santa Clara, Calif., USA) and confirmed by running 1 µl of each sample on the Agilent Bioanalyzer using the RNA 6,000 kit (Agilent Technologies, Santa Clara, Calif., USA). The fragmented cDNA was labeled using the Affymetrix GeneChip WT Terminal Labeling kit and added into the hybridization cocktail that was prepared according to the protocol included in the Affymetrix GeneTitan Hybridization Wash and Stain kit (Affymetrix). The samples were finally loaded into the Affymetrix GeneTitan MC for hybridization, washing and scanning.

Mice

For xenograft formation, 5-10 week-old female nude mice, were injected subcutaneously (SC) with 10 million A549 cells in the dorsal area in a volume of 100 µl. For SC inoculation of sorted cells, 1,500 cells of A549 Shh+ or Shh− cells were injected in a volume of 150 µl. For intravenous injection of sorted cells, 1,000 cells of A549 Shh+ or Shh− cells were injected in the tail vein. For the in vivo treatment assay, after xenograft formation, animals were injected intravenously with cisplatin (10 mg/kg, weekly), docetaxel (10 mg/kg, twice a week) or vehicle, and intraperitoneally with GDC0449 (20 mg/kg, daily) or vehicle. Each group consisted of 4-5 mice. Tumor size was determined twice a week, and tumor volumes were calculated using width (x) and length (y) ($x^2y/2$, where x<y). Tumors were collected after mice were euthanized, and cell dissociation was performed in the same way as for fresh human samples as described above. Flow cytometry and FACS were done as described above. All animals were cared for in accordance with guidelines from the Institutional Animal Care and Use Committee at the University of California, San Francisco (UCSF).

Statistical Analyses

Distribution of variables was analyzed by the Shapiro-Wilk test. For normally distributed variables, results were expressed as mean (±SD), and comparison between 2 populations was performed by a Student's t-test. For variables that were not normally distributed, results were expressed as a median (interquartile range IQR), and comparison between 2 populations was performed by a non-parametric Mann-Whitney test. For qRT-PCR data analyses, a Student's t-test was used. For ddPCR results, Poisson law was used, with Poisson confidence intervals. Time-to-progression was calculated with the Kaplan-Meyer log-rank test. For each test, results were considered as significant if $p<0.05$. Statistical analyses were performed using Xlstat 2.01 software (Addinsoft).

Results

Presence of NSCLC Shh+ Cells In Vitro

Figure 27A:
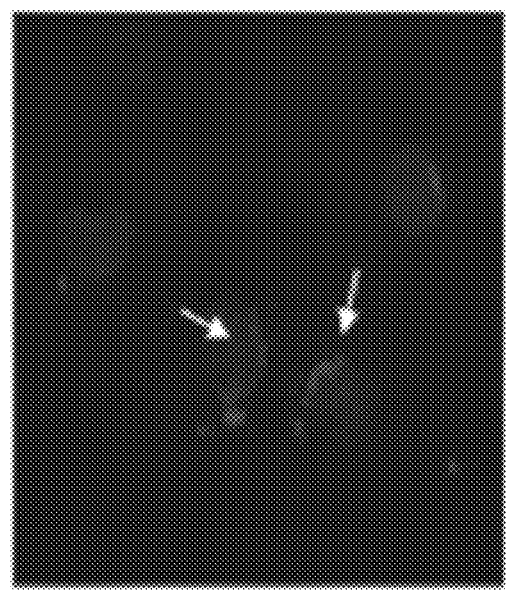
FIGS. 27A-27G show a collection of images showing that Shh+ cells were Shh-producing cells and represented a rare population in vitro.
Figure 27B:
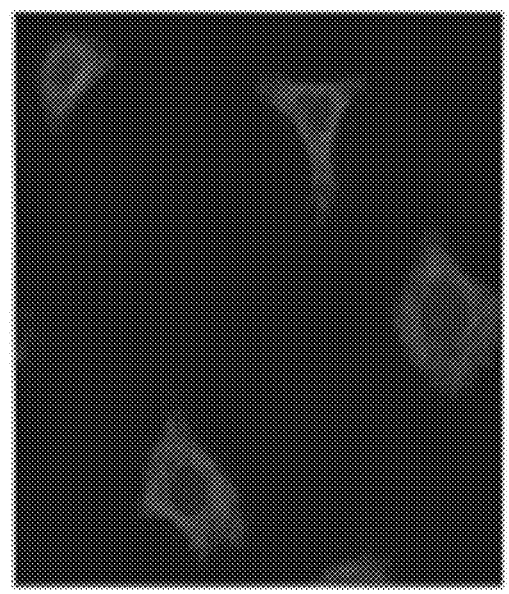
Figure 27C:
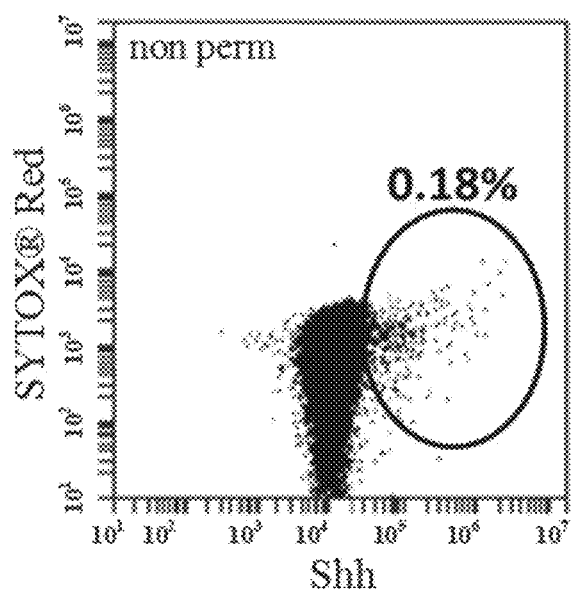
Figure 27D:
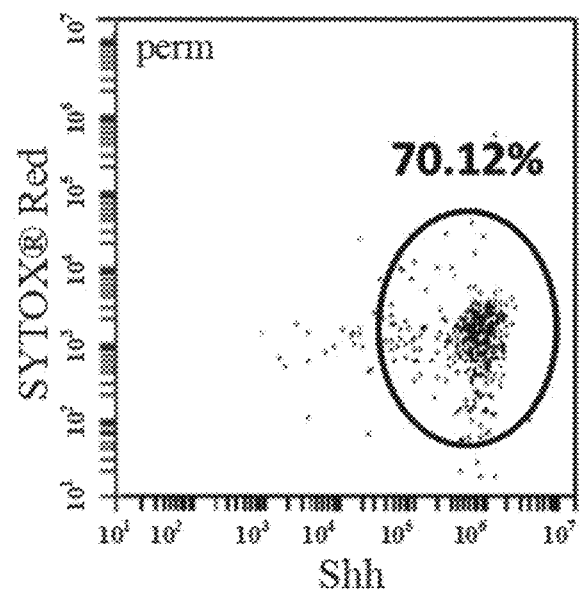
Figure 27E:
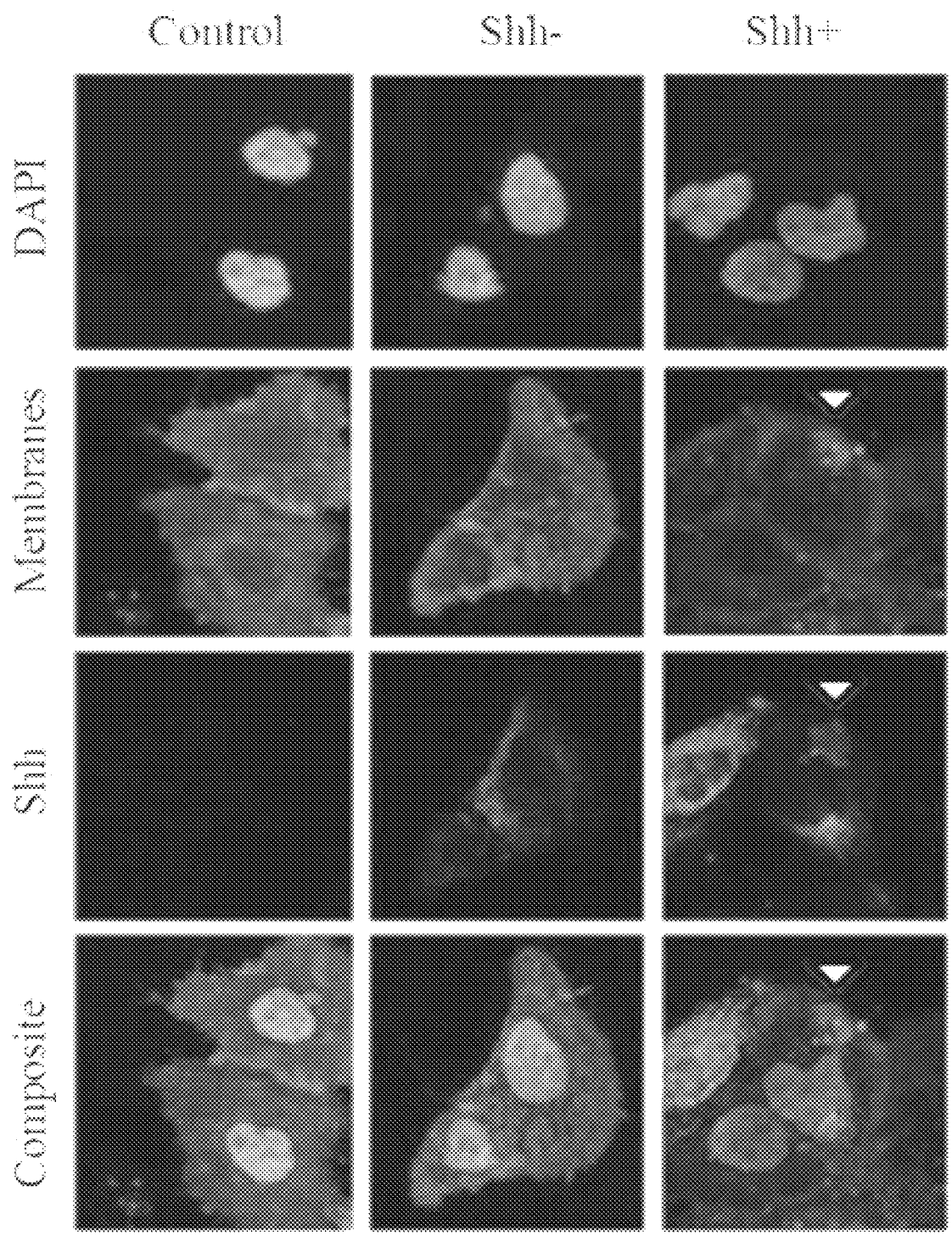
Figure 27F:
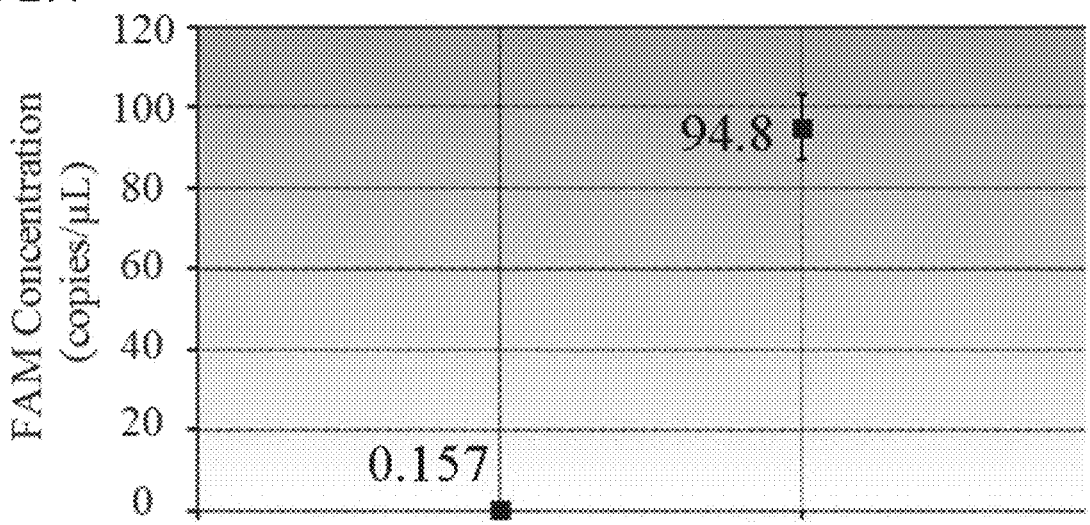
Figure 27G:
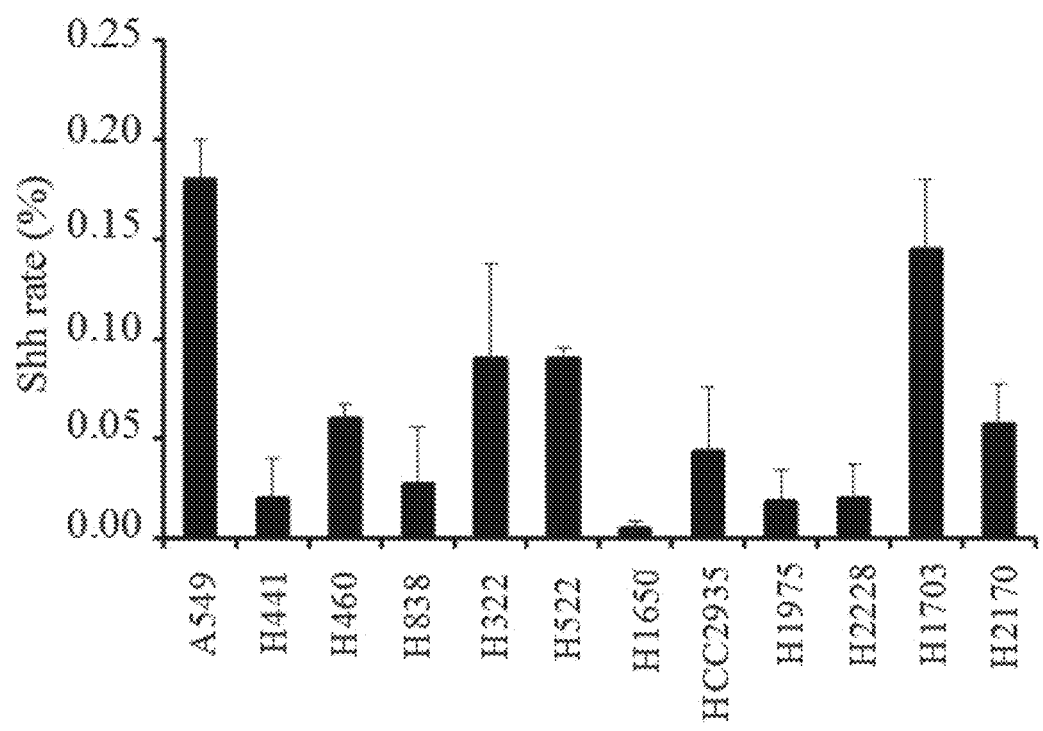

A peptide antibody against the C-terminal of Shh was developed and tested for its specificity with and without permeabilization on NSCLC cells. Immunofluorescence (IF) analysis showed that although only a very small number of cells stained positive (Shh+) without permeabilization, (FIG. 27A) most were positive with permeabilization (FIG. 27B). Flow cytometry analysis corroborated these findings and less than 0.20% (FIG. 27C) and more than 70% (FIG. 27D) of the cells were observed to be positive without and with permeabilization respectively. To better characterize these Shh+ cells by IF and flow cytometry, sorting via Fluorescence Activated Cell Sorting (FACS) without membrane permeabilization was performed. IF analysis on sorted cells confirmed that only Shh+ cells had a Shh membranous staining (indicated by arrows), whereas Shh− cells had low/no staining (FIG. 27E). Digital droplet PCR (ddPCR) analysis in sorted cells (Shh+ and Shh− cells) showed that Shh+ cells were Shh-producing cells. $Shh^+$ cells expressing high levels of the Shh gene [FAM concentration=94.8 copies/µl (Poisson confidence interval: 87.1-103)] were observed, whereas $Shh^−$ cells did not express the Shh gene [FAM concentration=0.157 copies/µl (Poisson confidence interval: 0.01-0.75)] (FIG. 27F). Next, 12 NSCLC cell lines (10 adenocarcinoma cell lines: A549, H322, H441, H460, H522, H838, H1650, H1975, H2228, HCC2935; 2 squamous cell lines: H1703, H2170) were screened by flow cytometry on non-permeabilized cells. 0.06% (±0.05%) of the cells were found to be Shh positive via flow cytometry analysis (FIG. 27G). The highest rate was for A549 at 0.18% (±0.02%).

Secretion of Full-Length Shh Protein by $Shh^+$ Cells

Figure 28A:
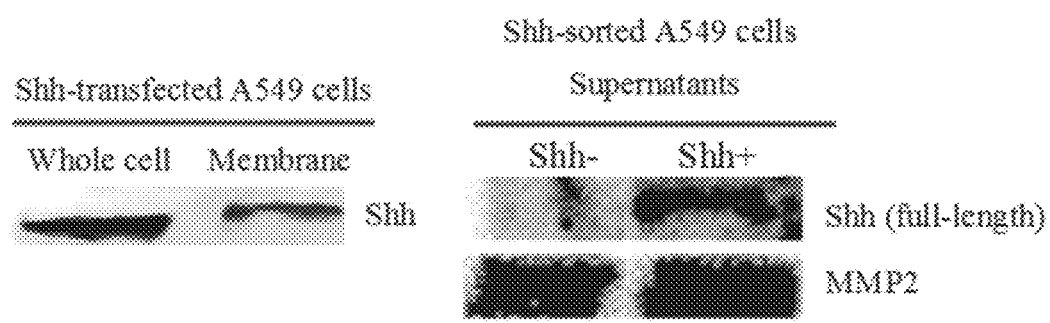
FIGS. 28A-28E show a collection of images showing that Shh+ cells produced Shh full-length protein.
Figure 28B:
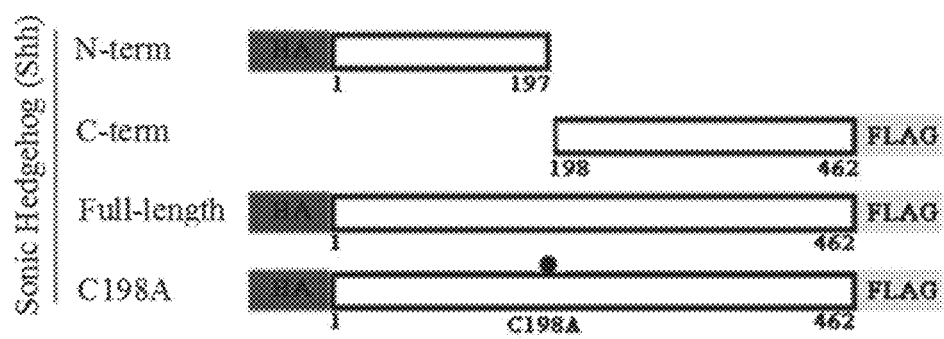
Figure 28C:
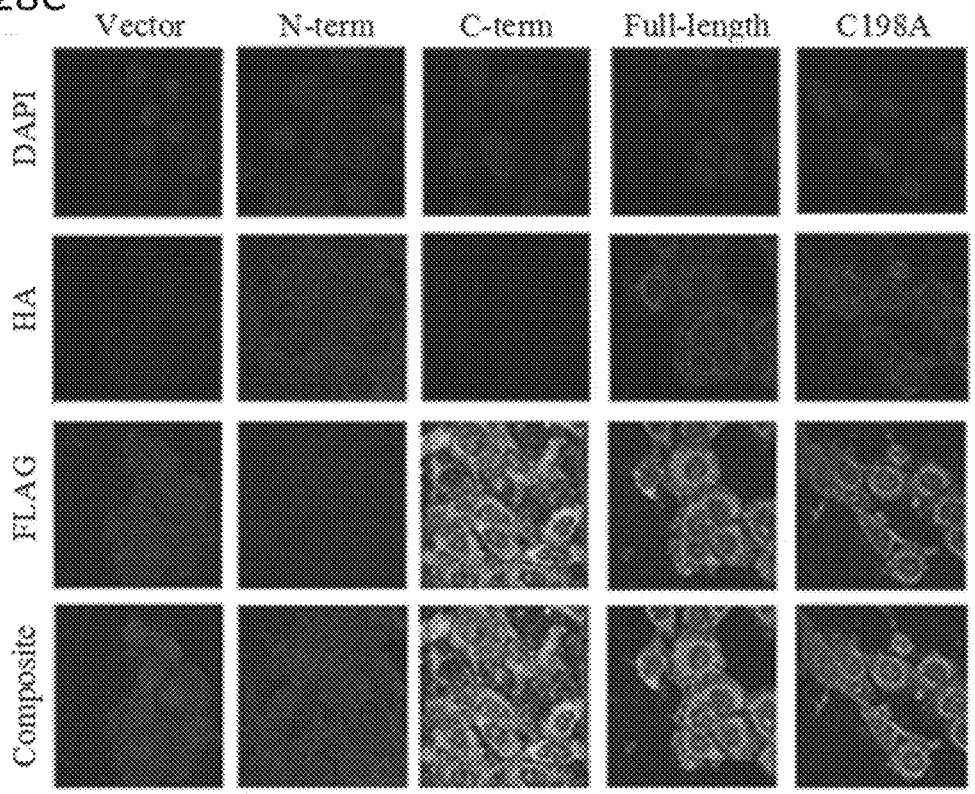
Figure 28D:
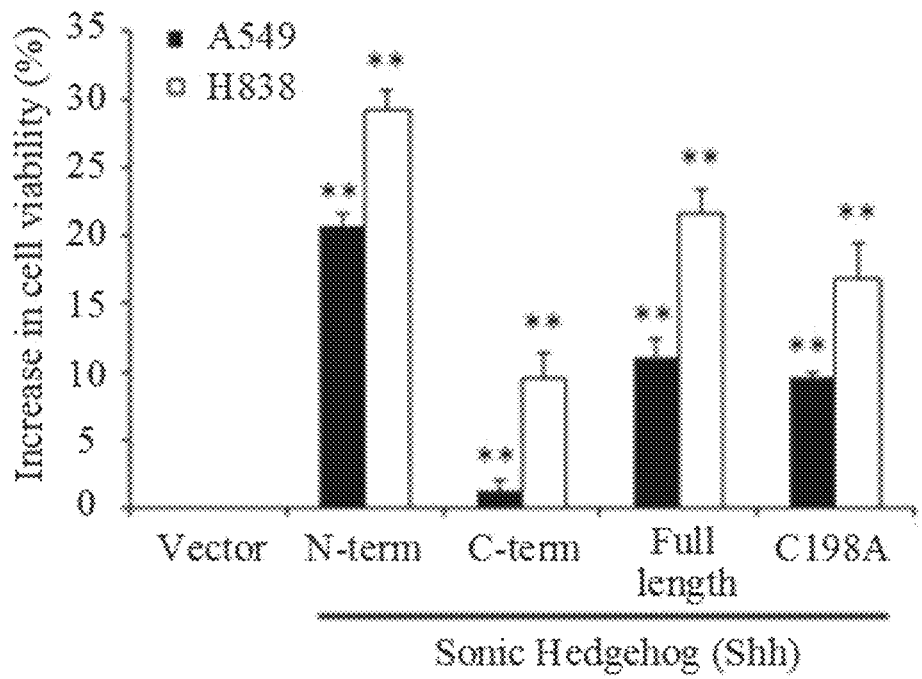
Figure 28E:
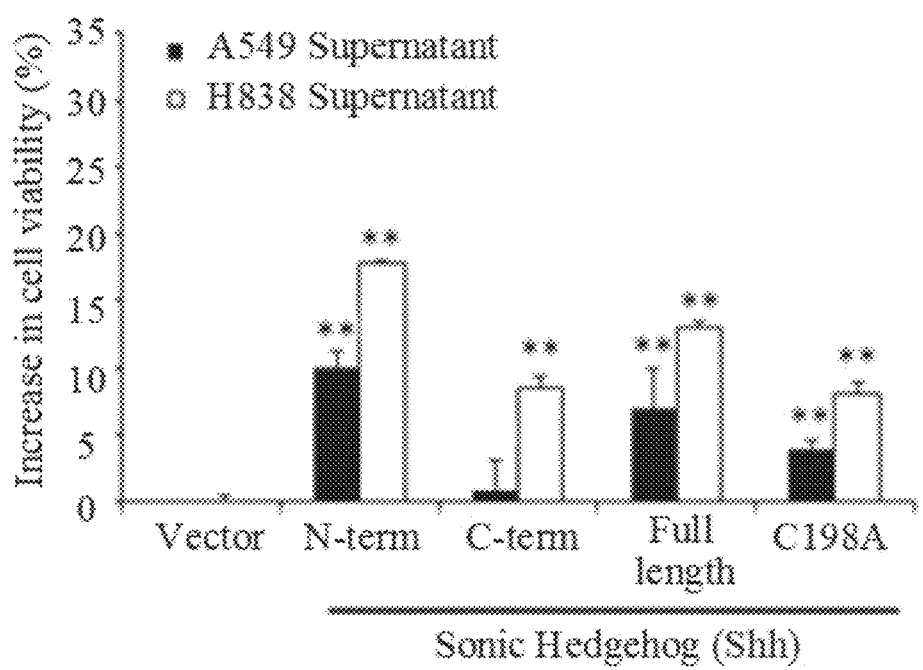
Figure 29A:
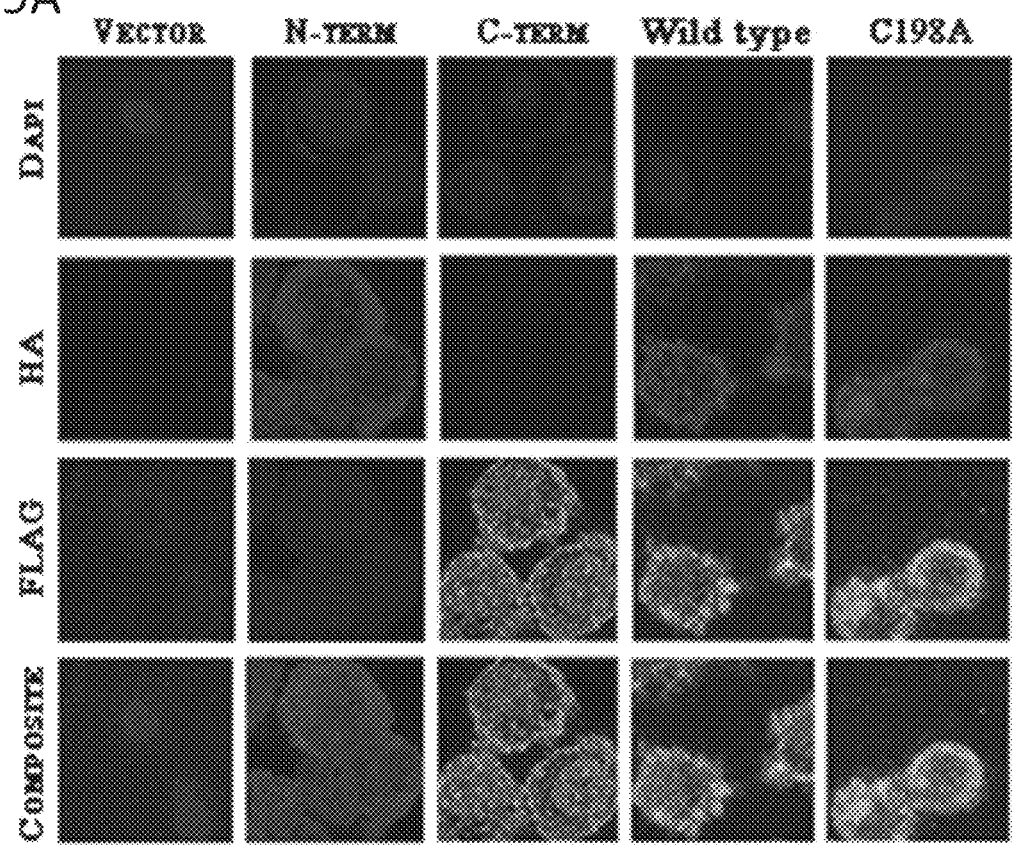
FIG. 29A shows immunofluorescence analysis of A549 cells showing cytosolic and membrane staining of N-term, C-term, wild-type Shh and C198A Shh constructs probed for the presence of HA (red) and FLAG (yellow).
Figure 29B:
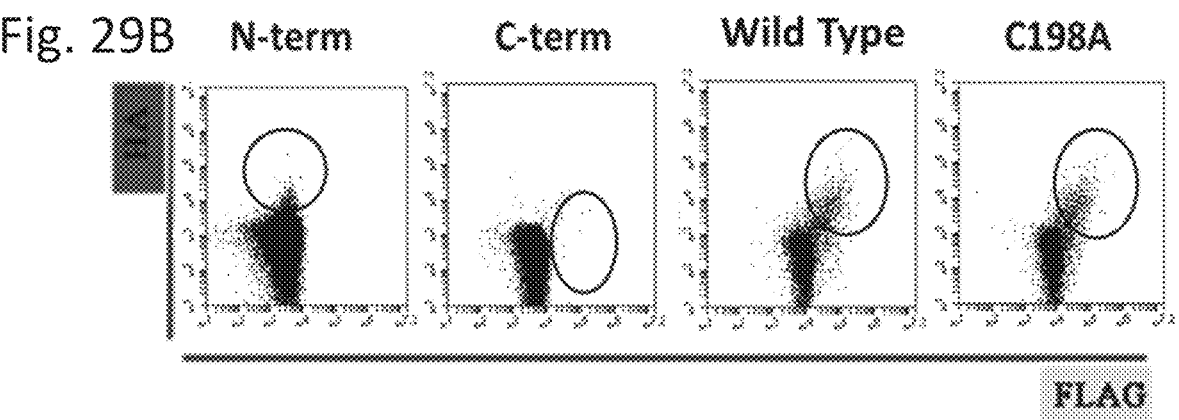
FIG. 29B shows flow analysis showing positive double-staining in H838 cells for HA and FLAG in cells bearing wild-type and C198A constructs and single staining for N-term and C-term.

To characterize the localization of the Shh protein recognized by the C-terminal Shh antibody, NSCLC cell line A549 transiently transfected with the Shh gene was used. Western blotting (WB) indicated the presence of the full-length Shh protein, both in the cytosol and on the membrane (FIG. 28A) recognized by the C-terminal Shh antibody. Moreover, WB analysis on the culture medium (supernatant) of non-transfected A549 sorted cells (3 days after sorting) showed the presence of the full-length Shh protein in the supernatant only for $Shh^+$ cells, but not for $Shh^−$ cells indicating that they did not secrete the protein (MMP2 served as a loading control). To further characterize the localization and functional significance of the Shh protein and its cleaved products, retrovirus-mediated gene transfer was used to stably express several versions of the Shh gene in A549 and H838 cells. N-term peptide hemagglutinin (HA)-tagged Shh (1-197aa), C-term peptide FLAG-tagged Shh (198-462aa), double-tagged wild-type Shh (N-HA and C-FLAG) and double-tagged cleavage mutant Shh C198A (N-HA and C-FLAG) were used as shown in FIG. 28B. Next peptide expression and membrane/cytosolic localization of N-term, C-term, wild-type and C198A mutant Shh were confirmed via immunofluorescence in both A549 (FIG. 29A) and H838 cells (FIG. 28C) with antibodies directed at HA and FLAG respectively. Flow analysis revealed positive double staining in H838 cells for HA and FLAG in cells bearing wild-type and C198A constructs and single staining for N-term and C-term (FIG. 29B). Functional analyses with stably expressing N-term Shh in A549 and H838 cells resulted in a 20-30% growth advantage compared with the vector control (FIG. 28D). Moreover, the wild-type and C198A-expressing lines also showed significant increases in viability (10-20% and 10-15%, respectively) relative to the vector. The C-term expressing lines only showed a 1-10% increase. Analogous results were observed when the supernatants from cells expressing (vector, N-term, C-term, wild-type, C198A) were applied to their respective parental cell lines and presented a percentage increase relative to the vector control (FIG. 28E).

Paracrine Effect of Shh+ Cells on Other Cancer Cells

To better understand the properties of $Shh^+$ and $Shh^−$ populations, functional analyses on sorted cells were performed. The total number of cells after 7 days in culture was 4 times higher for $Shh^+$ cells than for the $Shh^−$ cells (FIG.

Figure 30A:
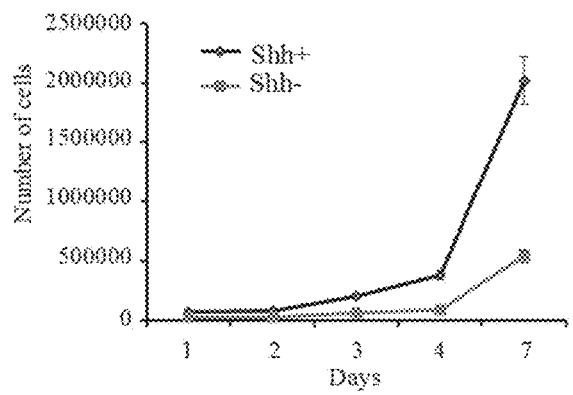
FIGS. 30A-30E show a collection of images showing that Shh+ cells had a paracrine effect on Shh− cells.
Figure 30B:
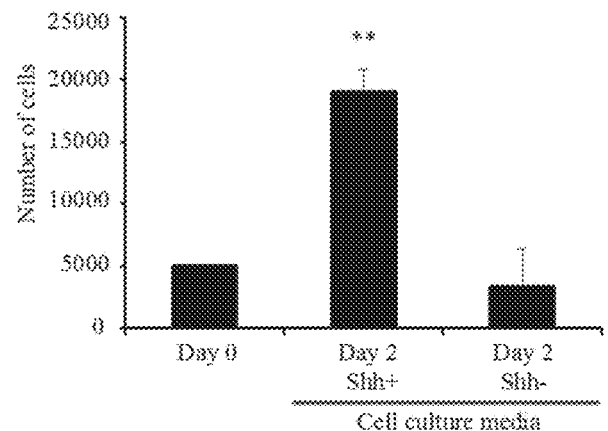
Figure 30C:
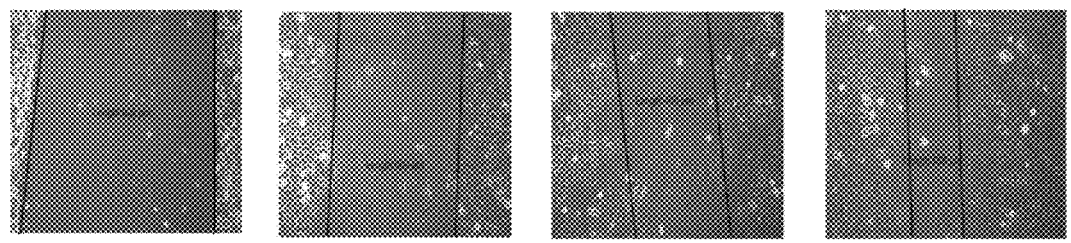
Figure 30D:
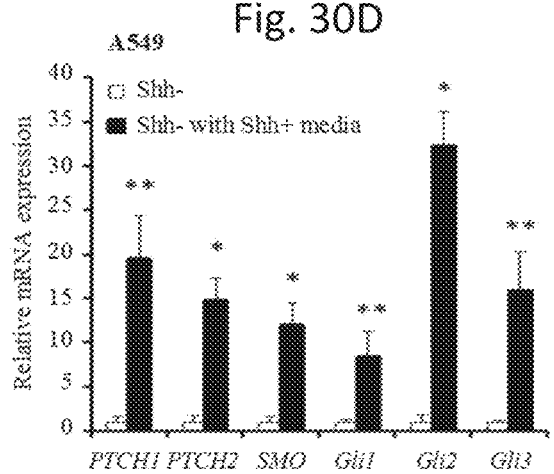
Figure 30E:
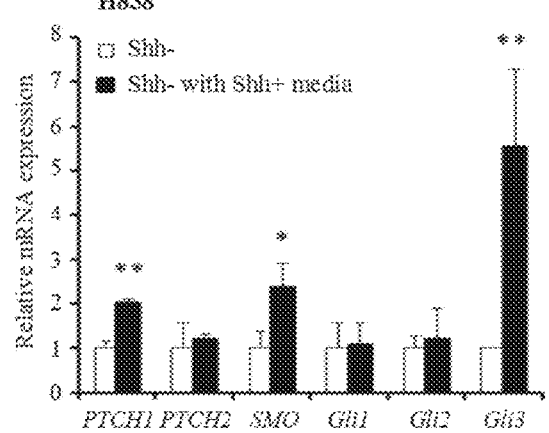

30A). Moreover, the addition of media from Shh⁺ cells to Shh⁻ cells induced a higher proliferation rate and increased the migration rate of the Shh⁻ cells by 50%. Addition of human recombinant N-terminal Shh peptide increased the migration rate by 15% (FIGS. 30B & 30C). The addition of media from Shh⁺ cells to Shh⁻ cells induced gene overexpression of the downstream components of the Shh pathway such as Ptch, Smo, Gli1, Gli2, and Gli3 in quantitative RT-PCR (qRT-PCR) (FIGS. 30D & 30E).

Effect of the Shh Rate Following Cisplatin, Docetaxel and GDC0449 Treatment

Figure 31A:
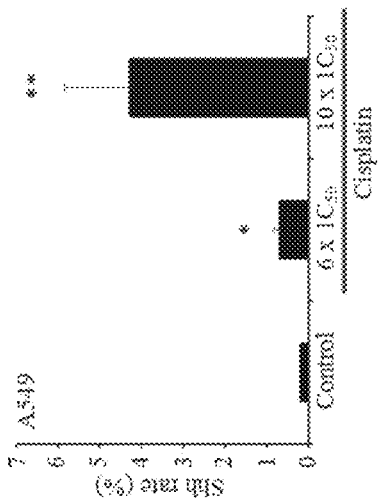
FIGS. 31A-31I show a collection of images showing that Shh+ cells were resistant to cisplatin but sensitive to GDC0449.
Figure 31B:
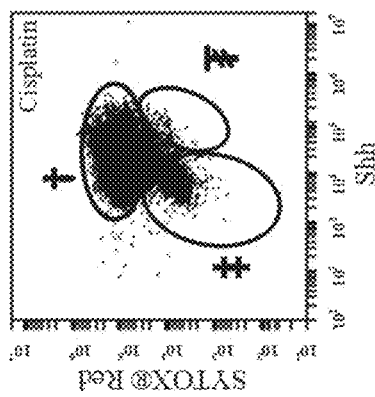
Figure 31C:
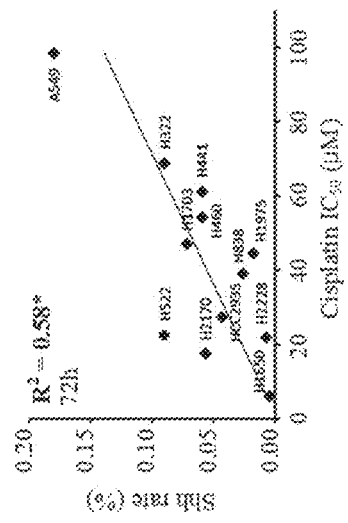
Figure 31D:
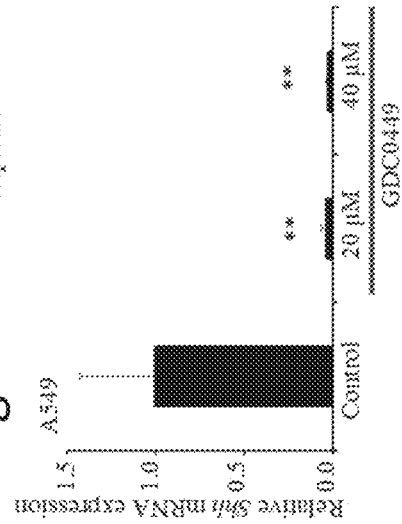
Figure 32A:
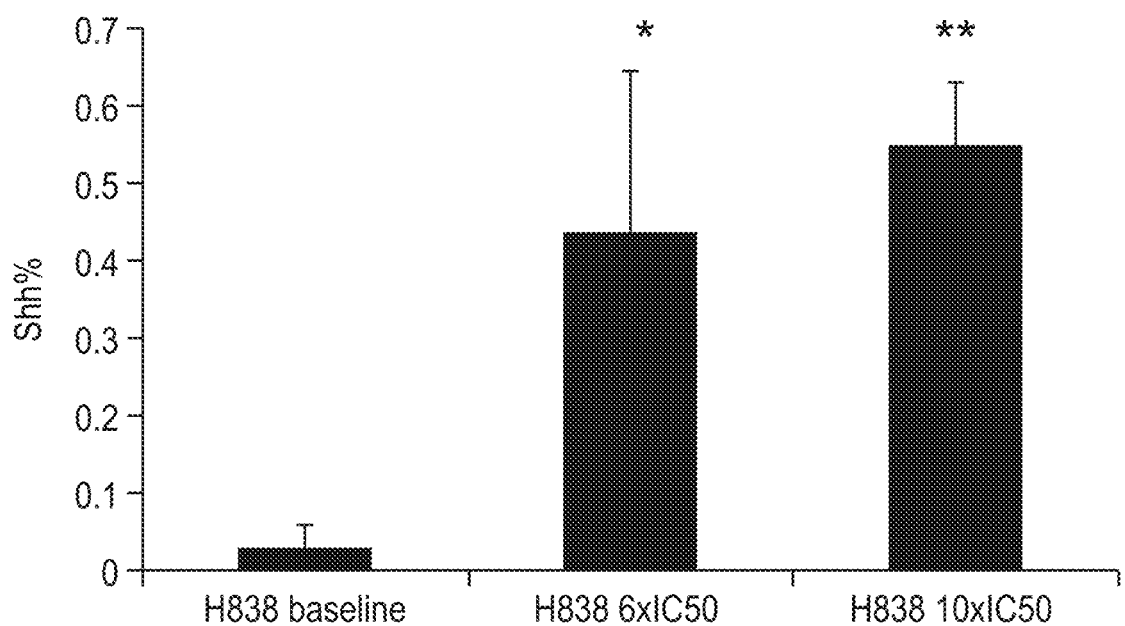
FIGS. 32A-32C show graphs of Shh rate (%) assessed by flow cytometry in H838 (FIG. 32A), H2228 (FIG. 32B) and H1650 (FIG. 32C) cells treated with 2 doses of cisplatin (6-fold and 10-fold $IC_{50}$, 72 h).
Figure 32B:
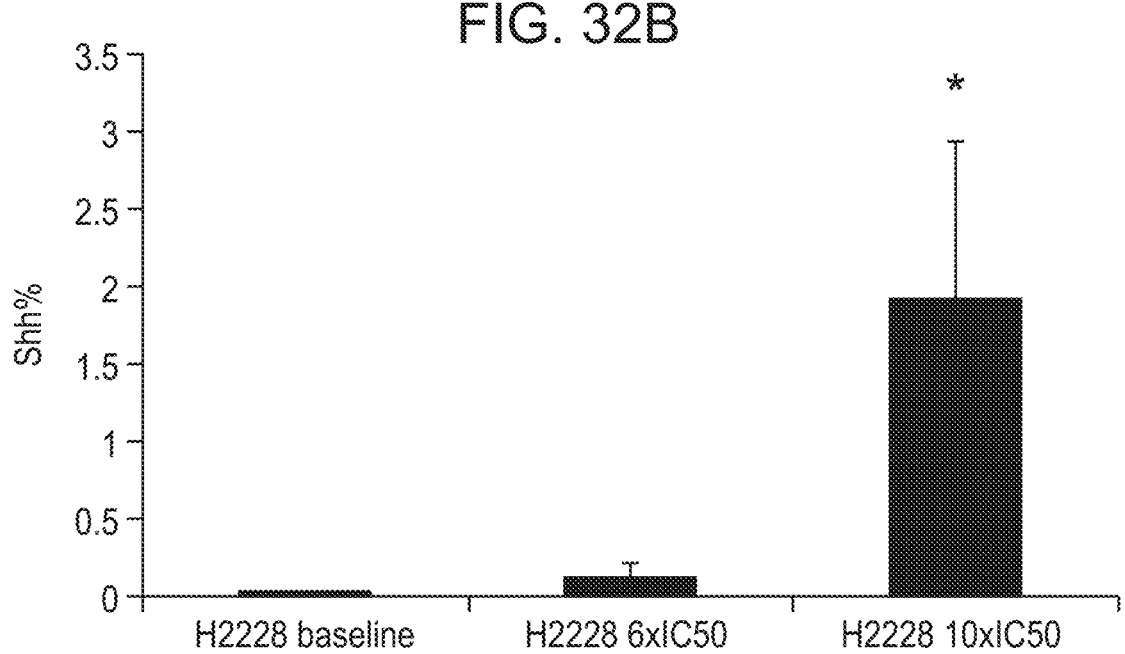
Figure 32C:
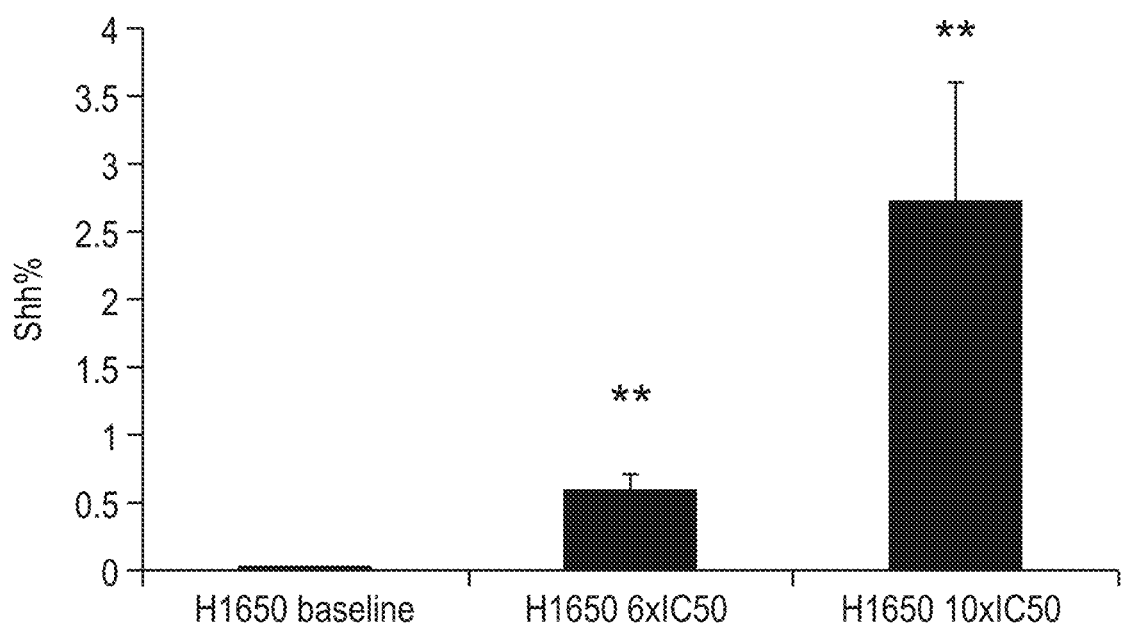
Figure 32D:
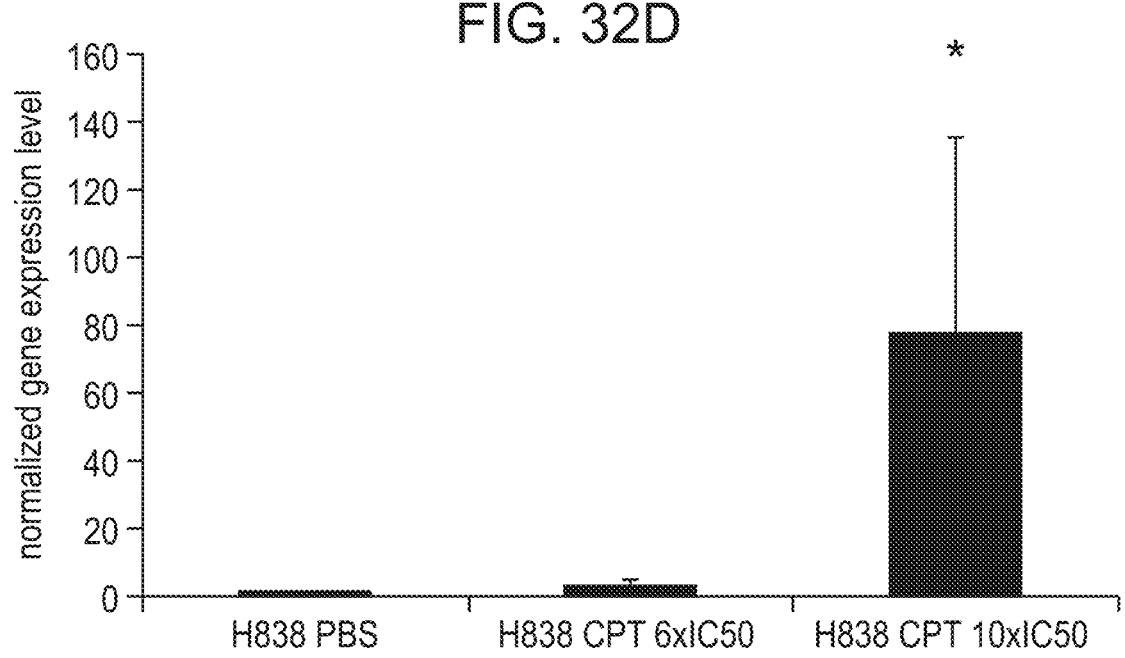
FIGS. 32D-32F shows graphs of Shh gene expression levels in H838 (FIG. 32D), H2228 (FIG. 32E) and H1650 (FIG. 32F) cells treated with 2 doses of cisplatin (6-fold and 10-fold $IC_{50}$, 72 h) analyzed by qRT-PCR (normalized to PBS-treated cells).
Figure 32E:
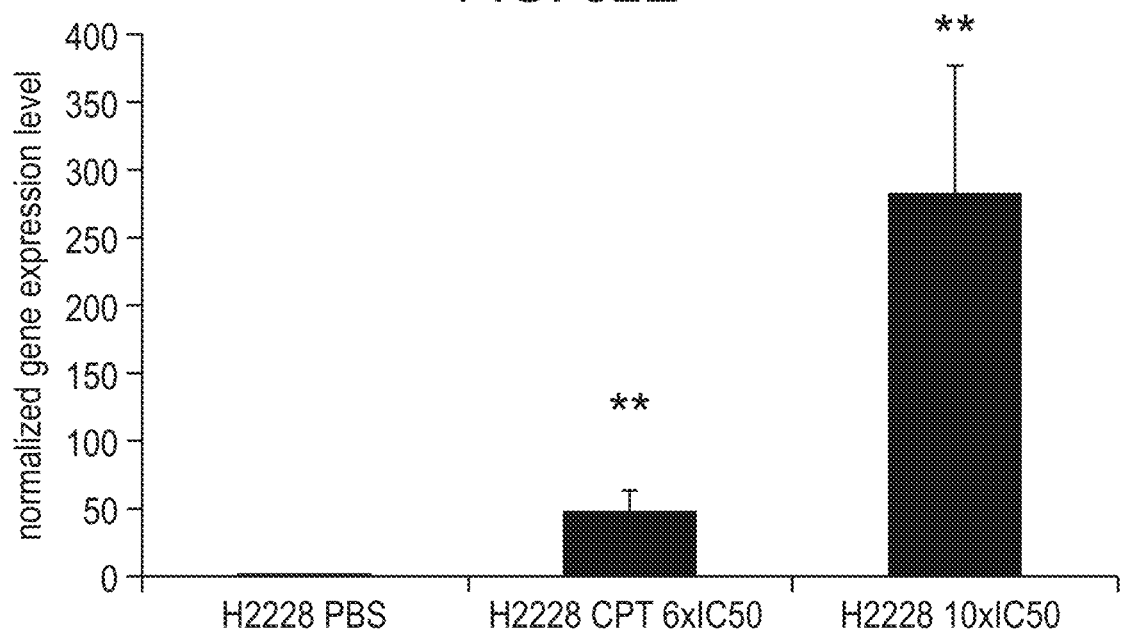
Figure 32F:
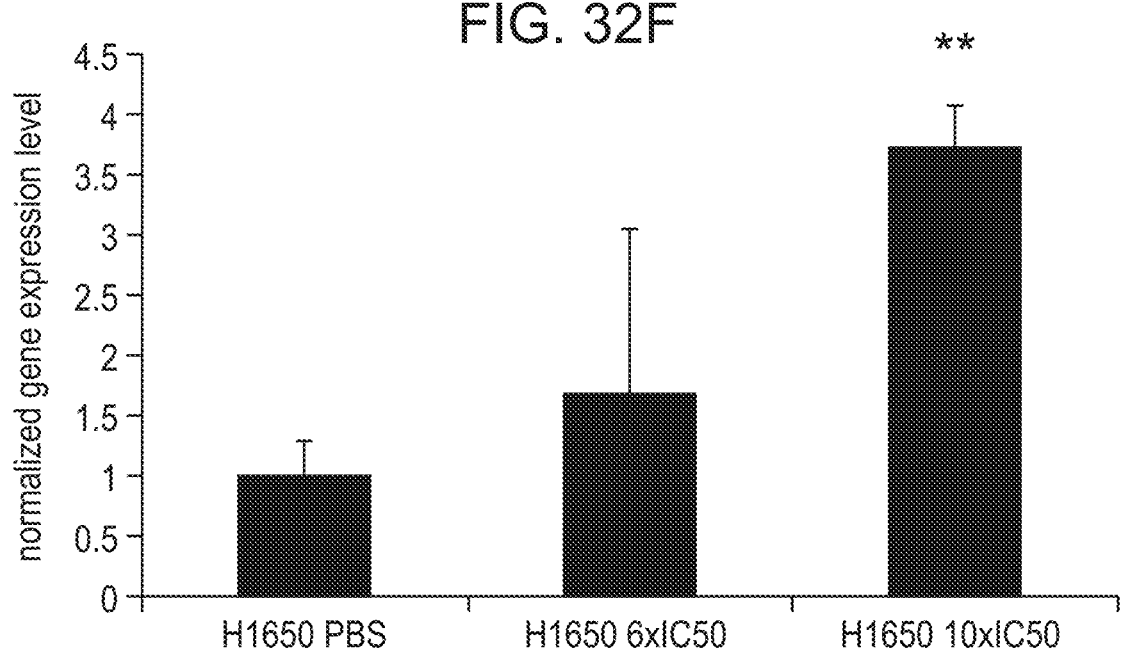

To examine the effect of cisplatin sensitivity on the rate of Shh+ cells, the resistance to cisplatin was compared with the level of Shh expression and a positive correlation between the $IC_{50}$ of cisplatin and the Shh+ rate assessed by flow cytometry (p=0.004, $R^2$=0.58, FIG. 31A) was observed. Further, when the cells were treated with escalating doses of cisplatin, a corresponding absolute augmentation in the Shh rate was observed (FIGS. 31B & 31C; FIGS. 32A-32C), with an increase in the total number of Shh⁺ cells subsequent to cisplatin treatment. This elevation in Shh gene expression was further confirmed by qRT-PCR after cisplatin treatment (FIG. 31D; FIGS. 32D-32F).

Figure 31E:
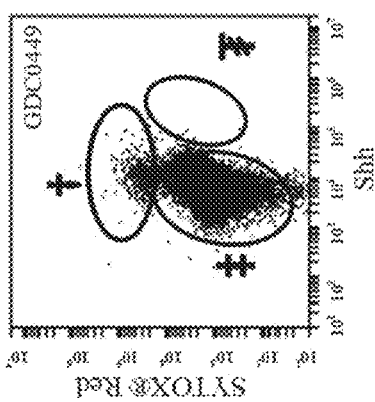
Figure 31F:
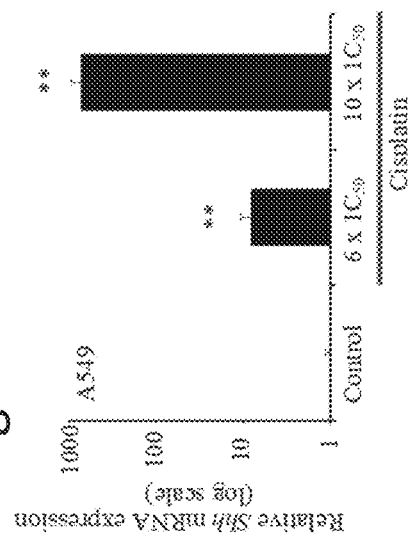
Figure 31G:
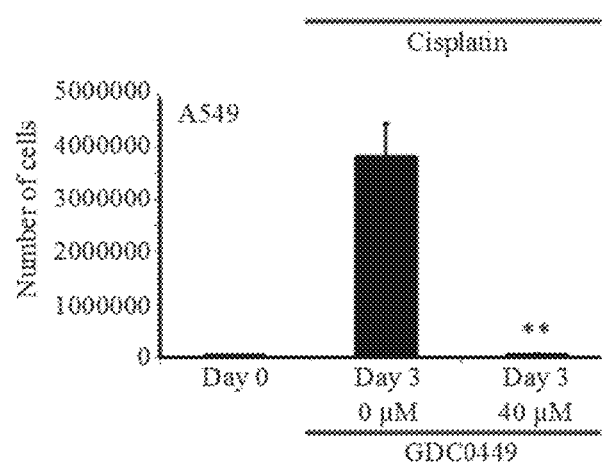
Figure 31H:
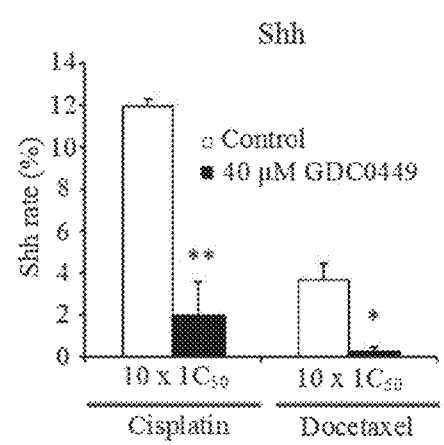
Figure 31I:
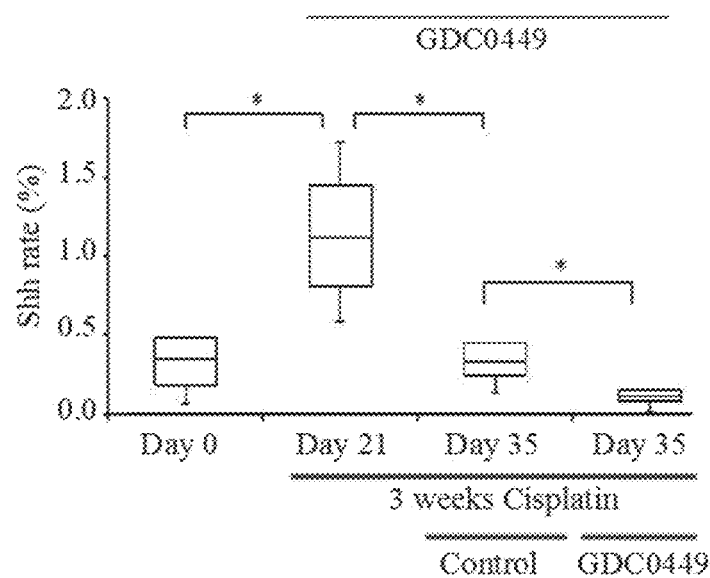
Figure 33A:
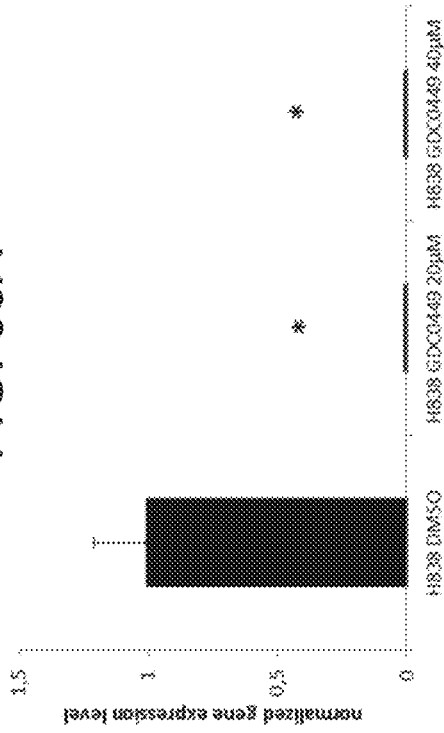
FIGS. 33A-33C show graphs of Shh gene expression levels (qRT-PCR) in H838 (FIG. 33A), H1650 (FIG. 33B) and H2228 (FIG. 33C) treated with GDC0449 (20 μM and 40 μM, 72 h) (normalized to DMSO-treated cells).
Figure 33C:
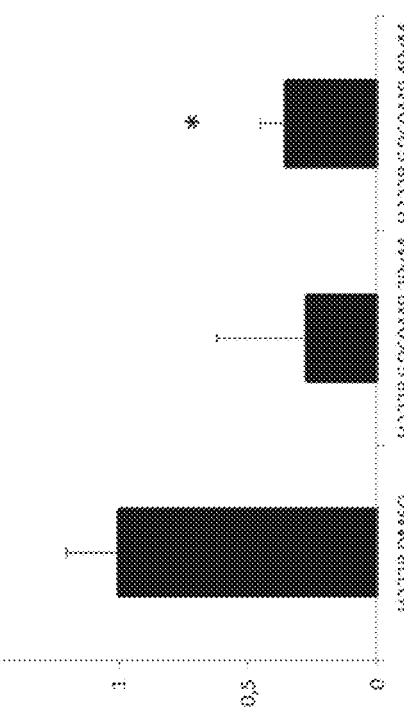
Figure 33B:
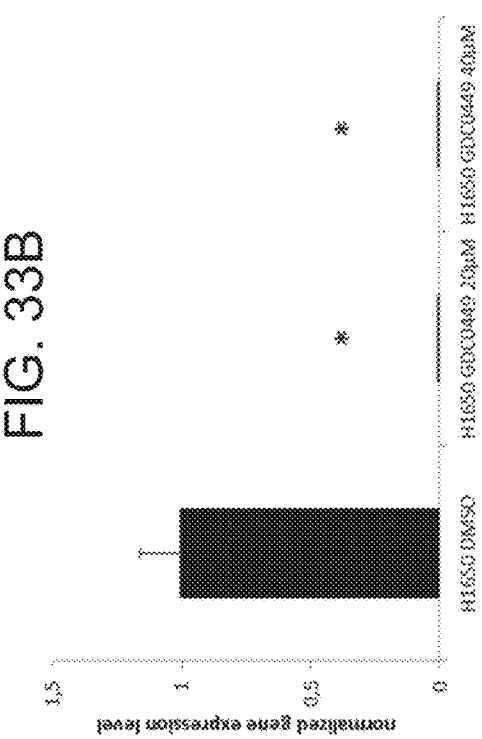
Figure 34A:
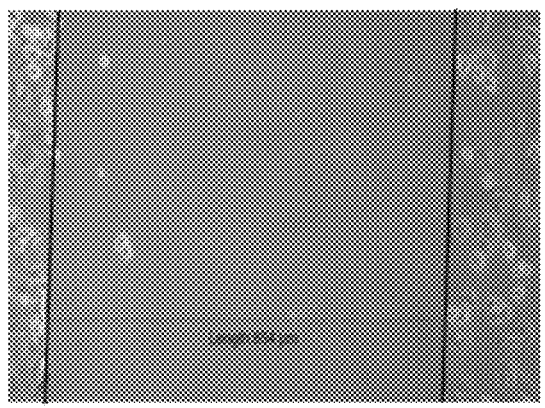
FIGS. 34A-34D show images of a migration/wound healing assay performed on A549 cells at d0 (FIG. 34A) and d3 (FIG. 34B: DMSO.
Figure 34B:
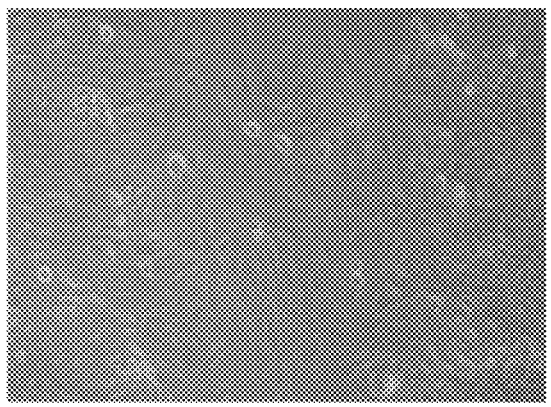
Figure 34C:
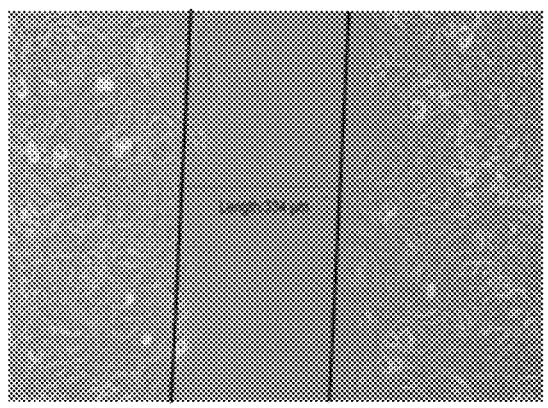
Figure 34D:
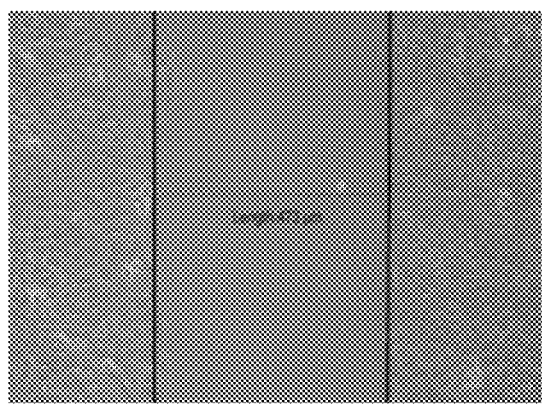
Figure 35:
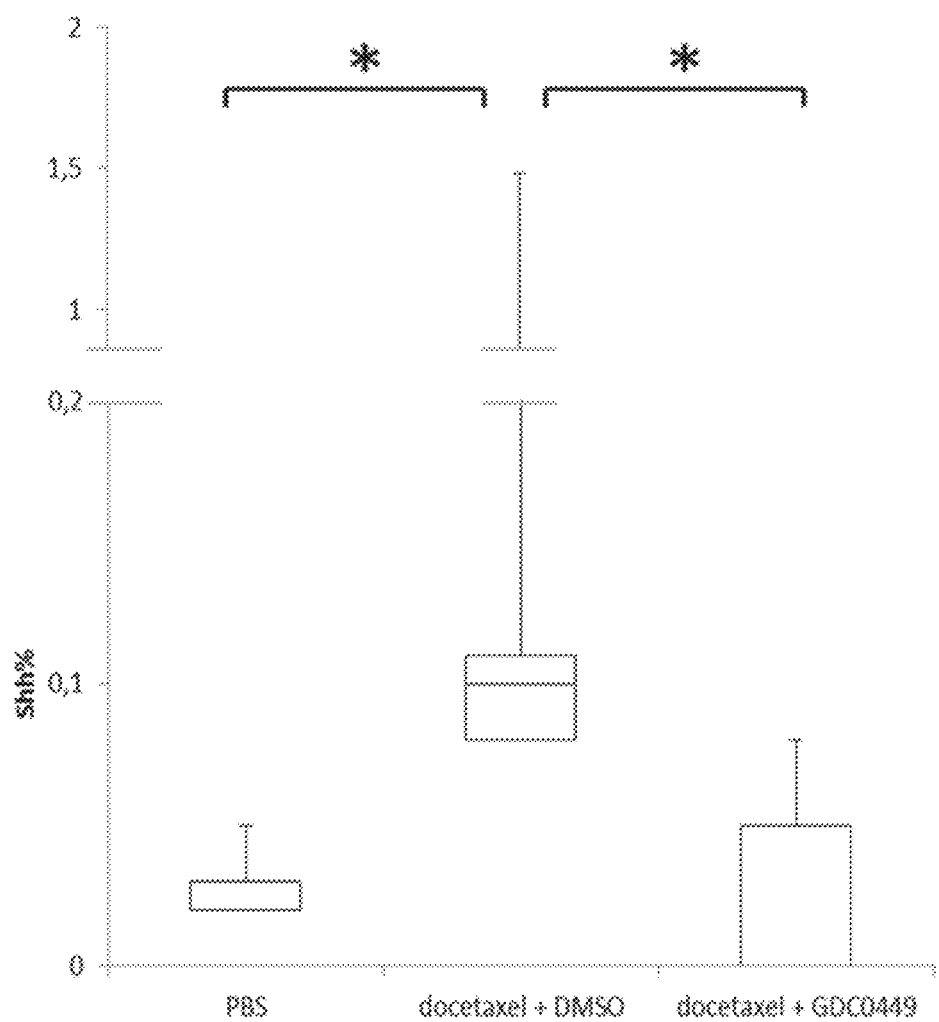
FIG. 35 shows a graph of Shh rate (%) at d21 in A549 xenografts (nude mice) treated with PBS or docetaxel (10 mg/kg, twice a week) plus vehicle or docetaxel (10 mg/kg, twice a week) and GDC0449 (20 mg/kg, IP daily). *p<0.05.

Treatment of A549 cells with 40 µM GDC0449 (vismodegib/commercial Smoothened inhibitor (Selleck Chemicals)) successfully inhibited the Shh pathway, as evidenced by a complete disappearance of Shh⁺ cells assessed by flow cytometry (FIG. 31E). qRT-PCR analyses confirmed this dramatic decrease in Shh gene expression post-GDC0449 treatment (FIG. 31F; FIGS. 33A-33C). Moreover, treatment with GDC0449 induced an inhibition of cell proliferation and migration (FIG. 31G; FIGS. 34A-34D). Also, when GDC0449 was combined with chemotherapy (cisplatin or docetaxel), the Shh rate post-chemotherapy (cisplatin or docetaxel) decreased significantly compared to chemotherapy alone (FIG. 31H). To confirm these results in vivo, A549 xenografts were used in nude mice treated sequentially with cisplatin and then GDC0449, or treated with the combination of docetaxel and GDC0449. A significant increase in the Shh⁺ rate after chemotherapy and a significant reduction in the Shh rate after GDC0449 treatment (sequential assay) were observed, and a significant reduction in the Shh rate following combination treatment, compared to chemotherapy alone (combined docetaxel and GDC0449 treatment) was also observed (FIG. 31I; FIG. 35).

CSC Features of Shh+ Cells

To elucidate the features of the two populations, gene expression microarray profiling of sorted Shh⁺ and Shh⁻ A549 cells were performed (FIG. 36). This analysis, revealed an overexpression of Shh pathway genes (notably Shh), several well-known CSC genes (POU5F1P3, NANOG, LIN28A, ALDH1A2, PROM1), genes involved in cell survival and proliferation [Cyclin D2 (CCND2), BCL2], Wnt pathway genes, and chemokine-related genes. Genes associated with differentiation (KRT7, PRDM1) were underexpressed in Shh⁺ cells.

Upon culturing sorted cells in serum-free media, the formation of floating spheroids with A549 Shh⁺ cells 10 to 15 days after sorting was observed (FIG. 37A), but not with A549 Shh⁻ cells (FIG. 37B). To prove the critical role of the Shh pathway in oncogenesis, cultured A549 cells were treated with 40 µM of GDC0449 (FIGS. 37C & 37D). Then, nude mice were inoculated subcutaneously with 1 million treated cells (still adherent to the culture flask after treatment with GDC0449). Tumor formation was completely inhibited with the pre-treated cells compared with the control group (DMSO pre-treated cells) (FIG. 37E). Next, nude mice were inoculated with a small number (1,500 cells) of Shh⁺ or Shh⁻ cells subcutaneously. At 3 weeks, 3 out of 4 mice (75%) inoculated with Shh⁺ cells developed a measurable xenograft, whereas 0 of 4 mice (0%) inoculated with Shh⁻ cells developed any tumors (FIGS. 37F-37I).

Presence of Shh+ Cells in Human Tumor Samples and Prognostic Impact

To evaluate the role of Shh as a prognostic marker in lung cancer, 48 fresh human surgical samples from 47 patients with NSCLC, obtained consecutively from the Surgery Department at UCSF were tested. There were 46 primary lung tumors, one tumor pleural effusion, and one adrenal metastasis of lung adenocarcinoma. Patient samples were not only probed for Shh to assess the percentage of positive cells but also for CD45 to exclude immune cells from the final analysis. Although the overall median Shh rate was 0.06% (interquartile range IQR 0.02-0.20), the rate in corresponding fresh normal lung tissue (n=48) was 0% (IQR 0-0%) (p<0.001) (FIGS. 38A-38C). The median Shh rate was 0.09% (IQR 0.03-0.21) for stage I (n=32), 0.02% (IQR 0.01-0.11) for stage II (n=6), 0.01% (IQR 0-0.02) for stage III (n=5) and 0.15% (IQR 0.01-0.56) for stage IV (n=5) (p<0.05 for each comparison). All the samples were chemonaive, except for 3 samples (stage I: n=1; stage IV: n=2) which received pre-surgery chemotherapy. One patient underwent surgery twice after systemic chemotherapy, with 6-weeks delay between the 2 surgeries (the first surgery for the primary lung tumor, the second for an adrenal metastasis), and without any chemotherapy between the 2 surgeries. Initial post-chemotherapy evaluation showed a tumor response in the primary lung tumor, but a tumor burden on the adrenal metastasis. Both the primary tumor and adrenal metastasis were analyzed, and a nearly 70-fold higher Shh rate was assessed via flow cytometry at the metastatic progressive site compared to the primary tumor that responded to chemotherapy (FIG. 38D). qRT-PCR analysis confirmed this result of Shh gene overexpression at the site with tumor progression compared to the site with tumor response (p=0.01, FIG. 39). Fresh lung metastases from other pathological subtypes were also tested via flow cytometry and the presence of Shh⁺ cells was observed in almost all of them (FIG. 40).

Microarray analysis was performed on 7 sorted fresh human tumor samples {4 primary lung adenocarcinoma and 3 secondary lung tumors [primary: melanoma (n=1); breast carcinoma (n=1); colorectal carcinoma (n=1)]}. Consistent with the microarray data from the NSCLC cell line, gene overexpression for Shh pathway genes, CSC genes, cell survival, EMT and aggressiveness genes, Wnt pathway and chemokine genes were observed (FIG. 41 and FIG. 42).

Finally, to ascertain a clinical impact of Shh⁺ cells in human NSCLC, all the patients in the study were prospectively followed. A statistically significant association between the Shh⁺ rate and the time-to-progression (TTP) for stage I NSCLC was found. Median TTP was 11.8 months in patients whose tumors showed a Shh⁺ rate of more than 0.10%, versus 'non reached' in those whose tumors showed a Shh+ rate of less than 0.10% (p=0.004, FIG. 38E). For stage I NSCLC, patients with tumor relapse within 12 months after surgery had a higher Shh⁺ rate in their tumors compared to those without tumor relapse within 12 months of surgery [median: 0.19% (IQR 0.14-0.36) versus 0.05% (IQR 0.02-0.09), respectively, p=0.01; analysis based on 22 stage I NSCLC with follow-up >12 months after surgery] (FIG. 38F).

In this study, a new in vitro and in vivo lung CSC marker, the membranous full-length Shh protein, was studied. CSCs identified by this marker were resistant to systemic chemotherapy but sensitive to GDC0449, a Smoothened inhibitor administered alone or in combination with systemic chemotherapy.

The existence of CSCs has been proven in several malignancies including lung cancer. They are believed to be responsible for tumor initiation and development, as well as resistance to chemotherapy, and thus could be responsible for rapid tumor recurrence or relapse after cancer treatment. Several CSC markers have been described for CSC characterization and isolation such as CD133, CD44, ABCG2 and aldehyde dehydrogenase (ALDH). However, the specificity of these markers is poor (32-34). CD133 is not usable for isolation of CSCs in NSCLC because some CD133− cells in NSCLC cell lines presented CSC features (colony formation, self-renewal, proliferation, differentiation and chemoresistance). This marker is probably more specific in SCLC than in NSCLC. Also, the use of ALDH activity is limited in practice because it lacks specificity; pneumocytes in smoking patients can also have high ALDH activity. Moreover the functional role of these markers in CSCs remains unclear. Based on the microarray results in A549 and fresh tumor sorted cells described herein, a great heterogeneity in the expression of the conventional CSC markers in Shh+ cells was found.

The association of the Shh pathway and CSCs was studied in multiple solid tumors. However, for the first time it has been demonstrated that Shh+ cells are CSCs in NSCLC. Whereas during biological development the full-length protein is truncated in the cytosol and only the N-terminal fragment has biological activity, described herein for the first time the presence and localization of the full-length protein on the membrane of CSCs. The biological activity of full-length Shh protein was determined in in vitro studies under physiological conditions, but never in cancer models. Shh+ cells exert a paracrine effect on other tumor cells, initiating induction of proliferation and migration signals. IF staining showed a diffuse Shh staining pattern and flow cytometry on permeabilized cells revealed that more than 70% of them were Shh-positive cells. However, only Shh+ cells are Shh producing cells as demonstrated by our ddPCR results on sorted cells and by the WB results on the supernatant from sorted cells. Shh− cells received the Shh protein secreted by Shh+ cells and internalize the protein immediately after receptor binding, explaining the cytosolic staining for Shh in permeabilized cells. The results herein also highlight the important role CSCs play in chemoresistance exhibited by NSCLC cell lines, in vivo models (xenografts), and also in patient prognosis (high Shh+ rates correlated with progressive metastases and responsive lung tumors had low Shh+ rates). The results herein show a substantial and significant impact of targeting these CSCs in order to improve clinical outcome of patients treated for lung cancer. The present experiments demonstrated herein that lung CSCs are sensitive to targeted therapy. In vivo treatment with GDC0449 resulted in a complete disappearance of Shh+ cells, and when combined with chemotherapy, a significant reduction of the Shh+ rate assessed via flow cytometry. The efficacy of GDC0449 on lung CSCs has been suggested in vitro and on a very limited number of cell lines. We have demonstrated in a previous study that the Shh pathway is overexpressed in chemo-refractory advanced NSCLC treated with platinum-based chemotherapy, and that inhibition of the Shh pathway with GDC0449 had a synergistic effect with cisplatin in vitro in the most chemo-resistant NSCLC cell lines. Only a few clinical studies have tested Smoothened inhibitors in lung cancer. The ECOG-ACRIN phase II trial (E1508) tested standard chemotherapy (cisplatin/etoposide) with or without vismodegib as the first line of treatment for advanced-stage SCLC. No effect in terms of response rate, PFS or OS was observed. A recent phase I trial testing another Smoothened antagonist (sonidegib) in addition to cisplatin/etoposide for advanced SCLC showed an interesting response rate (79%), frequently observed in SCLC treated with standard chemotherapy alone; but one patient in a group of 15 patients was found to have a SOX2 gene amplification with progression-free survival while on maintenance with sonidegib after 27 months. For NSCLC, no published clinical trial has reported tests with Shh pathway inhibitors.

Example 6: Preclinical Characterization of Therapeutic Antibodies Targeted at the Carboxy-Terminus of Sonic Hedgehog Materials and Methods
Generation and Purification of Monoclonal IgG Antibodies A proprietary algorithm (ThermoFisher) was used to analyze amino acid sequences and suggest the best small peptide sequences for antibody generation and development. The algorithm took into account specific structural motifs, charge, hydrophilicity and historically successful sequences. Two synthetic peptide mimics of the C-terminal human Sonic Hedgehog Protein (C-term: 198-462 AA) were selected: 1) Shh 247-264 AA and 2) Shh 448-462 AA. Both peptides were KLH-conjugated and injected as IP emulsions in Freund's Complete Adjuvant (CFA) into Sp2/0-Ag14 mice to mount an immune response (primary and first-booster). An ELISA employing the KLH free peptides as an antigen was used to confirm the production of the antibodies in the sera of the mice. Two mice with the strongest response were advanced into the fusion phase with myeloma cells in which the lymphocytes from the spleen/lymph nodes were seeded in 96-well plates with rich growth medium. Cell culture supernatants from proliferating colonies were screened against the free peptide antigens and full-length Shh in both 1) endogenous A549 cells and 2) exogenously transfected 293T+pCMV-Shh cells via flow cytometry and Western blotting. Expression of full-length Shh polypeptide in transfected cells increased the percentage of cells labeled with the Shh antibodies produced by two sub-clones (Ab 1C11-2D9 and Ab 1C11-2G4) identified after the screening, compared to the percentage of un-transfected cells labeled by the same antibodies, as measured by flow cytometry. Positively identified parental cell clones were re-plated to segregate into sub-clones followed by the above-mentioned screening procedure. About 51 clones and sub-clone producing antibodies were raised against the C-terminal Shh peptides. Finally, two selected sub-clones 1C11-2G4 and 1C11-2D9 were advanced to large-scale purification via chromatography of monoclonal antibodies from hybridoma cells, which recognize the C-terminal region of human Shh. These were used for subsequent in vitro and in vivo experimentation.

Octet Binding Studies

Purified Ab 1C11-2D9, Ab 1C11-2G4 OR control IgG antibodies in 1×HBS were covalently attached to amine-reactive second-generation (AR2G) biosensor tips (ForteBio) along with an amine coupling kit (GE Healthcare) by following the manufacturer's recommendations on an Octet RED 384 machine (ForteBio, PALL Octet System). Antibody immobilization was checked via Octet® Software (ForteBio) prior to introduction of increasing concentrations (37, 111, 333, 1000, 3000 nM) of Sonic Hedgehog peptide-mimic ligands (Shh 247-264 AA and Shh 448-462 AA).

Graphical output from the Octet® Software of representative data from two independent experiments is presented.

ELISA Screen

KLH-free Shh peptides used for antibody generation were used as the antigen and coated onto plastic ELISA plates followed by incubation with sera containing antibodies from immunized mice or cell culture supernatants. After PBS washes and the addition of secondary antibodies, the optical density (O.D.) values produced as a result of binding/TMB substrate system for ELISA were recorded.

Western Blot Analysis

Total protein from whole-cell lysates was prepared with M-PER buffer (ThermoFisher Scientific) and from frozen tissues with T-PER (ThermoFisher Scientific) supplemented with protease and phosphatase inhibitors (Roche). Subsequently protein concentrations were determined via a Bradford assay. Equal quantities of proteins were combined with 5× protein loading buffer and separated by SDS-PAGE followed by PVDF membrane transfer. Membranes were blocked with 5% milk followed by incubation with commercial Shh (Abcam 97029, 1:1000) and therapeutic test supernatant (1:20) antibodies. Blots were developed with ECL Reagents (Pierce).

Cell Lines and Reagents

All cells were obtained from American Type Culture Collection (ATCC) (Manassas, Va.) and were cultured in ATCC-recommended media supplemented with 10% fetal bovine serum (FBS) and 2% antibiotics (Penicillin-Streptomycin). Transient transfection of the pCMV-Shh plasmid (Origene) was introduced into 293T/A549 cells with Lipofectamine 2000 (Life Technologies) by following the manufacturer's recommendations.

Flow Cytometry Screening and Cell Sorting

A549, 293T or 293T (+pCMV Shh) cells were labeled with Sonic Hedgehog (Shh) antibody (Abcam 53281, 1:100) or therapeutic test antibodies (1:100) for 1 hour at RT post serum blocking. Following two PBS washes, a FITC-conjugated secondary antibody (Abcam 97029, 1:100) or an Alexa-Fluor 647 (Invitrogen, 1:1000) was used to label cells. Samples were screened by flow cytometry using an Accuri™ C6 machine (BD Biosciences). For fluorescence activated cell sorting, samples were sorted using an S3e™ Cell Sorter (Bio-Rad) and the Shh+ population was collected. For all experiments, cells processed without primary antibody served as a negative control. Experiments were performed in duplicates or triplicates.

Immunoglobulin Isotype Determination

Immunoglobulin class (IgG, IgA, IgE, IgM) and subclass identities of screened and isolated antibodies were determined using cell culture supernatant with an isotyping kit by following the manufacturer's recommendations—Pierce™ Rapid Mouse Antibody Isotyping Kit plus Kappa and Lambda (Cat. No. 26179).

Cell Viability Assay

Logarithmically growing cells were plated in antibiotic-free medium supplemented with 2% fetal bovine serum at a density of 5,000 cells per well in clear-bottom 96-well plates. The next day cells were treated (triplicates) with increasing doses of in-house therapeutic antibodies (reconstituted in PBS) or PBS controls for 96 hours and subsequently assessed for cell viability by measuring ATP content with CellTiter-Glo Luminescent Cell Viability Assay (Promega). Signal intensity was measured on a Glomax™ 96 Microplate Luminometer (Promega) and percent cell survival was calculated based on the reading of PBS control cells set as 100%.

Antitumor Efficacy in NSCLC Animal Model 7-week old female nude mice (Jackson Laboratories) were injected with $10 \times 10^6$ NSCLC A549 cells in 50% matrigel in the flank region. To assess establishment of tumors, mice were examined 10 days post inoculation and were randomly segregated into 2 treatment groups (IgG control and Ab 1C11-2G4, n=5 per group). 8 mg/kg therapeutic or control antibodies were administered three times a week for approximately 3 weeks. Tumor volumes were calculated using the formula ($V=L \times W^2$) with recorded caliper measurements. At the end point, tumors were harvested, weighed and imaged. All animal procedures were performed under IACUC-approved protocols and guidelines.

Immunofluorescence Staining

Control IgG and Ab 1C11-2G4-treated A549 tumors harvested from mice were sectioned (5 μM) and stained with a commercially available Sonic Hedgehog (Shh) antibody (Abcam 53281, 1:100) post acetone fixation, 0.2% Triton-X 100 permeabilization and serum blocking steps. A FITC-conjugated secondary antibody (1:1000) and VECTASHIELD DAPI (Vector Laboratories) mounting medium were used to stain sections prior to imaging at 20× magnification using a Zeiss Axiolmager 2 fluorescence microscope. Captured images were processed via ImageJ software (available at https://imagej.nih.gov/ij/download-.html) and representative images are presented.

Real-Time PCR

Antibody-treated tumors were harvested to extract total RNA using Trizol (Invitrogen) and cDNA was synthesized using reverse transcriptase from iScript's cDNA Synthesis Kit (Bio-Rad). Real-time quantitative reverse transcript-polymerase chain reaction (qRT-PCR) was performed with TaqMan® Universal PCR Master Mix (Life Technologies) using gene specific PCR primers for human Shh-FAM (Life Technologies). Triplicate samples were run on an AB7900HT Fast Real Time PCR System thermocycler (Applied Biosystems) and GAPDH was used as a housekeeping gene for normalization. Ct values were analyzed using the $2^{-\Delta\Delta CT}$ method and the data is presented as a fold change in target gene expression±standard deviation.

Statistical Analyses

All experiments were repeated a minimum of two times with duplicate or triplicate samples. Values including controls are expressed as the mean±SD. A two-tailed paired Student's t-test was used to assess differences between groups. Differences with p value ≤0.05 were considered statistically significant.

Results

Generation of a Repertoire of Novel Therapeutic Antibody Candidates Targeted at C-Terminal Sonic Hedgehog (Shh) Derived from Mouse Hybridoma Clones A novel murine repertoire of antibody candidates derived from hybridoma clone fusions isolated was constructed from the lymph nodes of Sonic Hedgehog-immunized mice. Specialized antigen-designing software was used to construct two synthetic peptide mimics of the C-terminal human Sonic hedgehog protein: 1) Shh 247-264 AA and 2) Shh 448-462 AA. Following dual intravenous (IV) administration of both KLH-conjugated peptides into Sp2/0-Ag14 mice to mount an immune response, the B-cells from the isolated lymph nodes were fused to myeloma cells to generate a diverse repertoire of hybridomas. Next, protein-based screening analyses for anti-Shh C-term therapeutic antibody hybridoma candidates by capture ELISA, Western blotting and flow cytometry for binding as well as correct antigen recognition using cancer cells and cells exogenously transfected for the expression of Shh were performed. One selected hybridoma clone, 1C11, from this screening strategy was isolated, sub-cloned and subjected to the same selection procedure as the parental clones using ELISAs, Western blots and flow cytometric evaluations. Large-scale protein purification of antibodies from hybridoma sub-clones designated 2G4 and 2D9 yielded sufficient protein required for ensuing in vitro and in vivo analyses.

Screening and Selection of Precursor Antibodies Directed at C-Terminal Shh

Figure 43C:
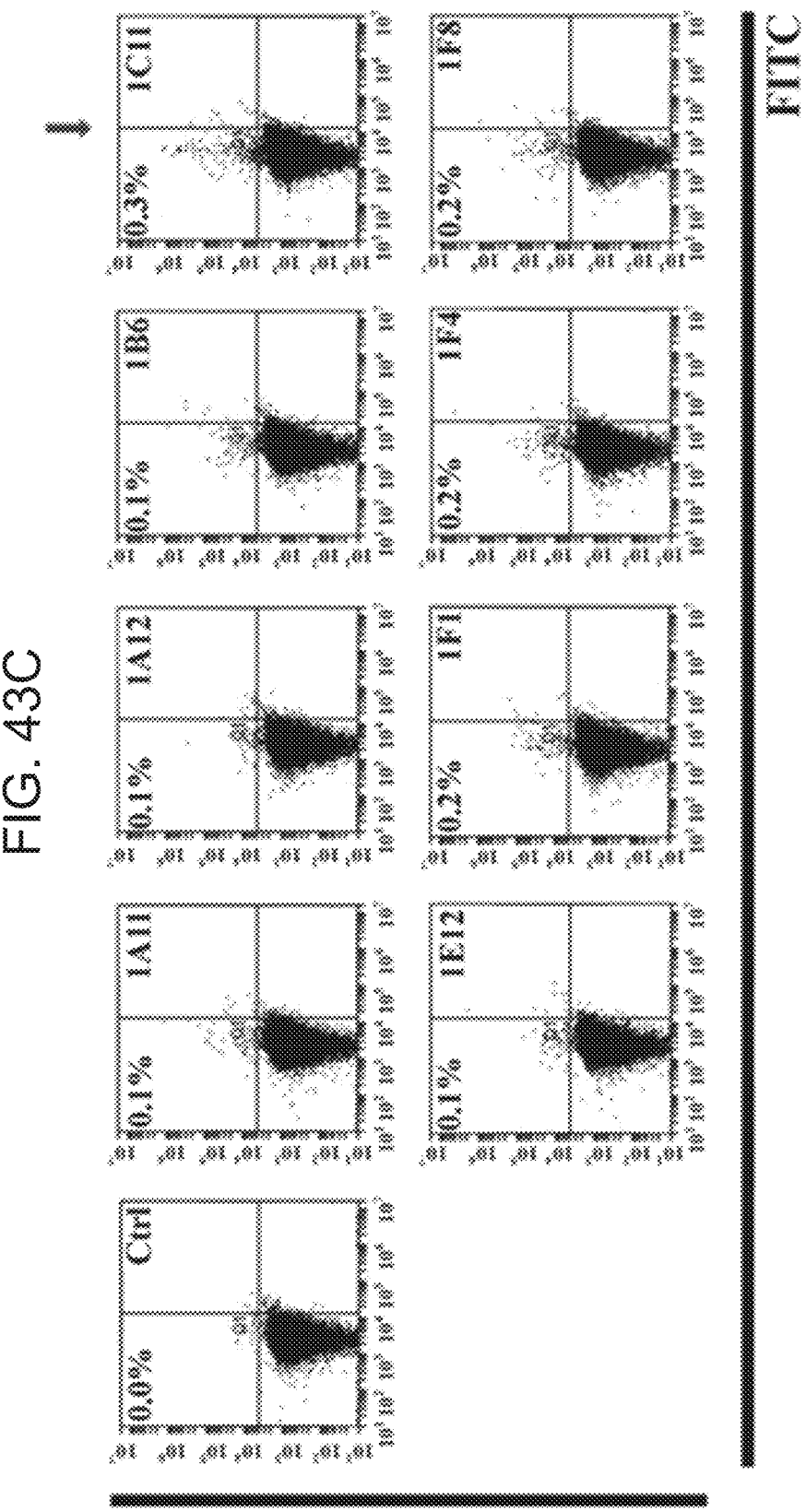
Figures 43D, 44A, 44B:
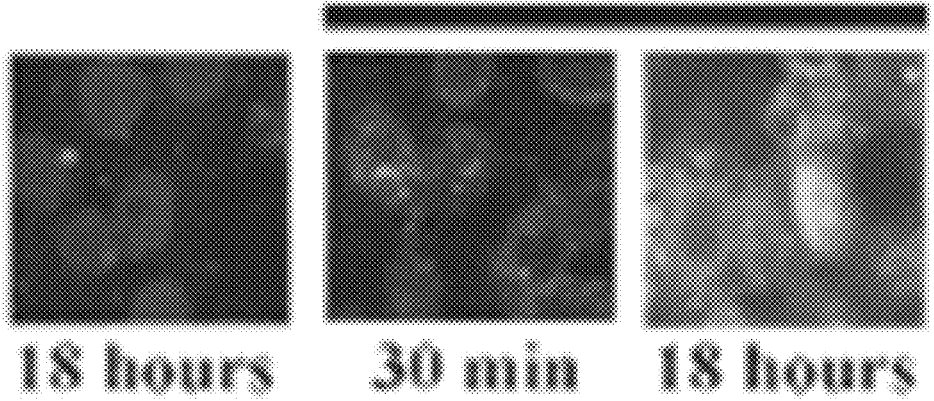

For the purpose of selecting the best C-term Shh antibodies from over 50 hybridoma clones, two sets of screening assays were designed. First, the same Shh C-term peptides (AA 247-264 and 448-462, KLH-free version) used to mount an immune response in mice was employed in an ELISA-based assay with supernatants from antibody-producing hybridoma clonal cells. The O.D. values of the best clones are presented as a measure of antibody binding to the original antigen/immunogen for which it was raised; 1C11 (indicated by an arrow) showed the highest binding value (FIG. 43A). The next set of screening assays comprised three cell lines: 1) 293T (endogenous Shh), 2) 293T (bearing exogenously transfected Shh) and 3) A549 (Shh-expressing), which were used for both Western blotting and flow cytometry. NSCLC A549 cells, which express a post-translationally distinct (different size via Western blotting) Shh protein, were also used as a positive control. Concomitant with the ELISA results, clone 1C11 was the most effective Shh antibody at detecting the Shh bands from the screening cell lysates (1-3) via Western blotting (FIG. 43B). More in-depth analyses by flow cytometry showed that 1C11 exhibited the ability to recognize and bind cell-surface endogenous Shh in 293T (FIG. 43C, 0.3%, 293T) and exogenous Shh in 293T cells (FIG. 47A, 1.2%, 293T+pCMV-Shh) more strongly compared with other clones and the negative control (0%, 0.1%, 2° antibody alone). Ab 1C11-producing hybridoma cells were sub-cloned in an iterative effort to isolate monoclonal antibodies with stronger binding properties. The above-mentioned screening analyses were used to cull out the most effective sub-clones (data not shown) and Abs 1C11-2G4 and 1C11-2D9 were both isotyped as IgG$_1$, κ (FIG. 43D). Thus from a large number of hybridoma clones, two sub-clones were selected that target the C-term of Shh for further investigation. Purified monoclonal antibodies 1C11-2G4 and 1C11-2D9 were used for the subsequent biolayer inferometry (BLI) binding studies and via flow cytometric evaluation in A549 cells to confirm specificity using the same C-term Shh peptides for which they were raised. To confirm specific recognition, A549 (+vector control) cells and A549 cells transfected with exogenous Shh were labeled with 2G4 and 2D9 and assessed via flow cytometry. Both sub-clones exhibited the ability to recognize and bind endogenous Shh in A549 (FIG. 47B top panel, 2G4-0.5%, 2D9-0.4%, commercial C-term Ab-1%) and exogenous Shh transfected in A549 cells (FIG. 47B bottom panel, 2G4-6%, 2D9-4.1%, commercial C-term Ab-5.1%) more strongly compared with the negative control (0%, 0.2%, 2° antibody alone). To further characterize the binding properties in a cell-free system using Shh peptides, it was first verified that Ab 1C11-2D9, Ab 1C11-2G4 OR control IgG antibodies were covalently bound and immobilized on amine-reactive sensor tips using an Octet RED 384 system (FIG. 48A). Upon introduction of increasing concentrations of Sonic Hedgehog peptide-mimic ligands (Shh 247-264 AA and Shh 448-462 AA), it was observed that both Abs 1C11-2G4 and 1C11-2D9 resulted in increases in binding response not observed with the IgG control antibody (FIG. 48B). Finally, the K$_d$ values of both antibodies with recombinant full-length Shh were calculated and nanomolar binding affinities were observed (FIG. 48C).

FIGS. 43A-43D. Screening of murine hybridoma clones for selection of candidate therapeutic anti-Shh antibodies directed at the C-terminal of the Sonic hedgehog protein. FIG. 43A: Supernatants from antibody producing hybridoma clone cells were incubated with synthetic peptide mimics of Shh as measure by an ELISA-based assay. Clone 1C11 (red arrow) showed the strongest binding to the same Shh peptide mimics used to generate an immune response. FIG. 43B: Hybridoma clonal supernatants were incubated with the following cell lysates to check for Shh protein detection and analyzed by Western blotting: 1) 293T (endogenous Shh), 2) 293T (exogenously transfected with pCMV-Shh) and 3) A549 (Shh expressing lung cancer cells) FIG. 43C: Flow cytometric evaluation of cell surface Shh recognition performed with clonal supernatants incubated with non-permeabilized 293T cells. Clone 1C11 detected the highest percentage of cell-surface Shh compared with the other clones. The secondary antibody alone incubated with cells was run as a negative control. FIG. 43D: Two sub-clones of 1C11, 2G4 and 2D9, exhibit IgG$_1$, kappa measured using an isotyping kit.

FIGS. 47A-47B. Screening of candidate therapeutic anti-Shh antibodies directed at the C-terminal of the Sonic Hedgehog protein. FIG. 47A: Flow cytometric evaluation of Shh recognition performed with clonal supernatants incubated with 293T cells transfected with exogenous Shh. Clone 1C11 detected the highest percentage of cell-surface Shh compared with the other clones. The secondary antibody alone incubated with cells was run as a negative control. FIG. 47B: Flow cytometric evaluation of Shh recognition performed with purified antibodies Ab 1C11-2G4, Ab 1C11-2D9 and a commercial (Comm) C-term antibody on vector control (pCMV) A549 cells (top panel) and A549 cells transfected with pCMV-Shh (bottom panel) compared with their respective negative controls of cells incubated with secondary antibody alone.

FIGS. 48A-48C. Biolayer interferometry (BLI) binding studies of C-term Shh antibodies to synthetic peptide mimics of the Sonic Hedgehog protein. FIG. 48A: Covalent binding and immobilization of control IgG, Ab11-2D9 or Ab11-2G4 antibodies to 5 amine reactive biosensors each. FIG. 48B: Sensor-bound antibodies exposed to increasing concentrations of two C-term Shh synthetic peptides (AA 247-264 and AA 448-462) show a binding response (nm). Antibody immobilization was checked via Octet® Software prior to introduction of increasing concentrations (37, 111, 333, 1000, 3000 nM) of Sonic Hedgehog peptide-mimic ligands (Shh 247-264 AA and Shh 448-462 AA). Graphical output from the Octet® Software of representative data from two independent experiments is presented. FIG. 48C: Binding affinities (K$_d$) of antibodies Ab 1C11-2D9 and Ab 1C11-2G4 for recombinant full-length Shh protein.

Figure 44D:
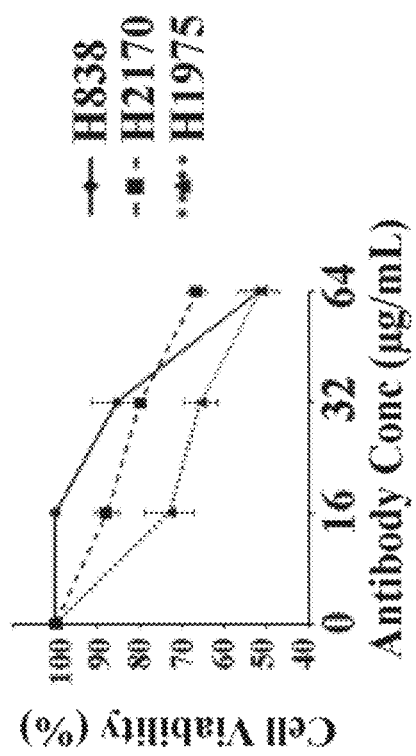
Figure 44E:
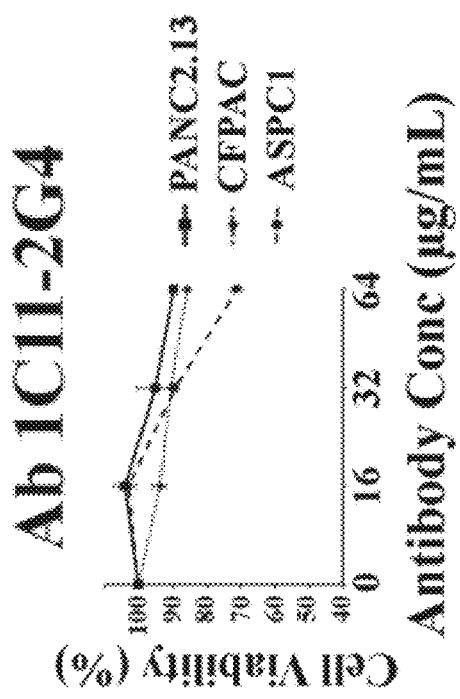
Figure 44C:
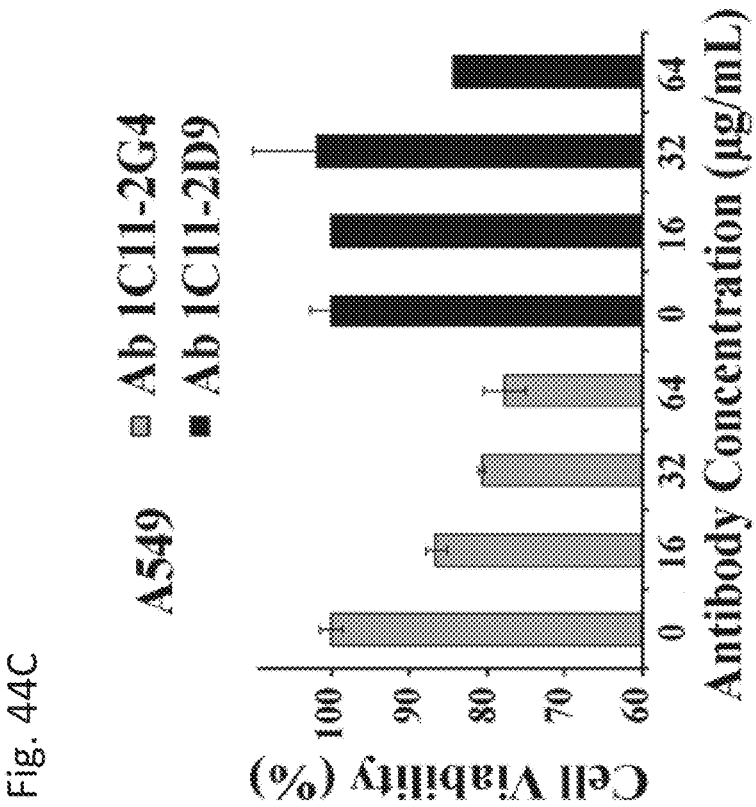

Ab 1C11 C-Term Shh Antibodies Recognize Shh+ Expressing Cell Populations and Inhibit the Growth of Cancer Cells In Vitro To corroborate that the two anti-Shh antibodies, 1C11-2G4 and 1C11-2D9, recognize cell-surface expression of Sonic Hedgehog, A549 cells were labeled with in-house antibodies and sorted via Fluorescence Activated Cell Sorting (FACS) without membrane permeabilization. Sub-clone Ab 1C11-2G4 recognized the most Shh+ cells from a mixed population (0.11%) compared with 1C11-2D9 (0.05%) and a commercially available C-term antibody (0.06%, Abcam) (FIG. 44A). Next an antibody labeling kit was used to conjugate Alexa Fluor®488 to Ab 1C11-2G4 to check for antibody internalization over a period of time. Higher intensities of Alexa Fluor®488-Ab 1C11-2G4 were observed 18 hours after antibody incubation compared with the 30 minute time point and also with a control FITC-IgG antibody assessed via confocal microscopy (FIG. 44B) indicating antibody internalization. Delivery of purified 1C11 anti-C-terminal Shh antibodies decreased NSCLC A549 tumor cell proliferation as evidenced by a reduction of cell viability compared with the controls; and sub-clone 2G4 showed marginally stronger anti-proliferative capacity compared with 2D9 (FIG. 44C). Finally, it was also observed that Ab 1C11-2G4 inhibited the growth of other lung and pancreatic cancer cell lines (FIG. 44D and FIG. 44E) possessing CSC populations as reported in Zakaria N, Yusoff N M, Zakaria Z, Lim M N, Baharuddin P J, Fakiruddin K S, Yahaya B. Human non-small cell lung cancer expresses putative cancer stem cell markers and exhibits the transcriptomic profile of multipotent cells. BMC Cancer. 15:84 (2015); Singh S, Trevino J, Bora-Singhal N, Coppola D, Haura E, Altiok S, Chellappan S P. EGFR/Src/Akt signaling modulates Sox2 expression and self-renewal of stem-like side-population cells in non-small cell lung cancer. Mol Cancer. 11:73 (2012); Cochrane C R, Szczepny A, Watkins D N, Cain J E. Hedgehog Signaling in the Maintenance of Cancer Stem Cells. Cancers (Basel). 7(3):1554-85; (2015); Seton-Rogers S. One of these things is not like the other. Nat Rev Cancer. 16(1):5 (2016); Herreros-Villanueva M, Zhang J S, Koenig A, Abel E V, Smyrk T C, Bamlet W R, de Narvajas A A, Gomez T S, Simeone D M, Bujanda L, Billadeau D D. SOX2 promotes dedifferentiation and imparts stem cell-like features to pancreatic cancer cells. Oncogenesis. 2:e61 (2013). Based on these collective observations, Ab 1C11-2G4 was advanced for further analyses via in vivo animal studies presented below.

FIGS. 44A-44E. Anti-Shh antibodies directed at the C-terminal of the Sonic Hedgehog protein recognize Shh+ cell populations and reduce cell viability of cancer cells in a dose-dependent manner. FIG. 44A: Fluorescence Activated Cell Sorting (FACS) of A549 cells labeled with Ab 1C11-2G4, Ab 1C11-2D9 and commercially purchased (Abcam) anti-Shh antibodies showing the % and number of Shh+ cells sorted. FIG. 44B: immunofluoresence analyses of non-fixed, non-permeabilized A549 cells treated with FITC-control IgG or Alexa Fluor®488-conjugated Ab C11-2G4, membrane dye and DAPI for indicated times to assess antibody internalization. FIG. 44C: NSCLC A549 cells were treated with indicated doses of C-term anti-Shh 1C11-2G4 and 1C11-2D9 antibodies (reconstituted in PBS) in triplicates for 96 hours and cell viability/ATP content was measured using CellTiter-Glo Luminescent Cell Viability Assay. PBS was used as a negative control. The results shown for all cell viability figures are representative of two independent experiments. Effect of Ab 1C11-2G4 on cell viability in lung cancer (FIG. 44D) and pancreatic cancer (FIG. 44E) performed as in (FIG. 44C).

Figure 45A:
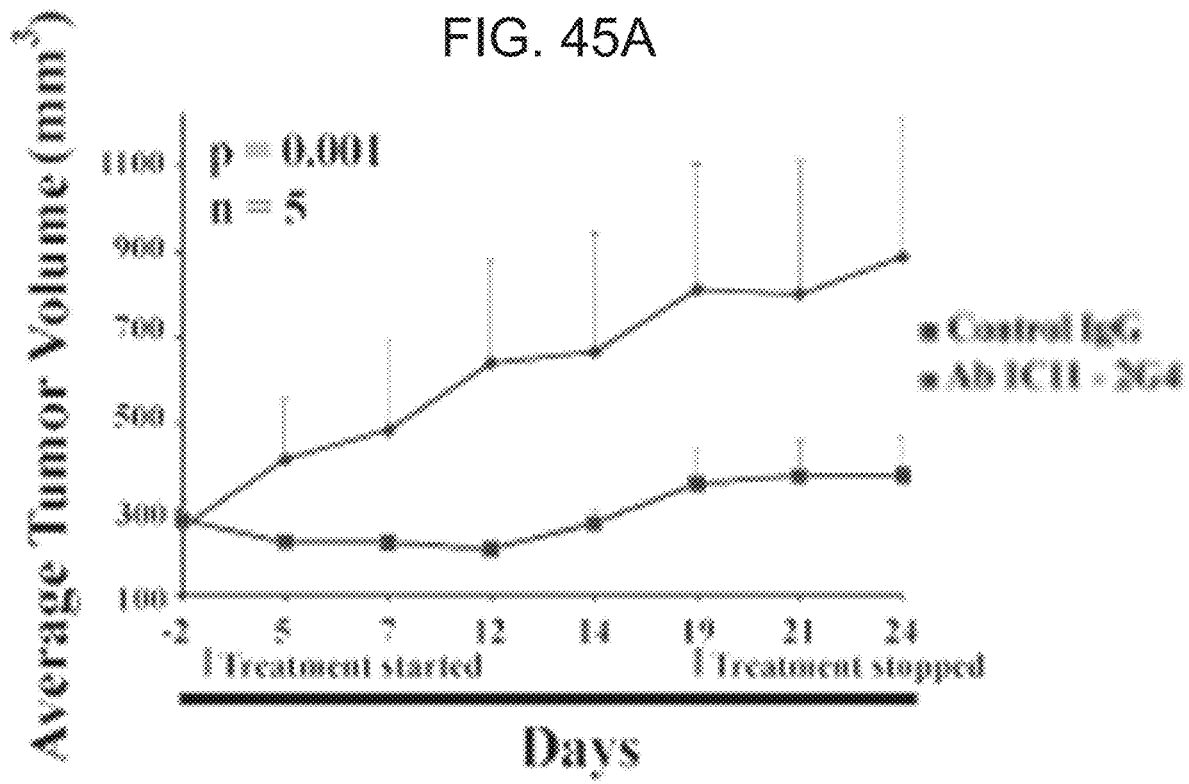
Figure 45B:
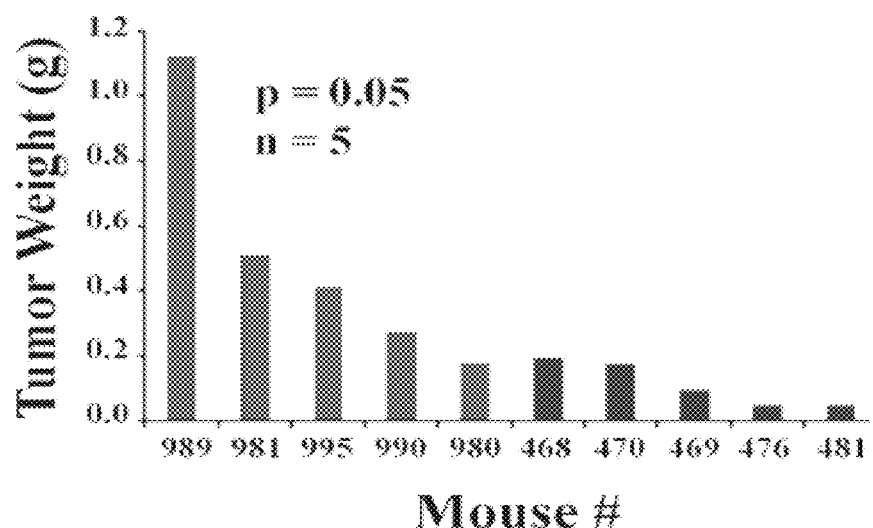
Figures 45C, 45D:
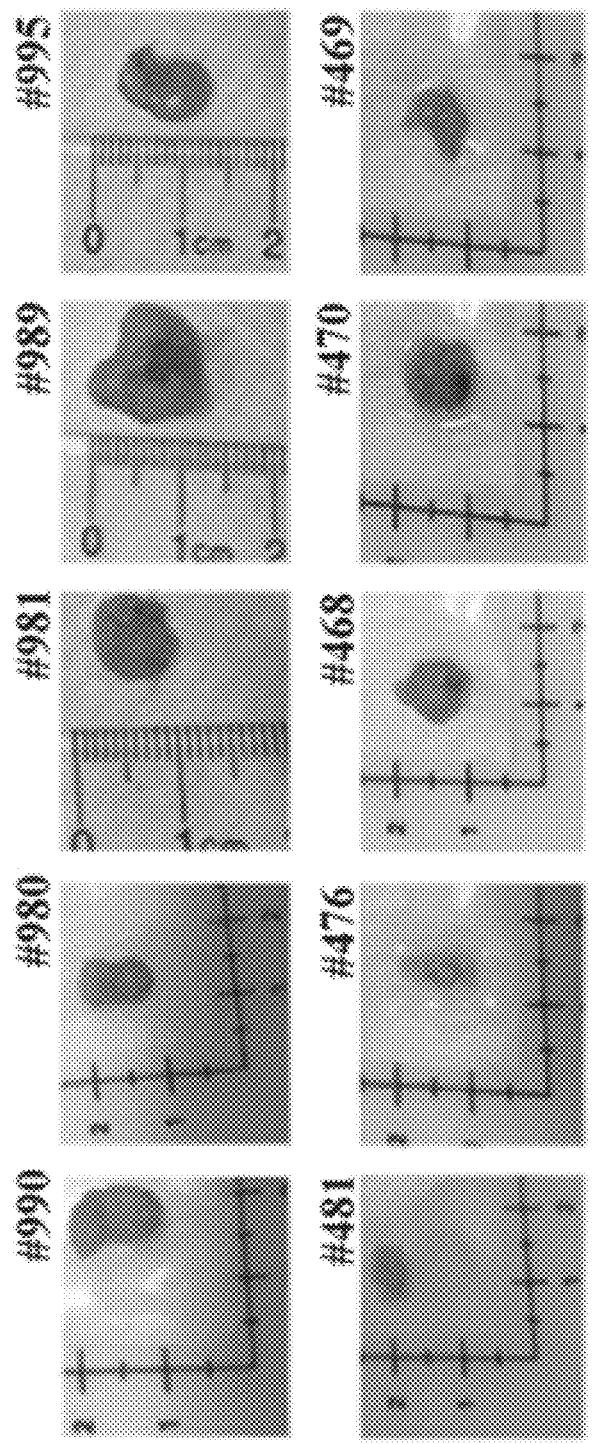

Reduction of Tumor Burden Upon In Vivo Xenograft Treatment with C-Term Shh Antibodies in Mice To determine the in vivo therapeutic utility of our C-term Shh antibody, 8 mg/kg Ab 1C11-2G4 or control IgG antibodies were injected into mice bearing A549-derived NSCLC xenografts. Mice were randomly assigned to control (n=5) or therapeutic antibody-recipient groups (n=5, 8 mg/kg, 3 times a week for 3 weeks) and tumor volume and body weight were recorded. During the course of the study, all mice survived but a significant reduction in tumor volume was observed in the Ab 1C11-2G4 C-term Shh-treated mice (FIG. 45A, p=0.001). All mice were subsequently sacrificed and their tumors excised for further investigation. Comparative analysis of harvested tumor size (FIG. 45C) exhibited a decrease in tumor weight (FIG. 45B, p=0.05) and tumor volume (FIG. 45D) in the C-term Shh antibody-treated group. Furthermore, antibody treatment did not cause toxicity because no drastic changes were observed in body weight in either group (FIG. 49A). Both antibodies presented here are efficacious in reducing tumor volume and are relatively non-toxic (FIGS. 49A and 49B).

FIGS. 45A-45D. C-term Shh Ab 1C11-2G4 treatment inhibits in vivo growth of NSCLC in a mouse xenograft model. FIG. 45A: 7-week-old female nude mice were inoculated with 10×10$^6$ NSCLC A549 cells in the flank region to establish tumors and randomly assigned to treatment regimens of IgG control or Ab 1C11-2G4 (8 mg/kg×3 times a week for 3 weeks). Changes in tumor volume of mice treated with the antibodies IgG control or Ab 1C11-2G4 (n=5, p=0.001) over the course of the study are shown. At the end point, tumor mass (FIG. 45B) was determined on harvested tumors by weighing (n=5, p=0.05) and the tumor volumes (FIG. 45D) were calculated using the formula (V=L×W$^2$). (FIG. 45C) Corresponding images of tumors collected from antibody-treated mice with their identifying ear-tag mouse numbers (#) showing a clear reduction in tumor burden in Ab 1C11-2G4-treated mice when compared with the control IgG antibody.

FIGS. 49A-49B. In vivo studies of C-term Shh Ab 1C11-2G4 and Ab 1C11-2D9 in lung NSCLC. FIG. 49A: Average body weight of all mice treated with Ab 1C11-2G4, Ab 1C11-2D9 or control IgG over the course of the study. FIG. 49B: Images of tumors collected from control IgG antibody-treated or Ab 1C11-2D9 antibody-treated mice.

Figure 46A:
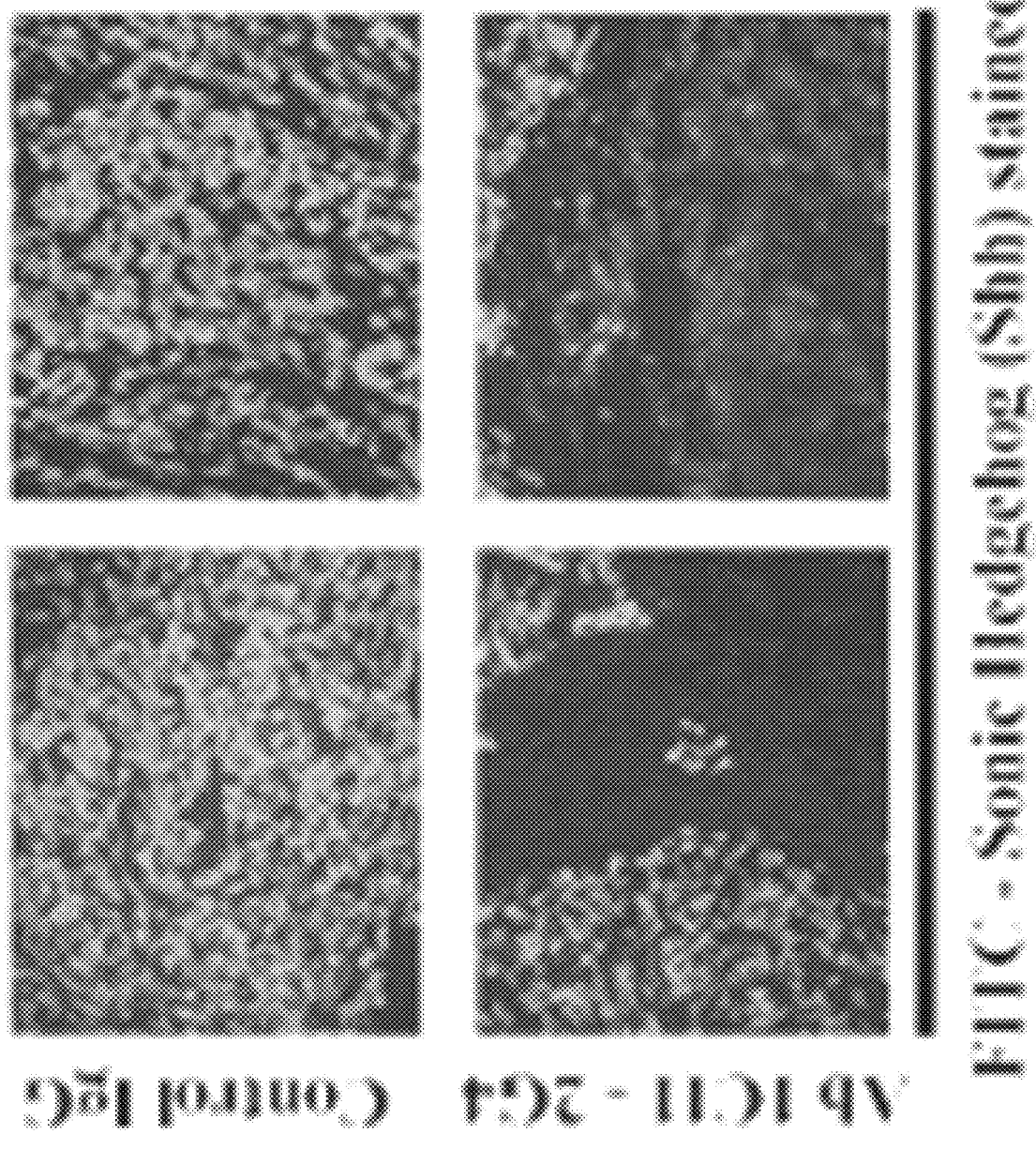
Figure 46B:
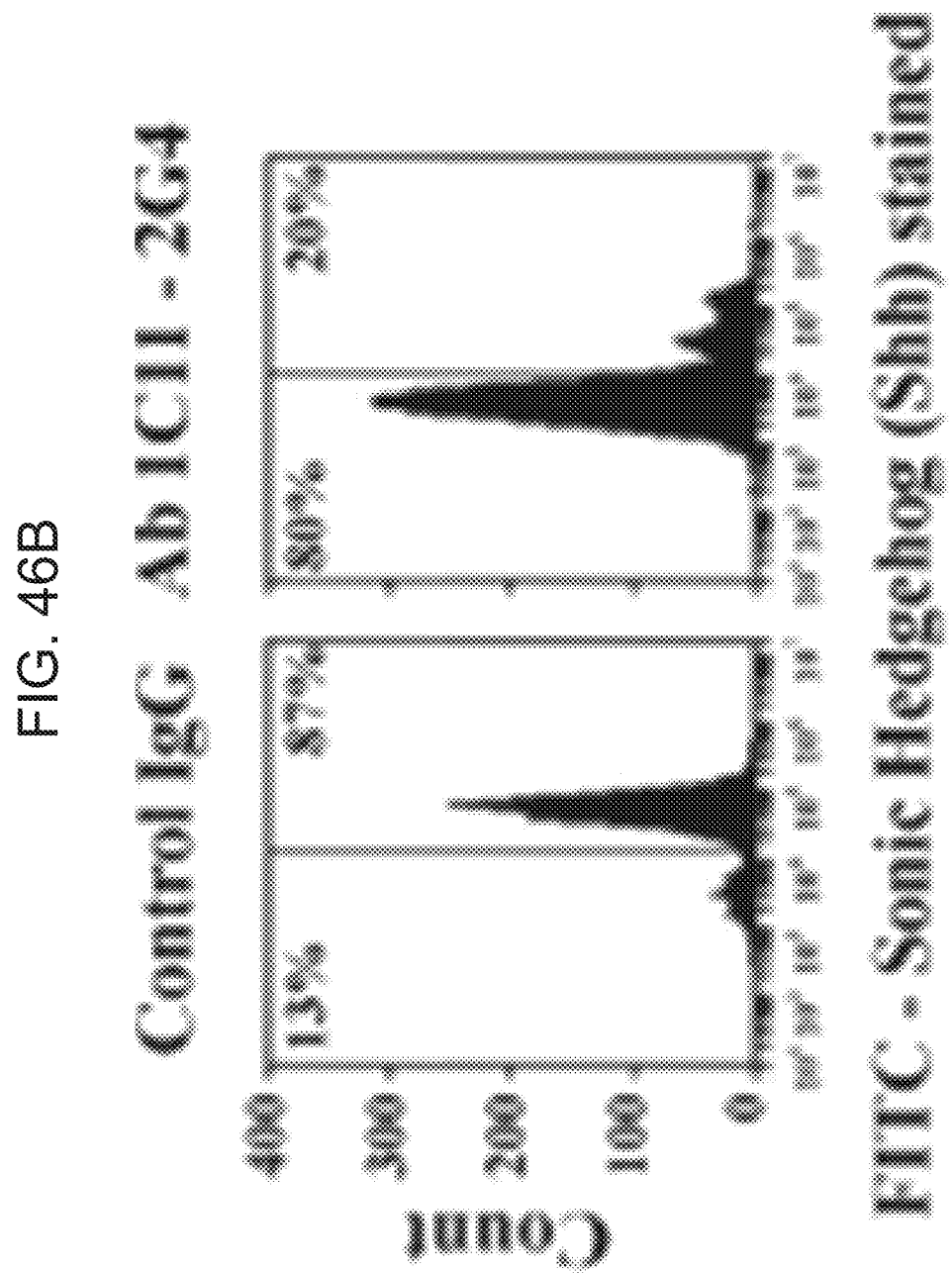
Figure 46C:
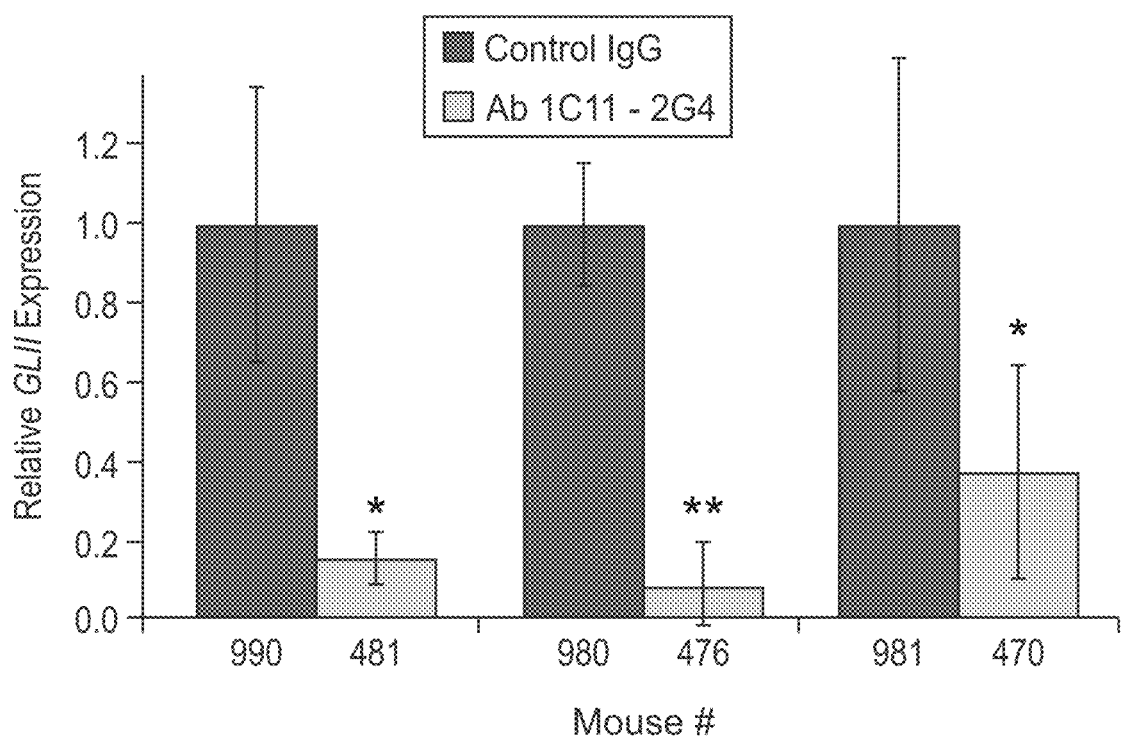
Figure 46D:
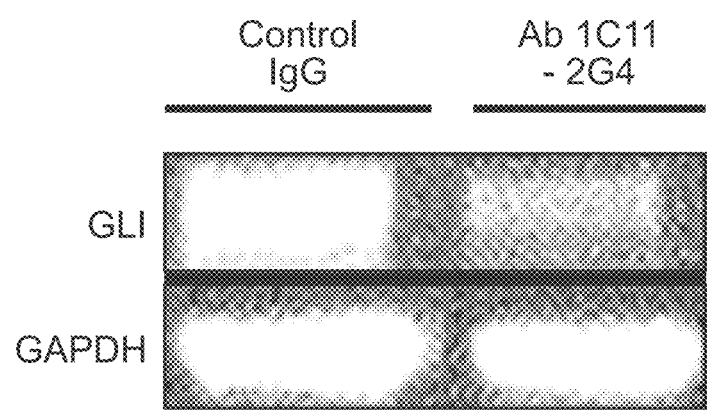

Ab1 C11-2G4 Treatment Down-Regulates Shh Expression Via Ex Vivo Xenograft Analyses To determine if the biologic presented here targets Shh and hampers cell-mediated hedgehog signaling as a result of C-term epitope binding, ex vivo analyses of human NSCLC A549 xenograft tumors from mice that were treated with anti-C-terminal Shh Ab 1C11-2G4 or with a control IgG were performed. To assess the effects of antibody administration on hedgehog epitope occupancy, tumors were sectioned and stained with a commercial antibody specific for sonic hedgehog (Shh). Immunofluorescent analysis of permeabilized tumor sections co-stained for Shh (FIG. 46A) revealed a significant reduction in the number of Shh-labeled cells from Ab 1C11-2G4-treated samples (bottom panel) compared with IgG controls (top panel). Confirmatory results were observed when ground up permeabilized tumor cells were labeled with the commercially available Shh antibody and assessed using flow cytometry; 1C11-2G4-treated tumors (20%-Shh-labeled) contrasted with IgG controls (80%-Shh-labeled) (FIG. 46B). To confirm whether functional targeting of cells expressing the C-term (or full-length) Shh protein impaired Shh signal transduction target genes in Ab 1C11-2G4-treated tumors, the effect of antibody treatment on transcription factor GLI gene and protein expression levels was tested. qRT-PCR and Western blot analysis with ground up tumors were performed and a significant reduction in GLI transcripts (FIG. 46C) and GLI polypeptide expression (FIG. 46D) compared with the IgG controls was observed.

FIGS. 46A-46D. Ex vivo analyses of Ab 1C11-2G4-treated tumors show Shh epitope occupancy and down-regulation of GLI expression in lung cancer xenografts. Permeabilized tumors harvested from nude mice after treatment with therapeutic C-term anti-Shh Ab 1C11-2G4 or IgG controls were stained for Shh with a commercial antibody to check for a Shh expression/epitope occupancy. Immunofluorescent analysis (FIG. 46A) and flow cytometric evaluation (FIG. 46B) show reduction of Shh (FITC) expression/epitope availability in Ab 1C11-2G4-treated tumors compared with IgG controls. (FIG. 46C) Quantitative RT-PCR analysis of GLI levels in A549 harvested tumors treated with IgG controls OR 8 mg/kg Ab 1C11-2G4, 3× per week for 3 weeks. Real-time PCR reactions were performed in triplicate and the data are presented as fold change in target gene expression (Mean±SD) after normalization with GAPDH. The results shown are representative of two independent experiments. (FIG. 46D) Corresponding tumors after control IgG OR Ab 1C11-2G4 treatments were lysed and analyzed by Western blot for the expression of GLI. GAPDH was used as a loading control.

Discussion

In this study, experiments were performed for the discovery and characterization of a novel C-terminal anti-Shh antibody, Ab 1C11-2G4, selected and purified from a screen of over 50 antibody-producing hybridoma candidates derived from murine clones. Mouse hybridomas were screened based on their ability to bind to recombinant fragments of Shh and Shh-expressing cells in both endogenous and exogenous systems. A proof-of-principle was demonstrated that the therapeutic anti-Shh antibody, Ab 1C11-2G4, recognized and bound its target, sonic hedgehog protein. In particular, Ab 2G4 recognized and bound not only the Shh peptide via biolayer inferometry and possesses nanomolar affinity for its ligand but also recognized cell-surface Shh+ expressing cell populations, appeared to get internalized and inhibited the viability of a 7 cancer cell lines in vitro. In addition, in studies using Ab 1C11-2G4 in an Shh-expressing xenograft model of lung cancer, efficacious doses of 2G4 exhibited an anti-proliferative effect on A549 tumors; a significant reduction in tumor volume (p=0.001, n=5) and tumor weight (p=0.05, n=5) is observed. Corresponding ex vivo analyses of A549 xenograft tumors from mice treated with the C-term Shh antibody Ab 1C11-2G4, provided further support that the Sonic Hedgehog epitope was occupied and Shh signal transduction programs were down-regulated post-treatment as evidenced by suppressed transcript and protein levels of downstream target protein GLI.

Taken together, these data highlighted a new therapeutic avenue of blocking the protein-protein interaction interface for regulating Shh signaling by use of anti-Shh antibodies directed at the C-term as a way to target full-length Shh implicated as the 'signal source' of CSCs. Activation of the pathway typically occurs upon binding of Shh to its receptor Patched, but in studies presented here, signaling was inhibited in a small population of cells if full-length Shh binds instead to the blocking antibody 2G4, a potential therapeutic, so that the protein cannot transmit downstream signals. The modest efficacy of the C-term anti-Shh antibody was associated with the fact that only a very small population (~1%) of tumor cells express full-length Shh. Thus, sustained treatment with 2G4 over time could be used to eradicate CSC-like Shh+ cells in Shh-dependent tumor types without severe toxicity. Another reason modest efficacy was observed may be that the antibody also binds cleaved C-term Shh produced by a majority of the cells (~99%) which has no known Shh signaling function and thus only modest changes in tumor inhibition upon treatment were observed.

The Ab 1C11-2G4 represents the first report of a therapeutic and inhibitory antibody designed to specifically target the carboxy-terminus of Sonic Hedgehog as an antigen. The present studies have established a new paradigm in which 2G4 shows modest anti-tumor activity in vivo accompanied by a lack of toxicity and it targets populations of CSC-harboring Shh+ cells.

In summary, a first-in-class therapeutic C-terminus antibody against Sonic Hedgehog was generated. This mouse antibody recognized Shh in cancer cell lines, lung xenografts in mice and inhibited Shh-mediated pathway activity. A hybridoma cell line expressing Ab 1C11-2G4 amenable to scale up production was developed to support IND enabling studies as well as advancement to phase 1 clinical testing.

While the present disclosure has been described with reference to the specific embodiments thereof, it should be understood by those skilled in the art that various changes may be made and equivalents may be substituted without departing from the true spirit and scope of the present disclosure. In addition, many modifications may be made to adapt a particular situation, material, composition of matter, process, process step or steps, to the objective, spirit and scope of the present disclosure. All such modifications are intended to be within the scope of the claims appended hereto.

What is claimed is:

1. An antibody, or an antigen binding fragment thereof, that specifically binds a Sonic Hedgehog (Shh) polypeptide comprising:

a heavy chain variable ($V_H$) region comprising:
- a complementarity determining region ($CDR_H1$) comprising the amino acid sequence: SYTMS (SEQ ID NO:10);
- a $CDR_H2$ comprising the amino acid sequence: TISGGGNTYYPDSVKG (SEQ ID NO:11); and
- a $CDR_H3$ comprising the amino acid sequence: DYRSLFAY (SEQ ID NO:12); and a light chain variable ($V_L$) region comprising:
- a $CDR_L1$ comprising the amino acid sequence: SASSSVSYMH (SEQ ID NO:13);
- a $CDR_L2$ comprising the amino acid sequence: STSNLAS (SEQ ID NO:14); and
- a $CDR_L3$ comprising the amino acid sequence: QQRSSYPFT (SEQ ID NO:15).

2. The antibody, or the antigen binding fragment thereof, of claim 1, wherein the antibody specifically binds a C-terminal Shh polypeptide.

3. The antibody, or the antigen binding fragment thereof, of claim 1, wherein the antibody, or the antigen binding fragment thereof, is humanized.

4. The antibody, or the antigen binding fragment thereof, of claim 1, comprising a $V_H$ region comprising an amino acid sequence at least about 80% identical to the sequence:

(SEQ ID NO: 16)
EVKLVESGGGLVKPGGSLKLSCAASGFTFSSYTMSWVRQTPAKRLE

WVATISSGGGNTYYPDSVKGRFTISRDNARNTLYLQMSSLRSEDTA

MYYCARDYRSLFAYWGQGTLVTVSA.

5. The antibody, or the antigen binding fragment thereof, of claim 1, comprising a $V_L$ region comprising an amino acid sequence at least 80% identical to the sequence:

(SEQ ID NO: 17)
QIVLTQSPAIMSASPGEKVTITCSASSSVSYMHWFQQKPGTSPKLW

IYSTSNLASGVPARFSGSGSGTSYSLTISRMEAEDAATYYCQQRSS

YPFTFGSGTKLEIK.

6. The antibody, or the antigen binding fragment thereof, of claim 1, wherein the antibody, or the antigen binding fragment thereof, is a scFV antibody, F(ab')$_2$, Fab', or Fab fragment or a diabody.

7. The antibody, or the antigen binding fragment thereof, of claim 1, wherein the antibody is an IgG$_1$ antibody.

8. An antibody conjugate comprising an antibody, or an antigen binding fragment thereof, comprising an immunoglobulin (Ig) polypeptide attached to a therapeutic agent, wherein the antibody specifically binds to full-length Shh polypeptide expressed on a cell surface and comprises:
  a heavy chain variable (VH) region comprising:
    a complementarity determining region (CDR$_H$1) comprising the amino acid sequence: SYTMS (SEQ ID NO:10);
    a CDR$_H$2 comprising the amino acid sequence: TISSGGGNTYYPDSVKG (SEQ ID NO:11); and
    a CDR$_H$3 comprising the amino acid sequence: DYRSLFAY (SEQ ID NO:12); and
  a light chain variable (VL) region comprising:
    a CDR$_L$1 comprising the amino acid sequence: SASSSVSYMH (SEQ ID NO:13);
    a CDR$_L$2 comprising the amino acid sequence: STSNLAS (SEQ ID NO:14); and
    a CDR$_L$3 comprising the amino acid sequence: QQRSSYPFT (SEQ ID NO:15).

9. The antibody conjugate of claim 8, wherein the antibody specifically binds to a C-terminal Shh polypeptide.

10. The antibody conjugate of claim 9, wherein the cell surface is a surface of a tumor cell.

11. The antibody conjugate of claim 10, wherein the tumor cell is a cancer stem cell.

12. The antibody conjugate of claim 8, wherein the therapeutic agent is covalently attached to the Ig polypeptide.

13. The antibody conjugate of claim 12, wherein the therapeutic agent is covalently attached through one or more cysteine residues in the Ig polypeptide.

14. The antibody conjugate of claim 13, wherein the therapeutic agent is attached to the polypeptide by one or more disulfide linkages.

15. The antibody conjugate of claim 12, wherein the therapeutic agent is attached to the Ig polypeptide through one or more linking groups.

16. The antibody conjugate of claim 8, wherein the Ig polypeptide comprises a light chain polypeptide.

17. The antibody conjugate of claim 8, wherein the Ig polypeptide comprises a heavy chain polypeptide.

18. The antibody conjugate of claim 16, wherein the therapeutic agent is attached to a constant region.

19. The antibody conjugate of claim 8, wherein the therapeutic agent is an inhibitor of a Shh signaling pathway.

20. The antibody conjugate of claim 19, wherein the inhibitor is a GLI inhibitor or a Smoothened (Smo) inhibitor.

21. A nucleic acid comprising a nucleotide sequence encoding a Ig polypeptide of the antibody, or the antigen binding fragment thereof, of claim 1.

22. An expression vector comprising the nucleic acid of claim 21, wherein the nucleotide sequence encoding the antibody, or the antigen binding fragment thereof, is operably linked to a promoter.

23. A composition comprising:
  the antibody of claim 1; and
  a pharmaceutically acceptable excipient.

24. The composition of claim 23, wherein the antibody is present in a therapeutically effective amount.

25. The composition of claim 23, comprising the antibody, and further comprising a therapeutic agent in a therapeutically effective amount.

26. The composition of claim 25, wherein the therapeutic agent is a chemotherapeutic agent.

27. The composition of claim 26, wherein the chemotherapeutic agent is an alkylating agent, antimetabolite, anti-microtubule agent, topoisomerase inhibitor, or a cytotoxic antibiotic.

28. The composition of claim 24, wherein the therapeutic agent is an inhibitor of a Shh signaling pathway.

29. The composition of claim 28, wherein the antibody is present in an amount such that the therapeutically effective amount of the therapeutic agent in the composition comprising the amount of the antibody is less than the therapeutically effective amount of the therapeutic agent in the composition that does not comprise the antibody.

30. The composition of claim 29, wherein the therapeutically effective amount of the therapeutic agent in the composition comprising the amount of the antibody is at least about 10% less than the therapeutically effective amount of the therapeutic agent in the composition that does not comprise the antibody.

31. The composition of claim 28, wherein the inhibitor is a GLI inhibitor or a Smo inhibitor.

32. A kit comprising:
  the antibody, or an antigen-binding fragment thereof, of claim 1; and
  a packaging configured to hold the antibody, or an antigen-binding fragment thereof.

33. The kit of claim 32, further comprising a buffer comprising the antibody, or an antigen-binding fragment thereof.

34. The kit of claim 33, wherein the buffer is a pharmaceutically acceptable excipient.

35. A composition comprising:
  the antibody conjugate of claim 8; and
  a pharmaceutically acceptable excipient.

36. The composition of claim 35, wherein the antibody conjugate is present in a therapeutically effective amount.

37. A kit comprising:
  the antibody conjugate of claim 8; and
  a packaging configured to hold the antibody conjugate.

38. The kit of claim 37, further comprising a buffer comprising the antibody conjugate.

39. The kit of claim 38, wherein the buffer is a pharmaceutically acceptable excipient.

40. A method of treating an individual for a cancer, comprising administering to an individual, a therapeutically effective amount of the antibody of claim 1.

* * * * *

SEQUENCE LISTING

```
<160> NUMBER OF SEQ ID NOS: 20

<210> SEQ ID NO 1
<211> LENGTH: 462
<212> TYPE: PRT
<213> ORGANISM: Artificial Sequence
<220> FEATURE:
<223> OTHER INFORMATION: Synthetic Sequence

<400> SEQUENCE: 1

Met Leu Leu Leu Ala Arg Cys Leu Leu Leu Val Leu Val Ser Ser Leu
1               5                   10                  15

Leu Val Cys Ser Gly Leu Ala Cys Gly Pro Gly Arg Gly Phe Gly Lys
                20                  25                  30

Arg Arg His Pro Lys Lys Leu Thr Pro Leu Ala Tyr Lys Gln Phe Ile
            35                  40                  45
```

```
Pro Asn Val Ala Glu Lys Thr Leu Gly Ala Ser Gly Arg Tyr Glu Gly
 50                  55                  60

Lys Ile Ser Arg Asn Ser Glu Arg Phe Lys Glu Leu Thr Pro Asn Tyr
 65                  70                  75                  80

Asn Pro Asp Ile Ile Phe Lys Asp Glu Glu Asn Thr Gly Ala Asp Arg
                     85                  90                  95

Leu Met Thr Gln Arg Cys Lys Asp Lys Leu Asn Ala Leu Ala Ile Ser
                100                 105                 110

Val Met Asn Gln Trp Pro Gly Val Lys Leu Arg Val Thr Glu Gly Trp
                115                 120                 125

Asp Glu Asp Gly His His Ser Glu Glu Ser Leu His Tyr Glu Gly Arg
    130                 135                 140

Ala Val Asp Ile Thr Thr Ser Asp Arg Asp Arg Ser Lys Tyr Gly Met
145                 150                 155                 160

Leu Ala Arg Leu Ala Val Glu Ala Gly Phe Asp Trp Val Tyr Tyr Glu
                165                 170                 175

Ser Lys Ala His Ile His Cys Ser Val Lys Ala Glu Asn Ser Val Ala
                180                 185                 190

Ala Lys Ser Gly Gly Cys Phe Pro Gly Ser Ala Thr Val His Leu Glu
            195                 200                 205

Gln Gly Gly Thr Lys Leu Val Lys Asp Leu Ser Pro Gly Asp Arg Val
    210                 215                 220

Leu Ala Ala Asp Asp Gln Gly Arg Leu Leu Tyr Ser Asp Phe Leu Thr
225                 230                 235                 240

Phe Leu Asp Arg Asp Asp Gly Ala Lys Lys Val Phe Tyr Val Ile Glu
                245                 250                 255

Thr Arg Glu Pro Arg Glu Arg Leu Leu Leu Thr Ala Ala His Leu Leu
            260                 265                 270

Phe Val Ala Pro His Asn Asp Ser Ala Thr Gly Glu Pro Glu Ala Ser
            275                 280                 285

Ser Gly Ser Gly Pro Pro Ser Gly Gly Ala Leu Gly Pro Arg Ala Leu
    290                 295                 300

Phe Ala Ser Arg Val Arg Pro Gly Gln Arg Val Tyr Val Val Ala Glu
305                 310                 315                 320

Arg Asp Gly Asp Arg Arg Leu Leu Pro Ala Ala Val His Ser Val Thr
                325                 330                 335

Leu Ser Glu Glu Ala Ala Gly Ala Tyr Ala Pro Leu Thr Ala Gln Gly
                340                 345                 350

Thr Ile Leu Ile Asn Arg Val Leu Ala Ser Cys Tyr Ala Val Ile Glu
                355                 360                 365

Glu His Ser Trp Ala His Arg Ala Phe Ala Pro Phe Arg Leu Ala His
    370                 375                 380

Ala Leu Leu Ala Ala Leu Ala Pro Ala Arg Thr Asp Arg Gly Gly Asp
385                 390                 395                 400

Ser Gly Gly Gly Asp Arg Gly Gly Gly Gly Arg Val Ala Leu Thr
                405                 410                 415

Ala Pro Gly Ala Ala Asp Ala Pro Gly Ala Gly Ala Thr Ala Gly Ile
                420                 425                 430

His Trp Tyr Ser Gln Leu Leu Tyr Gln Ile Gly Thr Trp Leu Leu Asp
            435                 440                 445

Ser Glu Ala Leu His Pro Leu Gly Met Ala Val Lys Ser Ser
450                 455                 460
```

<210> SEQ ID NO 2
<211> LENGTH: 1383
<212> TYPE: PRT
<213> ORGANISM: Artificial Sequence
<220> FEATURE:
<223> OTHER INFORMATION: Synthetic Sequence

<400> SEQUENCE: 2

```
Ala Thr Gly Ala Ala Cys Thr Thr Cys Gly Gly Cys Thr Cys Ala
1               5                   10                  15

Gly Cys Thr Thr Gly Ala Thr Thr Thr Cys Cys Thr Thr Gly Thr
                20                  25                  30

Cys Cys Thr Thr Gly Thr Thr Thr Ala Ala Ala Gly Gly Thr
                35              40                  45

Gly Thr Cys Cys Ala Gly Thr Gly Ala Ala Gly Thr Gly Ala
                50              55                  60

Ala Gly Cys Thr Gly Gly Thr Gly Gly Ala Gly Thr Cys Thr Gly Gly
65              70                  75                  80

Gly Gly Gly Ala Gly Gly Cys Thr Thr Ala Gly Thr Ala Ala Gly
                85                  90                  95

Cys Cys Thr Gly Gly Ala Gly Gly Thr Cys Cys Thr Gly Ala
                100                 105                 110

Ala Ala Cys Thr Cys Thr Cys Thr Gly Thr Gly Cys Ala Gly Cys
                115                 120                 125

Cys Thr Cys Thr Gly Gly Ala Thr Thr Cys Ala Cys Thr Thr Cys
                130                 135                 140

Ala Gly Thr Ala Gly Cys Thr Ala Thr Ala Cys Cys Ala Thr Gly
145                 150                 155                 160

Cys Thr Thr Gly Gly Gly Thr Cys Gly Cys Cys Ala Gly Ala Cys
                165                 170                 175

Thr Cys Cys Gly Gly Cys Gly Ala Ala Gly Ala Gly Cys Thr Gly
                180                 185                 190

Gly Ala Gly Thr Gly Gly Gly Thr Cys Gly Cys Ala Ala Cys Cys Ala
                195                 200                 205

Thr Thr Ala Gly Thr Ala Gly Thr Gly Gly Thr Gly Gly Thr Gly Gly
                210                 215                 220

Thr Ala Ala Cys Ala Cys Cys Thr Ala Cys Thr Ala Thr Cys Cys Ala
225                 230                 235                 240

Gly Ala Cys Ala Gly Thr Gly Thr Gly Ala Ala Gly Gly Gly Cys Cys
                245                 250                 255

Gly Ala Thr Thr Cys Ala Cys Cys Ala Thr Cys Thr Cys Cys Ala Gly
                260                 265                 270

Ala Gly Ala Cys Ala Ala Thr Gly Cys Cys Ala Gly Gly Ala Ala Cys
                275                 280                 285

Ala Cys Cys Cys Thr Gly Thr Ala Cys Cys Thr Gly Cys Ala Ala Ala
                290                 295                 300

Thr Gly Ala Gly Cys Ala Gly Thr Cys Thr Gly Ala Gly Gly Thr Cys
305                 310                 315                 320

Thr Gly Ala Gly Gly Ala Cys Ala Cys Gly Gly Cys Cys Ala Thr Gly
                325                 330                 335

Thr Ala Thr Thr Ala Cys Thr Gly Thr Gly Cys Ala Ala Gly Ala Gly
                340                 345                 350

Ala Cys Thr Ala Thr Ala Gly Gly Thr Cys Cys Thr Gly Thr Thr
                355                 360                 365

Thr Gly Cys Thr Thr Ala Cys Thr Gly Gly Gly Gly Cys Cys Ala Ala
```

-continued

```
    370                 375                 380

Gly Gly Gly Ala Cys Thr Cys Thr Gly Gly Thr Cys Ala Cys Thr Gly
385                 390                 395                 400

Thr Cys Thr Cys Thr Gly Cys Ala Gly Cys Cys Ala Ala Ala Ala Cys
                405                 410                 415

Gly Ala Cys Ala Cys Cys Cys Cys Cys Ala Thr Cys Thr Gly Thr Cys
            420                 425                 430

Thr Ala Thr Cys Cys Ala Cys Thr Gly Gly Cys Cys Cys Cys Thr Gly
        435                 440                 445

Gly Ala Thr Cys Thr Gly Cys Thr Gly Cys Cys Cys Ala Ala Ala Cys
    450                 455                 460

Thr Ala Ala Cys Thr Cys Cys Ala Thr Gly Gly Thr Gly Ala Cys Cys
465                 470                 475                 480

Cys Thr Gly Gly Gly Ala Thr Gly Cys Cys Thr Gly Gly Thr Cys Ala
                485                 490                 495

Ala Gly Gly Gly Cys Thr Ala Thr Thr Thr Cys Cys Cys Thr Gly Ala
            500                 505                 510

Gly Cys Cys Ala Gly Thr Gly Ala Cys Ala Gly Thr Gly Ala Cys Cys
        515                 520                 525

Thr Gly Gly Ala Ala Cys Thr Cys Thr Gly Gly Ala Thr Cys Cys Cys
    530                 535                 540

Thr Gly Thr Cys Cys Ala Gly Cys Gly Gly Thr Gly Thr Gly Cys Ala
545                 550                 555                 560

Cys Ala Cys Cys Thr Thr Cys Cys Cys Ala Gly Cys Thr Gly Thr Cys
                565                 570                 575

Cys Thr Gly Cys Ala Gly Thr Cys Thr Gly Ala Cys Cys Thr Cys Thr
            580                 585                 590

Ala Cys Ala Cys Thr Cys Thr Gly Ala Gly Cys Ala Gly Cys Thr Cys
        595                 600                 605

Ala Gly Thr Gly Ala Cys Thr Gly Thr Cys Cys Cys Cys Thr Cys Cys
    610                 615                 620

Ala Gly Cys Ala Cys Cys Thr Gly Gly Cys Cys Cys Ala Gly Cys Gly
625                 630                 635                 640

Ala Gly Ala Cys Cys Gly Thr Cys Ala Cys Cys Thr Gly Cys Ala Ala
                645                 650                 655

Cys Gly Thr Thr Gly Cys Cys Cys Ala Cys Cys Cys Gly Gly Cys Cys
            660                 665                 670

Ala Gly Cys Ala Gly Cys Ala Cys Cys Ala Ala Gly Gly Thr Gly Gly
        675                 680                 685

Ala Cys Ala Ala Gly Ala Ala Ala Ala Thr Thr Gly Thr Gly Cys Cys
    690                 695                 700

Cys Ala Gly Gly Gly Ala Thr Thr Gly Thr Gly Gly Thr Thr Gly Thr
705                 710                 715                 720

Ala Ala Gly Cys Cys Thr Thr Gly Cys Ala Thr Ala Thr Gly Thr Ala
                725                 730                 735

Cys Ala Gly Thr Cys Cys Cys Ala Gly Ala Ala Gly Thr Ala Thr Cys
            740                 745                 750

Ala Thr Cys Thr Gly Thr Cys Thr Thr Cys Ala Thr Cys Thr Thr Cys
        755                 760                 765

Cys Cys Cys Cys Cys Ala Ala Ala Gly Cys Cys Cys Ala Ala Gly Gly
    770                 775                 780

Ala Thr Gly Thr Gly Cys Thr Cys Ala Cys Cys Ala Thr Thr Ala Cys
785                 790                 795                 800
```

```
Thr Cys Thr Gly Ala Cys Thr Cys Cys Thr Ala Ala Gly Gly Thr Cys
                805                 810                 815

Ala Cys Gly Thr Gly Thr Gly Thr Thr Gly Thr Gly Gly Thr Ala Gly
            820                 825                 830

Ala Cys Ala Thr Cys Ala Gly Cys Ala Ala Gly Gly Ala Thr Gly Ala
        835                 840                 845

Thr Cys Cys Cys Gly Ala Gly Gly Thr Cys Cys Ala Gly Thr Thr Cys
    850                 855                 860

Ala Gly Cys Thr Gly Gly Thr Thr Thr Gly Thr Ala Gly Ala Thr Gly
865                 870                 875                 880

Ala Thr Gly Thr Gly Gly Ala Gly Gly Thr Gly Cys Ala Cys Ala Cys
                885                 890                 895

Ala Gly Cys Thr Cys Ala Gly Ala Cys Gly Cys Ala Ala Cys Cys Cys
            900                 905                 910

Cys Gly Gly Gly Ala Gly Gly Ala Gly Cys Ala Gly Thr Thr Cys Ala
        915                 920                 925

Ala Cys Ala Gly Cys Ala Cys Thr Thr Thr Cys Cys Gly Cys Thr Cys
    930                 935                 940

Ala Gly Thr Cys Ala Gly Thr Gly Ala Ala Cys Thr Thr Cys Cys Cys
945                 950                 955                 960

Ala Thr Cys Ala Thr Gly Cys Ala Cys Cys Ala Gly Gly Ala Cys Thr
                965                 970                 975

Gly Gly Cys Thr Cys Ala Ala Thr Gly Gly Cys Ala Ala Gly Gly Ala
            980                 985                 990

Gly Thr Thr Cys Ala Ala Ala Thr  Gly Cys Ala Gly Gly  Gly Thr Cys
        995                 1000                1005

Ala Ala  Cys Ala Gly Thr Gly  Cys Ala Gly Cys Thr  Thr Thr Cys
    1010                 1015                 1020

Cys Cys  Thr Gly Cys Cys Cys  Cys Cys Ala Thr Cys  Gly Ala Gly
    1025                 1030                 1035

Ala Ala  Ala Ala Cys Cys Ala  Thr Cys Thr Cys Cys  Ala Ala Ala
    1040                 1045                 1050

Ala Cys  Cys Ala Ala Ala Gly  Gly Cys Ala Gly Ala  Cys Cys Gly
    1055                 1060                 1065

Ala Ala  Gly Gly Cys Thr Cys  Cys Ala Cys Ala Gly  Gly Thr Gly
    1070                 1075                 1080

Thr Ala  Cys Ala Cys Cys Ala  Thr Thr Cys Cys Ala  Cys Cys Thr
    1085                 1090                 1095

Cys Cys  Cys Ala Ala Gly Gly  Ala Gly Cys Ala Gly  Ala Thr Gly
    1100                 1105                 1110

Gly Cys  Cys Ala Ala Gly Gly  Ala Thr Ala Ala Ala  Gly Thr Cys
    1115                 1120                 1125

Ala Gly  Thr Cys Thr Gly Ala  Cys Cys Thr Gly Cys  Ala Thr Gly
    1130                 1135                 1140

Ala Thr  Ala Ala Cys Ala Gly  Ala Cys Thr Thr Cys  Thr Thr Cys
    1145                 1150                 1155

Cys Cys  Thr Gly Ala Ala Gly  Ala Cys Ala Thr Thr  Ala Cys Thr
    1160                 1165                 1170

Gly Thr  Gly Gly Ala Gly Thr  Gly Gly Cys Ala Gly  Thr Gly Gly
    1175                 1180                 1185

Ala Ala  Thr Gly Gly Gly Cys  Ala Gly Cys Cys Ala  Gly Cys Gly
    1190                 1195                 1200
```

```
Gly Ala  Gly Ala Ala Cys  Thr Ala Cys  Ala Ala Gly  Ala Ala Cys
    1205              1210              1215

Ala Cys  Thr Cys Ala Gly  Cys Cys Ala  Thr Cys Ala  Thr Gly
    1220              1225              1230

Gly Ala  Cys Ala Cys Ala  Gly Ala Thr  Gly Gly Cys  Thr Cys Thr
    1235              1240              1245

Thr Ala  Cys Thr Thr Cys  Ala Thr Cys  Thr Ala Cys  Ala Gly Cys
    1250              1255              1260

Ala Ala  Gly Cys Thr Cys  Ala Ala Thr  Gly Thr Gly  Cys Ala Gly
    1265              1270              1275

Ala Ala  Gly Ala Gly Cys  Ala Ala Cys  Thr Gly Gly  Gly Ala Gly
    1280              1285              1290

Gly Cys  Ala Gly Gly Ala  Ala Thr Ala  Cys Thr Thr  Thr Thr Cys
    1295              1300              1305

Ala Cys  Cys Thr Gly Cys  Thr Cys Thr  Gly Thr Gly  Thr Thr Ala
    1310              1315              1320

Cys Ala  Thr Gly Ala Gly  Gly Cys Cys  Thr Gly Cys  Ala Cys
    1325              1330              1335

Ala Ala  Cys Cys Ala Cys  Ala Thr Ala  Cys Thr Gly  Ala Gly
    1340              1345              1350

Ala Ala  Gly Ala Gly Cys  Thr Cys Thr  Cys Cys Ala  Cys
    1355              1360              1365

Thr Cys  Thr Cys Cys Thr  Gly Gly Thr  Ala Ala Ala  Thr Gly Ala
    1370              1375              1380

<210> SEQ ID NO 3
<211> LENGTH: 460
<212> TYPE: PRT
<213> ORGANISM: Artificial Sequence
<220> FEATURE:
<223> OTHER INFORMATION: Synthetic Sequence

<400> SEQUENCE: 3

Met Asn Phe Gly Leu Ser Leu Ile Phe Leu Val Leu Val Leu Lys Gly
1               5                   10                  15

Val Gln Cys Glu Val Lys Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Ser Tyr Thr Met Ser Trp Val Arg Gln Thr Pro Ala Lys Arg Leu
    50                  55                  60

Glu Trp Val Ala Thr Ile Ser Ser Gly Gly Gly Asn Thr Tyr Tyr Pro
65                  70                  75                  80

Asp Ser Val Lys Gly Arg Phe Thr Ile Ser Arg Asp Asn Ala Arg Asn
                85                  90                  95

Thr Leu Tyr Leu Gln Met Ser Ser Leu Arg Ser Glu Asp Thr Ala Met
            100                 105                 110

Tyr Tyr Cys Ala Arg Asp Tyr Arg Ser Leu Phe Ala Tyr Trp Gly Gln
        115                 120                 125

Gly Thr Leu Val Thr Val Ser Ala Ala Lys Thr Thr Pro Pro Ser Val
    130                 135                 140

Tyr Pro Leu Ala Pro Gly Ser Ala Ala Gln Thr Asn Ser Met Val Thr
145                 150                 155                 160

Leu Gly Cys Leu Val Lys Gly Tyr Phe Pro Glu Pro Val Thr Val Thr
                165                 170                 175
```

Trp Asn Ser Gly Ser Leu Ser Ser Gly Val His Thr Phe Pro Ala Val
            180                 185                 190

Leu Gln Ser Asp Leu Tyr Thr Leu Ser Ser Val Thr Val Pro Ser
        195                 200                 205

Ser Thr Trp Pro Ser Glu Thr Val Thr Cys Asn Val Ala His Pro Ala
    210                 215                 220

Ser Ser Thr Lys Val Asp Lys Lys Ile Val Pro Arg Asp Cys Gly Cys
225                 230                 235                 240

Lys Pro Cys Ile Cys Thr Val Pro Glu Val Ser Ser Val Phe Ile Phe
                245                 250                 255

Pro Pro Lys Pro Lys Asp Val Leu Thr Ile Thr Leu Thr Pro Lys Val
            260                 265                 270

Thr Cys Val Val Val Asp Ile Ser Lys Asp Asp Pro Glu Val Gln Phe
        275                 280                 285

Ser Trp Phe Val Asp Asp Val Glu Val His Thr Ala Gln Thr Gln Pro
    290                 295                 300

Arg Glu Glu Gln Phe Asn Ser Thr Phe Arg Ser Val Ser Glu Leu Pro
305                 310                 315                 320

Ile Met His Gln Asp Trp Leu Asn Gly Lys Glu Phe Lys Cys Arg Val
                325                 330                 335

Asn Ser Ala Ala Phe Pro Ala Pro Ile Glu Lys Thr Ile Ser Lys Thr
            340                 345                 350

Lys Gly Arg Pro Lys Ala Pro Gln Val Tyr Thr Ile Pro Pro Pro Lys
        355                 360                 365

Glu Gln Met Ala Lys Asp Lys Val Ser Leu Thr Cys Met Ile Thr Asp
370                 375                 380

Phe Phe Pro Glu Asp Ile Thr Val Glu Trp Gln Trp Asn Gly Gln Pro
385                 390                 395                 400

Ala Glu Asn Tyr Lys Asn Thr Gln Pro Ile Met Asp Thr Asp Gly Ser
                405                 410                 415

Tyr Phe Ile Tyr Ser Lys Leu Asn Val Gln Lys Ser Asn Trp Glu Ala
            420                 425                 430

Gly Asn Thr Phe Thr Cys Ser Val Leu His Glu Gly Leu His Asn His
        435                 440                 445

His Thr Glu Lys Ser Leu Ser His Ser Pro Gly Lys
    450                 455                 460

<210> SEQ ID NO 4
<211> LENGTH: 707
<212> TYPE: PRT
<213> ORGANISM: Artificial Sequence
<220> FEATURE:
<223> OTHER INFORMATION: Synthetic Sequence

<400> SEQUENCE: 4

Ala Thr Gly Cys Ala Thr Thr Thr Cys Ala Ala Gly Thr Gly Cys
1               5                   10                  15

Ala Gly Ala Thr Thr Thr Thr Cys Ala Gly Cys Thr Thr Cys Cys Thr
            20                  25                  30

Gly Cys Thr Ala Ala Thr Cys Ala Gly Thr Gly Cys Cys Thr Cys Ala
        35                  40                  45

Gly Thr Cys Ala Thr Ala Ala Thr Gly Thr Cys Cys Ala Gly Ala Gly
    50                  55                  60

Gly Ala Cys Ala Ala Ala Thr Thr Gly Thr Thr Cys Thr Cys Ala Cys
65                  70                  75                  80

-continued

```
Cys Cys Ala Gly Thr Cys Thr Cys Cys Ala Gly Cys Ala Ala Thr Cys
                85                  90                  95

Ala Thr Gly Thr Cys Thr Gly Cys Ala Thr Cys Thr Cys Cys Ala Gly
            100                 105                 110

Gly Gly Gly Ala Gly Ala Ala Gly Gly Thr Cys Ala Cys Cys Ala Thr
        115                 120                 125

Ala Ala Cys Cys Thr Gly Cys Ala Gly Thr Gly Cys Cys Ala Gly Cys
    130                 135                 140

Thr Cys Ala Ala Gly Thr Gly Thr Ala Ala Gly Thr Thr Ala Cys Ala
145                 150                 155                 160

Thr Gly Cys Ala Cys Thr Gly Gly Thr Thr Cys Cys Ala Gly Cys Ala
                165                 170                 175

Gly Ala Ala Gly Cys Cys Ala Gly Gly Cys Ala Cys Thr Thr Cys Thr
            180                 185                 190

Cys Cys Cys Ala Ala Ala Cys Thr Cys Thr Gly Gly Ala Thr Thr Thr
        195                 200                 205

Ala Thr Ala Gly Cys Ala Cys Ala Thr Cys Cys Ala Ala Cys Cys Thr
    210                 215                 220

Gly Gly Cys Thr Thr Cys Thr Gly Gly Ala Gly Thr Cys Cys Cys Thr
225                 230                 235                 240

Gly Cys Thr Cys Gly Cys Thr Thr Cys Ala Gly Thr Gly Gly Cys Ala
                245                 250                 255

Gly Thr Gly Gly Ala Thr Cys Thr Gly Gly Gly Ala Cys Cys Thr Cys
            260                 265                 270

Thr Thr Ala Cys Thr Cys Thr Cys Thr Cys Ala Cys Ala Ala Thr Cys
        275                 280                 285

Ala Gly Cys Cys Gly Ala Ala Thr Gly Gly Ala Gly Gly Cys Thr Gly
    290                 295                 300

Ala Ala Gly Ala Thr Gly Cys Thr Gly Cys Cys Ala Cys Thr Thr Ala
305                 310                 315                 320

Thr Thr Ala Cys Thr Gly Cys Cys Ala Gly Cys Ala Ala Ala Gly Gly
                325                 330                 335

Ala Gly Thr Ala Gly Thr Thr Ala Cys Cys Cys Ala Thr Thr Cys Ala
            340                 345                 350

Cys Gly Thr Thr Cys Gly Gly Cys Thr Cys Gly Gly Gly Gly Ala Cys
        355                 360                 365

Ala Ala Ala Gly Thr Thr Gly Gly Ala Ala Ala Thr Ala Ala Ala Ala
    370                 375                 380

Cys Gly Gly Gly Cys Thr Gly Ala Thr Gly Cys Thr Gly Cys Ala Cys
385                 390                 395                 400

Cys Ala Ala Cys Thr Gly Thr Ala Thr Cys Cys Ala Thr Cys Thr Thr
                405                 410                 415

Cys Cys Cys Ala Cys Cys Ala Thr Cys Cys Ala Gly Thr Gly Ala Gly
            420                 425                 430

Cys Ala Gly Thr Thr Ala Ala Cys Ala Thr Cys Thr Gly Gly Ala Gly
        435                 440                 445

Gly Thr Gly Cys Cys Thr Cys Ala Gly Thr Cys Gly Thr Gly Thr Gly
    450                 455                 460

Cys Thr Thr Cys Thr Thr Gly Ala Ala Cys Ala Ala Cys Thr Thr Cys
465                 470                 475                 480

Thr Ala Cys Cys Cys Cys Ala Ala Ala Gly Ala Cys Ala Thr Cys Ala
                485                 490                 495

Ala Thr Gly Thr Cys Ala Ala Gly Thr Gly Gly Ala Ala Gly Ala Thr
```

-continued 500 505 510

Thr Gly Ala Thr Gly Gly Cys Ala Gly Thr Gly Ala Ala Cys Gly Ala
515 520 525

Cys Ala Ala Ala Ala Thr Gly Gly Cys Gly Thr Cys Cys Thr Gly Ala
530 535 540

Ala Cys Ala Gly Thr Thr Gly Gly Ala Cys Thr Gly Ala Thr Cys Ala
545 550 555 560

Gly Gly Ala Cys Ala Gly Cys Ala Ala Ala Gly Ala Cys Ala Gly Cys
565 570 575

Ala Cys Cys Thr Ala Cys Ala Gly Cys Ala Thr Gly Ala Gly Cys Ala
580 585 590

Gly Cys Ala Cys Cys Cys Thr Cys Ala Cys Gly Thr Thr Gly Ala Cys
595 600 605

Cys Ala Ala Gly Gly Ala Cys Gly Ala Gly Thr Ala Thr Gly Ala Ala
610 615 620

Cys Gly Ala Cys Ala Thr Ala Ala Cys Ala Gly Cys Thr Ala Thr Ala
625 630 635 640

Cys Cys Thr Gly Thr Gly Ala Gly Gly Cys Cys Ala Cys Thr Cys Ala
645 650 655

Cys Ala Ala Gly Ala Cys Ala Thr Cys Ala Ala Cys Thr Thr Cys Ala
660 665 670

Cys Cys Cys Ala Thr Thr Gly Thr Cys Ala Ala Gly Ala Gly Cys Thr
675 680 685

Thr Cys Ala Ala Cys Ala Gly Gly Ala Ala Thr Gly Ala Gly Thr Gly
690 695 700

Thr Thr Gly
705

<210> SEQ ID NO 5
<211> LENGTH: 235
<212> TYPE: PRT
<213> ORGANISM: Artificial Sequence
<220> FEATURE:
<223> OTHER INFORMATION: Synthetic Sequence

<400> SEQUENCE: 5

Met His Phe Gln Val Gln Ile Phe Ser Phe Leu Leu Ile Ser Ala Ser
1 5 10 15

Val Ile Met Ser Arg Gly Gln Ile Val Leu Thr Gln Ser Pro Ala Ile
20 25 30

Met Ser Ala Ser Pro Gly Glu Lys Val Thr Ile Thr Cys Ser Ala Ser
35 40 45

Ser Ser Val Ser Tyr Met His Trp Phe Gln Gln Lys Pro Gly Thr Ser
50 55 60

Pro Lys Leu Trp Ile Tyr Ser Thr Ser Asn Leu Ala Ser Gly Val Pro
65 70 75 80

Ala Arg Phe Ser Gly Ser Gly Ser Gly Thr Ser Tyr Ser Leu Thr Ile
85 90 95

Ser Arg Met Glu Ala Glu Asp Ala Ala Thr Tyr Tyr Cys Gln Gln Arg
100 105 110

Ser Ser Tyr Pro Phe Thr Phe Gly Ser Gly Thr Lys Leu Glu Ile Lys
115 120 125

Arg Ala Asp Ala Ala Pro Thr Val Ser Ile Phe Pro Pro Ser Ser Glu
130 135 140

Gln Leu Thr Ser Gly Gly Ala Ser Val Val Cys Phe Leu Asn Asn Phe

```
145                 150                 155                 160
Tyr Pro Lys Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
                180                 185                 190

Thr Tyr Ser Met Ser Ser Thr Leu Thr Leu Thr Lys Asp Glu Tyr Glu
                195                 200                 205

Arg His Asn Ser Tyr Thr Cys Glu Ala Thr His Lys Thr Ser Thr Ser
                210                 215                 220

Pro Ile Val Lys Ser Phe Asn Arg Asn Glu Cys
225                 230                 235

<210> SEQ ID NO 6
<211> LENGTH: 1383
<212> TYPE: PRT
<213> ORGANISM: Artificial Sequence
<220> FEATURE:
<223> OTHER INFORMATION: Synthetic Sequence

<400> SEQUENCE: 6

Ala Thr Gly Ala Ala Cys Thr Thr Cys Gly Gly Gly Cys Thr Cys Ala
1               5                   10                  15

Gly Cys Thr Thr Gly Ala Thr Thr Thr Cys Cys Thr Thr Gly Thr Thr
                20                  25                  30

Cys Cys Thr Thr Gly Thr Thr Thr Ala Ala Ala Gly Gly Thr
                35                  40                  45

Gly Thr Cys Cys Ala Gly Thr Gly Thr Gly Ala Ala Gly Thr Gly Ala
50                  55                  60

Ala Gly Cys Thr Gly Gly Thr Gly Gly Ala Gly Thr Cys Thr Gly Gly
65                  70                  75                  80

Gly Gly Gly Ala Gly Gly Cys Thr Thr Ala Gly Thr Gly Ala Ala Gly
                85                  90                  95

Cys Cys Thr Gly Gly Ala Gly Gly Gly Thr Cys Cys Cys Thr Gly Ala
                100                 105                 110

Ala Ala Cys Thr Cys Thr Cys Cys Thr Gly Thr Gly Cys Ala Gly Cys
                115                 120                 125

Cys Thr Cys Thr Gly Gly Ala Thr Thr Cys Ala Cys Thr Thr Thr Cys
                130                 135                 140

Ala Gly Thr Ala Gly Cys Thr Ala Thr Ala Cys Cys Ala Thr Gly Thr
145                 150                 155                 160

Cys Thr Thr Gly Gly Gly Thr Thr Cys Gly Cys Cys Ala Gly Ala Cys
                165                 170                 175

Thr Cys Cys Gly Gly Cys Gly Ala Ala Gly Ala Gly Gly Cys Thr Gly
                180                 185                 190

Gly Ala Gly Thr Gly Gly Gly Thr Cys Gly Cys Ala Ala Cys Cys Ala
                195                 200                 205

Thr Thr Ala Gly Thr Ala Gly Thr Gly Gly Thr Gly Gly Thr Gly Gly
                210                 215                 220

Thr Ala Ala Cys Ala Cys Cys Thr Ala Cys Thr Ala Thr Cys Cys Ala
225                 230                 235                 240

Gly Ala Cys Ala Gly Thr Gly Thr Gly Ala Ala Gly Gly Gly Cys Cys
                245                 250                 255

Gly Ala Thr Thr Cys Ala Cys Cys Ala Thr Cys Thr Cys Cys Ala Gly
                260                 265                 270

Ala Gly Ala Cys Ala Ala Thr Gly Cys Cys Ala Gly Gly Ala Ala Cys
```

-continued

```
        275                 280                 285

Ala Cys Cys Cys Thr Gly Thr Ala Cys Cys Thr Gly Cys Ala Ala Ala
    290                 295                 300

Thr Gly Ala Gly Cys Ala Gly Thr Cys Thr Gly Ala Gly Gly Thr Cys
305                 310                 315                 320

Thr Gly Ala Gly Gly Ala Cys Ala Cys Gly Gly Cys Cys Ala Thr Gly
                325                 330                 335

Thr Ala Thr Thr Ala Cys Thr Gly Thr Gly Cys Ala Ala Gly Ala Gly
            340                 345                 350

Ala Cys Thr Ala Thr Ala Gly Gly Thr Cys Cys Cys Thr Gly Thr Thr
        355                 360                 365

Thr Gly Cys Thr Thr Ala Cys Thr Gly Gly Gly Gly Cys Cys Ala Ala
    370                 375                 380

Gly Gly Gly Ala Cys Thr Cys Thr Gly Gly Thr Cys Ala Cys Thr Gly
385                 390                 395                 400

Thr Cys Thr Cys Thr Gly Cys Ala Gly Cys Cys Ala Ala Ala Ala Cys
                405                 410                 415

Gly Ala Cys Ala Cys Cys Cys Cys Cys Ala Thr Cys Thr Gly Thr Cys
            420                 425                 430

Thr Ala Thr Cys Cys Ala Cys Thr Gly Gly Cys Cys Cys Cys Thr Gly
        435                 440                 445
Gly Ala Thr Cys Thr Gly Cys Thr Gly Cys Cys Cys Ala Ala Ala Cys
    450                 455                 460

Thr Ala Ala Cys Thr Cys Cys Ala Thr Gly Gly Thr Gly Ala Cys Cys
465                 470                 475                 480
Cys Thr Gly Gly Gly Ala Thr Gly Cys Cys Thr Gly Gly Thr Cys Ala
                485                 490                 495

Ala Gly Gly Gly Cys Thr Ala Thr Thr Thr Cys Cys Cys Thr Gly Ala
            500                 505                 510

Gly Cys Cys Ala Gly Thr Gly Ala Cys Ala Gly Thr Gly Ala Cys Cys
        515                 520                 525

Thr Gly Gly Ala Ala Cys Thr Cys Thr Gly Gly Ala Thr Cys Cys Cys
    530                 535                 540

Thr Gly Thr Cys Cys Ala Gly Cys Gly Gly Thr Gly Thr Gly Cys Ala
545                 550                 555                 560

Cys Ala Cys Cys Thr Thr Cys Cys Cys Ala Gly Cys Thr Gly Thr Cys
                565                 570                 575

Cys Thr Gly Cys Ala Gly Thr Cys Thr Gly Ala Cys Cys Thr Cys Thr
            580                 585                 590

Ala Cys Ala Cys Thr Cys Thr Gly Ala Gly Cys Ala Gly Cys Thr Cys
        595                 600                 605

Ala Gly Thr Gly Ala Cys Thr Gly Thr Cys Cys Cys Cys Thr Cys Cys
    610                 615                 620

Ala Gly Cys Ala Cys Cys Thr Gly Gly Cys Cys Cys Ala Gly Cys Gly
625                 630                 635                 640

Ala Gly Ala Cys Cys Gly Thr Cys Ala Cys Cys Thr Gly Cys Ala Ala
                645                 650                 655

Cys Gly Thr Thr Gly Cys Cys Cys Ala Cys Cys Cys Gly Gly Cys Cys
            660                 665                 670

Ala Gly Cys Ala Gly Cys Ala Cys Cys Ala Ala Gly Gly Thr Gly Gly
        675                 680                 685

Ala Cys Ala Ala Gly Ala Ala Ala Ala Thr Thr Gly Thr Gly Cys Cys
    690                 695                 700
```

-continued

Cys Ala Gly Gly Gly Ala Thr Thr Gly Thr Gly Gly Thr Thr Gly Thr
705 710 715 720

Ala Ala Gly Cys Cys Thr Thr Gly Cys Ala Thr Ala Thr Gly Thr Ala
725 730 735

Cys Ala Gly Thr Cys Cys Cys Ala Gly Ala Ala Gly Thr Ala Thr Cys
740 745 750

Ala Thr Cys Thr Gly Thr Cys Thr Thr Cys Ala Thr Cys Thr Thr Cys
755 760 765

Cys Cys Cys Cys Cys Ala Ala Ala Gly Cys Cys Cys Ala Ala Gly Gly
770 775 780

Ala Thr Gly Thr Gly Cys Thr Cys Ala Cys Cys Ala Thr Thr Ala Cys
785 790 795 800

Thr Cys Thr Gly Ala Cys Thr Cys Cys Thr Ala Ala Gly Gly Thr Cys
805 810 815

Ala Cys Gly Thr Gly Thr Gly Thr Thr Gly Thr Gly Gly Thr Ala Gly
820 825 830

Ala Cys Ala Thr Cys Ala Gly Cys Ala Ala Gly Gly Ala Thr Gly Ala
835 840 845

Thr Cys Cys Cys Gly Ala Gly Gly Thr Cys Cys Ala Gly Thr Thr Cys
850 855 860

Ala Gly Cys Thr Gly Gly Thr Thr Thr Gly Thr Ala Gly Ala Thr Gly
865 870 875 880

Ala Thr Gly Thr Gly Gly Ala Gly Gly Thr Gly Cys Ala Cys Ala Cys
885 890 895

Ala Gly Cys Thr Cys Ala Gly Ala Cys Gly Cys Ala Ala Cys Cys Cys
900 905 910

Cys Gly Gly Gly Ala Gly Gly Ala Gly Cys Ala Gly Thr Thr Cys Ala
915 920 925

Ala Cys Ala Gly Cys Ala Cys Thr Thr Thr Cys Cys Gly Cys Thr Cys
930 935 940

Ala Gly Thr Cys Ala Gly Thr Gly Ala Ala Cys Thr Thr Cys Cys Cys
945 950 955 960

Ala Thr Cys Ala Thr Gly Cys Ala Cys Cys Ala Gly Gly Ala Cys Thr
965 970 975

Gly Gly Cys Thr Cys Ala Ala Thr Gly Gly Cys Ala Ala Gly Gly Ala
980 985 990

Gly Thr Thr Cys Ala Ala Ala Thr Gly Cys Ala Gly Gly Gly Thr Cys
995 1000 1005

Ala Ala Cys Ala Gly Thr Gly Cys Ala Gly Cys Thr Thr Thr Cys
1010 1015 1020

Cys Cys Thr Gly Cys Cys Cys Cys Cys Ala Thr Cys Gly Ala Gly
1025 1030 1035

Ala Ala Ala Ala Cys Cys Ala Thr Cys Thr Cys Cys Ala Ala Ala
1040 1045 1050

Ala Cys Cys Ala Ala Ala Gly Gly Cys Ala Gly Ala Cys Cys Gly
1055 1060 1065

Ala Ala Gly Gly Cys Thr Cys Cys Ala Cys Ala Gly Gly Thr Gly
1070 1075 1080

Thr Ala Cys Ala Cys Cys Ala Thr Thr Cys Cys Ala Cys Cys Thr
1085 1090 1095

Cys Cys Cys Ala Ala Gly Gly Ala Gly Cys Ala Gly Ala Thr Gly
1100 1105 1110

```
Gly Cys  Cys Ala Ala Gly Gly  Ala Thr Ala Ala  Ala Gly Thr Cys
    1115              1120                 1125

Ala Gly  Thr Cys Thr Gly Ala  Cys Cys Thr Gly  Cys Ala Thr Gly
    1130              1135                 1140

Ala Thr  Ala Ala Cys Ala Gly  Ala Cys Thr Thr  Cys Thr Thr Cys
    1145              1150                 1155

Cys Cys  Thr Gly Ala Ala Gly  Ala Cys Ala Thr  Ala Ala Cys Thr
    1160              1165                 1170

Gly Thr  Gly Gly Ala Gly Thr  Gly Gly Cys Ala  Gly Thr Gly Gly
    1175              1180                 1185

Ala Ala  Thr Gly Gly Gly Cys  Ala Gly Cys Cys  Ala Gly Cys Gly
    1190              1195                 1200

Gly Ala  Gly Ala Ala Cys Thr  Ala Cys Ala Ala  Gly Ala Ala Cys
    1205              1210                 1215

Ala Cys  Thr Cys Ala Gly Cys  Cys Cys Ala Thr  Cys Ala Thr Gly
    1220              1225                 1230

Gly Ala  Cys Ala Cys Ala Gly  Ala Thr Gly Gly  Cys Thr Cys Thr
    1235              1240                 1245

Thr Ala  Cys Thr Thr Cys Ala  Thr Cys Thr Ala  Cys Ala Gly Cys
    1250              1255                 1260

Ala Ala  Gly Cys Thr Cys Ala  Ala Thr Gly Thr  Gly Cys Ala Gly
    1265              1270                 1275

Ala Ala  Gly Ala Gly Cys Ala  Ala Cys Thr Gly  Gly Gly Ala Gly
    1280              1285                 1290

Gly Cys  Ala Gly Gly Ala Ala  Ala Thr Ala Cys  Thr Thr Thr Cys
    1295              1300                 1305

Ala Cys  Cys Thr Gly Cys Thr  Cys Thr Gly Thr  Gly Thr Thr Ala
    1310              1315                 1320

Cys Ala  Thr Gly Ala Gly Gly  Gly Cys Cys Thr  Gly Cys Ala Cys
    1325              1330                 1335

Ala Ala  Cys Cys Ala Cys Cys  Ala Thr Ala Cys  Thr Gly Ala Gly
    1340              1345                 1350

Ala Ala  Gly Ala Gly Cys Cys  Thr Cys Thr Cys  Cys Ala Cys
    1355              1360                 1365

Thr Cys  Thr Cys Cys Thr Gly  Thr Ala Ala Ala  Thr Gly Ala
    1370              1375                 1380
```

<210> SEQ ID NO 7
<211> LENGTH: 460
<212> TYPE: PRT
<213> ORGANISM: Artificial Sequence
<220> FEATURE:
<223> OTHER INFORMATION: Synthetic Sequence

<400> SEQUENCE: 7

```
Met Asn Phe Gly Leu Ser Leu Ile Phe Leu Val Leu Val Leu Lys Gly
1               5                   10                  15

Val Gln Cys Glu Val Lys Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Ser Tyr Thr Met Ser Trp Val Arg Gln Thr Pro Ala Lys Arg Leu
    50                  55                  60

Glu Trp Val Ala Thr Ile Ser Ser Gly Gly Gly Asn Thr Tyr Tyr Pro
65                  70                  75                  80
```

-continued

```
Asp Ser Val Lys Gly Arg Phe Thr Ile Ser Arg Asp Asn Ala Arg Asn
                 85                  90                  95

Thr Leu Tyr Leu Gln Met Ser Ser Leu Arg Ser Glu Asp Thr Ala Met
            100                 105                 110

Tyr Tyr Cys Ala Arg Asp Tyr Arg Ser Leu Phe Ala Tyr Trp Gly Gln
        115                 120                 125

Gly Thr Leu Val Thr Val Ser Ala Ala Lys Thr Thr Pro Pro Ser Val
    130                 135                 140

Tyr Pro Leu Ala Pro Gly Ser Ala Ala Gln Thr Asn Ser Met Val Thr
145                 150                 155                 160

Leu Gly Cys Leu Val Lys Gly Tyr Phe Pro Glu Pro Val Thr Val Thr
                165                 170                 175

Trp Asn Ser Gly Ser Leu Ser Ser Gly Val His Thr Phe Pro Ala Val
            180                 185                 190

Leu Gln Ser Asp Leu Tyr Thr Leu Ser Ser Ser Val Thr Val Pro Ser
        195                 200                 205

Ser Thr Trp Pro Ser Glu Thr Val Thr Cys Asn Val Ala His Pro Ala
    210                 215                 220

Ser Ser Thr Lys Val Asp Lys Lys Ile Val Pro Arg Asp Cys Gly Cys
225                 230                 235                 240

Lys Pro Cys Ile Cys Thr Val Pro Glu Val Ser Ser Val Phe Ile Phe
                245                 250                 255

Pro Pro Lys Pro Lys Asp Val Leu Thr Ile Thr Leu Thr Pro Lys Val
            260                 265                 270

Thr Cys Val Val Val Asp Ile Ser Lys Asp Asp Pro Glu Val Gln Phe
        275                 280                 285

Ser Trp Phe Val Asp Asp Val Glu Val His Thr Ala Gln Thr Gln Pro
    290                 295                 300

Arg Glu Glu Gln Phe Asn Ser Thr Phe Arg Ser Val Ser Glu Leu Pro
305                 310                 315                 320

Ile Met His Gln Asp Trp Leu Asn Gly Lys Glu Phe Lys Cys Arg Val
                325                 330                 335

Asn Ser Ala Ala Phe Pro Ala Pro Ile Glu Lys Thr Ile Ser Lys Thr
            340                 345                 350

Lys Gly Arg Pro Lys Ala Pro Gln Val Tyr Thr Ile Pro Pro Pro Lys
        355                 360                 365

Glu Gln Met Ala Lys Asp Lys Val Ser Leu Thr Cys Met Ile Thr Asp
    370                 375                 380

Phe Phe Pro Glu Asp Ile Thr Val Glu Trp Gln Trp Asn Gly Gln Pro
385                 390                 395                 400

Ala Glu Asn Tyr Lys Asn Thr Gln Pro Ile Met Asp Thr Asp Gly Ser
                405                 410                 415

Tyr Phe Ile Tyr Ser Lys Leu Asn Val Gln Lys Ser Asn Trp Glu Ala
            420                 425                 430

Gly Asn Thr Phe Thr Cys Ser Val Leu His Glu Gly Leu His Asn His
        435                 440                 445

His Thr Glu Lys Ser Leu Ser His Ser Pro Gly Lys
    450                 455                 460
```

<210> SEQ ID NO 8
<211> LENGTH: 707
<212> TYPE: PRT
<213> ORGANISM: Artificial Sequence
<220> FEATURE:
<223> OTHER INFORMATION: Synthetic Sequence

<400> SEQUENCE: 8

Ala Thr Gly Cys Ala Thr Thr Thr Thr Cys Ala Ala Gly Thr Gly Cys
1               5                   10                  15

Ala Gly Ala Thr Thr Thr Thr Cys Ala Gly Cys Thr Thr Cys Cys Thr
            20                  25                  30

Gly Cys Thr Ala Ala Thr Cys Ala Gly Thr Gly Cys Cys Thr Cys Ala
        35                  40                  45

Gly Thr Cys Ala Thr Ala Ala Thr Gly Thr Cys Cys Ala Gly Ala Gly
    50                  55                  60

Gly Ala Cys Ala Ala Ala Thr Thr Gly Thr Thr Cys Thr Cys Ala Cys
65                  70                  75                  80

Cys Cys Ala Gly Thr Cys Thr Cys Cys Ala Gly Cys Ala Ala Thr Cys
                85                  90                  95

Ala Thr Gly Thr Cys Thr Gly Cys Ala Thr Cys Thr Cys Cys Ala Gly
            100                 105                 110

Gly Gly Gly Ala Gly Ala Ala Gly Gly Thr Cys Ala Cys Cys Ala Thr
        115                 120                 125

Ala Ala Cys Cys Thr Gly Cys Ala Gly Thr Gly Cys Cys Ala Gly Cys
    130                 135                 140

Thr Cys Ala Ala Gly Thr Gly Thr Ala Ala Gly Thr Thr Ala Cys Ala
145                 150                 155                 160

Thr Gly Cys Ala Cys Thr Gly Gly Thr Thr Cys Cys Ala Gly Cys Ala
                165                 170                 175

Gly Ala Ala Gly Cys Cys Ala Gly Gly Cys Ala Cys Thr Thr Cys Thr
            180                 185                 190

Cys Cys Cys Ala Ala Ala Cys Thr Cys Thr Gly Gly Ala Thr Thr Thr
        195                 200                 205

Ala Thr Ala Gly Cys Ala Cys Ala Thr Cys Cys Ala Ala Cys Cys Thr
    210                 215                 220

Gly Gly Cys Thr Thr Cys Thr Gly Gly Ala Gly Thr Cys Cys Cys Thr
225                 230                 235                 240

Gly Cys Thr Cys Gly Cys Thr Thr Cys Ala Gly Thr Gly Gly Cys Ala
                245                 250                 255

Gly Thr Gly Gly Ala Thr Cys Thr Gly Gly Gly Ala Cys Cys Thr Cys
            260                 265                 270

Thr Thr Ala Cys Thr Cys Thr Cys Thr Cys Ala Cys Ala Ala Thr Cys
        275                 280                 285

Ala Gly Cys Cys Gly Ala Ala Thr Gly Gly Ala Gly Gly Cys Thr Gly
    290                 295                 300

Ala Ala Gly Ala Thr Gly Cys Thr Gly Cys Cys Ala Cys Thr Thr Ala
305                 310                 315                 320

Thr Thr Ala Cys Thr Gly Cys Cys Ala Gly Cys Ala Ala Ala Gly Gly
                325                 330                 335

Ala Gly Thr Ala Gly Thr Thr Ala Cys Cys Cys Ala Thr Thr Cys Ala
            340                 345                 350

Cys Gly Thr Thr Cys Gly Gly Cys Thr Cys Gly Gly Gly Gly Ala Cys
        355                 360                 365

Ala Ala Ala Gly Thr Thr Gly Gly Ala Ala Ala Thr Ala Ala Ala Ala
    370                 375                 380

Cys Gly Gly Gly Cys Thr Gly Ala Thr Gly Cys Thr Gly Cys Ala Cys
385                 390                 395                 400

Cys Ala Ala Cys Thr Gly Thr Ala Thr Cys Cys Ala Thr Cys Thr Thr

```
                405                 410                 415

Cys Cys Cys Ala Cys Cys Ala Thr Cys Cys Ala Gly Thr Gly Ala Gly
            420                 425                 430

Cys Ala Gly Thr Thr Ala Ala Cys Ala Thr Cys Thr Gly Gly Ala Gly
        435                 440                 445

Gly Thr Gly Cys Cys Thr Cys Ala Gly Thr Cys Gly Thr Gly Thr Gly
    450                 455                 460

Cys Thr Thr Cys Thr Thr Gly Ala Ala Cys Ala Ala Cys Thr Thr Cys
465                 470                 475                 480

Thr Ala Cys Cys Cys Cys Ala Ala Ala Gly Ala Cys Ala Thr Cys Ala
                485                 490                 495

Ala Thr Gly Thr Cys Ala Ala Gly Thr Gly Gly Ala Ala Gly Ala Thr
            500                 505                 510

Thr Gly Ala Thr Gly Gly Cys Ala Gly Thr Gly Ala Ala Cys Gly Ala
        515                 520                 525

Cys Ala Ala Ala Ala Thr Gly Gly Cys Gly Thr Cys Cys Thr Gly Ala
    530                 535                 540

Ala Cys Ala Gly Thr Thr Gly Gly Ala Cys Thr Gly Ala Thr Cys Ala
545                 550                 555                 560

Gly Gly Ala Cys Ala Gly Cys Ala Ala Ala Gly Ala Cys Ala Gly Cys
                565                 570                 575

Ala Cys Cys Thr Ala Cys Ala Gly Cys Ala Thr Gly Ala Gly Cys Ala
            580                 585                 590

Gly Cys Ala Cys Cys Cys Thr Cys Ala Cys Gly Thr Thr Gly Ala Cys
        595                 600                 605

Cys Ala Ala Gly Gly Ala Cys Gly Ala Gly Thr Ala Thr Gly Ala Ala
    610                 615                 620

Cys Gly Ala Cys Ala Thr Ala Ala Cys Ala Gly Cys Thr Ala Thr Ala
625                 630                 635                 640

Cys Cys Thr Gly Thr Gly Ala Gly Gly Cys Cys Ala Cys Thr Cys Ala
                645                 650                 655

Cys Ala Ala Gly Ala Cys Ala Thr Cys Ala Ala Cys Thr Thr Cys Ala
            660                 665                 670

Cys Cys Cys Ala Thr Thr Gly Thr Cys Ala Ala Gly Ala Gly Cys Thr
        675                 680                 685

Thr Cys Ala Ala Cys Ala Gly Gly Ala Ala Thr Gly Ala Gly Thr Gly
    690                 695                 700

Thr Thr Gly
705
```

<210> SEQ ID NO 9
<211> LENGTH: 235
<212> TYPE: PRT
<213> ORGANISM: Artificial Sequence
<220> FEATURE:
<223> OTHER INFORMATION: Synthetic Sequence

<400> SEQUENCE: 9

```
Met His Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile
            20                  25                  30

Met Ser Ala Ser Pro Gly Glu Lys Val Thr Ile Thr Cys Ser Ala Ser
        35                  40                  45

Ser Ser Val Ser Tyr Met His Trp Phe Gln Gln Lys Pro Gly Thr Ser
```

```
                50                  55                  60
Pro Lys Leu Trp Ile Tyr Ser Thr Ser Asn Leu Ala Ser Gly Val Pro
 65                  70                  75                  80

Ala Arg Phe Ser Gly Ser Gly Ser Gly Thr Ser Tyr Ser Leu Thr Ile
                 85                  90                  95

Ser Arg Met Glu Ala Glu Asp Ala Ala Thr Tyr Tyr Cys Gln Gln Arg
            100                 105                 110

Ser Ser Tyr Pro Phe Thr Phe Gly Ser Gly Thr Lys Leu Glu Ile Lys
        115                 120                 125

Arg Ala Asp Ala Ala Pro Thr Val Ser Ile Phe Pro Pro Ser Ser Glu
    130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Thr Lys Asp Glu Tyr Glu
        195                 200                 205

Arg His Asn Ser Tyr Thr Cys Glu Ala Thr His Lys Thr Ser Thr Ser
    210                 215                 220

Pro Ile Val Lys Ser Phe Asn Arg Asn Glu Cys
225                 230                 235

<210> SEQ ID NO 10
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 10

Ser Tyr Thr Met Ser
 1               5

<210> SEQ ID NO 11
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 11

Thr Ile Ser Ser Gly Gly Gly Asn Thr Tyr Tyr Pro Asp Ser Val Lys
 1               5                  10                  15

Gly

<210> SEQ ID NO 12
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 12

Asp Tyr Arg Ser Leu Phe Ala Tyr
 1               5

<210> SEQ ID NO 13
<211> LENGTH: 10
```

```
<212> TYPE: PRT
<213> ORGANISM: Artificial Sequence
<220> FEATURE:
<223> OTHER INFORMATION: Synthetic Sequence

<400> SEQUENCE: 13

Ser Ala Ser Ser Ser Val Ser Tyr Met His
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 14

Ser Thr Ser Asn Leu Ala Ser
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 15

Gln Gln Arg Ser Ser Tyr Pro Phe Thr
1               5

<210> SEQ ID NO 16
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 16

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Ala Lys Arg Leu Glu Trp Val
        35                  40                  45

Ala Thr Ile Ser Ser Gly Gly Gly Asn Thr Tyr Tyr Pro Asp Ser Val
    50                  55                  60

Lys Gly Arg Phe Thr Ile Ser Arg Asp Asn Ala Arg Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Asp Tyr Arg Ser Leu Phe Ala Tyr Trp Gly Gln Gly Thr Leu
            100                 105                 110

Val Thr Val Ser Ala
        115

<210> SEQ ID NO 17
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 17
```

```
Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Val Ser Tyr Met
            20                  25                  30

His Trp Phe Gln Gln Lys Pro Gly Thr Ser Pro Lys Leu Trp Ile Tyr
            35                  40                  45

Ser Thr Ser Asn Leu Ala Ser Gly Val Pro Ala Arg Phe Ser Gly Ser
        50                  55                  60

Gly Ser Gly Thr Ser Tyr Ser Leu Thr Ile Ser Arg Met Glu Ala Glu
65              70                  75                  80

Asp Ala Ala Thr Tyr Tyr Cys Gln Gln Arg Ser Ser Tyr Pro Phe Thr
                85                  90                  95

Phe Gly Ser Gly Thr Lys Leu Glu Ile Lys
                100                 105

<210> SEQ ID NO 18
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 18

Gly Ala Lys Lys Val Phe Tyr Val Ile Glu Thr Arg Glu Pro Arg Glu
1               5                   10                  15

Arg Leu

<210> SEQ ID NO 19
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 19

Asp Ser Glu Ala Leu His Pro Leu Gly Met Ala Val Lys Ser Ser
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 20

Asp Ser Glu Ala Leu His Pro Leu Gly Met Ala Val Lys Ser Ser
1               5                   10                  15
```